(12) United States Patent
Vergani et al.

(10) Patent No.: US 11,351,178 B2
(45) Date of Patent: Jun. 7, 2022

(54) SELECTIVE HDAC6 INHIBITORS

(71) Applicant: ITALFARMACO S.P.A., Milan (IT)

(72) Inventors: Barbara Vergani, Macherio (IT);
Gianluca Caprini, Somma Lombardo (IT); Gianluca Fossati, Milan (IT);
Maria Lattanzio, Milan (IT); Mattia Marchini, Milan (IT); Gianfranco Pavich, Desio (IT); Marcello Pezzuto, Paderno Dugnano (IT); Chiara Ripamonti, Monza (IT); Giovanni Sandrone, Novara (IT); Christian Steinkühler, Rome (IT); Andrea Stevenazzi, Milan (IT)

(73) Assignee: ITALFARMACO SPA, Milan (IT)

( * ) Notice: Subject to any disclaimer, the term of this patent is extended or adjusted under 35 U.S.C. 154(b) by 86 days.

(21) Appl. No.: 16/491,827

(22) PCT Filed: Apr. 12, 2018

(86) PCT No.: PCT/EP2018/059468
§ 371 (c)(1),
(2) Date: Sep. 6, 2019

(87) PCT Pub. No.: WO2018/189340
PCT Pub. Date: Oct. 18, 2018

(65) Prior Publication Data
US 2021/0128577 A1    May 6, 2021

(30) Foreign Application Priority Data

Apr. 14, 2017  (IT) .................. 102017000041723

(51) Int. Cl.
*A61K 31/4365*    (2006.01)
*A61K 31/427*    (2006.01)
(Continued)

(52) U.S. Cl.
CPC .............. *A61K 31/55* (2013.01); *A61K 31/41* (2013.01); *A61K 31/4196* (2013.01); *A61K 31/427* (2013.01); *A61K 31/4245* (2013.01); *A61K 31/433* (2013.01); *A61K 31/437* (2013.01); *A61K 31/4365* (2013.01); *A61K 31/4439* (2013.01); *A61K 31/454* (2013.01); *A61K 31/4709* (2013.01); *A61K 31/4725* (2013.01); *A61K 31/496* (2013.01); *A61K 31/497* (2013.01); *A61K 31/501* (2013.01);
(Continued)

(58) Field of Classification Search
CPC .. C07D 409/04; C07D 409/14; C07D 491/07; C07D 257/04; C07D 271/10; C07D 417/04; C07D 417/06; C07D 249/08; C07D 249/12; C07D 405/04; C07D 405/06; C07D 405/14; C07D 403/04; C07D 495/04; C07D 401/06; C07D 285/125; C07D 401/04; C07D 471/04; C07D 271/06; A61K 31/501; A61K 31/4365; A61K 31/437; A61K 31/496; A61K 31/454; A61K 31/4709; A61K 31/41; A61K 31/427; A61K 31/497; A61K 31/433; A61K 31/4245; A61K 31/55; A61K 31/506; A61K 31/5377; A61K 31/4439; A61P 27/00; A61P 29/00; A61P 35/00; A61P 25/00
See application file for complete search history.

(56) References Cited

U.S. PATENT DOCUMENTS

| | | |
|---|---|---|
| 2007/0232808 A1 | 10/2007 | Bacchi |
| 2009/0005374 A1 | 1/2009 | Melvin, Jr. et al. |
| 2011/0039027 A1 | 2/2011 | Blackburn et al. |

FOREIGN PATENT DOCUMENTS

| | | |
|---|---|---|
| JP | 2010-531875 | 9/2010 |
| JP | 2012-530703 | 12/2012 |

(Continued)

OTHER PUBLICATIONS

AD, 2021, https://www.mayoclinic.org/diseases-conditions/alzheimers-disease/in-depth/alzheimers/art-20048103.*

(Continued)

*Primary Examiner* — Sun Jae Yoo
(74) *Attorney, Agent, or Firm* — Hueschen and Sage

(57) ABSTRACT

The present invention relates to novel benzohydroxamic compounds of formula (I) and (II) and pharmaceutically acceptable salts, isomers and prodrugs thereof, exhibiting a high selective inhibitory activity against histone deacetylase 6 (HDAC6) enzyme.

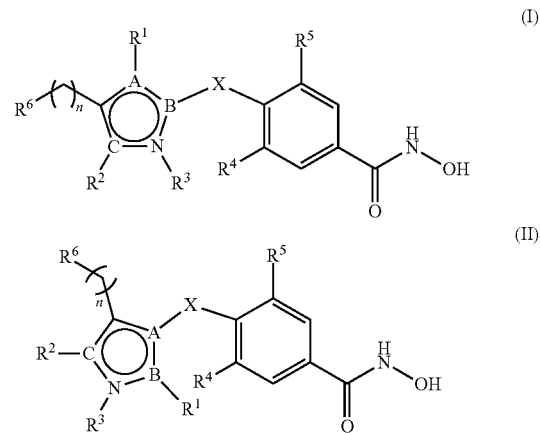

14 Claims, 6 Drawing Sheets

(51) Int. Cl.

| | | |
|---|---|---|
| A61K 31/506 | (2006.01) | |
| A61K 45/06 | (2006.01) | |
| A61K 31/496 | (2006.01) | |
| A61K 31/4196 | (2006.01) | |
| A61K 31/5377 | (2006.01) | |
| A61K 31/41 | (2006.01) | |
| A61K 31/55 | (2006.01) | |
| A61K 31/497 | (2006.01) | |
| A61K 31/4245 | (2006.01) | |
| A61K 31/437 | (2006.01) | |
| A61K 31/433 | (2006.01) | |
| A61K 31/4725 | (2006.01) | |
| A61K 31/4439 | (2006.01) | |
| A61K 31/4709 | (2006.01) | |
| A61K 31/501 | (2006.01) | |
| A61K 31/454 | (2006.01) | |
| C07D 249/12 | (2006.01) | |
| C07D 249/08 | (2006.01) | |
| C07D 401/06 | (2006.01) | |
| C07D 401/04 | (2006.01) | |
| C07D 271/06 | (2006.01) | |
| C07D 271/10 | (2006.01) | |
| C07D 405/04 | (2006.01) | |
| C07D 405/14 | (2006.01) | |
| C07D 417/06 | (2006.01) | |
| C07D 417/04 | (2006.01) | |
| C07D 471/04 | (2006.01) | |
| C07D 257/04 | (2006.01) | |
| C07D 409/14 | (2006.01) | |
| C07D 409/04 | (2006.01) | |
| C07D 403/04 | (2006.01) | |
| C07D 405/06 | (2006.01) | |
| C07D 495/04 | (2006.01) | |
| C07D 413/04 | (2006.01) | |
| A61P 35/00 | (2006.01) | |
| A61P 29/00 | (2006.01) | |
| A61P 27/00 | (2006.01) | |
| A61P 25/00 | (2006.01) | |
| C07D 271/113 | (2006.01) | |
| C07D 285/125 | (2006.01) | |
| C07D 491/107 | (2006.01) | |

(52) U.S. Cl.
CPC ........ *A61K 31/506* (2013.01); *A61K 31/5377* (2013.01); *A61K 45/06* (2013.01); *A61P 35/00* (2018.01); *C07D 249/08* (2013.01); *C07D 249/12* (2013.01); *C07D 257/04* (2013.01); *C07D 271/06* (2013.01); *C07D 271/10* (2013.01); *C07D 271/113* (2013.01); *C07D 285/125* (2013.01); *C07D 401/04* (2013.01); *C07D 401/06* (2013.01); *C07D 403/04* (2013.01); *C07D 405/04* (2013.01); *C07D 405/06* (2013.01); *C07D 405/14* (2013.01); *C07D 409/04* (2013.01); *C07D 409/14* (2013.01); *C07D 413/04* (2013.01); *C07D 417/04* (2013.01); *C07D 417/06* (2013.01); *C07D 471/04* (2013.01); *C07D 491/107* (2013.01); *C07D 495/04* (2013.01)

(56) References Cited

FOREIGN PATENT DOCUMENTS

| WO | 03062225 A1 | 7/2003 |
|---|---|---|
| WO | 2006003096 A1 | 1/2006 |
| WO | 2011021209 A1 | 2/2011 |
| WO | 2011106650 A2 | 9/2011 |
| WO | 2012106343 A2 | 8/2012 |
| WO | 2012106995 A1 | 8/2012 |
| WO | 2012178208 A2 | 12/2012 |
| WO | 2015087151 A1 | 6/2015 |
| WO | 2015102426 A1 | 7/2015 |
| WO | WO 2015/192078 | 12/2015 |

OTHER PUBLICATIONS

RA, 2021, https://www.mayoclinic.org/diseases-conditions/rheumatoid-arthritis/diagnosis-treatment/drc-20353653.*

Maurício T. Tavares, et al., "Synthesis and Pharmacological Evaluation of Selective Histone Deacetylase 6 Inhibitors in Melanoma Models", ACS Med. Chem. Lett. 2017, 8, 1031-1036.

Tatiana Akimova, et al., "Standardization, Evaluation, and Area-Under-Curve Analysis of Human and Murine Treg Suppressive Function", Suppression and Regulation of Immune Responses: Methods and Protocols, vol. II, Methods in Molecular Biology, vol. 1371, 2016.

Grace I. Aldana-Masangkay, et al., "The Role of HDAC6 in Cancer", Journal of Biomedicine and Biotechnology, vol. 2011, 10 pages, Jul. 2010.

Susan D. Aster, et al., "Bis-aryl triazoles as selective inhibitors of 11β-hydroxysteroid dehydrogenase type 1", Bioorg. Med. Chem. Lett. 18 (2008) 2799-2804.

Julia A. Brown, et al., "Blockade of Programmed Death-1 Ligands on Dendritic Cells Enhances T Cell Activation and Cytokine Production", J Immunol 2003; 170:1257-1266.

Sonja Schlimme, et al., "Carbamate Prodrug Concept for Hydroxamate HDAC Inhibitors", ChemMedChem 2011, 6, 1193-1198.

Georgette M. Castanedo, et al., "Rapid Synthesis of 1,3,5-Substituted 1,2,4-Triazoles from Carboxylic Acids, Amidines, and Hydrazines", J. Org. Chem. 2011, 76, 1177-1179.

Sarah J. Dolman, et al., "Superior Reactivity of Thiosemicarbazides in the Synthesis of 2-Amino-1,3,4-oxadiazoles", J. Org. Chem. 2006, 71, 9548-9551.

Jim P. Dompierre, et al., "Histone Deacetylase 6 Inhibition Compensates for the Transport Deficit in Huntington's Disease by Increasing Tubulin Acetylation", The Journal of Neuroscience, Mar. 28, 2007, 27(13):3571-3583.

Virginija Dudutienė, et al., "4-Substituted-2,3,5,6-tetrafluorobenzenesulfonamides as inhibitors of carbonic anhydrases I, II, VII, XII, and XIII", Bioorganic & Medicinal Chemistry 21 (2013) 2093-2106.

Warren Fiskus, et al., "Molecular and biologic characterization and drug sensitivity of pan-histone deacetylase inhibitor-resistant acute myeloid leukemia cells", Blood, Oct. 1, 2008, vol. 112, No. 7, 2896-2905.

Harish Rajak, et al., "2,5-Disubstituted-1,3,4-oxadiazoles/thiadiazole as surface recognition moiety: Design and synthesis of novel hydroxamic acid based histone deacetylase inhibitors", Bioorganic & Medicinal Chemistry Letters 21 (2011) 5735-5738.

Teru Hideshima, et al., "Small-molecule inhibition of proteasome and aggresome function induces synergistic antitumor activity in multiple myeloma", PNAS, Jun. 14, 2005, vol. 102, No. 24, 8567-8572.

Patil S.J., et al., "Prodrug Approach: An Effective Solution To Overcome Side-Effects", International Journal of Medical and Pharmaceutical Sciences (IJMPS), vol. 1, issue 7, 2011.

Jay H. Kalin, et al., "Second-Generation Histone Deacetylase 6 Inhibitors Enhance the Immunosuppressive Effects f Foxp3+ T-Regulatory Cells", Journal of Medicinal Chemistry, 2012, 55, 639-651.

Yoshiharu Kawaguchi, et al., "The Deacetylase HDAC6 Regulates Aggresome Formation and Cell Viability in Response to Misfolded Protein Stress", Cell, vol. 115, 727-738, Dec. 12, 2003.

Kazuhiro Ito, et al., "A molecular mechanism of action of theophylline: Induction of histone deacetylase activity to decrease inflammatory gene expression", PNAS, Jun. 25, 2002, vol. 99, No. 13, 8921-8926.

Sebastian Kreiter, et al., "Mutant MHC class II epitopes drive therapeutic immune responses to cancer", Nature, Apr. 30, 2015; 520 (7549): 692-696.

(56) References Cited

OTHER PUBLICATIONS

Lei Yan, et al., "Pyrimidine Triazole Thioether Derivatives as Toll-Like Receptor 5 (TLR5)/Flagellin Complex Inhibitors", ChemMedChem (2016) 11: 822-826.
Liang-Feng Niu, et al., "Efficient copper-catalyzed C—S cross-coupling of heterocyclic thiols with aryl iodides", Tetrahedron 67 (2011) 2878-2881.
Jaida Begum, et al., "Computationally motivated synthesis and enzyme kinetic evaluation of N-(β-D-glucopyranosyl)-1,2,4-triazolecarboxamides as glycogen phosphorylase inhibitors", Med. Chem. Commun., 2015, 6, 80-89.
Edwin F. De Zoeten, et al., "Histone Deacetylase 6 and Heat Shock Protein 90 Control the Functions of Foxp3+ T-Regulatory Cells", Molecular and Cellular Biology, May 2011, vol. 31, No. 10, p. 2066-2078.
Nadjet Rezki, et al., "Synthesis of Novel 2,5-Disubstituted-1,3,4-thiadiazoles Clubbed 1,2,4-Triazole, 1,3,4-Thiadiazole, 1,3,4-Oxadiazole and/or Schiff Base as Potential Antimicrobial and Antiproliferative Agents", Molecules 2015, 20, 16048-16067.
Tiago Fleming Outeiro, et al., "Sirtuin 2 Inhibitors Rescue α-Synuclein-Mediated Toxicity in Models of Parkinson's Disease", Science, vol. 317, Jul. 27, 2007.
Drew M. Pardoll, "The blockade of immune checkpoints in cancer immunotherapy", Nat Rev Cancer; 12(4):252-264, May 4, 2016.
Agustin Rodriguez-Gonzalez, et al., "Tubacin, An Inhibitor of HDAC6, Induces Apoptosis of Acute-Lymphoblastic Leukemia Cells in Vitro and in Vivo through a Na+/K+ATPase-Dependent Pathway", Blood, 2008, 112:1923.
Sergio Valente, et al., "1,3,4-Oxadiazole-Containing Histone Deacetylase Inhibitors: Anticancer Activities in Cancer Cells", Journal of Medicinal Chemistry, 2014, 57, 6259-6265.
Liqing Wang, et al., "Immunomodulatory effects of deacetylase inhibitors: therapeutic targeting of FOXP3+ regulatory T cells", Nat Rev Drug Discov. Dec. 2009, 8(12):969-981.
International Search Report dated May 16, 2018 issued in PCT/EP2018/059468.

\* cited by examiner

SELECTIVE HDAC6 INHIBITORS

This application is a National Stage of International Application PCT/EP2018/059468, filed Apr. 12, 2018, under PCT Article 21(2) in English; which claims the priority of Italian Application No. 102017000041723, filed Apr. 14, 2017. The contents of the above-identified applications are incorporated herein by reference in their entireties.

FIELD OF THE INVENTION

The present invention relates to novel selective benzohydroxamic inhibitors of histone deacetylase 6 (HDAC6) enzyme and pharmaceutical compositions thereof.

Therefore, these compounds are useful in treating diseases associated with HDAC6 activity such as graft rejection, GVHD, myositis, diseases associated with abnormal lymphocyte function, multiple myeloma, non-Hodgkin lymphoma, peripheral neuropathy, autoimmune diseases, inflammatory diseases, cancer and neurodegenerative pathologies.

STATE OF THE ART OF THE INVENTION

The genetic material of eukaryotic cells is organized in a complex and dynamic structure consisting of DNA and proteins, chromatin. The main protein components of chromatin are histones, basic proteins which interact with DNA forming the basic structural unit of chromatin, the nucleosome, the first level of chromosomal compaction within nucleus. The interaction between basic histone residues and DNA acid residues is crucial in determining the nucleosome compaction and the related DNA accessibility to molecular complexes regulating replication and transcription. This interaction is mainly influenced by histone degree of acetylation. Deacetylation of histone N-terminal lysine residues enables protonation of amine group, which carrying a positive charge, interacts with negative charges contained in DNA. Such interaction occurs in a more compact state of chromatin, involving the gene expression silencing. Conversely, acetylation of the same residues prevents ionic bonding formation, leading to a less compact form of chromatin which allows greater DNA exposure and the interaction with macromolecular complexes that activate gene transcription.

The degree of histone acetylation is regulated by the activity balance of two classes of enzymes: histone acetyl transferases (histone acetyl-transferases HAT) and histone deacetylase (histone deacetylases HDAC). An alteration of this delicate balance can lead to a loss of cellular homeostasis, commonly found in various human diseases, including cancer, neurological disorders, inflammation, and autoimmune diseases.

Histone deacetylases have been so classified as they reversibly catalyse the deacetylation of amine groups of histone N-terminus lysine residues. Subsequently, it has been found that there is a large number of substrates of these enzymes as their activity is also due to non-histone protein which are substrates of HAT enzymes containing N-acetyl-lysine, such as transcription factors, DNA repair enzymes and other nucleus and cytoplasmic proteins.

The human HDAC class consists of 18 enzymes, divided into two groups: zinc-dependent HDACs and HDAC NAD-dependent, also known as sirtuins (class III). Zinc-dependent HDACs are further distributed into four classes: 1) Class I, including HDAC1, 2, 3 and 8, ubiquitous isoenzymes mainly located in the nucleus; 2) Class IIa, including HDAC4, 5, 7 and 9, isoenzymes located both in the nucleus and the cytoplasm; 3) Class IIb, including HDAC6 and HDAC10, mainly located in the cytoplasm and 4) Class IV, including only HDAC11. Unlike Class I HDACs, Class IIa and IIb have a tissue-specific expression.

By regulating gene expression and acting on histones and transcription factors, it is clear that these enzymes are involved in a myriad of cellular functions. In addition, by acting on numerous other protein substrates, these enzymes, as well as phosphatases, are involved in many other processes such as signal transduction and cytoskeleton rearrangement.

In the recent decades, HDACs have become a well-studied therapeutic target. Several HDAC inhibitors have been synthesized, some of which are currently in advanced clinical trials and four of them have been approved for different types of cancer: Vorinostat and Romidepsin for Cutaneous T-cell lymphoma (CTLC), Belinostat for Cell Peripheral T-cell lymphoma (PTLC) and Panobinostat for multiple myeloma. These last inhibitors can interact to a varying extent with different HDAC isoforms.

Despite their clinical efficacy, the use of pan-inhibitors, thus non-selective for a particular isoform, is limited by their toxicity and side effects observed in both preclinical models and, most importantly, in clinical trials. Hence the need for developing HDAC inhibitors with a better pharmacological profile and therapeutic window (efficacy/toxicity ratio).

The attention of the scientific community has thus focused on the synthesis and study of selective inhibitors for individual HDAC isoforms, aiming to develop molecules with better pharmacological capabilities.

Therefore, the use of HDAC inhibitors can be an important therapeutic or diagnostic tool for pathologies caused by gene expression such as inflammatory disorders, diabetes, diabetes complications, homozygous thalassemia, fibrosis, cirrhosis, acute promyelocytic leukaemia (APL), organ transplant rejection, autoimmune pathologies, protozoal infections, cancers, etc. Selective inhibitors for a HDAC family or for a specific isoform, especially HDAC6, may be particularly useful for treating pathologies related to proliferative disorders and protein accumulation, immune system disorders and neurological and neurodegenerative disease, such as stroke, Huntington's disease, ALS and Alzheimer's disease.

Particularly for HDAC6 isoform, different substrates have been identified, such as α-tubulin, Hsp90 (Heat Shock Protein 90), cortactin, β-catenin. Modulation of these proteins acetylation by HDAC6 has been correlated with several important processes, such as immune response (Wang et al., Nat. Rev. Drug Disc. (2009), 8(12), 969-981; J. Med. Chem. (2012), 55, 639-651; Mol. Cell. Biol. (2011), 31(10), 2066-2078), regulation of microtubule dynamics, including cell migration and cell-cell interaction (Aldana-Masangkay et al., J. Biomed. Biotechnol. (2011), 2011, 875824), and degradation of degenerated proteins.

In addition, HDAC6 is involved in the process of catabolism of degraded proteins through the complex known as aggresome: HDAC6 is able to bind polyubiquitinated proteins and dynein, thus activating a kind of delivery of denatured proteins along the microtubules to the aggresome (Kawaguchi et al., Cell (2003) 115 (6), 727-738).

Alteration of this HDAC6 cytoprotective activity has been correlated with various neurodegenerative pathologies such as Parkinson's disease (Outerio et al., Science (2007), 317 (5837), 516-519) and Huntington's disease (Dompierre et al., J. Neurosci. (2007), 27(13), 3571-3583), wherein the accumulation of degraded proteins is a common pathological feature.

Further HDAC6 is involved in regulating many oncological proteins, especially in hematologic tumours, such as various types of leukaemia (Fiskus et al., Blood (2008), 112(7), 2896-2905; Rodriguez-Gonzales, Blood (2008), 112 (11), abstract 1923) and multiple myeloma (Hideshima et al., Proc. Natl. Acad. Sci. USA (2005), 102(24), 8567-8572). Regulation of α-tubulin acetylation by HDAC6 may be implicated in metastasis onset, wherein cellular motility plays an important role (Sakamoto et al., J. Biomed. Biotechnol. (2011), 2011, 875824).

International Patent Application WO 2011/021209 discloses 1,2,3-triazole compounds having HDAC inhibitory activity.

International Patent Application WO 2012/178208 discloses compounds with substituted heterocycles such as benzimidazole, benzimidazolone and benzotriazole having a selective HDAC6 inhibitory activity.

International Patent Application WO 2015/102426 discloses new indole derivatives with HDAC inhibitory activity.

International patent application WO 2015/087151 discloses new azaindole derivatives with HDAC inhibitory activity.

International Patent Application WO 2012/106343 discloses HDAC inhibitors and compositions containing the same. Methods of treating diseases and conditions wherein inhibition of HDAC provides a benefit, like a cancer, a neurodegenerative disorder, a peripheral neuropathy, a neurological disease, traumatic brain injury, stroke, hypertension, malaria, an autoimmune disease, autism, autism spectrum disorders, and inflammation, also are disclosed.

The paper "Valente et al., Journal of Medicinal Chemistry (2014), 57(14), 6259-6265" describes hydroxamates containing 1,3,4-oxadiazole (2) and 2-aminoanilides (3) as histone deacetylase inhibitors. Among these, compounds 2t, 2x, and 3i are described as being the most powerful and selective towards HDAC1.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, thus, the inclusion of such definitions herein should not be construed to represent a substantial difference over what is generally understood in the art.

The term "halogen" refers herein to fluorine (F), chlorine (C), bromine (Br), or iodine (I).

The term "C1-C4 alkyl" refers herein to a branched or linear hydrocarbon containing 1 to 4 carbon atoms. Examples of C1-C4 alkyl groups include, but are not limited to, methyl, ethyl, n-propyl, isopropyl, n-butyl, sec-butyl, isobutyl, tert-butyl.

The term "aryl" refers herein to mono- and poly-carbocyclic aromatic ring systems (i), wherein individual carbocyclic rings in the poly-carbocyclic ring systems may be fused or attached to each other by a single bond. Suitable aryl groups include, but are not limited to, phenyl, naphthyl and biphenyl.

The term "aryloxy" refers herein to O-aryl group, wherein "aryl" is as defined above.

The term "alkoxy" refers herein to O-alkyl group, wherein "alkyl" is as defined above.

The term "cycloalkyl" refers herein to a saturated or unsaturated hydrocarbon ring, preferably having 4 to 10 carbon atoms. Examples of cycloalkyl include cyclopropyl, cyclobutyl, cyclopentyl, cyclohexyl, cycloheptyl and cyclooctyl.

The term "arylalkyl" refers herein to an aryl radical as defined herein, attached to an alkyl radical as defined herein. An example of arylalkyl is benzyl.

The term "heterocycle" refers herein to a 4-, 5-, 6-, 7- or 8-membered monocyclic ring which is saturated or unsaturated and consisting of carbon atoms and one or more heteroatoms selected from N, O and S, and wherein the nitrogen and sulphur heteroatoms may optionally be oxidized and the nitrogen heteroatom can be optionally quaternized. The heterocyclic ring may be attached to any heteroatom or carbon atom, provided that the attachment results in the creation of a stable structure. The term also includes any bicyclic system wherein any of the above heterocyclic rings is fused to an aryl or another heterocycle. When the heterocyclic ring is an aromatic heterocyclic ring, it can be defined as a "heteroaromatic ring".

The term "unsaturated ring" refers herein to a partially or completely unsaturated ring.

For example, an unsaturated C6 monocyclic ring refers to cyclohexene, cyclohexadiene and benzene.

The term "substituted" refers herein to mono- or poly-substitution with a defined (or undefined) substituent provided that this single or multiple substitution is chemically allowed.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "pharmaceutically acceptable salts or derivatives thereof" herein refers to those salts or derivatives which possess the biological effectiveness and properties of the salified or derivatized compound and which do not produce adverse reactions when administered to a mammal, preferably a human. The pharmaceutically acceptable salts may be inorganic or organic salts, examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference. The pharmaceutically acceptable derivatives include the esters, the ethers and the N-oxides.

The terms "comprising", "having", "including" and "containing" are to be understood as open terms (meaning "including, but not limited to") and are to be considered as a support also for terms such as "essentially consist of", "essentially consisting of", "consist of" or "consisting of".

The terms "essentially consists of", "essentially consisting of" are to be understood as semi-closed terms, meanings that no other ingredient affecting the novel characteristics of the invention is included (therefore optional excipients can be included).

The terms "consists of", "consisting of" are to be understood as closed terms.

The term "isomers" refers to stereoisomers (or spatial isomers), i.e. diastereoisomers and enantiomers.

The term "prodrugs" refers to pharmacologically inactive derivatives, which can undergo in vivo metabolic transformation to afford an active compound included in the general formula of this invention. Many different prodrugs are known in the art (Prodrug approach: an effective solution to overcome side-effects, Patil S. J., Shirote P. J., International Journal of Medical and Pharmaceutical Sciences, 2011, 1-13; Carbamate Prodrug Concept for Hydroxamate HDAC Inhibitors, Jung, Manfred et al., ChemMedChem, 2011, 1193-1198).

The term "pathology" includes one or more of the following autoimmune diseases or disorders: diabetes mellitus, arthritis (including rheumatoid arthritis, juvenile rheumatoid arthritis, osteoarthritis, psoriatic arthritis), multiple sclerosis, severe myasthenia, systemic lupus erythematosus, autoimmune thyroiditis, dermatitis (including atopic dermatitis and eczematous dermatitis), psoriasis, Sjogren's syndrome, including dry keratoconjunctivitis secondary to Sjogren's syndrome, alopecia areata, allergic reactions due to arthropod bites, Chron's disease, stomach ulcer, iritis, conjunctivitis, keratoconjunctivitis, ulcerative colitis, asthma, allergic asthma, lupus erythematous cutaneous, scleroderma, vaginitis, proctitis, reaction to drug, leprosy, lupus erythema, autoimmune uveitis, allergic encephalomyelitis, acute necrotizing haemorrhagic encephalopathy, progressive bilateral idiopathic hearing loss, aplastic anaemia, anaemia, idiopathic thrombocytopenia, policondrite, Wegener's granulomatosis, chronic active hepatitis, Stevens-Jonhson syndrome, idiopathic sprues, lichen planus, Graves's ophthalmopathy, sarcoidosis, primary biliary cirrhosis, posterior uveitis, intestinal pulmonary fibrosis.

The term "pathology" refers to one or more of the following neurological or neurodegenerative diseases: Wilson's disease, spinocerebellar ataxia, prion diseases, Parkinson's disease, Huntington's disease, amyotrophic lateral sclerosis (ALS), amyloidosis, Alzheimer's disease, Alexander's disease, alcoholic liver disease, cystic fibrosis, Pick's disease, spinal muscular atrophy, and Lewy body dementia.

The term "pathology" further includes one or more of the following diseases: rheumatoid spondylitis, post-ischemic reperfusion injury, intestinal inflammation, chronic inflammatory pulmonary disease, eczema, asthma, acute respiratory distress syndrome, infectious arthritis, chronic progressive arthritis, deforming arthritis, post-traumatic arthropathy, gouty arthritis, Reiter syndrome, acute sinovitis, acute spondylitis, glomerulonephritis, haemolytic anaemia, aplastic anaemia, neutropenia, graft-versus-host (GVHD), transplant rejection, chronic thyroiditis, Grave's disease, binary primary cirrhosis, contact dermatitis, sunburn, chronic renal failure, Guillain-Barre syndrome, uveitis, otitis media, periodontal disease, pulmonary intestinal fibrosis, bronchitis, sinusitis, pneumoconiosis, pulmonary failure syndrome, pulmonary emphysema, pulmonary fibrosis, silicosis or pulmonary chronic inflammatory diseases.

The term "pathology" further comprise one or more of the following diseases: cancer, tumour growth, colon, breast, bone, brain and other cancer (e.g. osteosarcoma, neuroblastoma, colon adenocarcinoma), chronic myeloid leukaemia (CML), acute myeloid leukaemia (AML), acute promyelocytic leukaemia (APL), cardiac cancer (sarcoma, myxoma, rhabdomyoma, fibroma, lipoma and teratoma), lung cancer (e.g. bronchogenic carcinoma, alveolar carcinoma, bronchial adenoma, sarcoma, lymphoma, chondromatous hamartoma, mesothelioma), gastrointestinal cancer (e.g. oesophagus, stomach, pancreas, small intestine, large intestine cancer), genitourinary tract cancer (e.g. kidney, bladder and urethra, prostate, testicular cancer), liver cancer (e.g. hepatocellular carcinoma, cholangiocarcinoma, hepatoblastoma, angiosarcoma, hepatocellular adenoma, haemangioma), bone cancer (e.g. osteogenic sarcoma, fibrosarcoma, fibrous histiocytomas malignant, chondrosarcoma, Ewing's Sarcoma, malignant lymphoma, multiple myeloma, malignant giant cell tumour, chordoma, chondrosteoma, benign chordoma, chondroblastoma, condromixofibroma, osteoid osteoma), nervous system tumours (e.g. skull, meningitis, brain, spinal cord), gynecological tumours (e.g. uterus, cervix, ovaries, vulva and vagina), hematologic cancer (e.g. blood tumours, Hodgkin's disease, non-Hodgkin's disease), skin cancer (e.g. malignant melanoma, basal cell carcinoma, malignant squamous cell tumour, Kaposi's sarcoma, dysplastic naevus, lipoma, angioma, dermatofibroma, cheloid, psoriasis) and adrenal gland tumors (e.g. neuroblastoma).

DESCRIPTION OF THE INVENTION

Figure 1:
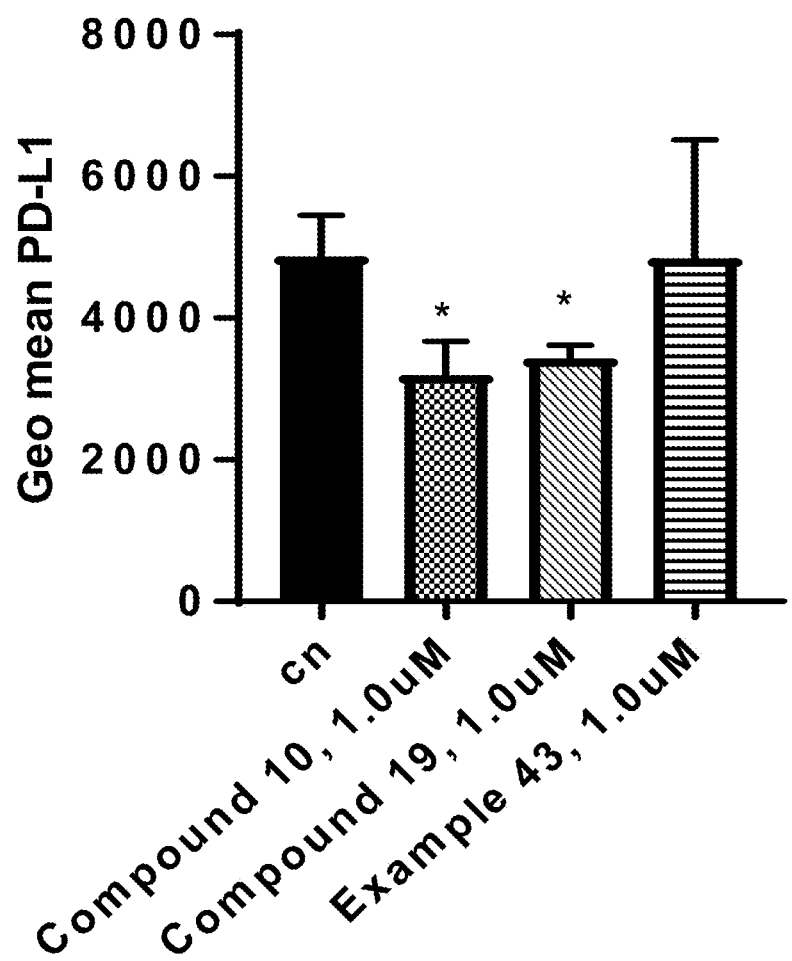
FIG. 1: The inhibition of PD-L1 expression in iDC (GMCSF-IL-4 stimulated monocytes). Human monocytes were treated with HDAC6 inhibitors and stimulated with GMCSF-IL-4 for 5 days. After incubation, cells were collected and labelled with an anti PD-L1 antibody. Cells were then washed and fluorescence data were acquired using a flow cytometer (BD FACSVerse). Values on the graphs represent the mean of 3 experiment carried out on 3 different donors (n=3). The expression of PD-L1 is represented by the geometric mean of the fluorescence. *=P<0.05 determined by Student's t test.

Inventors have experimentally found that benzo-hydroxamic compounds, characterized by a pentaheterocyclic central core, exhibit a high and selective inhibitory activity against HDAC6 enzyme.

These compounds also demonstrated a low cytotoxicity, thus allowing their chronic use. According to a first aspect, the present invention relates to compounds of formulas (I) and (II) and pharmaceutically acceptable salts, isomers and prodrugs thereof:

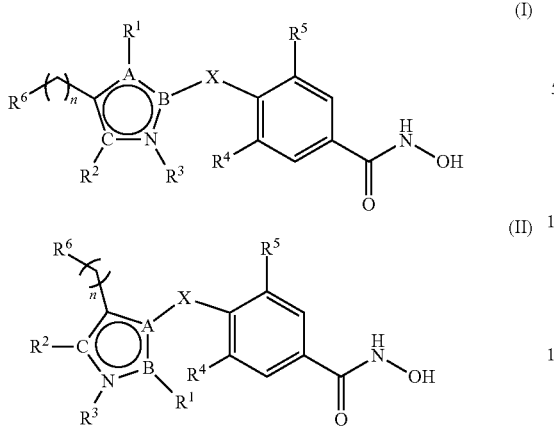

wherein
A=N, O, S in formula (I), while A=N in formula (II);
B=C, N;
C=N, O in formula (I), while C=N in formula (II);
X=CH$_2$, S, NH, O, CD$_2$;
n=0, 1;
when n=1, the carbon atom may be substituted with R$^{12}$ and R$^{13}$ being independently selected from the group comprising H, D, -Me, -phenyl, —F and —OH or together R$^{12}$ and R$^{13}$ can form a saturated cyclic moiety, preferably cyclopropane, cyclobutane, cyclopentane or cyclohexane;
when n=1, R$^6$ may be absent;
R$^4$=R$^5$=H, F;
R$^1$ is absent or it is selected from the group comprising —H, —NH$_2$, C1-C4 alkyl, phenyl, phenyl substituted with one or more halogens, arylalkyl, cycloalkyl, methylfuran, cyclobutylmethyl, tetrahydrofuran-2-yl-methyl, 3-(diethylamino)propyl, 2-methoxyethyl, vinyl, 2-(methylsulfanyl) ethyl, 1-cyclopropylethyl, pyridin-2-yl, (pyridin-3-yl) methyl, 2-(pyridin-2-yl)ethyl, 2-(thiophen-2-yl)ethyl, 3,4-dimethoxyphenyl, 4-methoxyphenyl, methylphenyl, 2-chloro-5-(morpholin-4-sulfonyl)phenyl, 4-[(difluoromethyl)sulfanyl]phenyl, 4-(morpholin-4-sulfonyl)phenyl, 5-(dimethylsulfamoyl)-2-methylphenyl, 3-(trifluoromethyl) phenyl, 4-(trifluoromethyl)phenyl, 2-(morpholin-4-yl) ethyl, 3-(morpholin-4-yl)propyl, 1-naphthyl, 2,3-dihydro-1,4-benzodioxin-6-yl, benzhydryl, 5-indanyl, thiophene and methylthiophene;

R$^2$ is absent or it is selected from H, alkyl, cycloalkyl, cycloalkyl-methyl, heteroaryl, phenyl, phenyl substituted with one or more halogens, phenyl substituted with one or more alkoxy groups, phenyl substituted with one or more nitro groups, benzyl, alkyl-substituted benzyl, (2,2-difluorocyclopentyl)methyl, 2-bromo-3-fluorophenyl, (2,2-dimethylcyclopropyl)methyl, 4-hydroxyphenyl, 2-(benzyloxy) ethyl, 2-bromo-4-methoxyphenyl, 2-methyl-quinoline, 3-methylpyridin-4-yl, 4-methanesulfonyl-2-methylphenyl, 2-chloro-4,6-dinitrophenyl, 1,3-benzodioxol-5-ylmethyl, or 2-benzyloxyphenyl;

R$^3$ is absent or it is selected from H, alkoxyaryl, phenyl, phenyl substituted with CF$_3$, benzyl, pyridyl, alkyl, cycloalkyl, cycloalkyl-methyl, heteroaryl, phenyl substituted with one or more halogens, phenyl substituted with one or more alkoxy groups, phenyl substituted with one or more nitro groups, benzyl, alkyl-substituted benzyl, (2,2-difluorocyclopentyl)methyl, 2-bromo-3-fluorophenyl, (2,2-dimethylcyclopropyl)methyl, 4-hydroxyphenyl, 2-(benzyloxy)ethyl, 2-bromo-4-methoxyphenyl, methyl-2-quinoline, 3-methylpyridin-4-yl, 4-methanesulfonyl-2-methylphenyl, 2-chloro-4,6-dinitrophenyl, 1,3-benzodioxol-5-ylmethyl, or 2-benzyloxyphenyl;

R$^6$ is a substituted or non-substituted mono or polycyclic residue, optionally partially or totally unsaturated, comprising carbon atoms and optionally one or more heteroatoms selected from N, S or O;
or R$^6$ can be selected from:

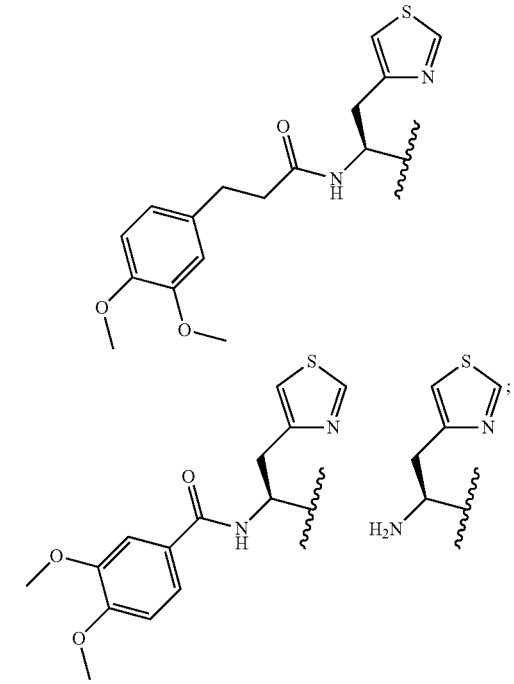 [SMILES: *[C@H](Cc1cscn1)NC(=O)CCc1ccc(OC)c(OC)c1 ; *[C@H](Cc1cscn1)NC(=O)c1ccc(OC)c(OC)c1 ; *[C@@H](N)Cc1cscn1]

with the proviso that in the compounds of formula (I), when the pentaheterocyclic core is 1,3,4-oxadiazole, R$^6$ is not naphthyl.

A further class of preferred compounds comprises compounds of formula (I) and (II) and pharmaceutically acceptable salts, isomers and pharmacologically acceptable esters thereof, wherein the pentaheterocyclic core is selected from the group consisting of tetrazole, 1,2,4-triazole, 1,3,4-oxadiazole, 1,2,4-oxadiazole, 1,3,4-thiadiazole.

Another class of preferred compounds comprises compounds of formula (I) and (II) and pharmaceutically acceptable salts, isomers and pharmaceutically acceptable salts thereof, wherein:
A=N, O, S in formula (I), while A=N in formula (II);
B=C, N;
C=N, O in formula (I), while C=N in formula (II);
X=CH$_2$, S;
n=0, 1;
when n=1, the carbon atom may be substituted with R$^{12}$ and R$^{13}$ being independently selected from the group comprising H, -Me, -phenyl, —F and —OH or together R$^{12}$ and R$^{13}$ can form a saturated cyclic moiety, preferably cyclopropane, cyclobutane, cyclopentane or cyclohexane;
when n=1, R$^6$ may be absent;
R$^4$=R$^5$=H, F;
R$^1$ is absent or it is selected from the group comprising —H, —NH$_2$, —CH$_3$, —CH$_2$CH$_3$, phenyl, p-fluorophenyl, m-chlorophenyl, p-chlorophenyl, benzyl, methylfuran, cyclopropyl, isobutyl, methylphenyl, trifluorophenyl, thiophene and 2-(morpholin-4-yl) ethyl;

R² is absent or it is selected from H, phenyl, or p-dichlorophenyl;
R³ is absent or it is selected from H, o-methoxyphenyl, p-trifluoromethylphenyl, benzyl, or pyridyl;
R⁶ is selected from the group comprising:
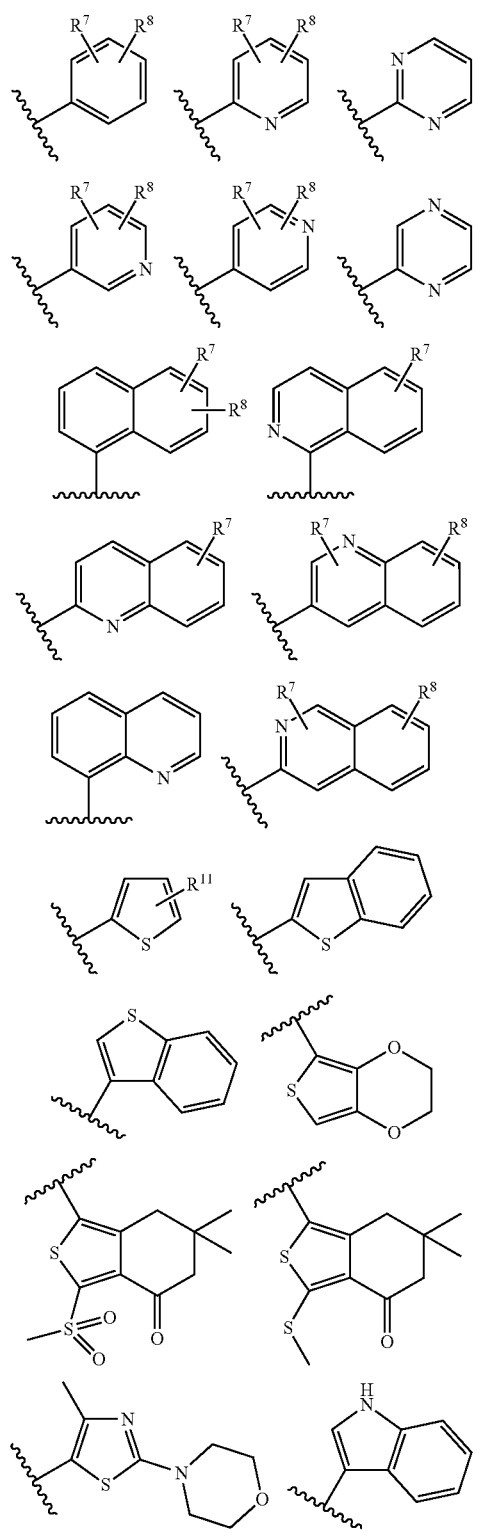
-continued
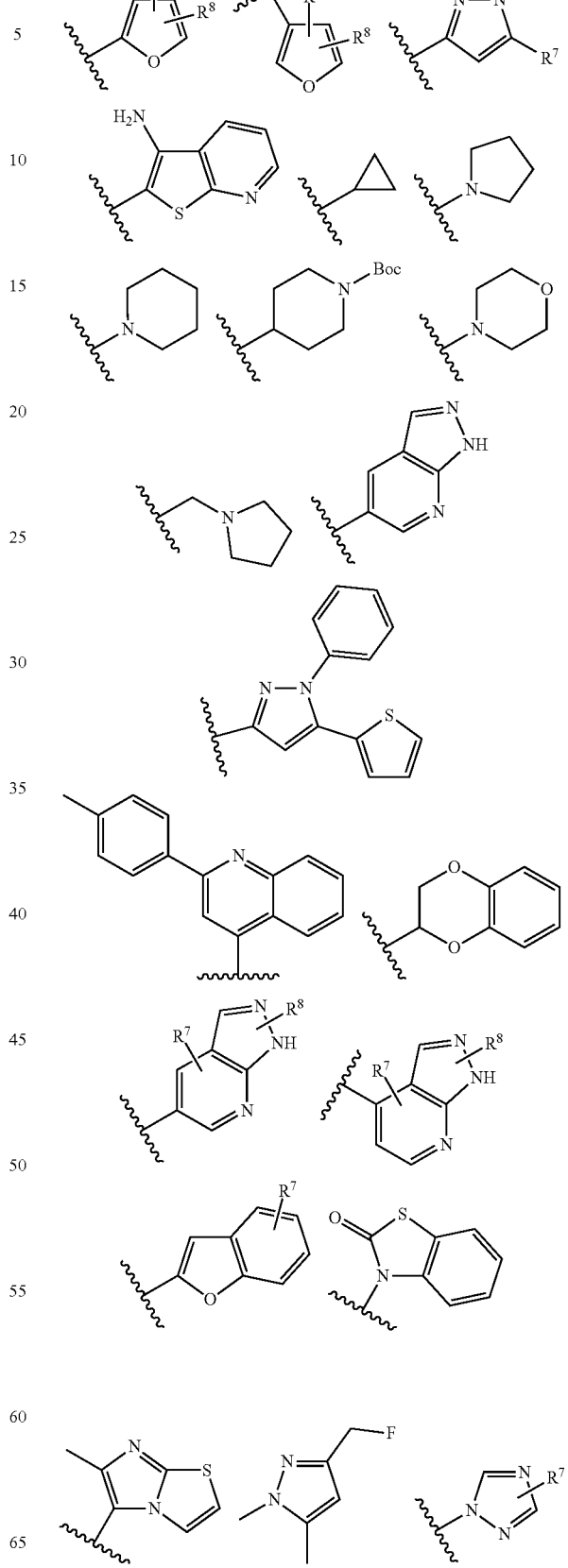

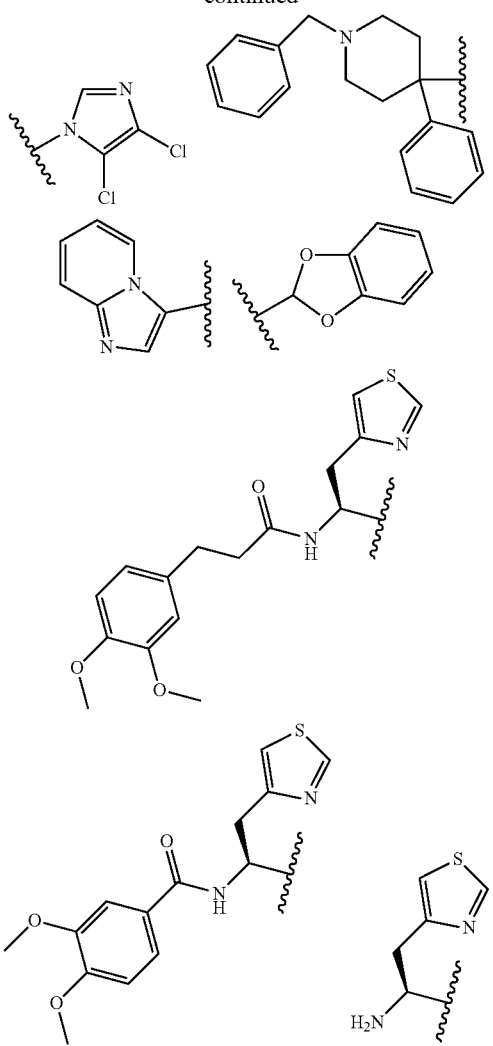

wherein:

R⁷ and R⁸ are independently selected from the group comprising H, D, —Cl, —F, —Br, —CF₃, -Me, -Et, —OMe, —OBenzyl, —SF₅, —OCH₂F, —CH₂NH₂, —NH₂, —CH₂NMe₂, —NMe₂, —N(CH₂CH₂OCH₃)₂, —COOH, —COOMe, —OH, —NHNH₂, —NO₂, —OEt, —OCHF₂, —OiPr, —CHF₂, —NEt₂,

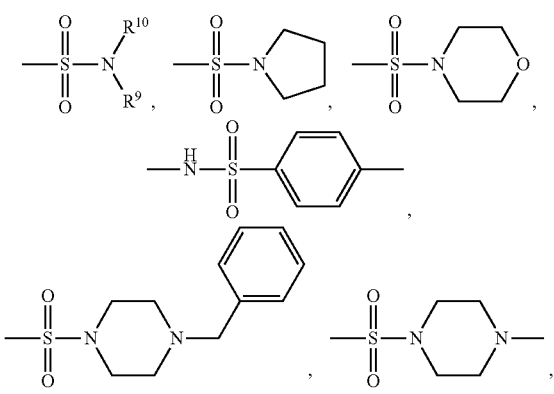

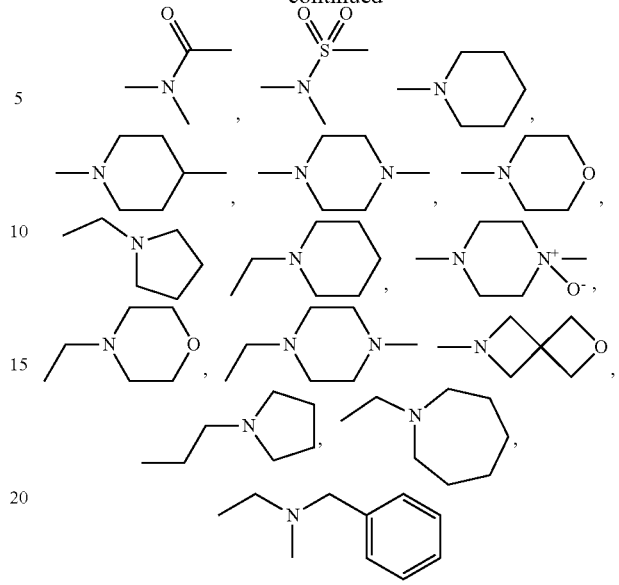

or R⁷ and R⁸ together can form a heteropentacyclic moiety (—OCH₂O—);

R⁹=R¹⁰=—H, -Me, -Et;

R¹¹ is selected from the group comprising —H, —Cl, —CH₃, —NO₂ and —Br.

The following compounds of formulas (I) and (II) are particularly preferred:

(S)—N-(1-(3-(4-(hydroxycarbamoyl)benzyl)-1,2,4-oxadiazol-5-yl)-2-(thiazol-4-yl)ethyl)-3,4-dimethoxybenzamide (comp. 1);

3,5-difluoro-N-hydroxy-4-((4-methyl-5-(naphthalen-1-yl)-4H-1,2,4-triazol-3-yl)thio)benzamide (comp. 2);

4-((5-(3-(N,N-dimethylsulfamoyl)phenyl)-1,3,4-oxadiazol-2-yl)methyl)-N-hydroxybenzamide (comp. 3);

3,5-difluoro-N-hydroxy-4-((4-methyl-5-(2-phenylpropan-2-yl)-4H-1,2,4-triazol-3-yl)thio)benzamide (comp. 4);

4-((5-(2,3-dihydrothieno[3,4-b][1,4]dioxin-5-yl)-1H-tetrazol-1-yl)methyl)-3,5-difluoro-N-hydroxybenzamide (comp. 5);

3,5-difluoro-N-hydroxy-4-((5-(pyridin-2-yl)-2H-tetrazol-2-yl)methyl)benzamide (comp. 6);

difluoro-N-hydroxy-4-((5-(pyrimidin-2-yl)-2H-tetrazol-2-yl)methyl)benzamide (comp. 7);

N-hydroxy-4-((5-(thiophen-2-yl)-1H-tetrazol-1-yl)methyl)benzamide (comp. 8);

3,5-difluoro-N-hydroxy-4-((4-methyl-5-(4-methyl-2-morpholinothiazo-5-yl)-4H-1,2,4-triazol-3-yl)thio)benzamide (comp. 9);

N-hydroxy-4-((4-methyl-5-(thiophen-2-yl)-4H-1,2,4-triazol-3-yl)thio)benzamide (comp. 10);

4-((5-(furan-2-yl)-2H-tetrazol-2-yl)methyl)-N-hydroxybenzamide (comp. 12);

3,5-difluoro-N-hydroxy-4-((5-(pyridin-2-yl)-1H-tetrazol-1-yl)methyl)benzamide (comp. 13);

3,5-difluoro-N-hydroxy-4-((4-methyl-5-(pyridin-2-yl)-4H-1,2,4-triazol-3-yl)thio)benzamide (comp. 14);

3,5-difluoro-N-hydroxy-4-((5-(thiophen-2-yl)-1H-tetrazol-1-yl)methyl)benzamide (comp. 15);

3,5-difluoro-N-hydroxy-4-((4-methyl-5-(4-(piperidin-1-ylmethyl)phenyl)-4H-1,2,4-triazol-3-yl)thio)benzamide (comp. 16);

3,5-difluoro-N-hydroxy-4-((4-methyl-5-(thiophen-2-yl)-4H-1,2,4-triazol-3-yl)thio)benzamide (comp. 17);
3,5-difluoro-4-((5-(furan-2-yl)-2H-tetrazol-2-yl)methyl)-N-hydroxybenzamide (comp. 19);
N-hydroxy-4-((5-(pyridin-2-yl)-1H-tetrazol-1-yl)methyl)benzamide (comp. 20);
3-(3,4-dimethoxyphenyl)-N-[(1S)-1-[3-[[4-(hydroxycarbamoyl)phenyl]methyl]-1,2,4-oxadiazol-5-yl]-2-thiazol-4-yl-ethyl]propanamide (comp. 21);
4-[[5-[4-(trifluoromethyl)phenyl]tetrazol-2-yl]methyl]benzenecarbohydroxamic acid (comp. 23);
4-[(4,5-diphenyl-1,2,4-triazol-3-yl)sulfanyl]benzenecarbohydroxamic acid (comp. 24);
4-[[4-(2-furylmethyl)-5-(1H-indol-3-yl)-1,2,4-triazol-3-yl]sulfanyl]benzenecarbohydroxamic acid;2,2,2-trifluoroacetic acid (comp. 25);
4-[5-[(3,4-dimethoxyphenyl)methyl]-1,3,4-oxadiazol-2-yl]benzenecarbohydroxamic acid (comp. 26);
4-[[5-benzyl-4-(4-fluorophenyl)-1,2,4-triazol-3-yl]sulfanyl]benzenecarbohydroxamic acid;2,2,2-trifluoroacetic acid (comp. 27);
4-[[4-amino-5-[4-(difluoromethoxy)phenyl]-1,2,4-triazol-3-yl]sulfanyl]benzenecarbohydroxamic acid (comp. 28);
4-[[5-(4-fluorophenyl)-4H-1,2,4-triazol-3-yl]sulfanyl]benzenecarbohydroxamic acid (comp. 29);
4-[[4-ethyl-5-(4-fluorophenyl)-1,2,4-triazol-3-yl]sulfanyl]benzenecarbohydroxamic acid (comp. 30);
4-[[5-(4-chlorophenyl)tetrazol-2-yl]methyl]benzenecarbohydroxamic acid (comp. 31);
4-[[5-(5-chloro-2-thienyl)tetrazol-2-yl]methyl]benzenecarbohydroxamic acid (comp. 32);
4-[[5-(2-fluorophenyl)tetrazol-2-yl]methyl]benzenecarbohydroxamic acid (comp. 33);
4-[[5-(4-fluorophenyl)tetrazol-2-yl]methyl]benzenecarbohydroxamic acid (comp. 34);
4-[[5-(4-methoxyphenyl)tetrazol-2-yl]methyl]benzenecarbohydroxamic acid (comp. 35);
4-[(5-benzyltetrazol-2-yl)methyl]benzenecarbohydroxamic acid (comp. 36);
4-[(5-benzyltetrazol-1-yl)methyl]benzenecarbohydroxamic acid (comp. 37);
4-[[5-(2,4-dichlorophenyl)tetrazol-2-yl]methyl]benzenecarbohydroxamic acid (comp. 38);
4-[[5-(3-methyl-2-thienyl)tetrazol-2-yl]methyl]benzenecarbohydroxamic acid (comp. 39);
4-[[5-(5-methyl-2-thienyl)tetrazol-2-yl]methyl]benzenecarbohydroxamic acid (comp. 41);
4-[[5-(benzothiophen-3-yl)tetrazol-2-yl]methyl]benzenecarbohydroxamic acid (comp. 42);
4-[[5-(2,3-dihydrothieno[3,4-b][1,4]dioxin-5-yl)tetrazol-2-yl]methyl]benzenecarbohydroxamic acid (comp. 43);
4-[[5-[(3,4-dimethoxyphenyl)methyl]-2-[4-(trifluoromethyl)phenyl]-1,2,4-triazol-3-yl]methyl]benzenecarbohydroxamic acid (comp. 44);
4-[[5-[(3,4-dimethoxyphenyl)methyl]-1,3,4-oxadiazol-2-yl]methyl]benzenecarbohydroxamic acid (comp. 45);
4-[[5-(2-fluorophenyl)tetrazol-2-yl]methyl]benzenecarbohydroxamic acid (comp. 46);
4-[[5-[(1S)-1-amino-2-thiazol-4-yl-ethyl]-1,2,4-oxadiazol-3-yl]methyl]benzenecarbohydroxamic acid;2,2,2-trifluoroacetic acid (comp. 48);
4-[[5-(3,4-dimethoxyphenyl)-1,2,4-oxadiazol-3-yl]methyl]benzenecarbohydroxamic acid (comp. 49);
4-[[5-(2-thienyl)tetrazol-2-yl]methyl]benzenecarbohydroxamic acid (comp. 50);
4-[[2-benzyl-5-(4-chlorophenyl)-1,2,4-triazol-3-yl]methyl]benzenecarbohydroxamic acid (comp. 51);
4-[[2-(2-pyridyl)-5-(2-thienyl)-1,2,4-triazol-3-yl]methyl]benzenecarbohydroxamic acid (comp. 52);
4-[[2-(2-methoxyphenyl)-5-(2-thienyl)-1,2,4-triazol-3-yl]methyl]benzenecarbohydroxamic acid (comp. 53);
4-[[5-(6,6-dimethyl-3-methylsulfanyl-4-oxo-5,7-dihydro-2-benzothiophen-1-yl)tetrazol-2-yl]methyl]benzenecarbohydroxamic acid (comp. 54);
4-[[5-(benzothiophen-2-yl)tetrazol-2-yl]methyl]benzenecarbohydroxamic acid (comp. 55);
4-[[5-(3,4-dimethoxyphenyl)-1,3,4-oxadiazol-2-yl]methyl]benzenecarbohydroxamic acid (comp. 57);
4-[[5-(2,4-difluorophenyl)-1,3,4-oxadiazol-2-yl]methyl]benzenecarbohydroxamic acid (comp. 58);
4-[[5-[3-(dimethylsulfamoyl)phenyl]tetrazol-2-yl]methyl]benzenecarbohydroxamic acid (comp. 59);
4-[(5-phenyl-1,3,4-oxadiazol-2-yl)amino]benzenecarbohydroxamic acid (comp. 60);
4-[[4-amino-5-[3-(diethylsulfamoyl)phenyl]-1,2,4-triazol-3-yl]sulfanyl]benzenecarbohydroxamic acid (comp. 61);
4-[[1-(2,4-dichlorophenyl)-5-methyl-1,2,4-triazol-3-yl]sulfanyl]benzenecarbohydroxamic acid (comp. 62);
4-[[5-(3-pyrrolidin-1-ylsulfonylphenyl)-1,3,4-oxadiazol-2-yl]amino]benzenecarbohydroxamic acid (comp. 63);
4-[[5-(3-morpholinosulfonylphenyl)-1,3,4-oxadiazol-2-yl]methyl]benzenecarbohydroxamic acid (comp. 64);
3,5-difluoro-4-[[5-(2-thienyl)tetrazol-2-yl]methyl]benzenecarbohydroxamic acid (comp. 65);
4-[[5-[3-(diethylsulfamoyl)phenyl]-4-methyl-1,2,4-triazol-3-yl]sulfanyl]benzenecarbohydroxamic acid (comp. 66);
4-[[4-methyl-5-[2-(p-tolyl)-4-quinolyl]-1,2,4-triazol-3-yl]sulfanyl]benzenecarbohydroxamic acid (comp. 67);
4-[(5-phenyl-1,3,4-oxadiazol-2-yl)methyl]benzenecarbohydroxamic acid (comp. 68);
4-[[5-(4-pyrrolidin-1-ylsulfonylphenyl)-1,3,4-oxadiazol-2-yl]methyl]benzenecarbohydroxamic acid (comp. 69);
4-[[5-(3-benzyloxy-4-methoxy-phenyl)tetrazol-2-yl]methyl]benzenecarbohydroxamic acid (comp. 70);
4-[[5-(3-benzyloxy-4-methoxy-phenyl)tetrazol-1-yl]methyl]benzenecarbohydroxamic acid (comp. 71);
4-[(5-cyclopropyl-1-phenyl-1,2,4-triazol-3-yl)sulfanyl]benzenecarbohydroxamic acid (comp. 72);
4-[[5-[4-(dimethylamino)phenyl]-4-methyl-1,2,4-triazol-3-yl]sulfanyl]benzenecarbohydroxamic acid (comp. 73);
4-[[5-(4-methyl-2-morpholino-thiazol-5-yl)-1,3,4-oxadiazol-2-yl]methyl]benzenecarbohydroxamic acid (comp. 75);
4-[[5-[3-(dimethylamino)phenyl]-4-methyl-1,2,4-triazol-3-yl]sulfanyl]benzenecarbohydroxamic acid (comp. 77);
4-[[5-(3-methoxyphenyl)-4-methyl-1,2,4-triazol-3-yl]sulfanyl]benzenecarbohydroxamic acid (comp. 78);
4-[[5-(2,3-dihydrothieno[3,4-b][1,4]dioxin-5-yl)tetrazol-2-yl]methyl]-3,5-difluoro-benzenecarbohydroxamic acid (comp. 79);
4-[[5-[3-(dimethylamino)phenyl]-4-methyl-1,2,4-triazol-3-yl]sulfanyl]-3,5-difluoro-benzenecarbohydroxamic acid (comp. 80);
tert-butyl 4-[5-[4-(hydroxycarbamoyl)phenyl]sulfanyl-4-methyl-1,2,4-triazol-3-yl]piperidine-1-carboxylate (comp. 82);
4-[[5-(2,3-dihydro-1,4-benzodioxin-5-yl)-4-methyl-1,2,4-triazol-3-yl]sulfanyl]benzenecarbohydroxamic acid (comp. 83);
4-[[5-(1,3-benzodioxol-5-yl)-4-methyl-1,2,4-triazol-3-yl]sulfanyl]benzenecarbohydroxamic acid (comp. 84);
4-[[5-(1,5-dimethylpyrazol-3-yl)-4-methyl-1,2,4-triazol-3-yl]sulfanyl]benzenecarbohydroxamic acid (comp. 85);

4-[[5-(2-furyl)tetrazol-1-yl]methyl]benzenecarbohydroxamic acid (comp. 86);
4-[[5-(1-isoquinolyl)tetrazol-2-yl]methyl]benzenecarbohydroxamic acid (comp. 87);
4-[[5-(1-isoquinolyl)tetrazol-1-yl]methyl]benzenecarbohydroxamic acid (comp. 88);
4-[[5-(2-pyridyl)tetrazol-2-yl]methyl]benzenecarbohydroxamic acid (comp. 89);
4-[[5-(2-quinolyl)tetrazol-2-yl]methyl]benzenecarbohydroxamic acid (comp. 90);
4-[[5-(2-quinolyl)tetrazol-1-yl]methyl]benzenecarbohydroxamic acid (comp. 91);
3,5-difluoro-4-[[5-(2-furyl)tetrazol-1-yl]methyl]benzenecarbohydroxamic acid (comp. 92);
3,5-difluoro-4-[[5-(1-isoquinolyl)tetrazol-2-yl]methyl]benzenecarbohydroxamic acid (comp. 93);
3,5-difluoro-4-[[5-(1-isoquinolyl)tetrazol-1-yl]methyl]benzenecarbohydroxamic acid (comp. 94);
3,5-difluoro-4-[[5-(2-quinolyl)tetrazol-2-yl]methyl]benzenecarbohydroxamic acid (comp. 95);
3,5-difluoro-4-[[5-(2-quinolyl)tetrazol-1-yl]methyl]benzenecarbohydroxamic acid (comp. 96);
3,5-difluoro-4-[[5-(2-thienyl)-4H-1,2,4-triazol-3-yl]sulfanyl]benzenecarbohydroxamic acid (comp. 97);
4-[(5-benzhydryl-4-methyl-1,2,4-triazol-3-yl)sulfanyl]-3,5-difluoro-benzenecarbohydroxamic acid (comp. 98);
4-[[5-(3-aminothieno[2,3-b]pyridin-2-yl)-4-methyl-1,2,4-triazol-3-yl]sulfanyl]-3,5-difluoro-benzenecarbohydroxamic acid (comp. 99);
4-[[5-(1,5-dimethylpyrazol-3-yl)-4-methyl-1,2,4-triazol-3-yl]sulfanyl]-3,5-difluoro-benzenecarbohydroxamic acid (comp. 100);
3,5-difluoro-4-[[4-methyl-5-(1-phenylcyclobutyl)-1,2,4-triazol-3-yl]sulfanyl]benzenecarbohydroxamic acid (comp. 101);
3,5-difluoro-4-[[5-[1-(3-fluorophenyl)cyclopentyl]-4-methyl-1,2,4-triazol-3-yl]sulfanyl]benzenecarbohydroxamic acid (comp. 102);
3,5-difluoro-4-[[5-[1-(4-methoxyphenyl)cyclohexyl]-4-methyl-1,2,4-triazol-3-yl]sulfanyl]benzenecarbohydroxamic acid (comp. 103);
3,5-difluoro-4-[[5-[1-(4-methoxyphenyl)cyclopropyl]-4-methyl-1,2,4-triazol-3-yl]sulfanyl]benzenecarbohydroxamic acid (comp 104);
4-[[5-[3-(pentafluoro-lambda6-sulfanyl)phenyl]tetrazol-2-yl]methyl]benzenecarbohydroxamic acid (comp. 106);
4-[[5-[3-(pentafluoro-lambda6-sulfanyl)phenyl]tetrazol-1-yl]methyl]benzenecarbohydroxamic acid (comp. 107);
3,5-difluoro-4-[[5-[3-(pentafluoro-lambda6-sulfanyl)phenyl]tetrazol-2-yl]methyl]benzenecarbohydroxamic acid (comp. 108);
3,5-difluoro-4-[[5-[3-(pentafluoro-lambda6-sulfanyl)phenyl]tetrazol-1-yl]methyl]benzenecarbohydroxamic acid (comp. 109);
4-[[5-[4-(pentafluoro-lambda6-sulfanyl)phenyl]tetrazol-2-yl]methyl]benzenecarbohydroxamic acid (comp. 110);
4-[[5-[4-(pentafluoro-lambda6-sulfanyl)phenyl]tetrazol-1-yl]methyl]benzenecarbohydroxamic acid (comp. 111);
3,5-difluoro-4-[[5-[4-(pentafluoro-lambda6-sulfanyl)phenyl]tetrazol-2-yl]methyl]benzenecarbohydroxamic acid (comp. 112);
3,5-difluoro-4-[[5-[4-(pentafluoro-lambda6-sulfanyl)phenyl]tetrazol-1-yl]methyl]benzenecarbohydroxamic acid (comp. 113);
3,5-difluoro-4-[[4-methyl-5-[3-(4-methyl-4-oxido-piperazin-4-ium-1-yl)phenyl]-1,2,4-triazol-3-yl]sulfanyl]benzenecarbohydroxamic acid (comp. 114);
3,5-difluoro-4-[[4-(4-fluorophenyl)-5-(1-piperidylmethyl)-1,2,4-triazol-3-yl]sulfanyl]benzenecarbohydroxamic acid (comp. 115);
3,5-difluoro-4-[[4-(2-furylmethyl)-5-pyrrolidin-1-yl-1,2,4-triazol-3-yl]sulfanyl]benzenecarbohydroxamic acid (comp. 116);
4-[(4-benzyl-5-morpholino-1,2,4-triazol-3-yl)sulfanyl]-3,5-difluoro-benzenecarbohydroxamic acid (comp. 117);
4-[[5-(2,3-dihydrothieno[3,4-b][1,4]dioxin-5-yl)-4-methyl-1,2,4-triazol-3-yl]sulfanyl]-3,5-difluoro-benzenecarbohydroxamic acid (comp. 118);
3,5-difluoro-4-[[5-(1-isoquinolyl)-4-methyl-1,2,4-triazol-3-yl]sulfanyl]benzenecarbohydroxamic acid (comp. 121);
3,5-difluoro-4-[[4-methyl-5-(2-quinolyl)-1,2,4-triazol-3-yl]sulfanyl]benzenecarbohydroxamic acid (comp. 122);
4-[(5-pyrimidin-2-yltetrazol-2-yl)methyl]benzenecarbohydroxamic acid (comp. 123);
4-[(5-pyrimidin-2-yltetrazol-1-yl)methyl]benzenecarbohydroxamic acid (comp. 124);
3,5-difluoro-4-[(5-pyrimidin-2-yltetrazol-1-yl)methyl]benzenecarbohydroxamic acid (comp. 125);
4-[[5-[5-(trifluoromethyl)-2-pyridyl]tetrazol-2-yl]methyl]benzenecarbohydroxamic acid (comp. 126);
4-[[5-[5-(trifluoromethyl)-2-pyridyl]tetrazol-1-yl]methyl]benzenecarbohydroxamic acid (comp. 127);
3,5-difluoro-4-[[5-[5-(trifluoromethyl)-2-pyridyl]tetrazol-2-yl]methyl]benzenecarbohydroxamic acid (comp. 128);
3,5-difluoro-4-[[5-[5-(trifluoromethyl)-2-pyridyl]tetrazol-1-yl]methyl]benzenecarbohydroxamic acid (comp. 129);
4-[[5-[3-morpholino-5-(trifluoromethyl)-2-pyridyl]tetrazol-2-yl]methyl]benzenecarbohydroxamic acid (comp. 130);
4-[[5-[3-morpholino-5-(trifluoromethyl)-2-pyridyl]tetrazol-1-yl]methyl]benzenecarbohydroxamic acid (comp. 131);
4-[[5-(2-pyridylmethyl)tetrazol-2-yl]methyl]benzenecarbohydroxamic acid;2,2,2-trifluoroacetic acid (comp. 132);
4-[[5-(2-pyridylmethyl)tetrazol-1-yl]methyl]benzenecarbohydroxamic acid;2,2,2-trifluoroacetic acid (comp. 133);
3,5-difluoro-4-[[5-(2-pyridylmethyl)tetrazol-2-yl]methyl]benzenecarbohydroxamic acid;2,2,2-trifluoroacetic acid (comp. 134);
3,5-difluoro-4-[[5-(2-pyridylmethyl)tetrazol-1-yl]methyl]benzenecarbohydroxamic acid;2,2,2-trifluoroacetic acid (comp. 135);
3,5-difluoro-4-[[4-methyl-5-[1-phenyl-5-(2-thienyl)pyrazol-3-yl]-1,2,4-triazol-3-yl]sulfanyl]benzenecarbohydroxamic acid (comp. 136);
3,5-difluoro-4-[[5-(6-fluoro-2-methyl-3-quinolyl)-4-methyl-1,2,4-triazol-3-yl]sulfanyl]benzenecarbohydroxamic acid (comp. 137);
3,5-difluoro-4-[[5-(4-fluorophenyl)-4-(2-morpholinoethyl)-1,2,4-triazol-3-yl]sulfanyl]benzenecarbohydroxamic acid (comp. 138);
3,5-difluoro-4-[[4-(2-furylmethyl)-5-pyrazin-2-yl-1,2,4-triazol-3-yl]sulfanyl]benzenecarbohydroxamic acid (comp. 139);
3,5-difluoro-4-[[4-(2-furylmethyl)-5-(2-pyridyl)-1,2,4-triazol-3-yl]sulfanyl]benzenecarbohydroxamic acid (comp. 140);
4-[[4-benzyl-5-(pyrrolidin-1-yl-methyl)-1,2,4-triazol-3-yl]sulfanyl]-3,5-difluoro-benzenecarbohydroxamic acid (comp. 141);
4-[[4-benzyl-5-(2-furyl)-1,2,4-triazol-3-yl]sulfanyl]-3,5-difluoro-benzenecarbohydroxamic acid (comp. 142);
4-[[4-benzyl-5-(2-thienyl)-1,2,4-triazol-3-yl]sulfanyl]-3,5-difluoro-benzenecarbohydroxamic acid (comp. 143);

3,5-difluoro-4-[[4-(2-furylmethyl)-5-(2-thienyl)-1,2,4-triazol-3-yl]sulfanyl]benzenecarbohydroxamic acid (comp. 144);
3,5-difluoro-4-[[5-(2-fluorophenyl)-4-(2-furylmethyl)-1,2,4-triazol-3-yl]sulfanyl]benzenecarbohydroxamic acid (comp. 145);
3,5-difluoro-4-[[4-(2-furylmethyl)-5-(4-pyridyl)-1,2,4-triazol-3-yl]sulfanyl]benzenecarbohydroxamic acid (comp. 146);
3,5-difluoro-4-[[4-(2-furylmethyl)-5-(3-pyridyl)-1,2,4-triazol-3-yl]sulfanyl]benzenecarbohydroxamic acid (comp. 147);
3,5-difluoro-4-[[5-(3-isoquinolyl)-4-methyl-1,2,4-triazol-3-yl]sulfanyl]benzenecarbohydroxamic acid (comp. 148);
3,5-difluoro-4-[(5-imidazo[1,2-a]pyridin-3-yl-4-methyl-1,2,4-triazol-3-yl)sulfanyl]benzenecarbohydroxamic acid (comp. 149);
4-[[5-(1-benzyl-4-phenyl-4-piperidyl)-4-methyl-1,2,4-triazol-3-yl]sulfanyl]-3,5-difluoro-benzenecarbohydroxamic acid (comp. 150);
3,5-difluoro-4-[[4-methyl-5-[3-(4-methylpiperazin-1-yl)sulfonylphenyl]-1,2,4-triazol-3-yl]sulfanyl]benzenecarbohydroxamic acid (comp. 151);
4-[[5-[3-(4-benzylpiperazin-1-yl)sulfonylphenyl]-4-methyl-1,2,4-triazol-3-yl]sulfanyl]-3,5-difluoro-benzenecarbohydroxamic acid (comp. 152);
3,5-difluoro-4-[[4-methyl-5-(3-pyridyl)-1,2,4-triazol-3-yl]sulfanyl]benzenecarbohydroxamic acid (comp. 153);
methyl 4-[[2-[[2,6-difluoro-4-(hydroxycarbamoyl)phenyl]methyl]tetrazol-5-yl]methyl]benzoate (comp. 154);
methyl 4-[[1-[[2,6-difluoro-4-(hydroxycarbamoyl)phenyl]methyl]tetrazol-5-yl]methyl]benzoate (comp. 155);
methyl 6-[2-[[4-(hydroxycarbamoyl)phenyl]methyl]tetrazol-5-yl]pyridine-3-carboxylate (comp. 156);
methyl 6-[1-[[4-(hydroxycarbamoyl)phenyl]methyl]tetrazol-5-yl]pyridine-3-carboxylate (comp. 157);
4-[[2-[[4-(hydroxycarbamoyl)phenyl]methyl]tetrazol-5-yl]methyl]benzoic acid (comp. 158);
4-[[1-[[4-(hydroxycarbamoyl)phenyl]methyl]tetrazol-5-yl]methyl]benzoic acid (comp. 159);
4-[[2-[[2,6-difluoro-4-(hydroxycarbamoyl)phenyl]methyl]tetrazol-5-yl]methyl]benzoic acid (comp. 160);
4-[[1-[[2,6-difluoro-4-(hydroxycarbamoyl)phenyl]methyl]tetrazol-5-yl]methyl]benzoic acid (comp. 161);
6-[2-[[4-(hydroxycarbamoyl)phenyl]methyl]tetrazol-5-yl]pyridine-3-carboxylic acid (comp. 162);
3-[2-[[4-(hydroxycarbamoyl)phenyl]methyl]tetrazol-5-yl]benzoic acid (comp. 163);
3,5-difluoro-4-[[4-methyl-5-(8-quinolylmethyl)-1,2,4-triazol-3-yl]sulfanyl]benzenecarbohydroxamic acid (comp. 164);
4-[[5-(2,6-difluorophenyl)-4-methyl-1,2,4-triazol-3-yl]sulfanyl]-3,5-difluoro-benzenecarbohydroxamic acid (comp. 165);
3,5-difluoro-4-[[4-methyl-5-[3-(4-methylpiperazin-1-yl)phenyl]-1,2,4-triazol-3-yl]sulfanyl]benzenecarbohydroxamic acid (comp. 166);
4-[[5-[3-(azepan-1-ylmethyl)phenyl]-4-methyl-1,2,4-triazol-3-yl]sulfanyl]-3,5-difluoro-benzenecarbohydroxamic acid (comp. 167);
4-[[5-[4-(azepan-1-ylmethyl)phenyl]-4-methyl-1,2,4-triazol-3-yl]sulfanyl]-3,5-difluoro-benzenecarbohydroxamic acid (comp. 168);
4-[[5-(4-aminophenyl)tetrazol-2-yl]methyl]benzenecarbohydroxamic acid (comp. 169);
4-[[5-(4-aminophenyl)tetrazol-1-yl]methyl]benzenecarbohydroxamic acid (comp. 170);
4-[[5-(4-aminophenyl)tetrazol-2-yl]methyl]-3,5-difluoro-benzenecarbohydroxamic acid (comp. 171);
4-[[5-(4-aminophenyl)tetrazol-1-yl]methyl]-3,5-difluoro-benzenecarbohydroxamic acid (comp. 172);
4-[[5-[4-(aminomethyl)phenyl]tetrazol-2-yl]methyl]benzenecarbohydroxamic acid (comp. 173);
4-[[5-[4-(aminomethyl)phenyl]tetrazol-1-yl]methyl]benzenecarbohydroxamic acid (comp. 174);
4-[[5-[4-(aminomethyl)phenyl]tetrazol-2-yl]methyl]-3,5-difluoro-benzenecarbohydroxamic acid (comp. 175);
4-[[5-[4-(aminomethyl)phenyl]tetrazol-1-yl]methyl]-3,5-difluoro-benzenecarbohydroxamic acid (comp. 176);
3,5-difluoro-4-[[4-methyl-5-[1-(2-pyridyl)cyclopropyl]-1,2,4-triazol-3-yl]sulfanyl]benzenecarbohydroxamic acid (comp. 177);
3,5-difluoro-4-[[4-methyl-5-[1-(3-pyridyl)cyclopropyl]-1,2,4-triazol-3-yl]sulfanyl]benzenecarbohydroxamic acid (comp. 178);
3,5-difluoro-4-[(4-methyl-5-pyridazin-3-yl-1,2,4-triazol-3-yl)sulfanyl]benzenecarbohydroxamic acid (comp. 179);
3,5-difluoro-4-[[5-(3-fluoro-2-pyridyl)-4-methyl-1,2,4-triazol-3-yl]sulfanyl]benzenecarbohydroxamic acid (comp. 180);
3,5-difluoro-4-[[4-methyl-5-[3-(1-piperidylmethyl)phenyl]-1,2,4-triazol-3-yl]sulfanyl]benzenecarbohydroxamic acid (comp. 181);
3,5-difluoro-4-[[4-methyl-5-[3-(morpholinomethyl)phenyl]-1,2,4-triazol-3-yl]sulfanyl]benzenecarbohydroxamic acid (comp. 182);
4-((3-((1H-indol-3-yl)methyl)-5-(thiophen-2-yl)-4H-1,2,4-triazol-4-yl)methyl)-N-hydroxybenzamide (comp. 183);
4-[[5-[3-[[benzyl(methyl)amino]methyl]phenyl]-4-methyl-1,2,4-triazol-3-yl]sulfanyl]-3,5-difluoro-benzenecarbohydroxamic acid (comp. 184);
4-[[3-[(3,4-dimethoxyphenyl)methyl]-5-(2-thienyl)-1,2,4-triazol-4-yl]methyl]benzenecarbohydroxamic acid (comp. 185);
3,5-difluoro-4-[[4-methyl-5-[1-methyl-1-(3-pyridyl)ethyl]-1,2,4-triazol-3-yl]sulfanyl]benzenecarbohydroxamic acid (comp. 186);
3,5-difluoro-4-[[5-[4-[methyl(methylsulfonyl)amino]phenyl]-1,3,4-thiadiazol-2-yl]sulfanyl]benzenecarbohydroxamic acid (comp. 187);
4-[(5-phenyl-1,3,4-oxadiazol-2-yl)sulfanyl]benzenecarbohydroxamic acid (comp. 188);
4-[(5-phenyl-1,2,4-oxadiazol-3-yl)methyl]benzenecarbohydroxamic acid (comp. 189);
4-[(5-phenyl-1,3,4-thiadiazol-2-yl)methyl]benzenecarbohydroxamic acid (comp. 190);
3,5-difluoro-N-hydroxy-4-((5-(pyridin-3-yl)-1,3,4-thiadiazol-2-yl)thio)benzamide (comp. 191);
3,5-difluoro-4-[(5-phenyl-1,3,4-oxadiazol-2-yl)sulfanyl]benzenecarbohydroxamic acid (comp. 192);
4-[[5-(2-morpholino-4-pyridyl)-1,2,4-oxadiazol-3-yl]methyl]benzenecarbohydroxamic acid (comp. 193);
3,5-difluoro-N-hydroxy-4-((5-phenyl-1,2,4-oxadiazol-3-yl)methyl)benzamide (comp. 194);
3,5-difluoro-4-[[5-(4-pyridyl)-1,3,4-thiadiazol-2-yl]methyl]benzenecarbohydroxamic acid (comp. 195);
4-[[5-(5-bromo-3-pyridyl)-1,3,4-thiadiazol-2-yl]sulfanyl]-3,5-difluoro-benzenecarbohydroxamic acid (comp. 196);

3,5-difluoro-4-[[5-(5-morpholino-3-pyridyl)-1,3,4-thiadi-azol-2-yl]methyl]benzenecarbohydroxamic acid (comp. 197);

3,5-difluoro-N-hydroxy-4-((5-phenyl-1,3,4-thiadiazol-2-yl)methyl)benzamide (comp. 198);

3,5-difluoro-4-[[5-(2-furyl)-4-methyl-1,2,4-triazol-3-yl]sulfanyl]benzenecarbohydroxamic acid (comp. 199);

4-[[5-[5-[bis(2-methoxyethyl)amino]-3-pyridyl]-1,2,4-oxadiazol-3-yl]methyl]-3,5-difluoro-benzenecarbohydroxamic acid (comp. 200);

3,5-difluoro-4-[[5-[5-(2-oxa-6-azaspiro[3.3]heptan-6-yl)-3-pyridyl]-1,2,4-oxadiazol-3-yl]methyl]benzenecarbohydroxamic acid (comp. 201);

3,5-difluoro-4-[[5-[5-(pyrrolidin-1-ylmethyl)-2-furyl]-1,2,4-oxadiazol-3-yl]methyl]benzenecarbohydroxamic acid (comp. 202);

3,5-difluoro-4-[[4-methyl-5-[5-(morpholinomethyl)-3-furyl]-1,2,4-triazol-3-yl]sulfanyl]benzenecarbohydroxamic acid (comp. 203);

3,5-difluoro-4-[[4-methyl-5-[5-(morpholinomethyl)-2-furyl]-1,2,4-triazol-3-yl]sulfanyl]benzenecarbohydroxamic acid (comp. 204);

3,5-difluoro-4-[[4-methyl-5-[5-[(4-methylpiperazin-1-yl)methyl]-2-furyl]-1,2,4-triazol-3-yl]sulfanyl]benzenecarbohydroxamic acid (comp. 205);

4-[[5-[5-[(dimethylamino)methyl]-2-furyl]-4-methyl-1,2,4-triazol-3-yl]sulfanyl]-3,5-difluoro-benzenecarbohydroxamic acid (comp. 206);

3,5-difluoro-4-[[4-methyl-5-[5-(pyrrolidin-1-ylmethyl)-2-furyl]-1,2,4-triazol-3-yl]sulfanyl]benzenecarbohydroxamic acid (comp. 207);

4-[[5-[5-ethyl-4-(pyrrolidin-1-ylmethyl)-2-furyl]-4-methyl-1,2,4-triazol-3-yl]sulfanyl]-3,5-difluoro-benzenecarbohydroxamic acid (comp. 208);

4-[[4-methyl-5-[5-[(4-methylpiperazin-1-yl)methyl]-2-furyl]-1,2,4-triazol-3-yl]sulfanyl]benzenecarbohydroxamic acid (comp. 209);

3,5-difluoro-4-[[4-methyl-5-[6-(2-pyrrolidin-1-ylethyl)-3-pyridyl]-1,2,4-triazol-3-yl]sulfanyl]benzenecarbohydroxamic acid (comp. 210);

4-[[5-[5-(diethylaminomethyl)-2-furyl]-4-methyl-1,2,4-triazol-3-yl]sulfanyl]-3,5-difluoro-benzenecarbohydroxamic acid (comp. 211);

3,5-difluoro-4-[[4-methyl-5-[5-(1-piperidylmethyl)-2-furyl]-1,2,4-triazol-3-yl]sulfanyl]benzenecarbohydroxamic acid (comp. 212);

4-[[5-[5-(diethylaminomethyl)-2-methyl-3-furyl]-4-methyl-1,2,4-triazol-3-yl]sulfanyl]-3,5-difluoro-benzenecarbohydroxamic acid (comp. 213);

4-[(5-phenyltetrazol-2-yl)methyl]benzenecarbohydroxamic acid (comp. 214);

4-[(5-phenyltetrazol-1-yl)methyl]benzenecarbohydroxamic acid (comp. 215);

4-[(5-phenyl-4H-1,2,4-triazol-3-yl)methyl]benzenecarbohydroxamic acid (comp. 216);

N-hydroxy-4-((4-methyl-5-phenyl-4H-1,2,4-triazol-3-yl)methyl)benzamide (comp. 217).

The following compounds of formulas (I) and (II) are particularly preferred:

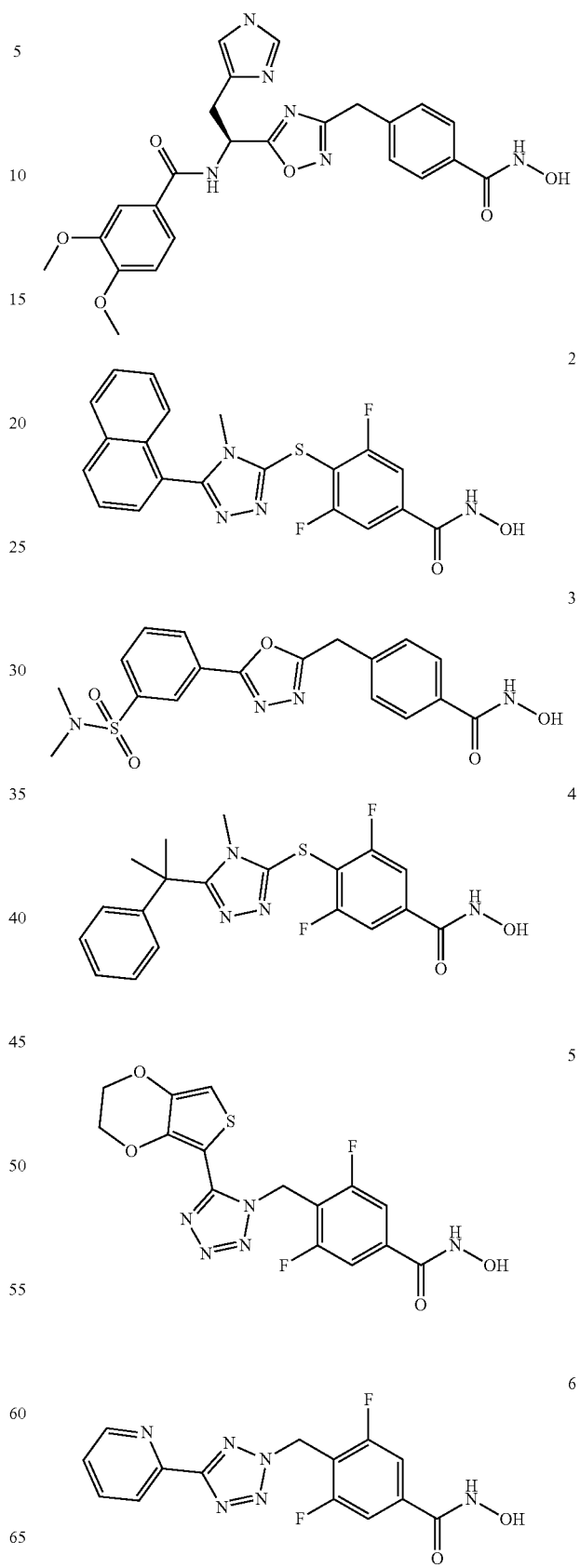

7
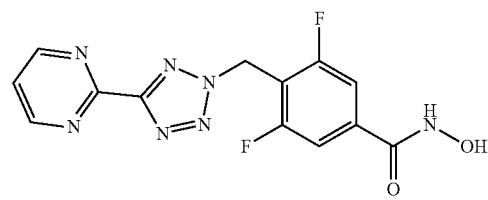
8
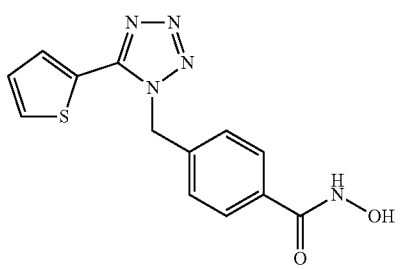
9
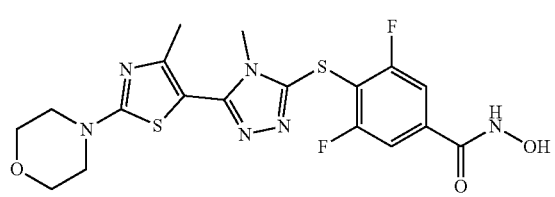
10
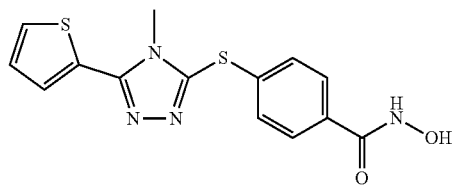
12
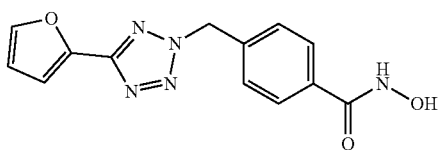
13
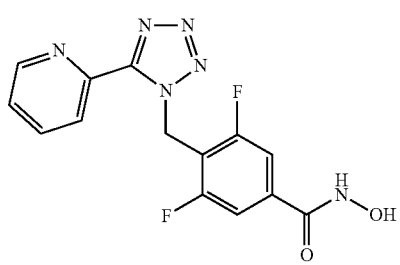
14
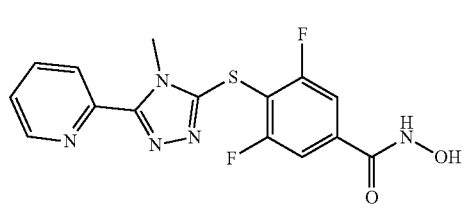
15
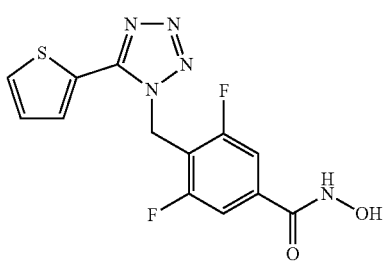
16
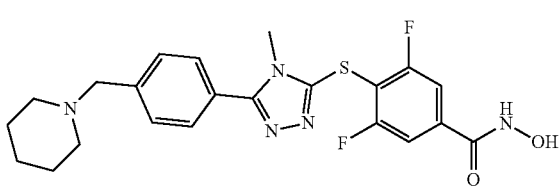
17
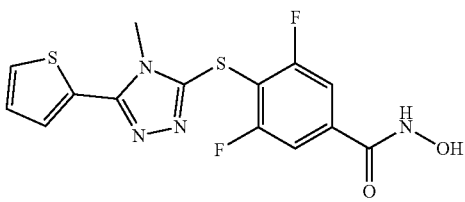
19
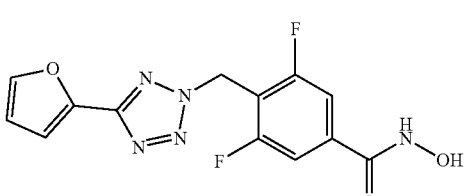
20
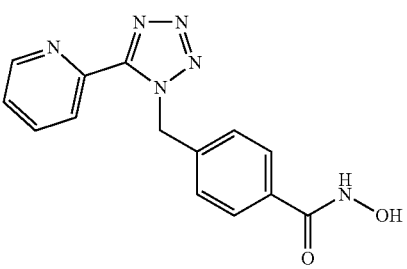
68
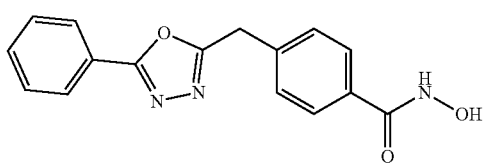
74
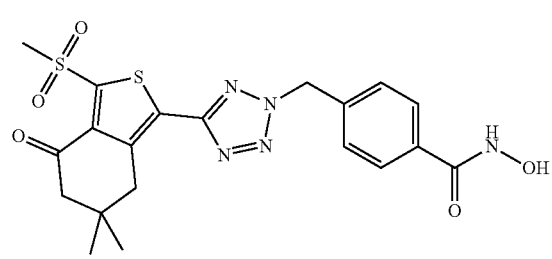

75
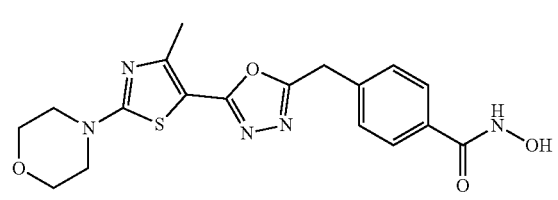
76
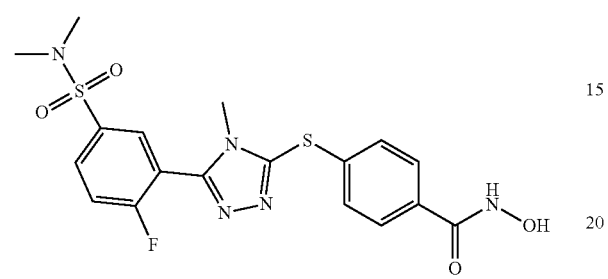
77
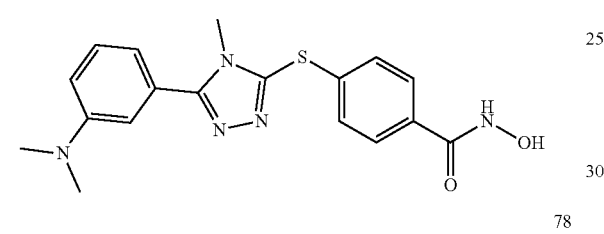
78
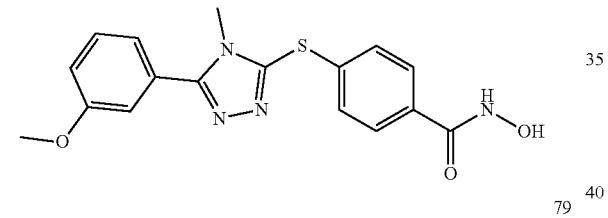
79
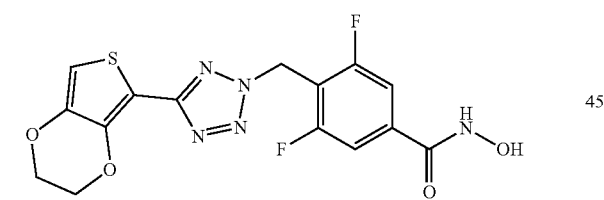
82
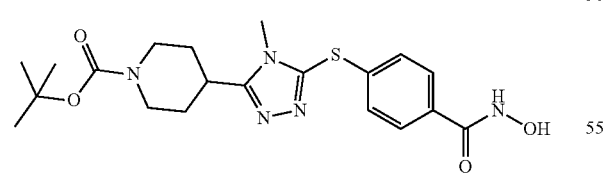
84
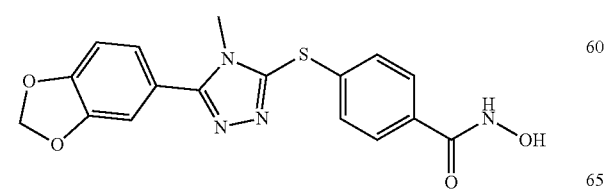
85
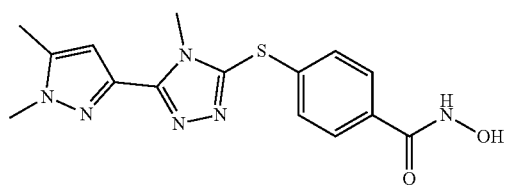
87
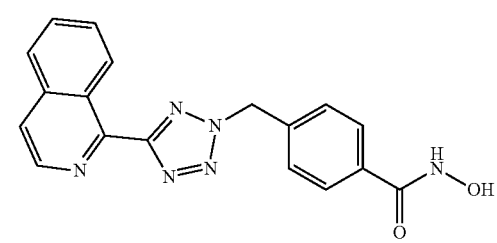
91
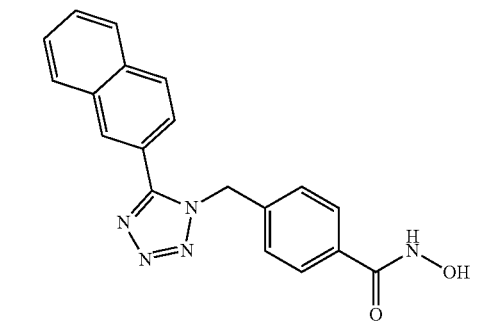
92
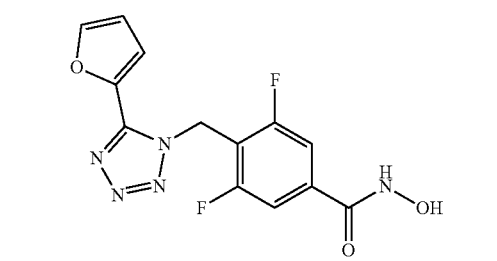
93
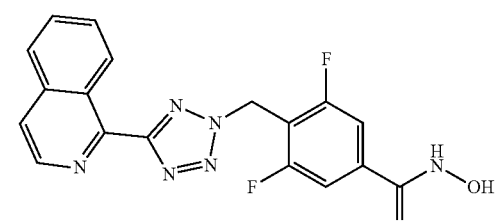
94
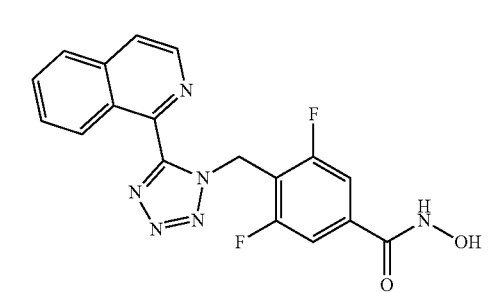

95
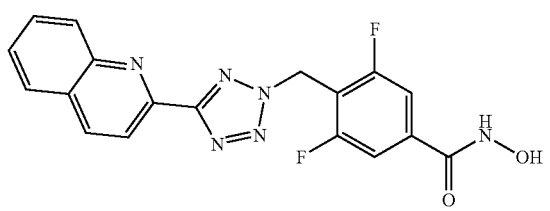
121
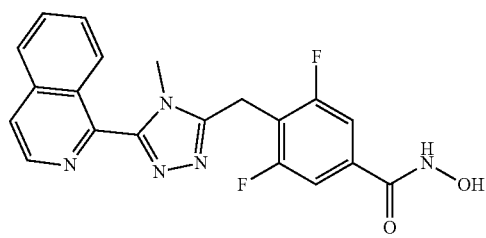
122
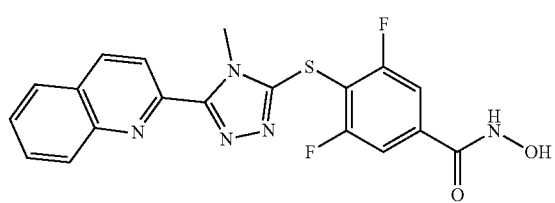
123
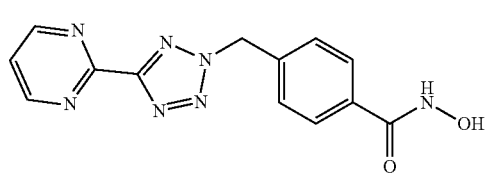
125
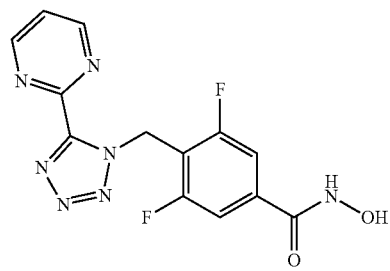
129
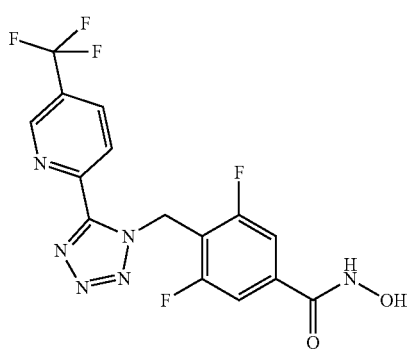
134
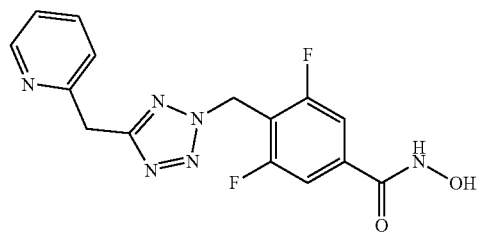
138
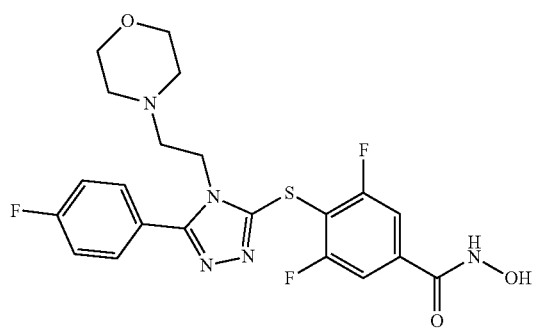
140
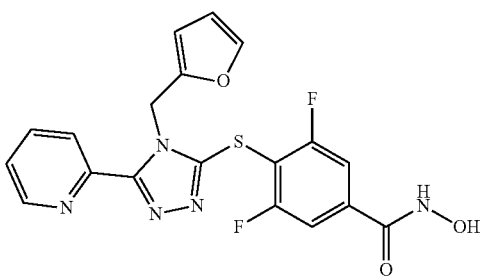
141
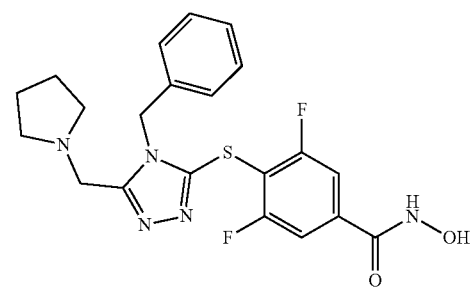
145
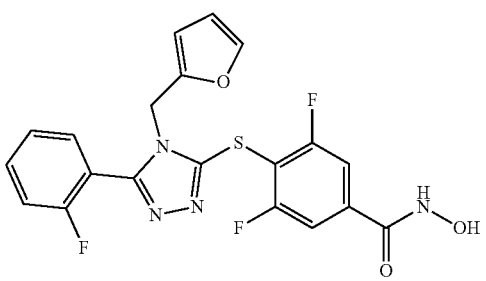

146
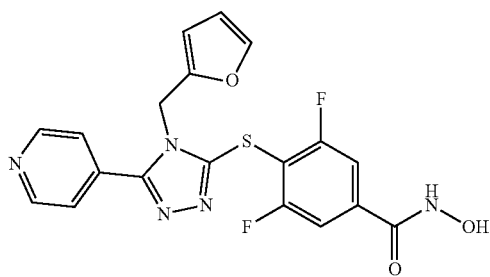
147
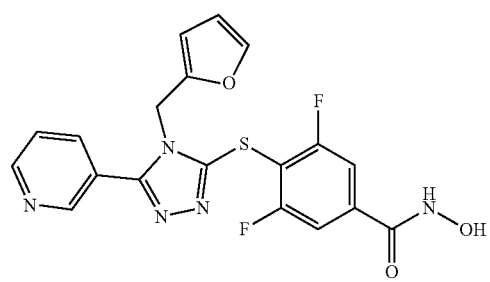
149
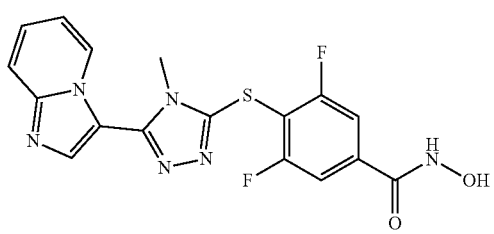
150
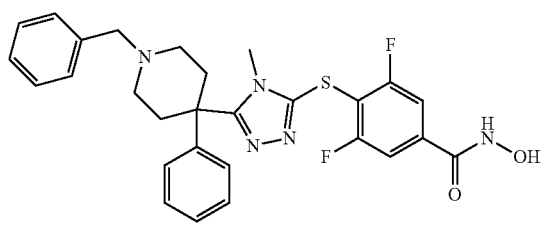
151
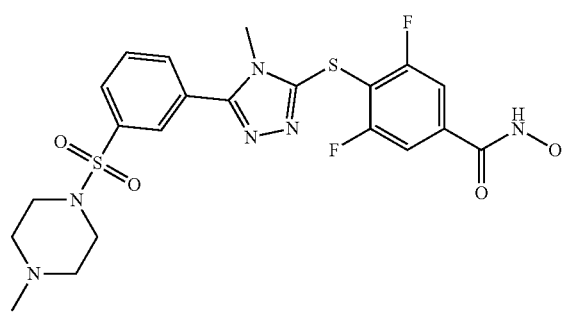
152
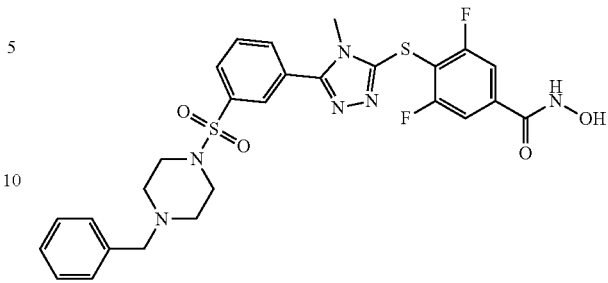
153
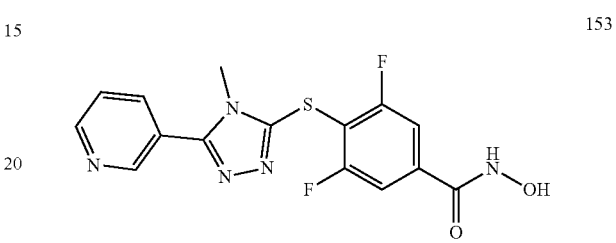
165
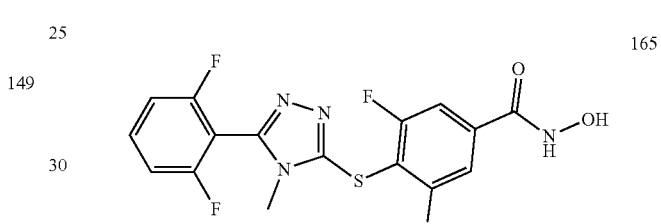
166
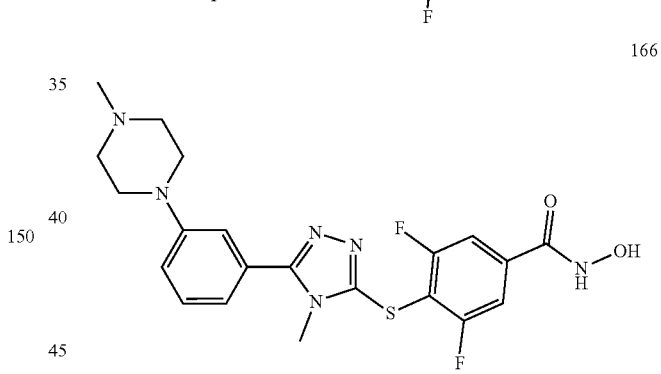
167
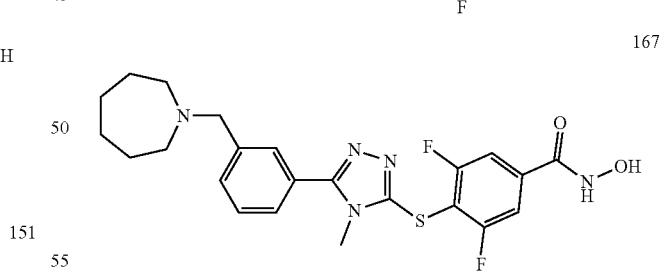
168
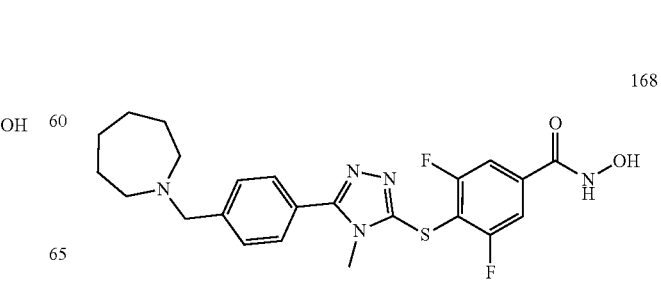

169
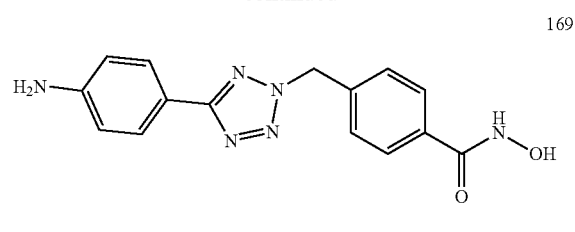
171
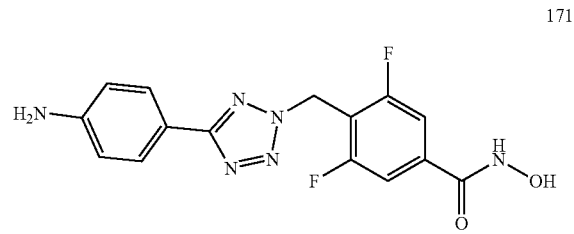
172
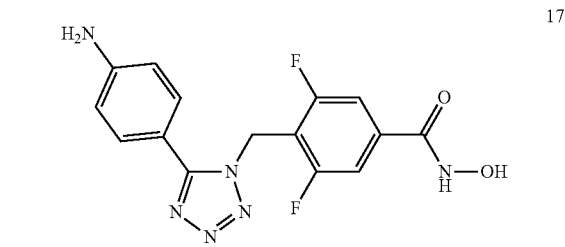
175
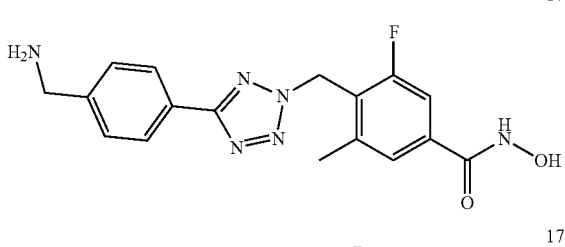
177
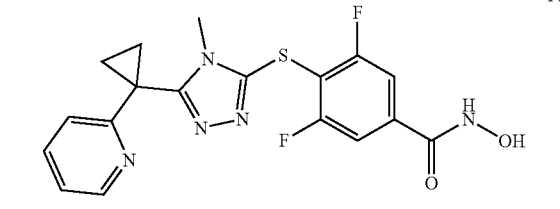
178
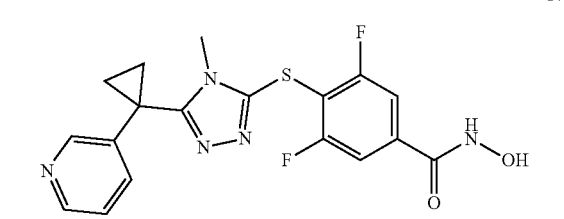
179
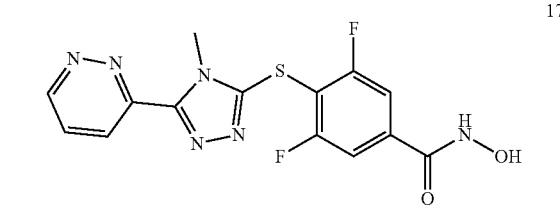
180
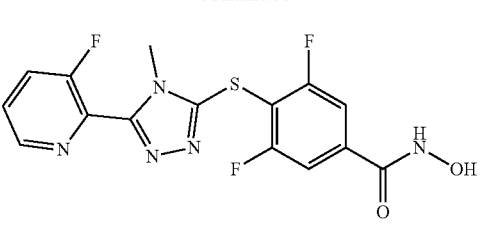
181
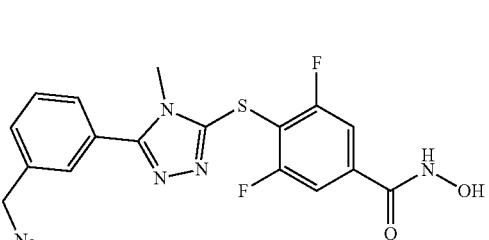
182
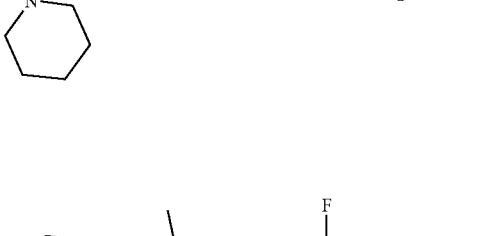
186
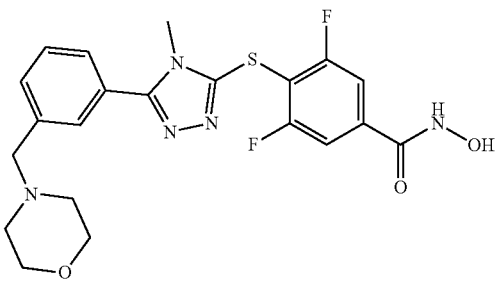
191
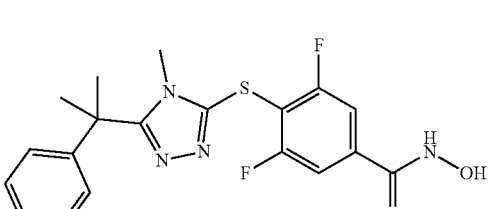
195
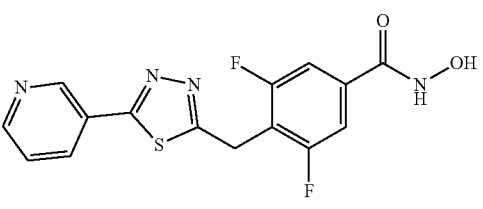

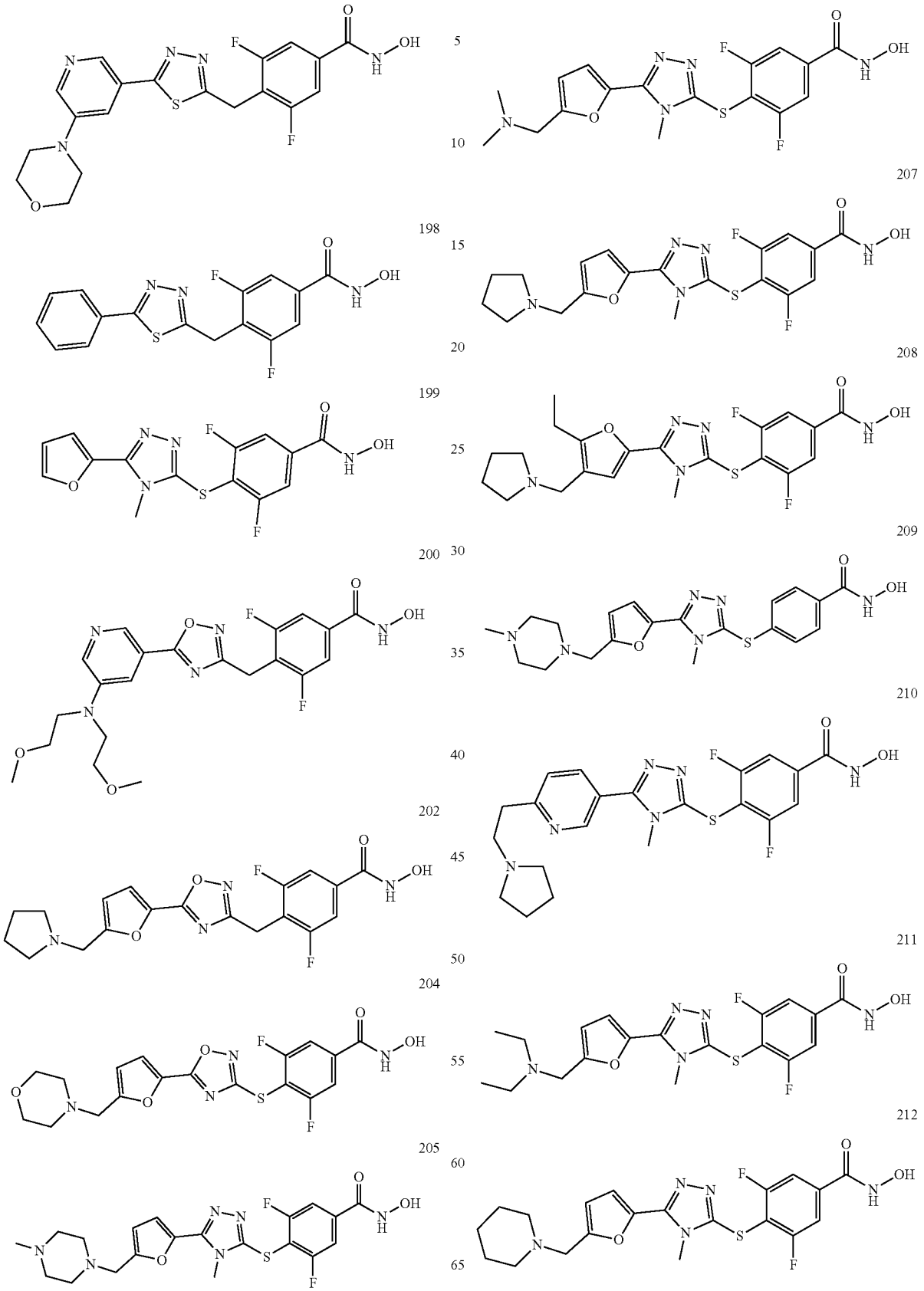

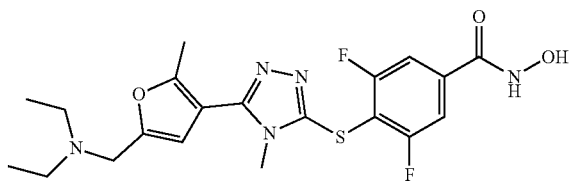

213

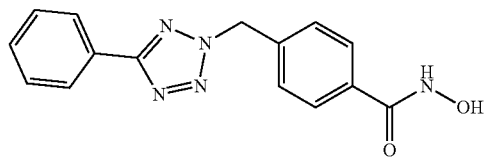

214

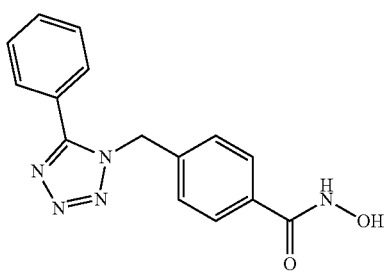

215

Compounds of the present invention may contain one or more chiral centres (asymmetric carbon atoms), therefore they may exist in enantiomeric and/or diastereoisomeric forms.

All possible optical isomers, alone or in a mixture with each other, fall within the scope of the present invention.

Compounds according to the invention may be used alone or in combination with other drugs such as proteasome inhibitors, immunochemical inhibitors, steroids, bromodomain inhibitors and other epigenetic drugs, traditional chemotherapeutic agents, kinase inhibitors, such as, for example, but not limited to, JAK family, CTLA4, PD1 or PDL1 checkpoints inhibitors, such as nivolumab, pemprolizumab, pidilizumab or BMS-936559 (anti-PD1), atezolizumab or avelumab (anti-PDL1), ipilimumab or tremelimumab (anti-CTLA4).

The compounds of the invention alone or in combination are preferably useful for the treatment of HDAC6-mediated diseases.

The compounds of the invention alone or in combination are preferably useful for the treatment of graft rejection, GVHD, myositis, diseases associated with abnormal lymphocyte functions, multiple myeloma, non-Hodgkin lymphoma, peripheral neuropathy, autoimmune diseases, inflammatory diseases, cancer and neurodegenerative diseases, ocular diseases (e.g. uveitis).

Therefore, the present invention also provides pharmaceutical compositions comprising a therapeutically effective amount of compounds of formula (I) or (II) or pharmaceutically acceptable salts, isomers and pharmacologically acceptable prodrugs thereof, together with at least one pharmaceutically acceptable excipient.

Such compositions can be liquid, suitable for enteral or parenteral administration, or solid, for example, in the form of capsules, tablets, pills, powders or granules for oral administration, or in forms suitable for cutaneous administration such as creams or ointments, or for inhalation delivery.

The pharmaceutical compositions of the present invention can be prepared by using known methods.

General Synthetic Pathway

The compounds described in the present invention can be prepared by using methods known to those skilled in the art.

All starting materials, reagents, acids, bases, solvents and catalysts used in the synthesis of the described compounds are commercially available.

Reaction progression was monitored by HPLC, UPLC or HPLC-MS analysis.

The triazole-thiol core compounds were obtained by reaction of 1,2,4-triazole-thiols, optionally substituted with methyl-4-iodo-benzoate or methyl-3,4,5-trifluoro-benzoate, in the presence of potassium carbonate in DMF under heating overnight. The reaction with methyl 4-iodo-benzoate was catalysed with copper iodide and L-proline (Scheme 1) and was heated at 120° C. (Liang-Feng et al., Tetrahedron (2011), 67, 2878-2881). On the other hand, the reaction with methyl 3,4,5-trifluoro-benzoate proceeds even under mild conditions (55° C.) and without catalysis (Scheme 2) (Dudutiene et al., Bioorg. Med. Chem. (2013), 21(7), 2093-2106; WO03/062225).

The same conditions were used to synthesize 1,3,4-thiadiazole-2-thiol and 1,3,4-oxadiazole-2-thiol core compounds.

The conversion of ester derivatives into the corresponding hydroxamic acids was achieved by treating with a large excess of aqueous hydroxylamine in a basic medium (NaOH), in methanol. Hydroxamic acid can also be synthesized by methyl ester hydrolysis with NaOH and subsequent condensation with hydroxylamine, upon activation with HATU or other coupling reagents.

Scheme 1- Synthesis of Benzohydroxamic Derivatives with Triazole, Thiadiazole and Oxadiazole Core

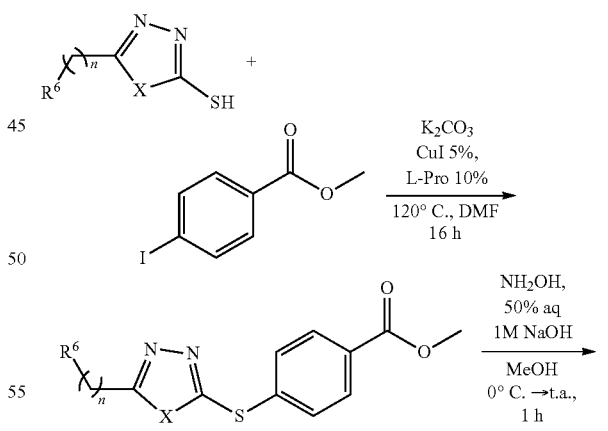

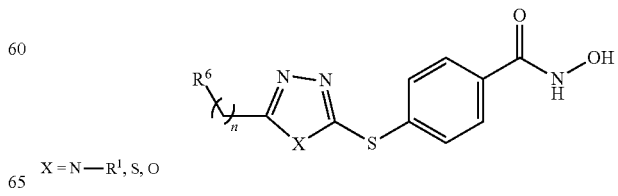

Scheme 2- Synthesis of 3,5-Difluorobenzohydroxamic Derivatives with Triazole, Thiadiazole and Oxadiazole Core

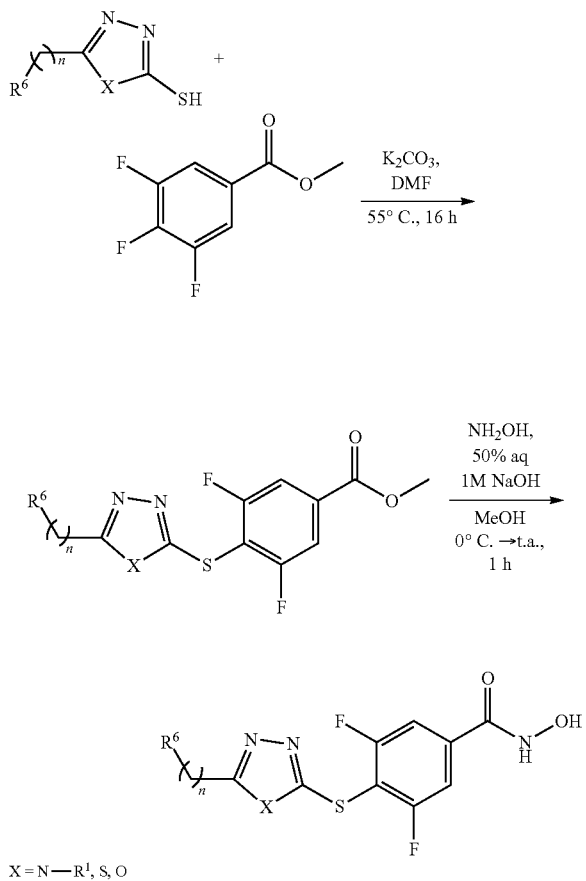

X = N—R¹, S, O

Many of the starting 1,2,4-triazole-thiols are commercially available. In some cases they have been synthesized according to the two routes shown in Scheme 3. The open intermediate was prepared from carboxylic acid by activation with T3P and condensation with N-substituted hydrazine carbothioamide in the presence of DIPEA in DMF (US2007/0232808). The same intermediate was obtained starting from hydrazide, which was treated with N-substituted isothiocyanate in refluxing ethanol (Lei et al., ChemMedChem (2016), 11, 822-826; Nadjet et al., Molecules (2015), 20, 16048-16067). Cyclization of the open intermediate was achieved by addition of aqueous NaOH to the reaction mixture.

1,3,4-thiadiazole-2-thiols not commercially available were synthesized by treating the corresponding hydrazide with KOH and $CS_2$ at low temperature (0-5° C.) for 1 hour and with $H_2SO_4$ in a second step, as described in Scheme 4.

Scheme 4- Synthesis of 1,3,4-Thiadiazole-thiols

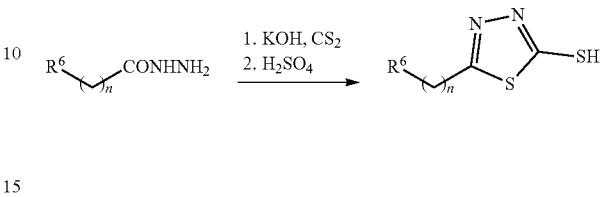

Compounds with triazole core were prepared as described in Scheme 5a starting from 2-(4-(methoxycarbonyl)phenyl) acetic acid by reaction with a carboxyimidamide in the presence of HATU and DIPEA in DMF. Upon complete conversion of starting products into the intermediate, a substituted hydrazine and an excess of acetic acid were added to the reaction mixture. The formation of triazole cycle was achieved by heating the mixture overnight (Castanedo et al., J. Org. Chem. (2011), 76(4), 1177-1179).

Compounds with 1,3,4-thiadiazole and 1,3,4-oxadiazole scaffold were also obtained by cyclization of an open intermediate, prepared by condensation of 2-(4-(methoxycarbonyl)phenyl)acetic acid or 2-(2,6-difluoro-4-(methoxycarbonyl)phenyl)acetic acid with appropriate hydrazide by usual HATU, DIPEA activation. Hydrazides were either commercially available or could be easily prepared from the corresponding carboxylic acid (Scheme 5c). Lawesson's Reagent was used as cyclizing agent for 1,3,4-thiadiazole derivatives, while the same intermediate cyclized upon treatment with an excess of Burgess' Reagent in refluxing toluene or THF to provide 1,3,4-oxadiazoles (Scheme 5b). As 2-(2,6-difluoro-4-(methoxycarbonyl)phenyl)acetic acid is not commercially available, it was synthesized reacting methyl 3,4,5-trifluorobenzoate and di-ter-butyl malonate in presence of sodium hydride in anhydrous DMF. The resulting di-tert-butyl 2-(2,6-difluoro-4-(methoxycarbonyl)phenyl)malonate was then decarboxylated by treating with TFA under reflux (Scheme 5c).

Due to the lower reactivity of 2-(2,6-difluoro-4-(methoxycarbonyl)phenyl)acetic acid, it was necessary to activate it with thionyl chloride to achieve the condensation (Scheme 5c). The conversion of ester derivatives into the corresponding hydroxamic acids was achieved by hydroxylaminolysis, as already described in the above cases.

Scheme 3- Synthesis of 1,2,4-Triazole-thiols

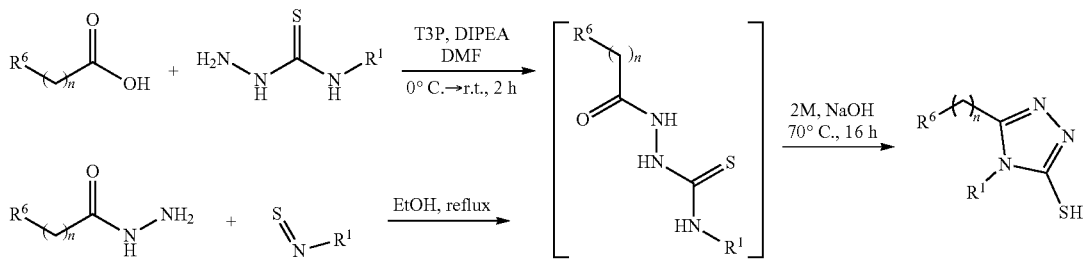

Scheme 5- Synthesis of Benzohydroxamic Derivatives with Triazole, Thiadiazole and Oxadiazole Core
a)
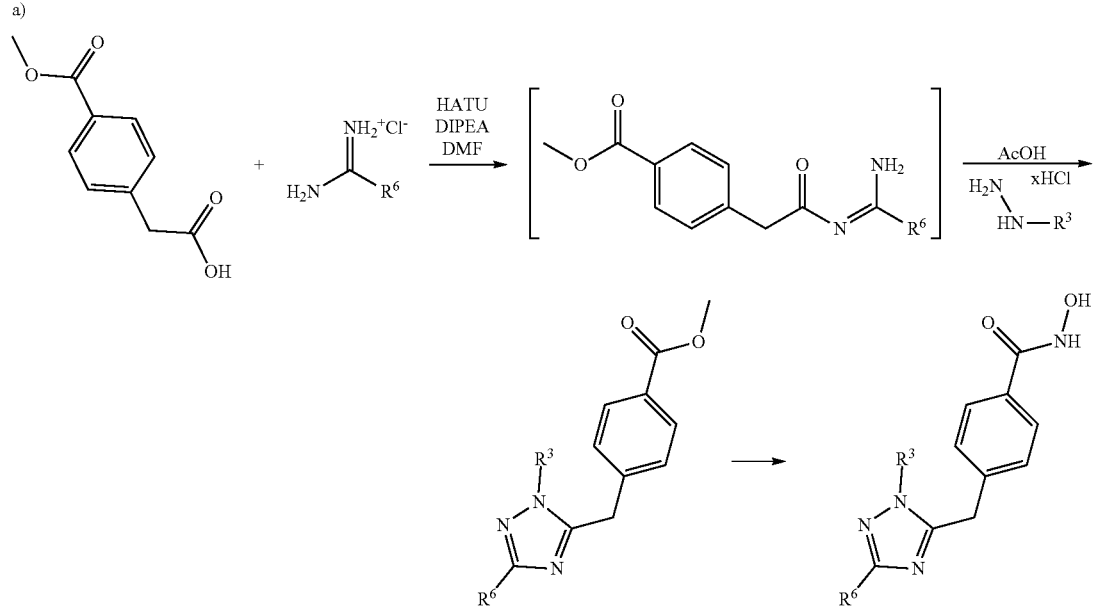
b)
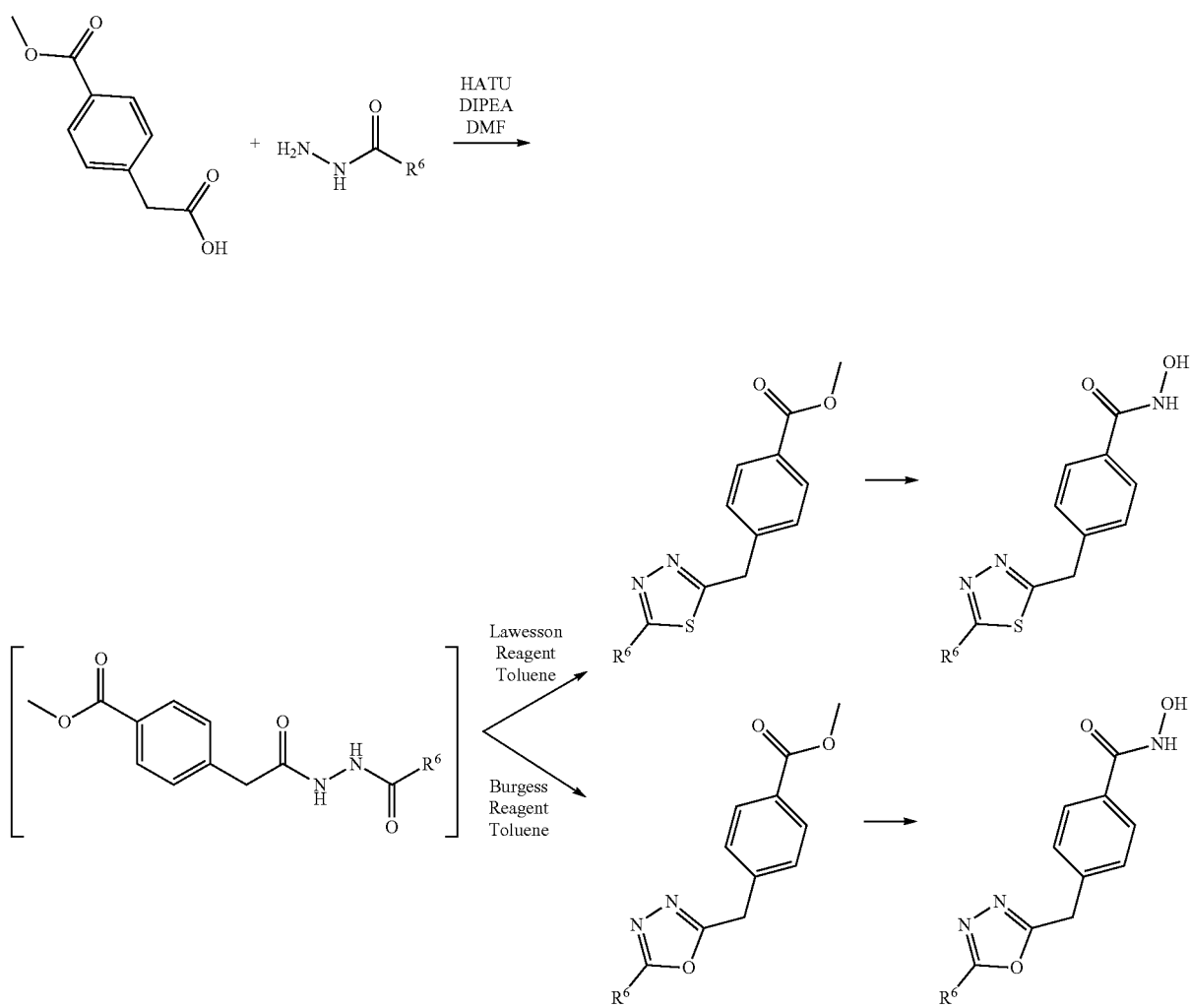

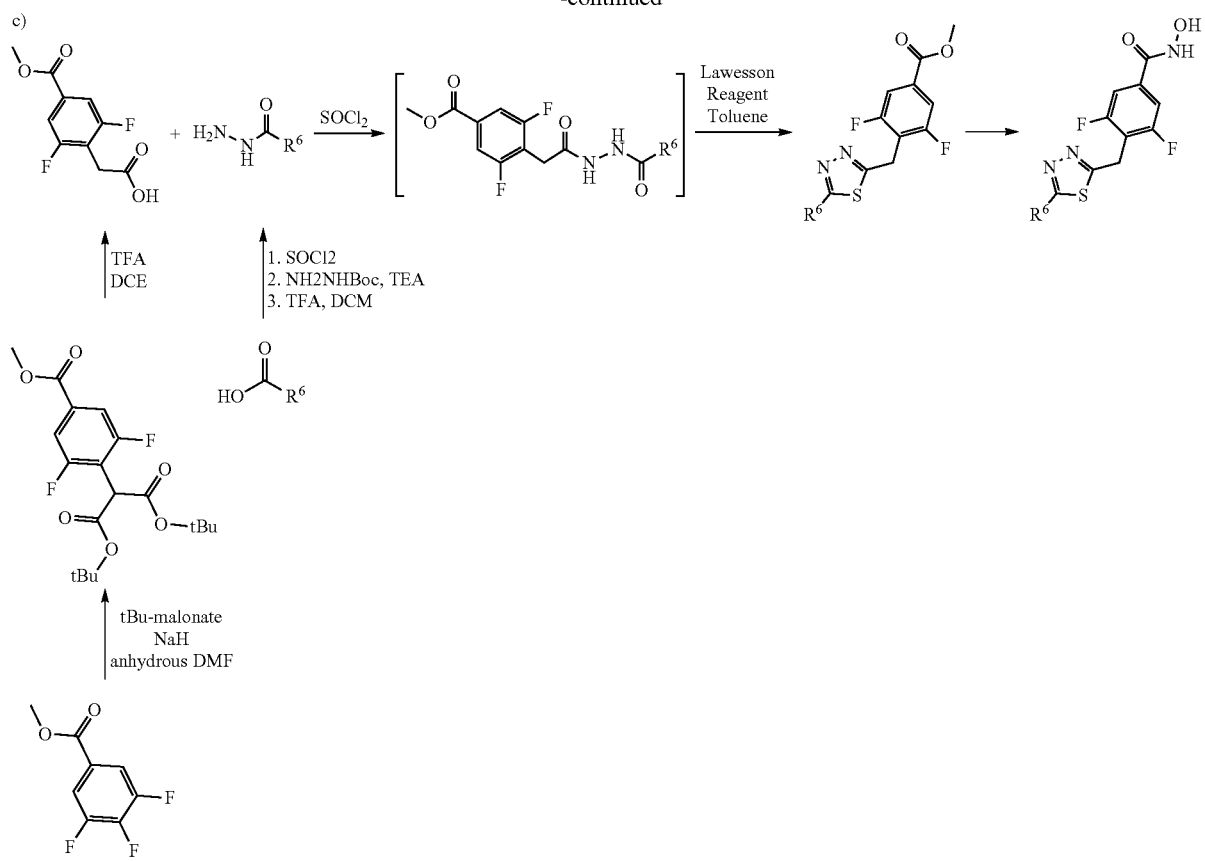

1,3,4-oxadiazol derivatives were used as starting material for the synthesis of compounds bearing triazole core. The conversion was obtained by heating the oxadiazole in THF in presence of MeNH$_2$, as described in Scheme 6.

Scheme 6
Synthesis of 1,2,3-Triazole derivatives.

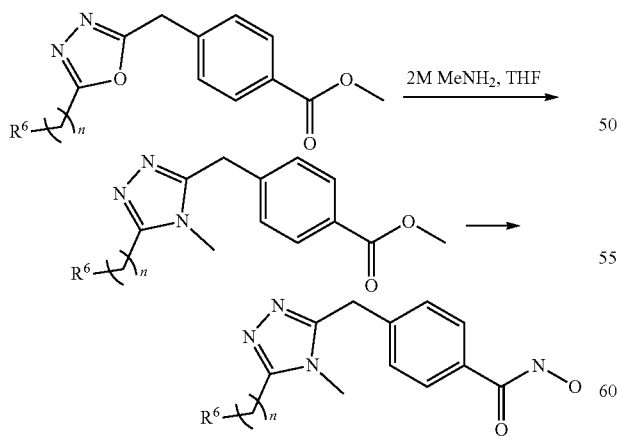

Compounds bearing a 3,4,5-trisubstituted 1,2,4-triazole as a scaffold were prepared starting from methyl p-aminomethylbenzoate hydrochloride and the corresponding acyl-chloride in presence of trimethylamine. The amide thus obtained was refluxed in thionyl chloride to form an intermediate imidoyl chloride, which gave the desired product upon reaction with the corresponding hydrazide and subsequent cyclization in refluxing toluene (Scheme 7). (WO2011106650 (A2)—2011 Sep. 1; Begum et al Med. Chem. Commun. 2015, 6, 80-89; Aster et al. Bioorg. Med. Chem. Lett. 2008, 18, 2799-2804.)

Scheme 7-Synthesis of Benzohydroxamic Derivatives with 3,4,5-Trisubstituted 1,2,4-Triazole Core

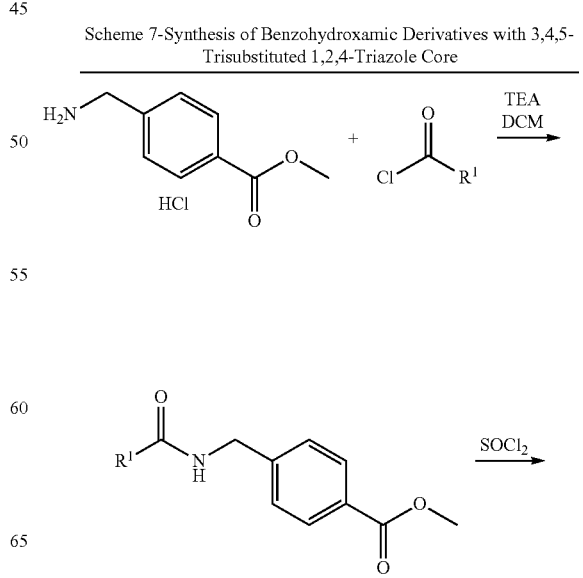

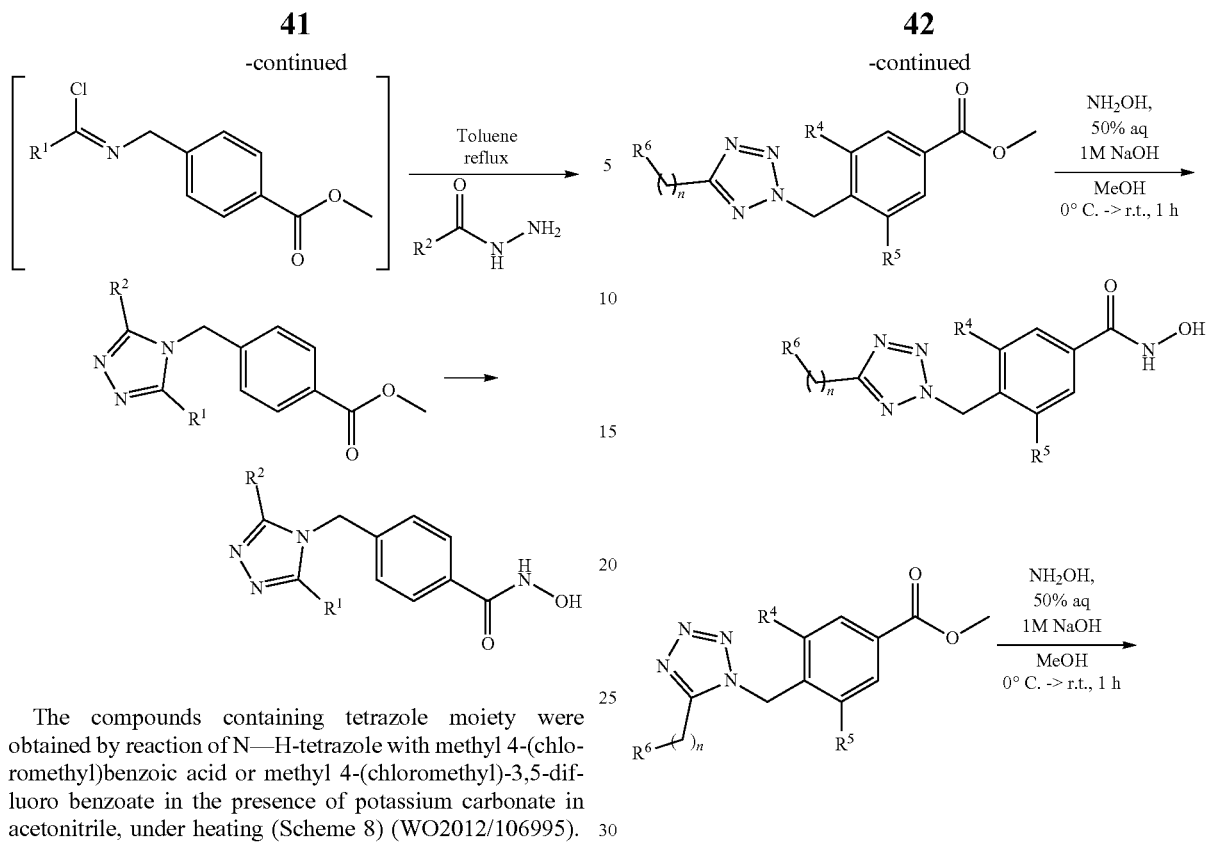

The compounds containing tetrazole moiety were obtained by reaction of N—H-tetrazole with methyl 4-(chloromethyl)benzoic acid or methyl 4-(chloromethyl)-3,5-difluoro benzoate in the presence of potassium carbonate in acetonitrile, under heating (Scheme 8) (WO2012/106995).

Scheme 8-Synthesis of Benzo-hydroxamic and 3,5-DifluoroBenzo-Hydroxamic Derivatives with Tetrazole Core

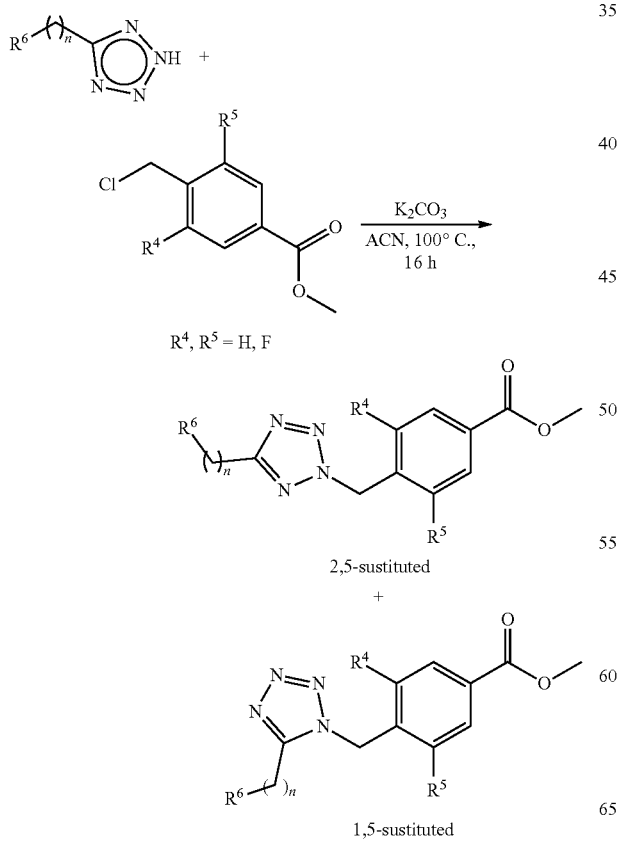

Regioselectivity is dependent on the tetrazole substrate, usually being the 2,5-disubstituted product 2-10 fold favoured with respect to the 1,5-disubstituted product. The regioisomers, separated by chromatography on silica, were treated separately with an excess of hydroxylamine and aqueous sodium hydroxide to obtain the respective hydroxamic products.

Some of the starting N—H-tetrazoles are commercially available while others were synthesized by treating the respective nitrile with sodium azide and ammonium chloride in DMF under heating (Scheme 9).

Scheme 9-Synthesis of NH-Tetrazoles

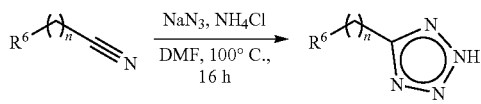

Compounds containing the 2-amino-1,3,4-oxadiazole moiety were obtained by combining an acyl hydrazide with methyl 4-isocyanatobenzoate in THF at room temperature (rt) and refluxing the intermediate just formed in the presence of an excess of Burgess Reagent (Scheme 10) (Dolman et al., J. Org. Chem. (2006), 71(25), 9548).

Scheme 10-Synthesis of Benzo-Hydroxamic Derivatives with 2-Amino-1,3,4-Oxadiazole Core

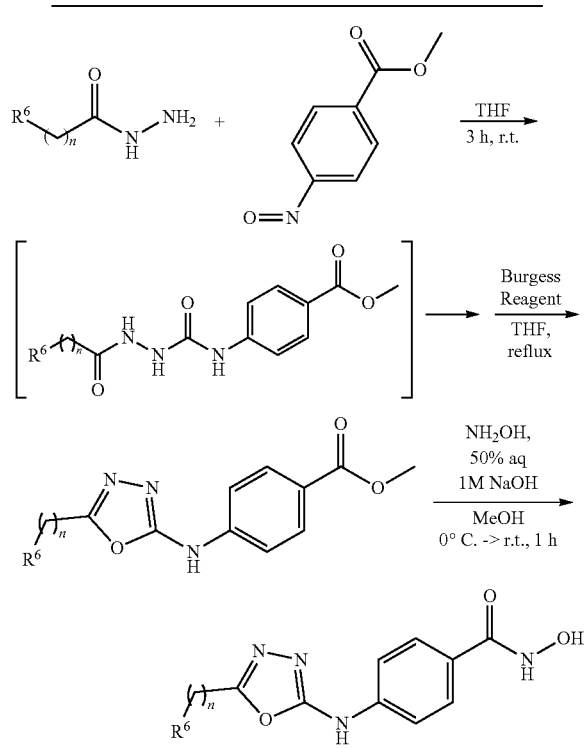

Conversion of ester compounds into hydroxamic acid has been achieved, as described in the above cases, by hydroxylaminolysis.

The 1,2,4-oxadiazole core compounds were synthesized from 4-(cyanomethyl)benzoic acid, or from the corresponding methyl ester, by treatment with hydroxylamine hydrochloride in the presence of an excess of potassium hydroxide or sodium bicarbonate in refluxing ethanol (Scheme 11). The (Z)-4-(2-amino-2-(hydroxyimino)ethyl)benzoic acid thus obtained was then reacted with a suitable carboxylic acid previously activated with HATU and DIPEA or other activators to give an open intermediate, which undergoes cyclization by heating at 100° C. and in the presence of molecular sieves or cyclizing agents, such as carbonyldiimidazole.

Scheme 11-Synthesis of Benzohydroxamic Derivatives with 1,2,4-Oxadiazole Core

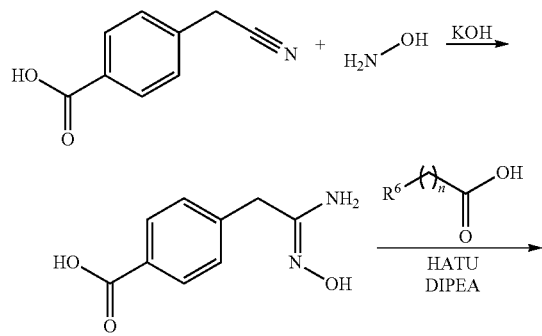

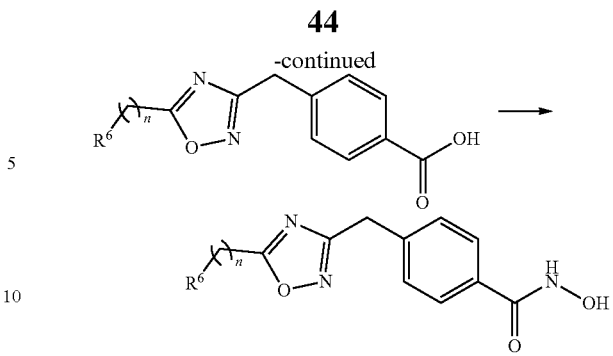

The conversion of the carboxylic acid into hydroxamic acid can be accomplished with any method known in the art. Generally it is obtained by activation with HATU, DCC or acyl chloride and reaction of the activated compound with aqueous hydroxylamine. In some cases it has been necessary to condense the carboxylic acid with 0-(tetrahydro-2H-pyran-2-yl)hydroxylamine in order to obtain an hydroxamic acid protected form which can be released by treatment with TFA (Scheme 12).

Scheme 12-Conversion of the carboxylic acid into hydroxamic acid through a protected form thereof

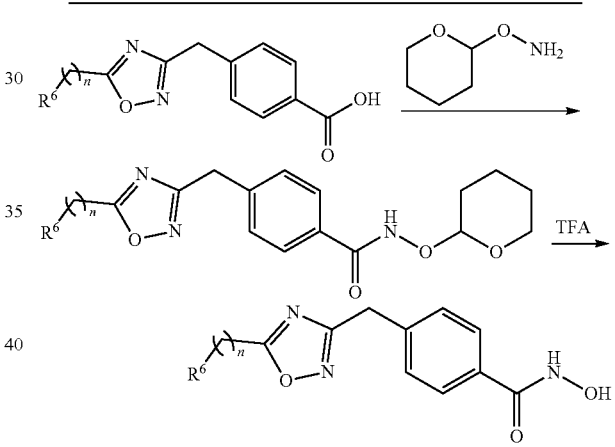

For the synthesis of compounds with 1,3,4-oxadiazole core (Scheme 13) the appropriate hydrazide was prepared by reaction of the corresponding acid, activated by acyl chloride, with Boc-hydrazine and subsequent deprotection by TFA treatment. The hydrazide was then condensed with 2-(4-(methoxycarbonyl)phenyl)acetic acid, previously activated with HATU and DIPEA. The cyclisation of the open intermediate was achieved by treatment with an excess of Burgess Reagent in toluene or THF under reflux.

Scheme 13-Synthesis of Hydroxamic Derivatives with 1,3,4-Oxadiazole Core

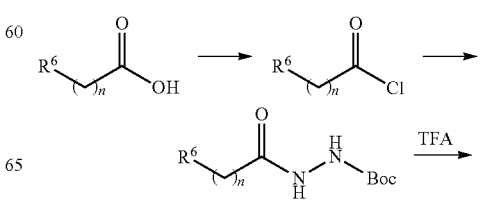

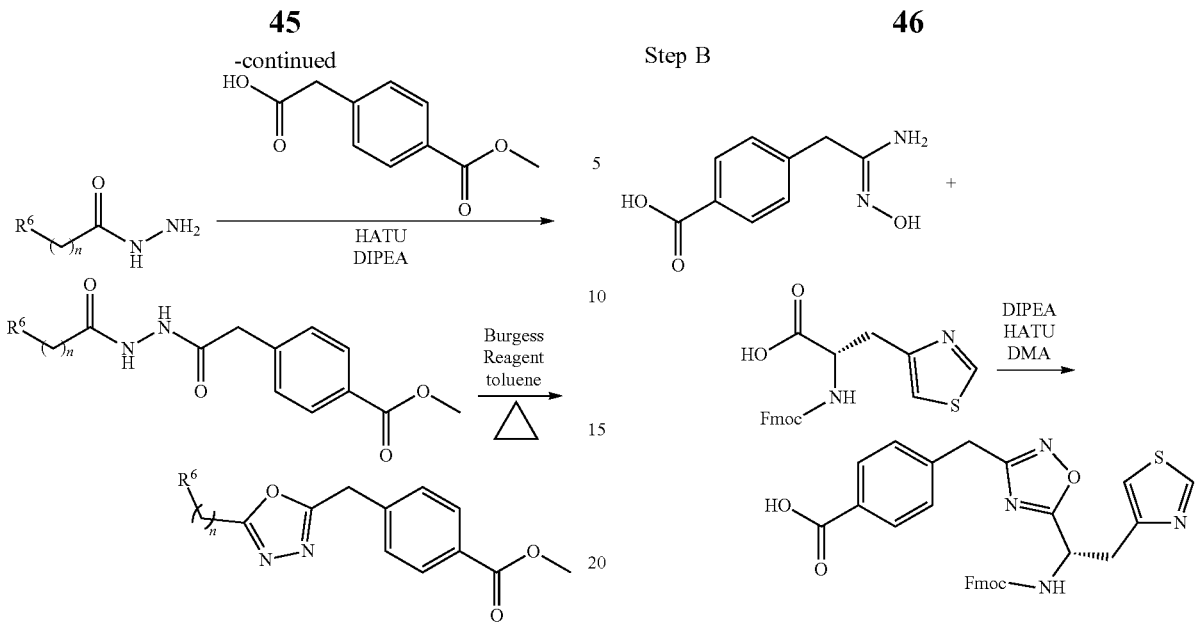

As previously shown, it is possible to obtain the final hydroxamic derivative by methyl ester hydroxylaminolysis reacting it with hydroxylamine, in the presence of a large excess of sodium hydroxide.

The following examples are intended to further illustrate the invention but not limiting it.

Example 1—Synthesis of (S)—N-(1-(3-(4-(hydroxycarbamoyl)benzyl)-1,2,4-oxadiazol-5-yl)-2-(thiazol-4yl)ethyl-3,4-dimethoxybenzamide (comp. 1)

Step A

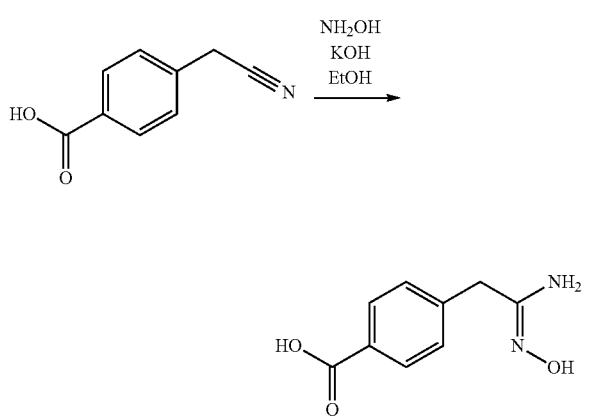

To a solution of 4-(cyanomethyl)benzoic acid (3.04 g, 1 eq) in EtOH (250 ml), KOH (3.17 g, 3 eq) and hydroxylamine hydrochloride (2.62 g, 2 eq) were added. The reaction mixture was refluxed 20 hours. The solution was then cooled, diluted with water (300 ml) and acidified to pH 6 with conc. HCl. The precipitated white solid was filtered and dried under vacuum at 50° C. overnight. 2.6 g of product were obtained, which was used for the next step without any further purification.

Step B

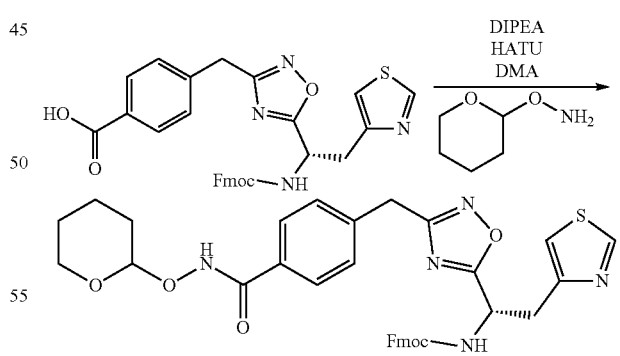

(S)-2-(N-Fmoc-amino)-3-(thiazol-4-il)propanoic acid (2 g, 1 eq) was activated by treatment with HATU (2.5 g, 1.3 eq) and DIPEA (1.4 ml) in DMA at room temperature for 1 hour. Additional DIPEA (1.4 mL) and (Z)-4-(2-amino-2-(hydroxyimino)ethyl)benzoic acid (985 mg, 1 eq) were then added to the reaction mixture. After complete dissolution of the starting products, molecular sieves were added in order to remove the forming water and aid the cyclization of the open intermediate. After two hours, the molecular sieves were removed by filtration and the solvent evaporated under reduced pressure. The residue was taken up in methanol. The white solid separating was removed by filtration. The solvent was partially evaporated. An additional precipitation of a white solid was observed, which was filtered. The solution was evaporated to dryness and the residue was purified by reverse phase flash chromatography ($C_{18}$) in $H_2O$/ACN/TFA gradient.

Step C

The acid obtained in step B (82 mg, 1 eq) was activated by treatment with HATU (73 mg, 1.3 eq) and DIPEA (41μ1.3 eq) in DMF at room temperature. O-(tetrahydro-2H-pyran-2-yl)hydroxylamine (17 mg, 1 eq) was then added to the reaction mixture. After 2 hours stirring at room temperature, the solvent was evaporated in a vacuum centrifuge. The residue was used for the next step without any further purification.

Step D

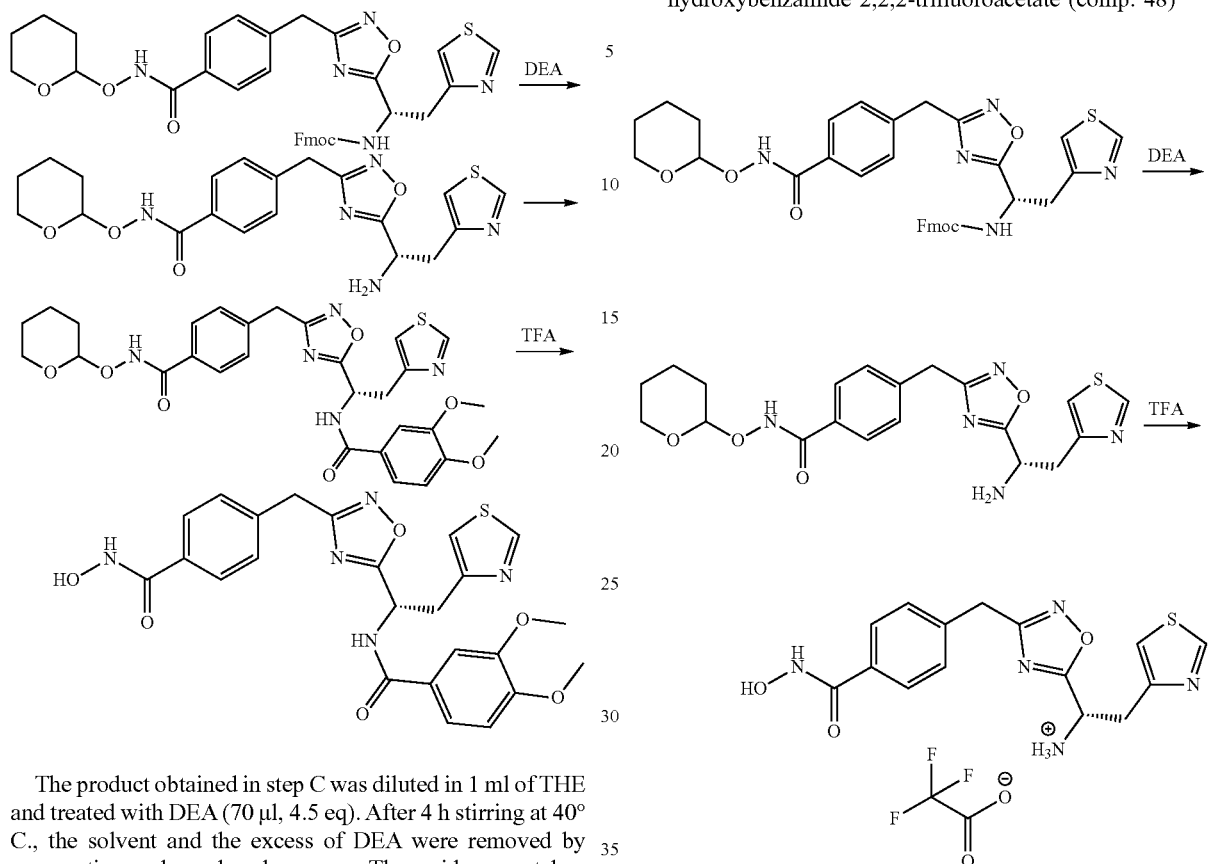

The product obtained in step C was diluted in 1 ml of THF and treated with DEA (70 μl, 4.5 eq). After 4 h stirring at 40° C., the solvent and the excess of DEA were removed by evaporation under reduced pressure. The residue was taken up with 1 ml of DMF and 3,4-dimethoxybenzoic acid (27 mg, 1 eq), previously activated with HATU (74 mg, 1.3 eq) and DIPEA (41μl.3 eq) in DMF (1 ml), was added to the solution. The reaction mixture was stirred at room temperature 4 hours. Finally, 0.4 ml of TFA was added to deprotect the hydroxamic functionality. After 4 hours, the solvent and the excess of TFA were removed by evaporation and the residue was purified via semipreparative LC-MS (m/z 509.84 [MH+]).

The following compound was synthesized using the same procedure:

Example 2—Synthesis of (S)-4-((5-(1-amino-2-(thiazol-4-yl)ethyl)-1,2,4-oxadiazol-3-yl)methyl)-N-hydroxybenzamide 2,2,2-trifluoroacetate (comp. 48)

(9H-Fluoren-9-yl)methyl((1S)-1-(3-(4-(((tetrahydro-2H-pyran-2-yl)oxy)carbamoyl)benzyl)-1,2,4-oxadiazol-5-yl)-2-(thiazol-4-yl)ethyl)carbamate (obtained in Step C of Synthesis of Compound 1) (222 mg, 1 eq) was treated with DEA (159 μl, 4.5 eq) in DMF (1 ml) overnight at RT. Then 0.520 ml of TFA (20 eq) were added to the reaction mixture. Solvent was removed by evaporation and the residue was purified in semipreparative LC-MS (m/z 346.04 [MH+]).

| Comp. | Structure | m/z [MH+] |
|---|---|---|
| 21 | 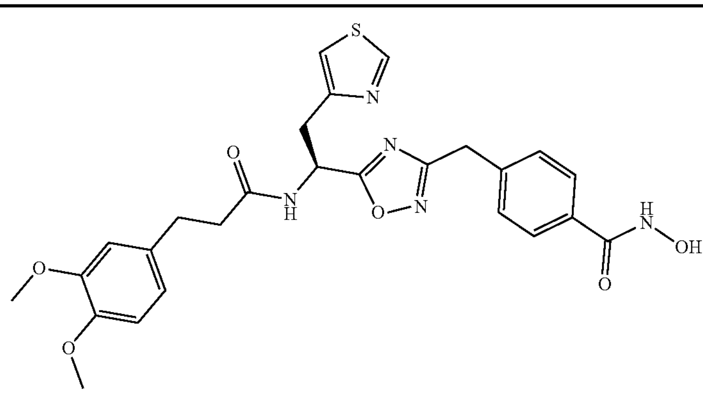 | 537.97 |

Example 3—Synthesis of 4-[[5-(3,4-dimethoxyphenyl)-1,2,4-oxadiazol-3-yl]methyl]benzenecarbohydroxamic acid (comp. 49)

Step A

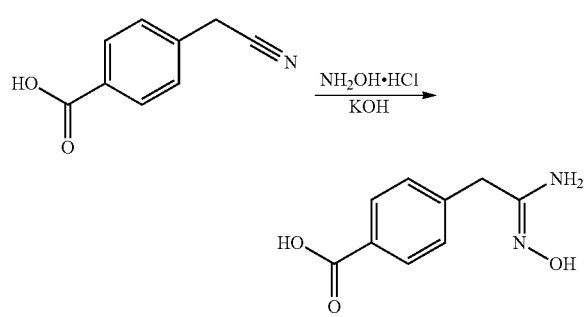

A mixture of 4-(cyanomethyl)benzoic acid (3 g, 1 eq), hydroxylamine hydrochloride (2.6 g, 2 eq) and potassium hydroxide (3.2 g, 3 eq) in ethanol (250 ml) was heated overnight under reflux. After cooling to RT, 300 ml of water and 15 ml of 1N HCl (pH 5) were added to the reaction mixture. The desired product, obtained as a precipitate, was filtered off on a sintered septum and dried under vacuum overnight. 320 mg of clean product was recovered.

Step B

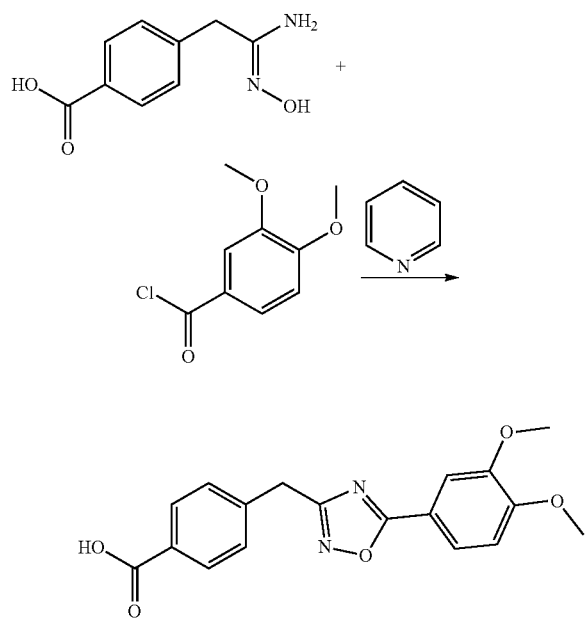

(Z)-4-(2-amino-2-(hydroxyimino)ethyl)benzoic acid (319 mg, 1.1 eq) obtained in step A was dissolved in toluene (6 ml) and pyridine (3 ml) was added. 3,4-Dimethoxybenzoyl chloride (300 mg, 1 eq), previously prepared by reacting 3,4-dimethoxybenzoic acid with an excess of thionyl chloride, was added to the reaction mixture. The reaction mixture was refluxed 4 hours. Solvent was evaporated under reduced pressure and the product was purified by semipreparative LC-MS.

Step C

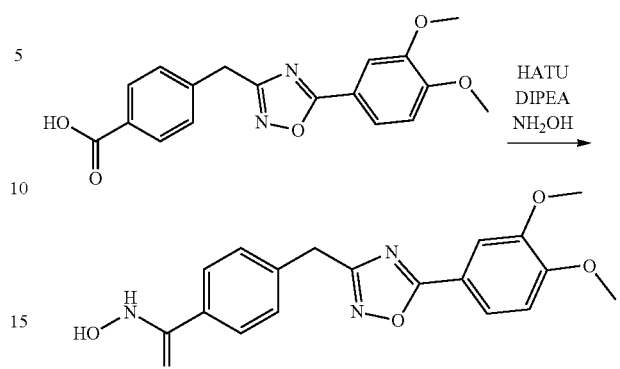

4-((5-(3,4-dimethoxyphenyl)-1,2,4-oxadiazol-3-yl)methyl)benzoic acid (71 mg, 1 eq) obtained in Step B was activated by treating with HATU (103 mg, 1.3 eq) and DIPEA (47 µl, 1.3 eq) in DMF (1 mL) 30 minutes at room temperature. Hydroxylamine hydrochloride (14 mg, 1 eq) and additional DIPEA (47 µl, 1.3 eq) were then added to the reaction mixture. After stirring at room temperature overnight, the solvent was removed evaporating under reduced pressure and the residue was purified by semipreparative LC-MS. 33 mg of clean product was recovered (m/z 356.08 [MH+]).

Example 4. Synthesis of 4-((5-(2,4-difluorophenyl)-1,3,4-oxadiazol-2-yl)methyl)-N-hydroxybenzamide (comp. 58)

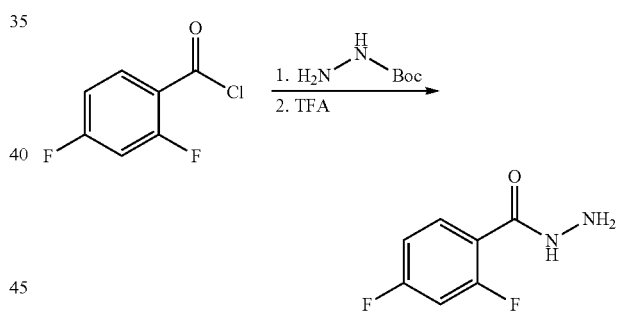

A solution of Boc-hydrazine (150 mg, 1 eq) in ACN (2 ml) and 95 mg of NaHCO$_3$ (1 eq) were added to a solution of 2,4-difluorobenzoyl chloride (200 mg, 1 eq) in ACN (3 ml). After three hours at RT, solvent was evaporated in air flow. Residue was treated with TFA for three hours. Acid was removed in air stream and the residue was taken up with EtOAc and washed with 2.5% NaHCO$_3$ solution. The combined organic phases were dried on Na$_2$SO$_4$, filtered and evaporated to dryness. 159 mg of product was obtained, which was used for the next step without any further purification.

Step B

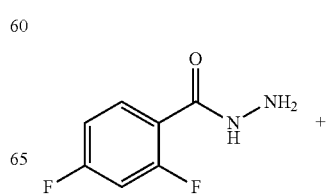

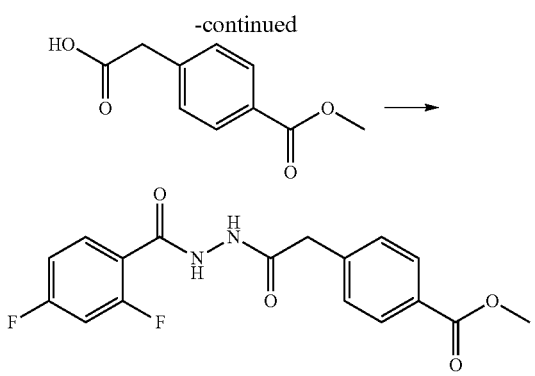

HATU (439 mg, 1.3 eq) and DIPEA (0.4 mL, 2.6 eq) were added to a solution of 2-(4-(methoxycarbonyl)phenyl)acetic acid (224 mg, 1.3 eq) in 5 ml of THF). The reaction mixture was stirred at room temperature for 1 h until complete dissolution of reagents. A solution of 2,4-difluorobenzohydrazide (153 mg, 1 eq) in THF (2 ml) was then added to the mixture. After 4 hours at RT, complete conversion of the starting reagents to the desired product was observed. Solvent was removed by evaporation in air stream. The residue was taken up in H$_2$O and the formed precipitate was filtered on a sintered septum. The product (149 mg) was used in the subsequent step without any further purification.

Step C

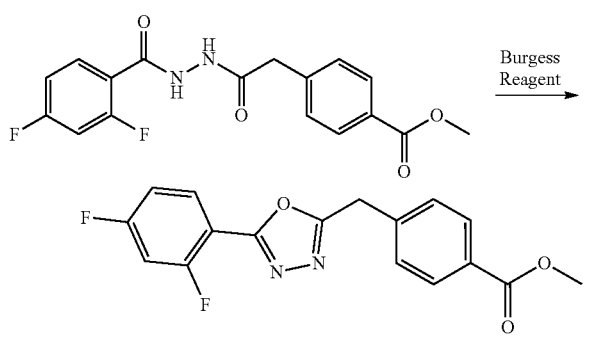

175 mg of Burgess Reagent (1.72 eq) was added to a suspension of compound obtained in Step B (149 mg, 1 eq) in 5 ml of dry toluene heated under reflux. After one hour, complete conversion of the starting compound into the cyclic product was observed. Solvent was removed evaporating under vacuum. The residue was taken up with DCM and washed with 1N HCl and H$_2$O. Organic phase was dried on Na$_2$SO$_4$, filtered and evaporated to dryness. 132.3 mg of product was recovered, which was used in the following step without any further purification.

Step D

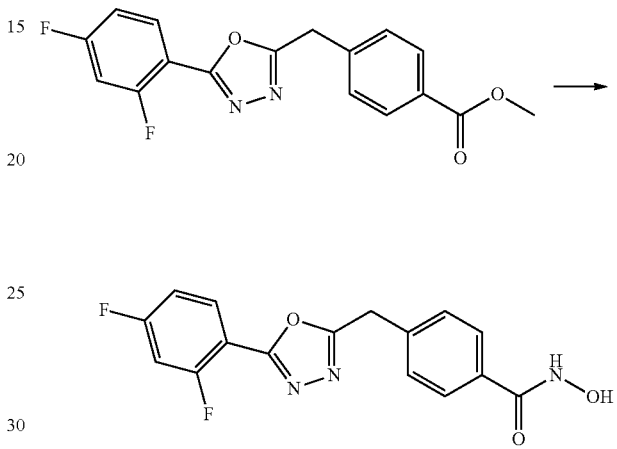

0.707 ml of aqueous hydroxylamine (60 eq) was added to a solution of compound obtained in step C (132 mg, 1 eq) in 4 ml of MeOH/THF. 1,998 ml of 1N NaOH (5 eq) was slowly added dropwise. Approximately after one hour, the system was neutralized by addition of 1N HCl (2 ml). The solvent was evaporated under vacuum and the residue was diluted with a 2.5% NaHCO$_3$ solution, filtered and washed with H$_2$O. Solid was suspended in Et$_2$O and filtered. 53 mg of pure product was obtained (m/z 332.01 [MH+]).

The following compounds were synthesized using the same procedure:

| Comp. | Structure | m/z [MH+] |
|---|---|---|
| 3 | 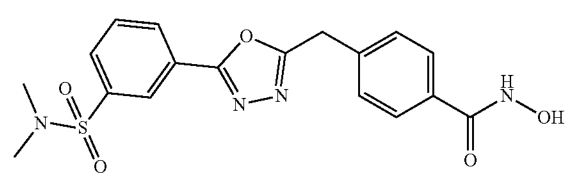 [SMILES: CN(C)S(=O)(=O)c1cccc(-c2nnc(Cc3ccc(C(=O)NO)cc3)o2)c1] | 403.05 |
| 64 | 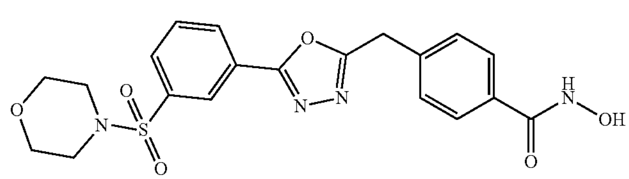 [SMILES: O=C(NO)c1ccc(Cc2nnc(-c3cccc(S(=O)(=O)N4CCOCC4)c3)o2)cc1] | 445.05 |

| Comp. | Structure | m/z [MH+] |
|---|---|---|
| 57 | 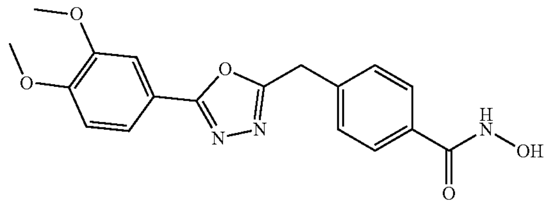 [SMILES: COc1ccc(-c2nnc(Cc3ccc(C(=O)NO)cc3)o2)cc1OC] | 356.01 |
| 45 | 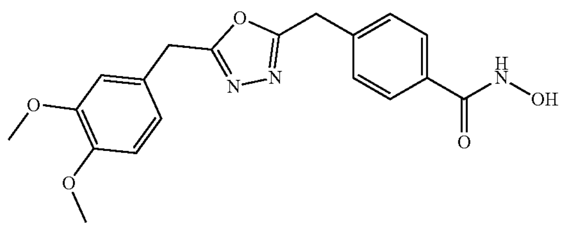 [SMILES: COc1ccc(Cc2nnc(Cc3ccc(C(=O)NO)cc3)o2)cc1OC] | 370.08 |
| 68 | 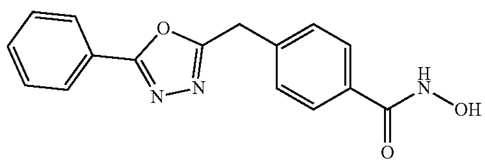 [SMILES: O=C(NO)c1ccc(Cc2nnc(-c3ccccc3)o2)cc1] | 296.04 |
| 69 | 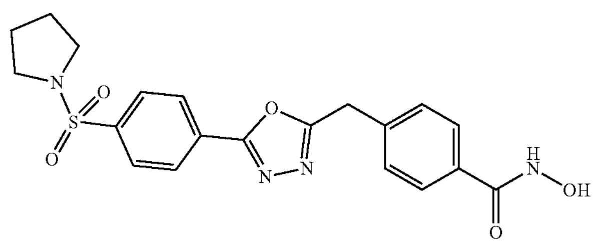 [SMILES: O=C(NO)c1ccc(Cc2nnc(-c3ccc(S(=O)(=O)N4CCCC4)cc3)o2)cc1] | 428.94 |
| 75 | 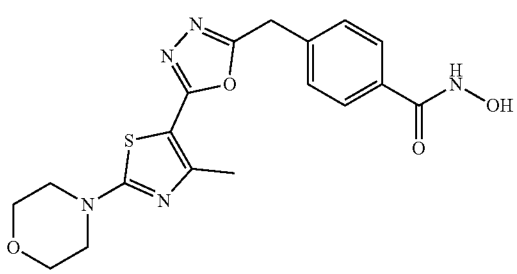 [SMILES: Cc1nc(N2CCOCC2)sc1-c1nnc(Cc2ccc(C(=O)NO)cc2)o1] | 401.96 |
Example 5. Synthesis of 4-[(5-phenyl-1,3,4-oxadiazol-2-yl)amino]benzenecarbohydroxamic acid (comp. 60)
Step A
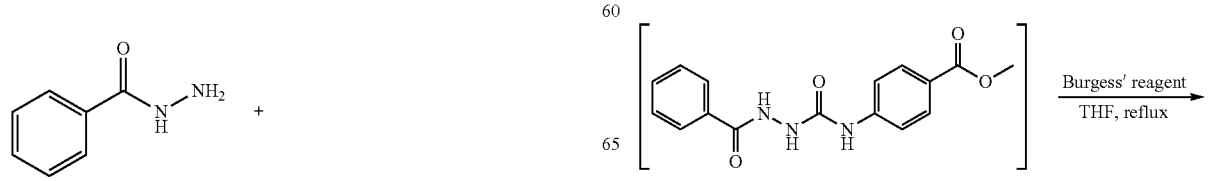

-continued

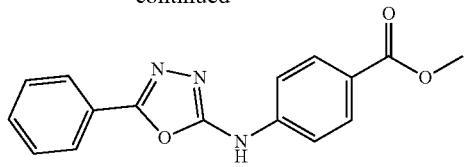

68 mg of benzohydrazide (1 eq) and methyl 4-isocyanobenzoate (88.5 mg, 1 eq) were mixed in THF (5 mL) at room temperature. The resulting solution was stirred for 3 hours. The intermediate formation was verified by HPLC and LC-MS. The solvent was removed by evaporation under reduced pressure. The residue was taken up with toluene. The mixture was refluxed and Burgess Reagent (298 mg, 2.5 eq) was added in small portions until complete conversion of the intermediate into cyclic product. After cooling down to room temperature, washing with water was carried out. The organic phase was dried, filtered and evaporated to dryness. The product was purified by crystallization from DCM. 172 mg of clean product was obtained (Dolman et al., J. Org. Chem. (2006), 71(25), 9548).

Step B

The ester obtained in step A (172 mg, 1 eq) was suspended in 4 ml of methanol and the reaction mixture was cooled with ice bath at 0° C. and magnetically stirred. After hydroxylamine (50%, aqueous solution, 1.365 ml, 40 eq) addition, 1M sodium hydroxide (6 ml, 10 eq) aqueous solution was slowly added dropwise. The ice bath was removed, allowing the solution to reach room temperature. The conversion of the starting product into hydroxamic acid was confirmed by HPLC after 1 hour. The methanolic portion was removed evaporating under reduced pressure, and the reaction was subsequently quenched by adding 6 ml of 1M HCl aqueous solution and 6 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 26 mg of pure product was recovered (m/z 297.09 [MH+]).

The following compound was synthesized using the same procedure:

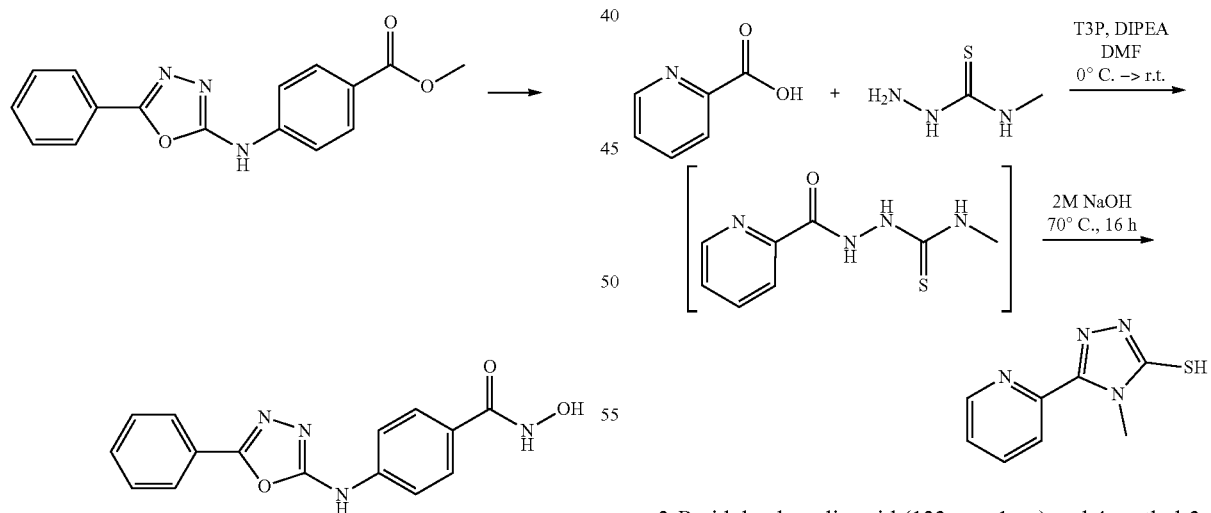

| Comp. | Structure | m/z [MH+] |
|---|---|---|
| 63 | 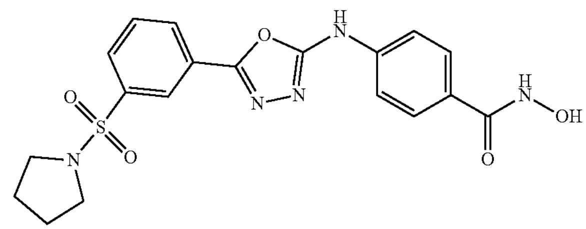 [SMILES: O=C(NO)c1ccc(Nc2nnc(-c3cccc(S(=O)(=O)N4CCCC4)c3)o2)cc1] | 430.00 |

Example 6. Synthesis of 3,5-difluoro-N-hydroxy-4-((4-methyl-5-(pyridin-2-yl)-4H-1,2,4-triazol-3-yl)thio)benzamide (comp. 14)

Step A

2-Pyridylcarboxylic acid (123 mg, 1 eq) and 4-methyl-3-thiosemicarbazide (116 mg, 1.1 eq) were suspended in 2 ml of DMF and the mixture was cooled to 0° C. with an ice bath. T3P (50% DMF solution, 893 μL, 1.5 eq) and diisopropylethylamine (310 μL, 1.78 eq) were added slowly to the reaction mixture under stirring. The ice bath was removed and the mixture was reacted at room temperature for 16 hours. The complete conversion of the starting material was confirmed by HPLC. 2 ml of ethyl acetate, 2 ml of water and 2 ml of 4M NaOH aqueous solution were added to the reaction mixture. The phases were separated, and the organic layer was re-extracted with 4M NaOH aqueous solution. The combined aqueous phases were stirred 16 hours at 70° C. Conversion of the open intermediate into the desired product was confirmed by LC-MS. The reaction mixture pH was adjusted to 5 by dropwise addition of conc. hydrochloric acid under stirring. The precipitate was collected by filtration. 157 mg of product was obtained, which was used in the following step without any further purification.

Step B

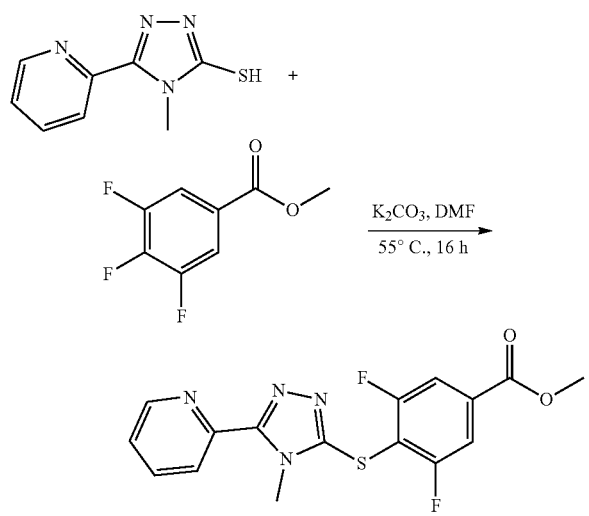

4-Methyl-5-(pyridin-2-yl)-4H-1,2,4-triazole-3-thiol (157 mg, 1 eq), methyl 3,4,5-trifluorobenzoate (156 mg, eq) and potassium carbonate (261 mg, 2.3 eq) were suspended in 2 ml of DMF under an argon atmosphere. The resulting mixture was warmed to 40° C. and stirred overnight.

The reaction mixture was diluted with 10 ml of ethyl acetate and 10 ml of water. The phases were separated and the aqueous layer was re-extracted with additional ethyl acetate (3×). The organic phases were combined and washed with brine (2×), dried over sodium sulphate, filtered and concentrated.

The crude reaction was purified by flash chromatography (Grace Reveleris X2, hexane:ethyl acetate). 149 mg of clean product was obtained (Dudutiene et al., Bioorg. Med. Chem. (2013), 21(7), 2093-2106; International Patent Application WO03/062225).

Step C

The ester obtained in step B (149 mg, 1 eq) was suspended in 5 ml of methanol and the reaction mixture was cooled with ice bath at 0° C. and magnetically stirred. After hydroxylamine (50%, aqueous solution, 0.97 ml, 40 eq) addition, 1M sodium hydroxide (4.1 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 4.1 ml of 1M hydrochloric acid aqueous solution and 6 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 113 mg of pure product was recovered (m/z 363.94 [MH+]).

The following compounds were synthesized using this procedure:

| Comp. | Structure | m/z [MH+] |
|---|---|---|
| 2 | 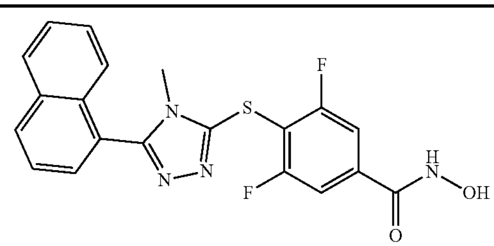 | 412.89 |
| 4 | 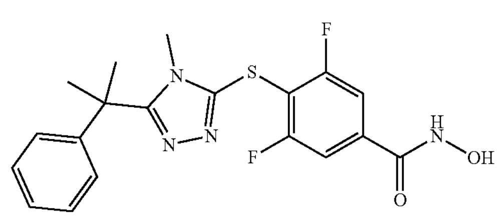 [SMILES: Cn1c(Sc2c(F)cc(C(=O)NO)cc2F)nnc1C(C)(C)c1ccccc1] | 405.01 |

-continued

| Comp. | Structure | m/z [MH+] |
|---|---|---|
| 9 | 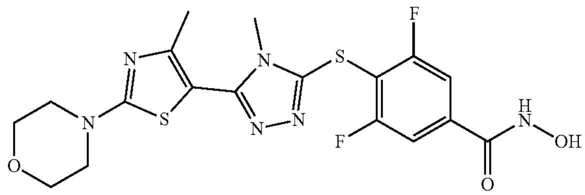 [SMILES: Cc1nc(N2CCOCC2)sc1-c1nnc(Sc2c(F)cc(C(=O)NO)cc2F)n1C] | 468.97 |
| 16 | 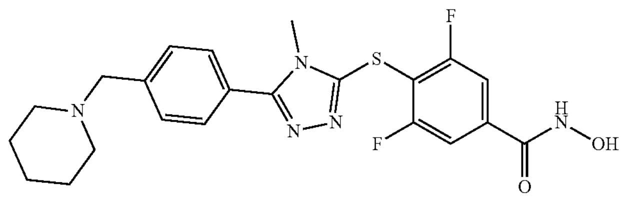 [SMILES: Cn1c(Sc2c(F)cc(C(=O)NO)cc2F)nnc1-c1ccc(CN2CCCCC2)cc1] | 460.01 |
| 17 | 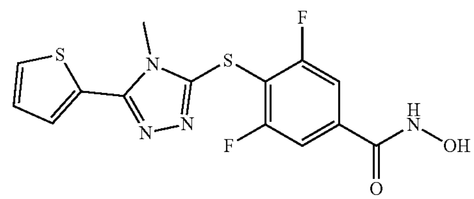 [SMILES: Cn1c(Sc2c(F)cc(C(=O)NO)cc2F)nnc1-c1cccs1] | 368.91 |
| 80 | 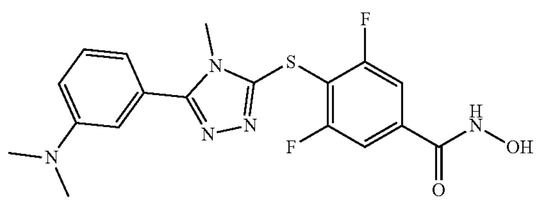 [SMILES: CN(C)c1cccc(-c2nnc(Sc3c(F)cc(C(=O)NO)cc3F)n2C)c1] | 405.92 |
| 97 | 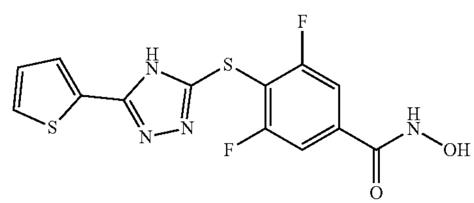 [SMILES: O=C(NO)c1cc(F)c(Sc2nnc(-c3cccs3)[nH]2)c(F)c1] | 354.92 |
| 98 | 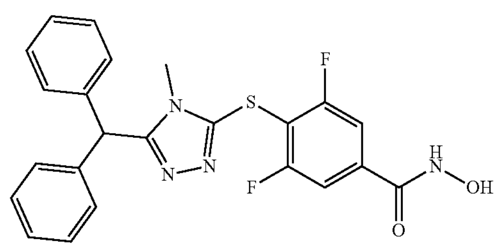 [SMILES: Cn1c(Sc2c(F)cc(C(=O)NO)cc2F)nnc1C(c1ccccc1)c1ccccc1] | 452.94 |
| 99 | 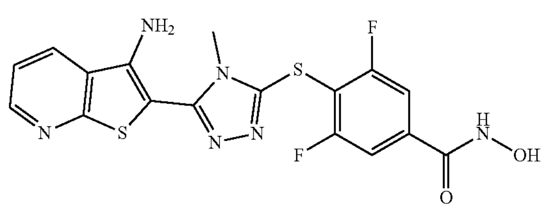 [SMILES: Cn1c(Sc2c(F)cc(C(=O)NO)cc2F)nnc1-c1sc2ncccc2c1N] | 434.89 |

-continued

| Comp. | Structure | m/z [MH+] |
|---|---|---|
| 100 | 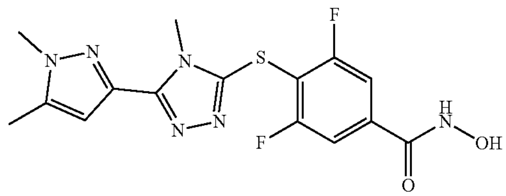 [SMILES: Cc1cc(-c2nnc(Sc3c(F)cc(C(=O)NO)cc3F)n2C)nn1C] | 380.94 |
| 104 | 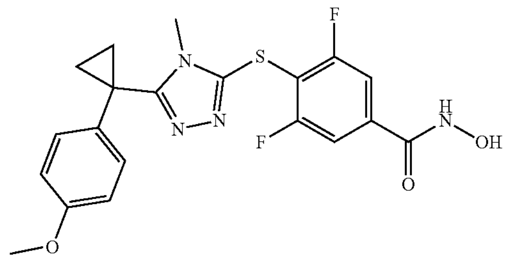 [SMILES: COc1ccc(C2(c3nnc(Sc4c(F)cc(C(=O)NO)cc4F)n3C)CC2)cc1] | 432.93 |
| 101 | 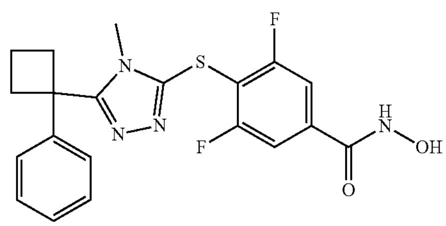 [SMILES: Cn1c(Sc2c(F)cc(C(=O)NO)cc2F)nnc1C1(c2ccccc2)CCC1] | 417.04 |
| 102 | 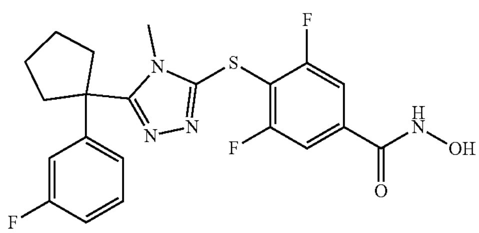 [SMILES: Cn1c(Sc2c(F)cc(C(=O)NO)cc2F)nnc1C1(c2cccc(F)c2)CCCC1] | 449.02 |
| 103 | 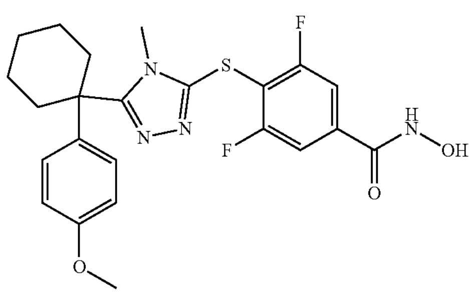 [SMILES: COc1ccc(C2(c3nnc(Sc4c(F)cc(C(=O)NO)cc4F)n3C)CCCCC2)cc1] | 475.05 |
| 114 | 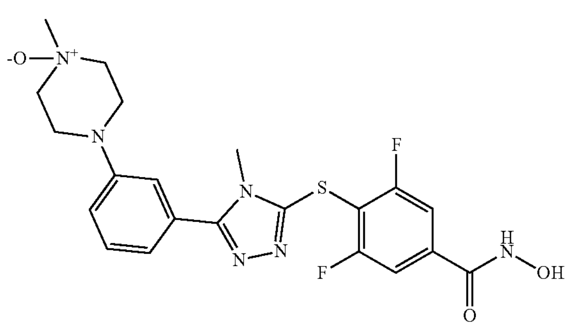 | 477.08 |

-continued

| Comp. | Structure | m/z [MH+] |
|---|---|---|
| 115 | 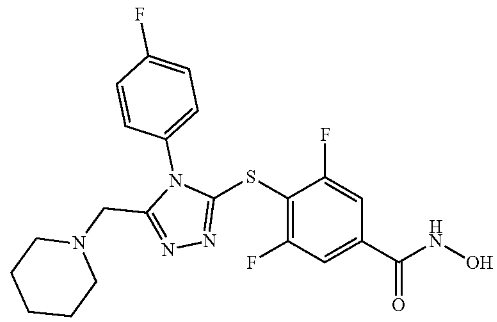 [SMILES: O=C(NO)c1cc(F)c(Sc2nnc(CN3CCCCC3)n2-c2ccc(F)cc2)c(F)c1] | 464.00 |
| 116 | 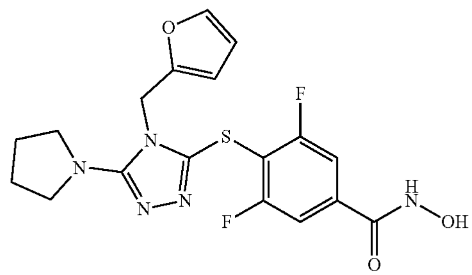 [SMILES: O=C(NO)c1cc(F)c(Sc2nnc(N3CCCC3)n2Cc2ccco2)c(F)c1] | 422.01 |
| 117 | 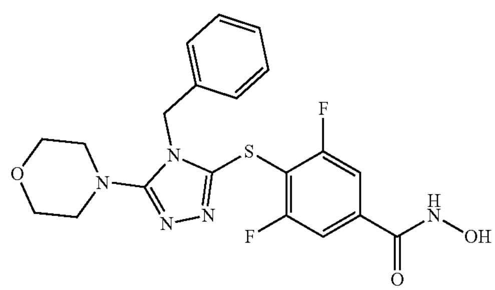 [SMILES: O=C(NO)c1cc(F)c(Sc2nnc(N3CCOCC3)n2Cc2ccccc2)c(F)c1] | 448.04 |
| 118 | 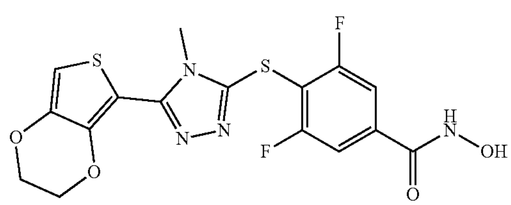 [SMILES: Cn1c(Sc2c(F)cc(C(=O)NO)cc2F)nnc1-c1scc2c1OCCO2] | 426.91 |
| 121 | 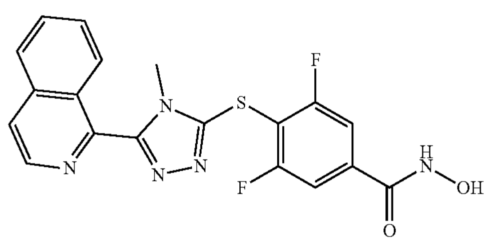 [SMILES: Cn1c(Sc2c(F)cc(C(=O)NO)cc2F)nnc1-c1nccc2ccccc12] | 413.89 |
| 122 | 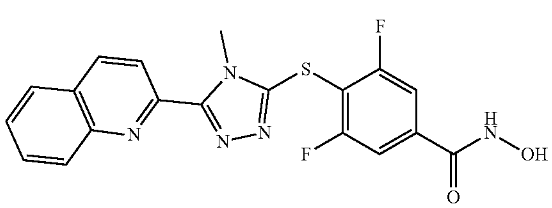 [SMILES: Cn1c(Sc2c(F)cc(C(=O)NO)cc2F)nnc1-c1ccc2ccccc2n1] | 413.96 |

| Comp. | Structure | m/z [MH+] |
|---|---|---|
| 136 | 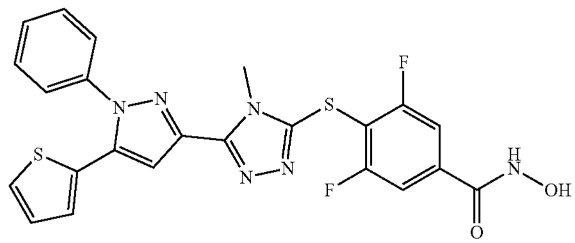 [SMILES: Cn1c(Sc2c(F)cc(C(=O)NO)cc2F)nnc1-c1cc(-c2cccs2)n(-c2ccccc2)n1] | 510.89 |
| 137 | 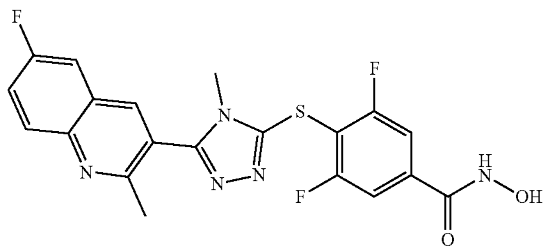 [SMILES: Cc1nc2ccc(F)cc2cc1-c1nnc(Sc2c(F)cc(C(=O)NO)cc2F)n1C] | 445.87 |
| 138 | 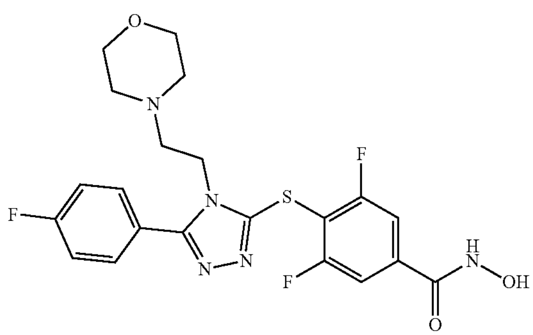 [SMILES: O=C(NO)c1cc(F)c(Sc2nnc(-c3ccc(F)cc3)n2CCN2CCOCC2)c(F)c1] | 479.88 |
| 139 | 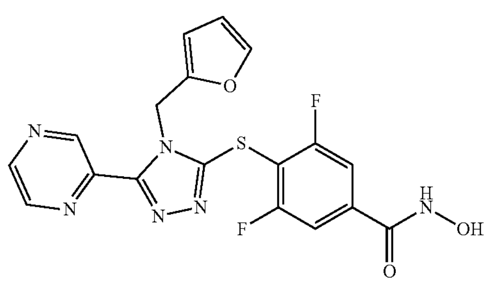 [SMILES: O=C(NO)c1cc(F)c(Sc2nnc(-c3cnccn3)n2Cc2ccco2)c(F)c1] | 430.9 |
| 140 | 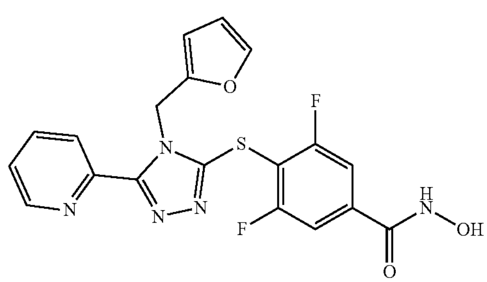 [SMILES: O=C(NO)c1cc(F)c(Sc2nnc(-c3ccccn3)n2Cc2ccco2)c(F)c1] | 429.78 |

-continued

| Comp. | Structure | m/z [MH+] |
|---|---|---|
| 141 | 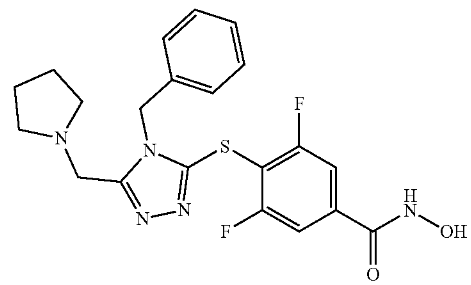 [SMILES: O=C(NO)c1cc(F)c(Sc2nnc(CN3CCCC3)n2Cc2ccccc2)c(F)c1] | 445.94 |
| 142 | 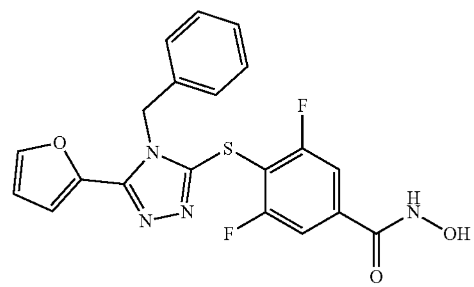 [SMILES: O=C(NO)c1cc(F)c(Sc2nnc(-c3cccs3)n2Cc2ccccc2)c(F)c1] | 428.87 |
| 143 | 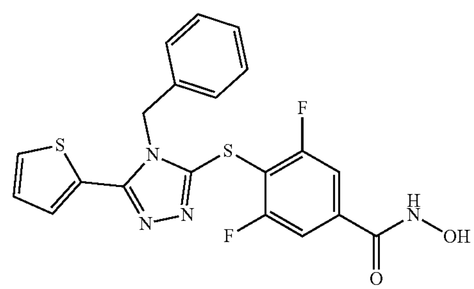 | 444.82 |
| 144 | 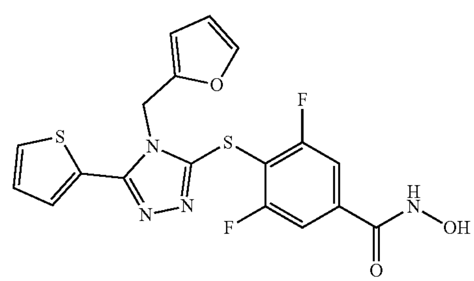 [SMILES: O=C(NO)c1cc(F)c(Sc2nnc(-c3cccs3)n2Cc2ccco2)c(F)c1] | 434.82 |
| 145 | 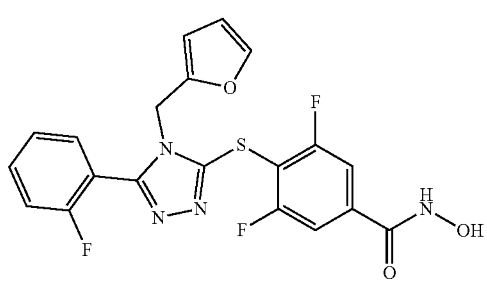 [SMILES: O=C(NO)c1cc(F)c(Sc2nnc(-c3ccccc3F)n2Cc2ccco2)c(F)c1] | 447.00 |

-continued

| Comp. | Structure | m/z [MH+] |
|---|---|---|
| 146 | 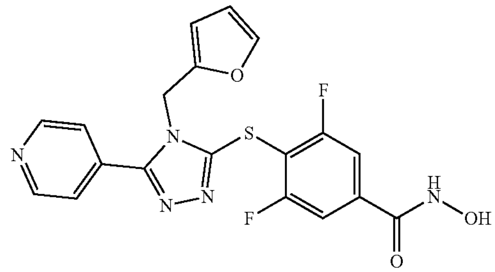 [SMILES: O=C(NO)c1cc(F)c(Sc2nnc(-c3ccncc3)n2Cc2ccco2)c(F)c1] | 430.10 |
| 147 | 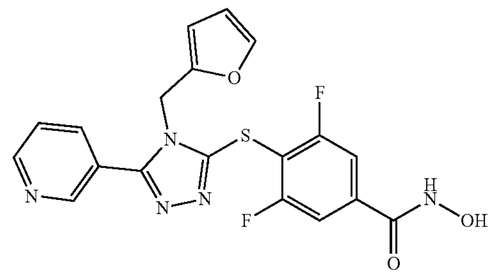 [SMILES: O=C(NO)c1cc(F)c(Sc2nnc(-c3cccnc3)n2Cc2ccco2)c(F)c1] | 430.10 |
| 148 | 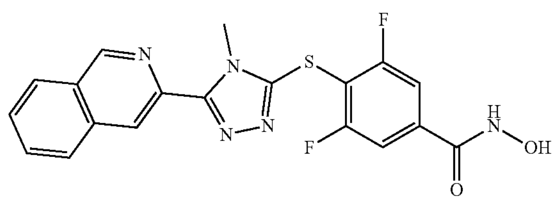 [SMILES: Cn1c(Sc2c(F)cc(C(=O)NO)cc2F)nnc1-c1cc2ccccc2cn1] | 414.00 |
| 149 | 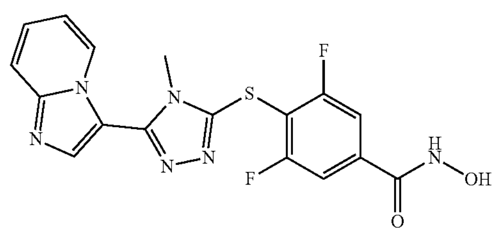 [SMILES: Cn1c(Sc2c(F)cc(C(=O)NO)cc2F)nnc1-c1cnc2ccccn12] | 403.1 |
| 150 | 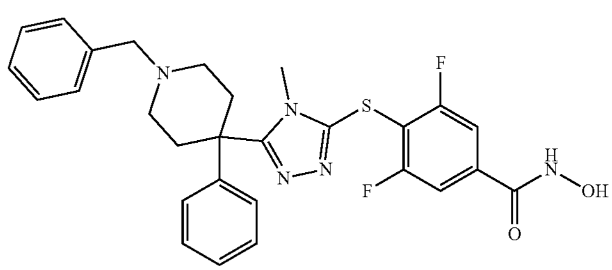 [SMILES: Cn1c(Sc2c(F)cc(C(=O)NO)cc2F)nnc1C1(c2ccccc2)CCN(Cc2ccccc2)CC1] | 536.1 |
| 151 | 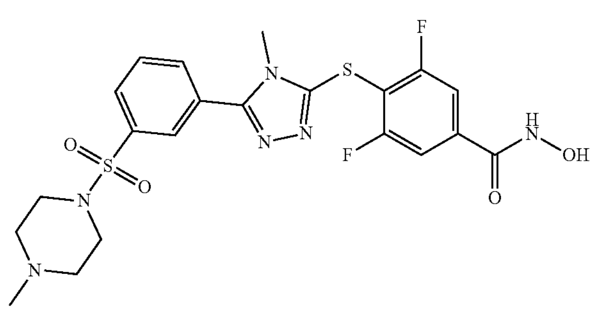 [SMILES: CN1CCN(S(=O)(=O)c2cccc(-c3nnc(Sc4c(F)cc(C(=O)NO)cc4F)n3C)c2)CC1] | 525.1 |

-continued

| Comp. | Structure | m/z [MH+] |
|---|---|---|
| 152 | 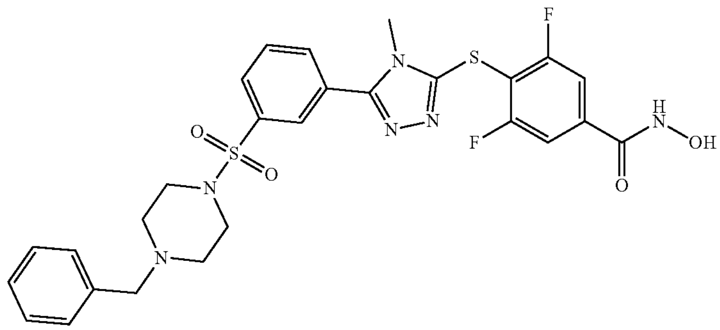 [SMILES: Cn1c(Sc2c(F)cc(C(=O)NO)cc2F)nnc1-c1cccc(S(=O)(=O)N2CCN(Cc3ccccc3)CC2)c1] | 601.2 |
| 153 | 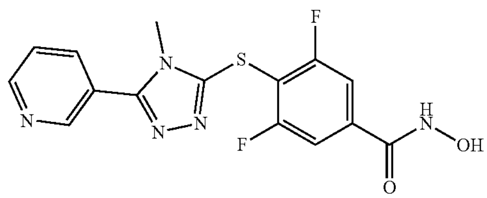 [SMILES: Cn1c(Sc2c(F)cc(C(=O)NO)cc2F)nnc1-c1cccnc1] | 364.1 |
| 164 | 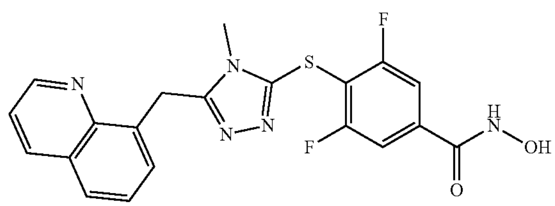 [SMILES: Cn1c(Cc2cccc3cccnc23)nnc1Sc1c(F)cc(C(=O)NO)cc1F] | 428.3 |
| 165 | 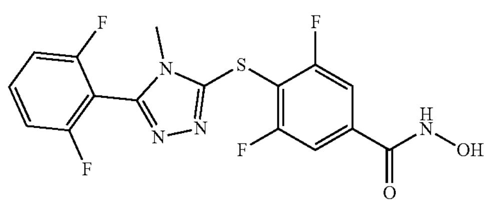 [SMILES: Cn1c(Sc2c(F)cc(C(=O)NO)cc2F)nnc1-c1c(F)cccc1F] | 399.5 |
| 166 | 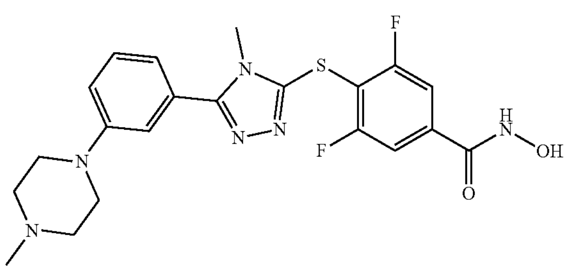 [SMILES: CN1CCN(c2cccc(-c3nnc(Sc4c(F)cc(C(=O)NO)cc4F)n3C)c2)CC1] | 461.3 |
| 167 | 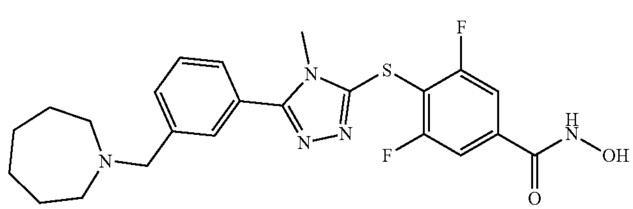 [SMILES: Cn1c(Sc2c(F)cc(C(=O)NO)cc2F)nnc1-c1cccc(CN2CCCCCC2)c1] | 474.4 |

-continued

| Comp. | Structure | m/z [MH+] |
|---|---|---|
| 168 | 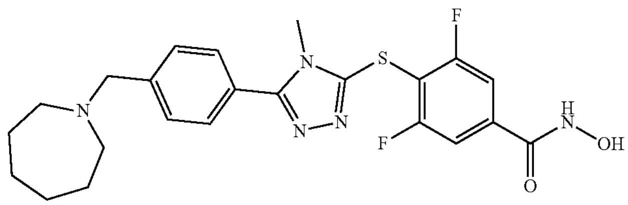 [SMILES: Cn1c(Sc2c(F)cc(C(=O)NO)cc2F)nnc1-c1ccc(CN2CCCCCC2)cc1] | 474.5 |
| 177 | 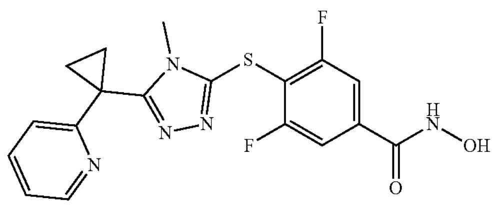 [SMILES: Cn1c(Sc2c(F)cc(C(=O)NO)cc2F)nnc1C1(c2ccccn2)CC1] | 404.8 |
| 178 | 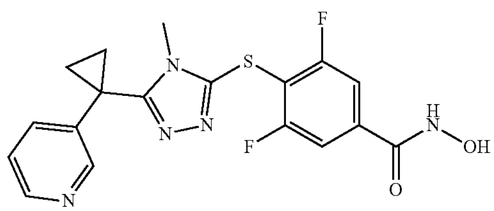 [SMILES: Cn1c(Sc2c(F)cc(C(=O)NO)cc2F)nnc1C1(c2cccnc2)CC1] | 404.8 |
| 179 | 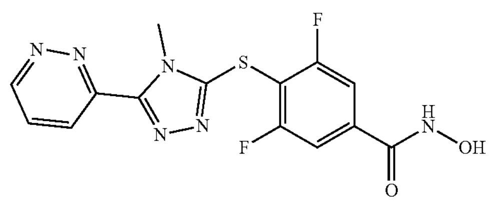 [SMILES: Cn1c(Sc2c(F)cc(C(=O)NO)cc2F)nnc1-c1cccnn1] | 365.1 |
| 180 | 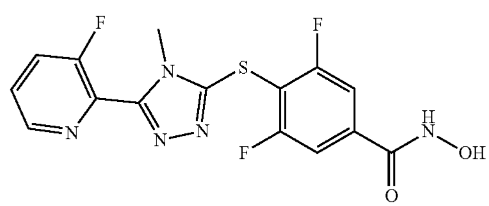 [SMILES: Cn1c(Sc2c(F)cc(C(=O)NO)cc2F)nnc1-c1ncccc1F] | 382.1 |
| 181 | 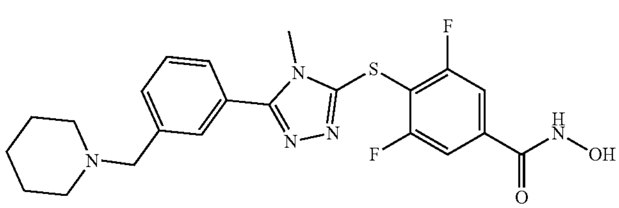 [SMILES: Cn1c(Sc2c(F)cc(C(=O)NO)cc2F)nnc1-c1cccc(CN2CCCCC2)c1] | 460.7 |
| 182 | 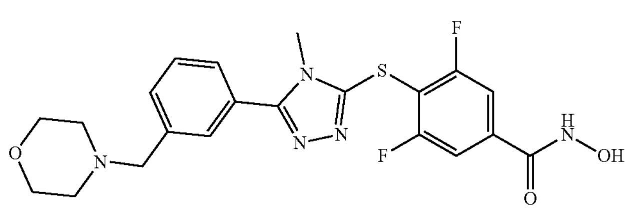 [SMILES: Cn1c(Sc2c(F)cc(C(=O)NO)cc2F)nnc1-c1cccc(CN2CCOCC2)c1] | 462.2 |

-continued
| Comp. | Structure | m/z [MH+] |
|---|---|---|
| 184 | 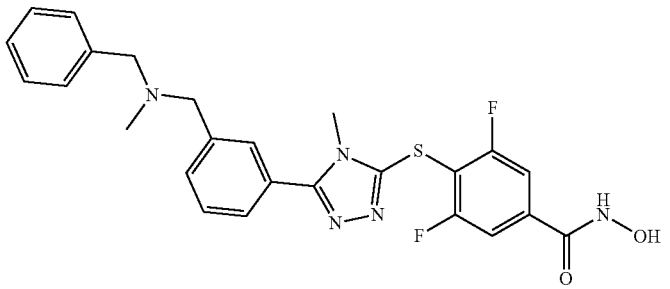 [SMILES: CN(Cc1ccccc1)Cc1cccc(-c2nnc(Sc3c(F)cc(C(=O)NO)cc3F)n2C)c1] | 496.3 |
| 186 | 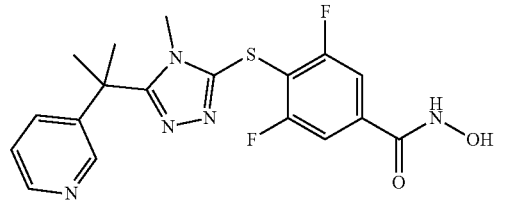 [SMILES: Cn1c(Sc2c(F)cc(C(=O)NO)cc2F)nnc1C(C)(C)c1cccnc1] | 406.5 |
| 199 | 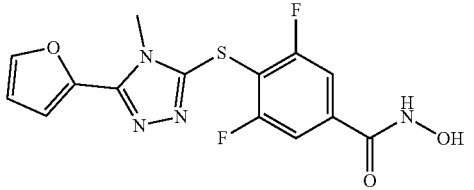 [SMILES: Cn1c(Sc2c(F)cc(C(=O)NO)cc2F)nnc1-c1ccco1] | 353.12 |
| 203 | 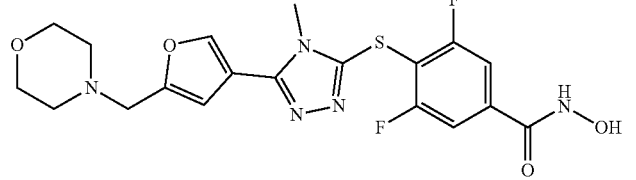 | 452.07 |
| 204 | 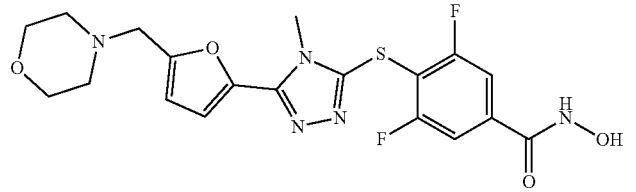 [SMILES: Cn1c(Sc2c(F)cc(C(=O)NO)cc2F)nnc1-c1ccc(CN2CCOCC2)o1] | 452.09 |
| 205 | 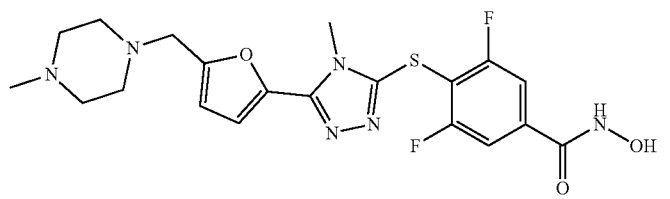 [SMILES: CN1CCN(Cc2ccc(-c3nnc(Sc4c(F)cc(C(=O)NO)cc4F)n3C)o2)CC1] | 465.08 |
| 206 | 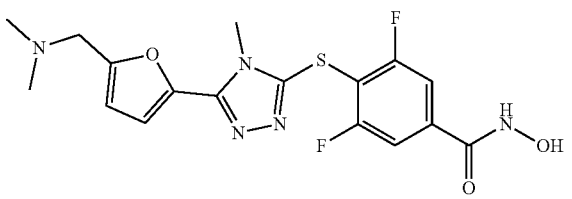 [SMILES: CN(C)Cc1ccc(-c2nnc(Sc3c(F)cc(C(=O)NO)cc3F)n2C)o1] | 410.1 |

| Comp. | Structure | m/z [MH+] |
|---|---|---|
| 207 | 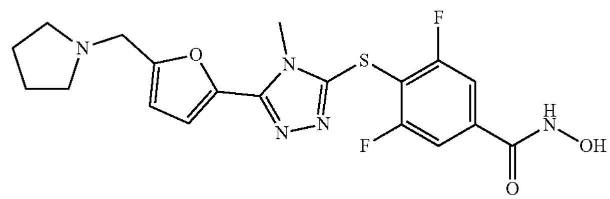 [SMILES: Cn1c(Sc2c(F)cc(C(=O)NO)cc2F)nnc1-c1ccc(CN2CCCC2)o1] | 433.8 |
| 208 | 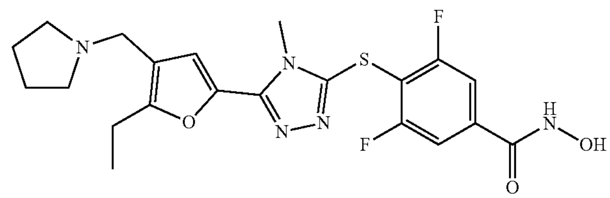 [SMILES: CCc1oc(-c2nnc(Sc3c(F)cc(C(=O)NO)cc3F)n2C)cc1CN1CCCC1] | 464.04 |
| 210 | 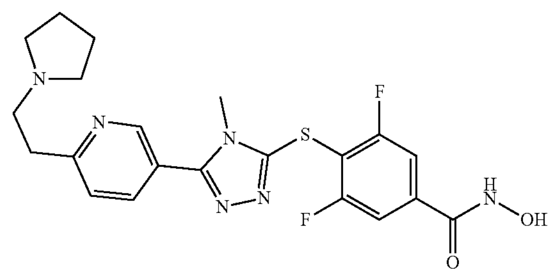 [SMILES: Cn1c(Sc2c(F)cc(C(=O)NO)cc2F)nnc1-c1ccc(CCN2CCCC2)nc1] | 461.05 |
| 211 | 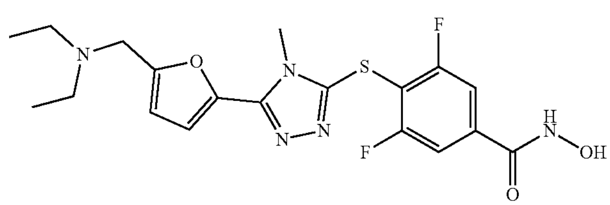 [SMILES: CCN(CC)Cc1ccc(-c2nnc(Sc3c(F)cc(C(=O)NO)cc3F)n2C)o1] | 438.0 |
| 212 | 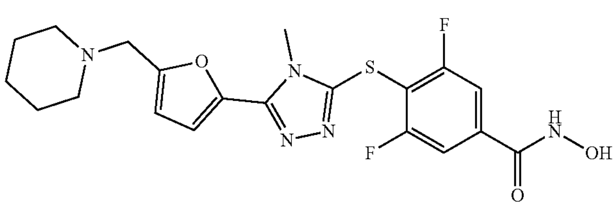 [SMILES: Cn1c(Sc2c(F)cc(C(=O)NO)cc2F)nnc1-c1ccc(CN2CCCCC2)o1] | 449.76 |
| 213 | 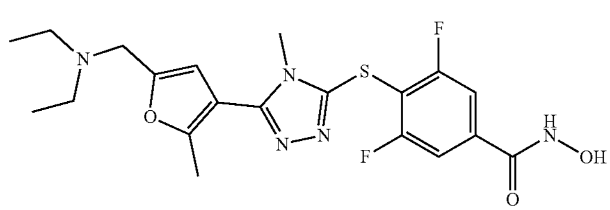 [SMILES: CCN(CC)Cc1cc(-c2nnc(Sc3c(F)cc(C(=O)NO)cc3F)n2C)c(C)o1] | 452.05 |

The following compound was synthesized using this procedure, starting from 2-mercapto-1,3,4-oxadiazole instead of 2-mercapto-1,3,4-triazole:

The crude product was purified by flash chromatography (Grace Reveleris X2, hexane:ethyl acetate). 236 mg of product was obtained.

| Comp. | Structure | m/z [MH+] |
|---|---|---|
| 192 | 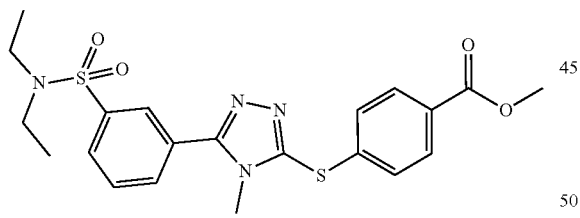 | 350.03 |

Example 7. Synthesis of 4-[[5-[3-(diethylsulfamoyl)phenyl]-4-methyl-1,2,4-triazol-3-yl]sulfanyl]benzenecarbohydroxamic acid (comp. 66)

Step A

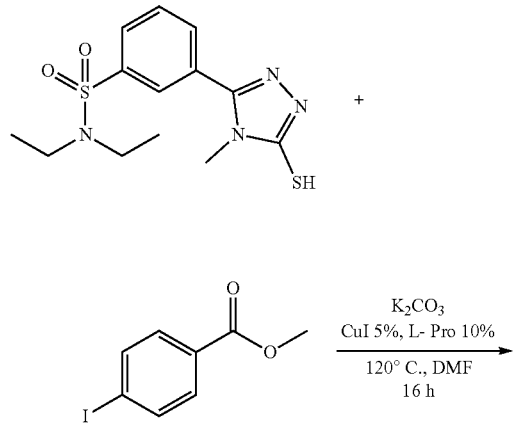

Step B

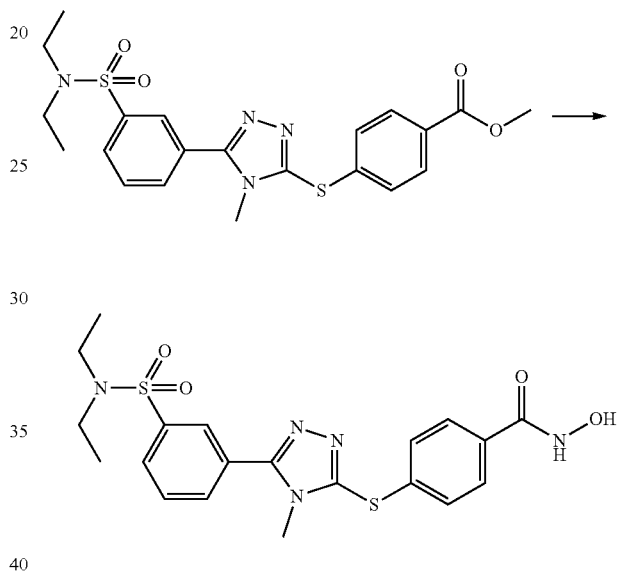

To a solution of copper iodide (10 mg, 0.05 eq), L-proline (11 mg, 0.1 eq) and potassium carbonate (152 mg, 1.1 eq) in 1 mL of DMF under argon atmosphere, methyl 4-iodobenzoate (288 mg, 1.1 eq) and N,N-diethyl-3-(5-mercapto-4-methyl-4H-1,3,4-triazol-3-yl)benzenesulfonamide (326 mg, 1 eq) were added sequentially. The reaction mixture was heated at 120° C. and stirred overnight. The consumption of heteroaromatic thiol was observed by HPLC.

The reaction mixture was diluted with 10 ml of ethyl acetate and 10 ml of water. The phases were separated and the aqueous layer was re-extracted with additional ethyl acetate (3×). The organic phases were combined and washed with brine (2×), dried over sodium sulphate, filtered and concentrated.

The ester obtained in step A (236 mg, 1 eq) was suspended in 15 ml of methanol and the reaction mixture was cooled with ice bath at 0° C. and magnetically stirred. After hydroxylamine (50%, aqueous solution, 1.2 ml, 40 eq) addition, 1M sodium hydroxide (4.1 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 4.1 ml of 1M hydrochloric acid aqueous solution and 6 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 207 mg of pure product was recovered (m/z 432.00 [MH+]).

The following compounds were synthesized using this procedure:

| Comp. | Structure | m/z [MH+] |
|---|---|---|
| 10 | 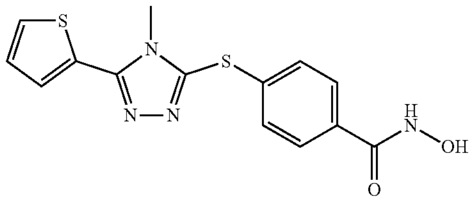 [SMILES: Cn1c(Sc2ccc(C(=O)NO)cc2)nnc1-c1cccs1] | 332.99 |
| 24 | 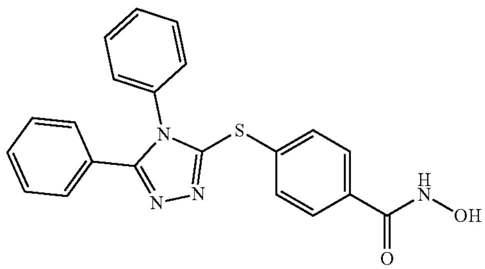 [SMILES: O=C(NO)c1ccc(Sc2nnc(-c3ccccc3)n2-c2ccccc2)cc1] | 389.05 |
| 25 | 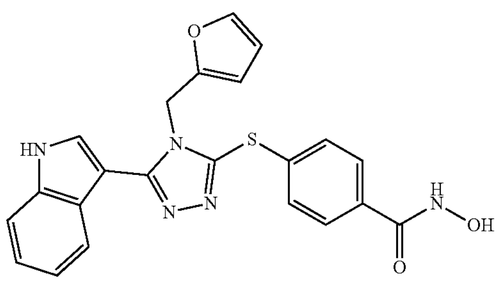 [SMILES: O=C(NO)c1ccc(Sc2nnc(-c3c[nH]c4ccccc34)n2Cc2ccco2)cc1] | 432.03 |
| 27 | 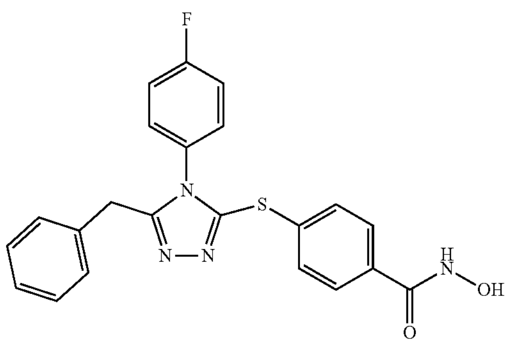 [SMILES: O=C(NO)c1ccc(Sc2nnc(Cc3ccccc3)n2-c2ccc(F)cc2)cc1] | 421.11 |
| 28 | 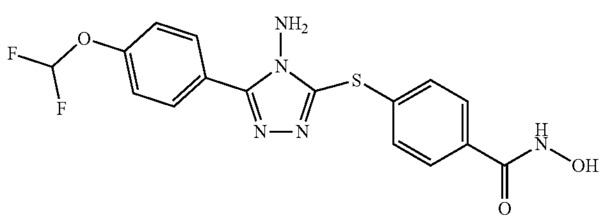 [SMILES: Nn1c(Sc2ccc(C(=O)NO)cc2)nnc1-c1ccc(OC(F)F)cc1] | 393.11 |
| 29 | 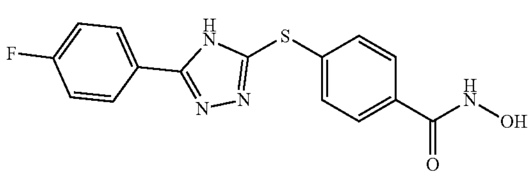 [SMILES: O=C(NO)c1ccc(Sc2nnc(-c3ccc(F)cc3)[nH]2)cc1] | 331.03 |

| Comp. | Structure | m/z [MH+] |
|---|---|---|
| 30 | 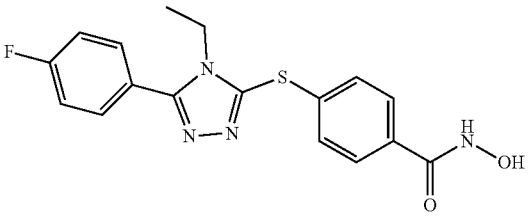 [SMILES: CCn1c(Sc2ccc(C(=O)NO)cc2)nnc1-c1ccc(F)cc1] | 359.09 |
| 61 | 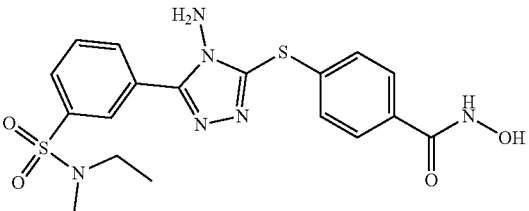 | 463.12 |
| 67 | 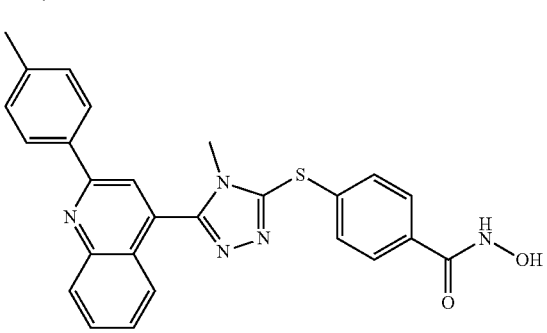 | 468.02 |
| 72 | 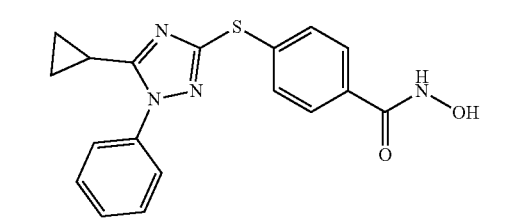 [SMILES: O=C(NO)c1ccc(Sc2nc(C3CC3)n(-c3ccccc3)n2)cc1] | 353.07 |
| 73 | 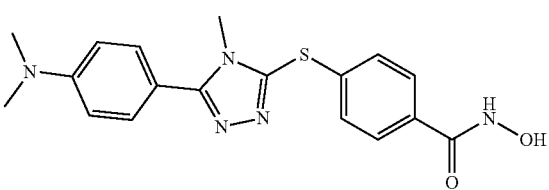 [SMILES: CN(C)c1ccc(-c2nnc(Sc3ccc(C(=O)NO)cc3)n2C)cc1] | 369.96 |
| 77 | 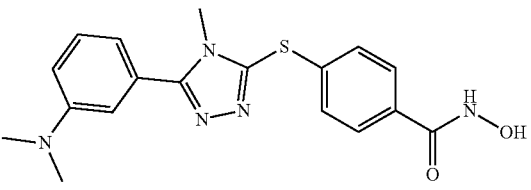 [SMILES: CN(C)c1cccc(-c2nnc(Sc3ccc(C(=O)NO)cc3)n2C)c1] | 370.03 |
| 78 | 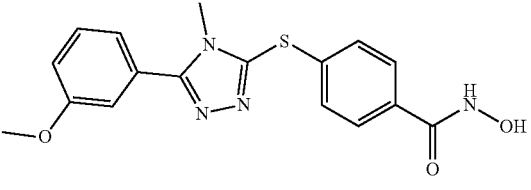 [SMILES: COc1cccc(-c2nnc(Sc3ccc(C(=O)NO)cc3)n2C)c1] | 356.94 |

-continued

| Comp. | Structure | m/z [MH+] |
|---|---|---|
| 82 | 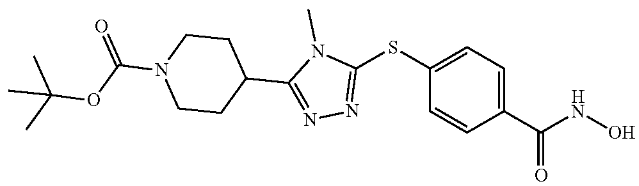 [SMILES: Cn1c(Sc2ccc(C(=O)NO)cc2)nnc1C1CCN(C(=O)OC(C)(C)C)CC1] | 434.05 |
| 83 | 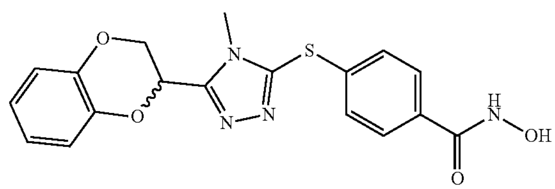 [SMILES: Cn1c(Sc2ccc(C(=O)NO)cc2)nnc1C1COc2ccccc2O1] | 384.93 |
| 84 | 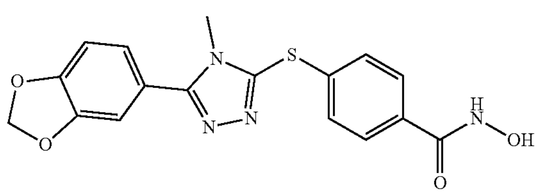 [SMILES: Cn1c(Sc2ccc(C(=O)NO)cc2)nnc1-c1ccc2c(c1)OCO2] | 370.94 |
| 85 | 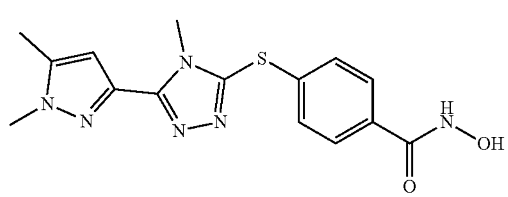 [SMILES: Cc1cc(-c2nnc(Sc3ccc(C(=O)NO)cc3)n2C)nn1C] | 344.98 |
| 209 | 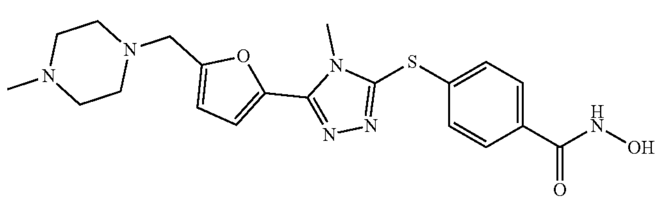 [SMILES: CN1CCN(Cc2ccc(-c3nnc(Sc4ccc(C(=O)NO)cc4)n3C)o2)CC1] | 429.07 |

The following compound was synthesized using this procedure, starting from 2-mercapto-1,3,4-oxadiazole instead of 2-mercapto-1,3,4-triazole:

| Comp. | Structure | m/z [MH+] |
|---|---|---|
| 188 | 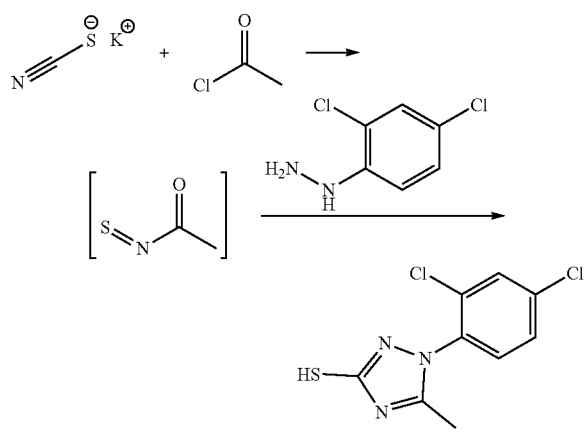 | 314.3 |

Example 8. Synthesis of 4-[[1-(2,4-dichlorophenyl)-5-methyl-1,2,4-triazol-3-yl]sulfanyl]benzenecarbohydroxamic acid (comp. 62)

Step A

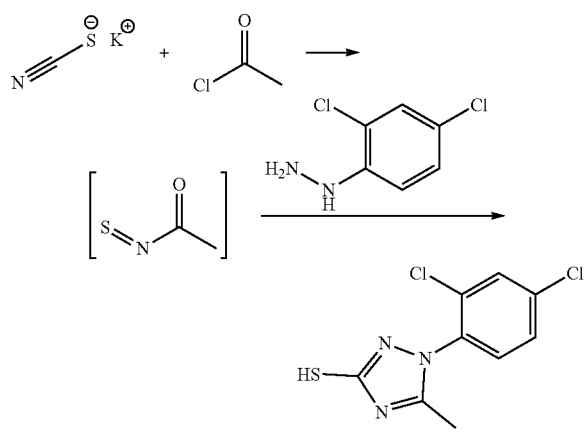

To a solution of potassium thiocyanate (194 mg, 1 eq) in dry acetonitrile (6 ml) acetyl chloride (143 µL, 1 eq) was added slowly. The mixture was refluxed one hour, then the formed potassium chloride was removed by filtration. (2,4-dichlorophenyl)hydrazine (427 mg, 1 eq) was added to the solution and the reaction mixture was heated under reflux. After 1.5 h, LC-MS analysis showed complete hydrazine consumption. The reaction mixture was abundantly diluted with cold water (50 mL) and the precipitated solid was recovered by filtration. The product was purified by crystallization from n-Hex/EtOAc 75:25. 60 mg of product was recovered.

Step B

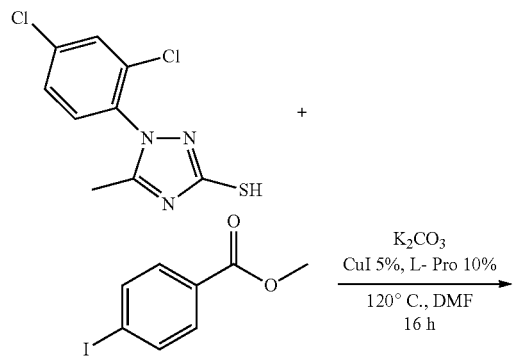

-continued

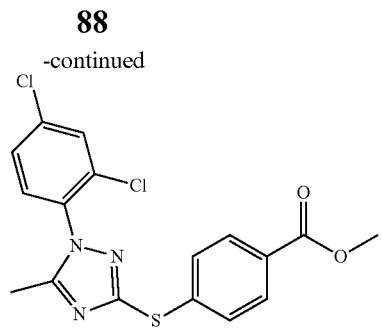

To a solution of copper iodide (2 mg, 0.05 eq), L-proline (3 mg, 0.1 eq) and potassium carbonate (35 mg, 1.1 eq) in 2 ml of DMF under argon atmosphere, methyl 4-iodobenzoate (66.5 mg, 1.1 eq) and 1-(2,4-dichlorophenyl)-5-methyl-1H-1,2,4-triazole-3-thiol (60 mg, eq) were added. The reaction mixture was heated at 120° C. and stirred overnight. The consumption of heteroaromatic thiol was observed by HPLC.

The reaction mixture was diluted with 6 ml of ethyl acetate and 6 ml of water. The phases were separated and the aqueous layer was re-extracted with additional ethyl acetate (3×). The organic phases were combined and washed with brine (2×), dried over sodium sulphate, filtered and concentrated. The obtained residue was used in the following step without any further purification.

Step C

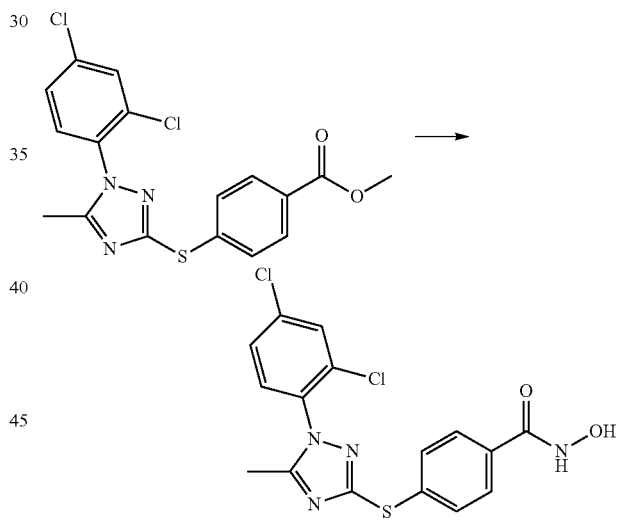

The ester obtained in step B (40 mg, 1 eq) was suspended in 6 ml of methanol and the reaction mixture was cooled with ice bath at 0° C. and magnetically stirred. After hydroxylamine (50%, aqueous solution, 236 µl, 40 eq) addition, 1M sodium hydroxide (1 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 1 ml of 1M hydrochloric acid aqueous solution and 1 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 30 mg of pure product was recovered (m/z 396.89 [MH+]).

Example 9. Synthesis of 4-[[5-[(3,4-dimethoxyphenyl)methyl]-2-[4-(trifluoromethyl)phenyl]-1,2,4-triazol-3-yl]methyl]benzenecarbohydroxamic acid (comp. 44)

Step A

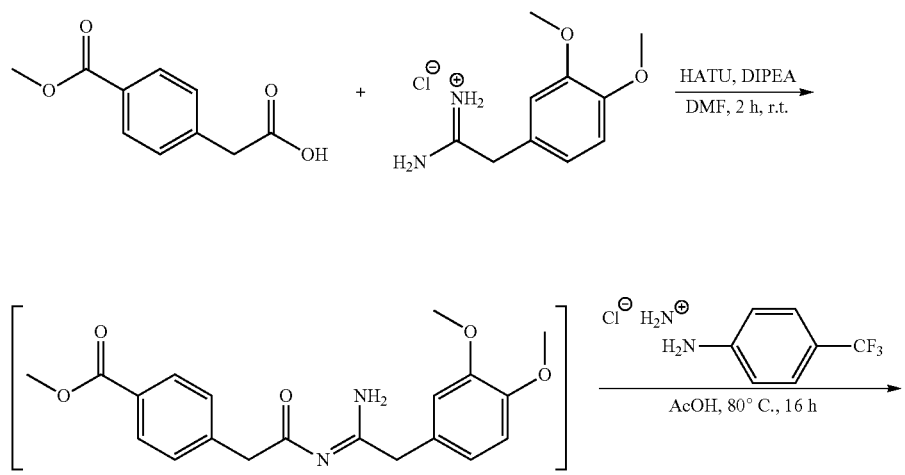

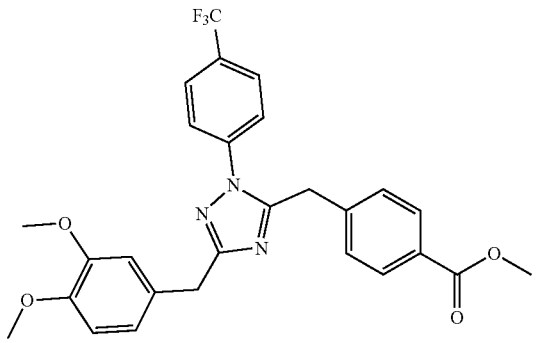

A vial with screw cap was charged with 2-(4-(methoxycarbonyl)phenyl)acetic acid (97 mg, 0.5 mmol), 1-amino-2-(3,4-dimethoxyphenyl)ethan-1-imino hydrochloride 200 mg, 1.73 eq) and HATU (209 mg, 1.1 eq). 2 ml of DMF and DIPEA (248 μL, 3 eq) were added sequentially under argon atmosphere. The reaction mixture was stirred at room temperature and checked by HPLC for carboxylic acid consumption and acylamidine intermediate formation. The complete conversion into intermediate was observed within 2-3 hours.

(4-(trifluoromethyl)phenyl)hydrazine hydrochloride (187 mg, 1.76 eq) and acetic acid (286 μL, 10 eq) were then added to the reaction mixture. The vial was sealed and the mixture was heated to 80° C. and stirred overnight.

Consumption of acylamidine intermediate was observed by HPLC.

The mixture was allowed to reach room temperature before diluting it with ethyl acetate and sequentially washing with saturated sodium bicarbonate aqueous solution and brine. The organic layer was dried over sodium sulphate, filtered and concentrated to dryness.

The product was purified by flash chromatography (hexane:ethyl acetate) (Castanedo et al., J. Org. Chem. (2011), 76(4), 1177-1179).

Step B

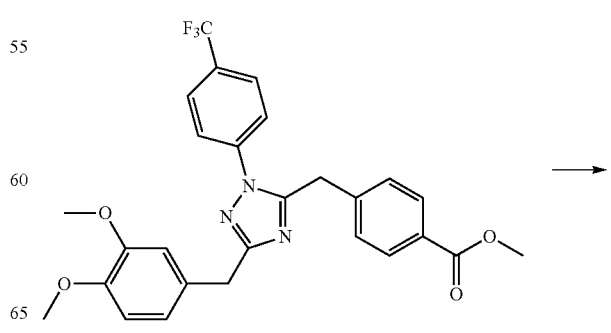

The ester obtained in step A (82 mg, 1 eq) was suspended in 5 ml of methanol and the resulting reaction mixture was cooled with ice bath at 0° C. and magnetically stirred. After hydroxylamine (50%, aqueous solution, 189 µl, 20 eq) addition, 1M sodium hydroxide (1.6 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 1.6 ml of 1M hydrochloric acid aqueous solution and 3 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 27 mg of pure product was recovered (m/z 513.18 [MH+]).

The following compounds were synthesized using this procedure:

| Comp. | Structure | m/z [MH+] |
|---|---|---|
| 51 | 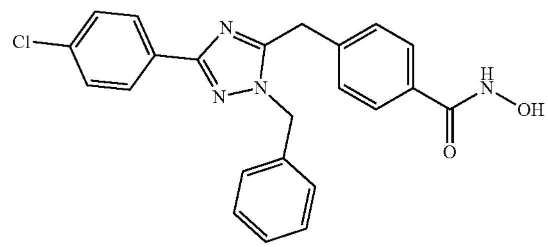 [SMILES: O=C(NO)c1ccc(Cc2nc(-c3ccc(Cl)cc3)nn2Cc2ccccc2)cc1] | 419.01 |
| 52 | 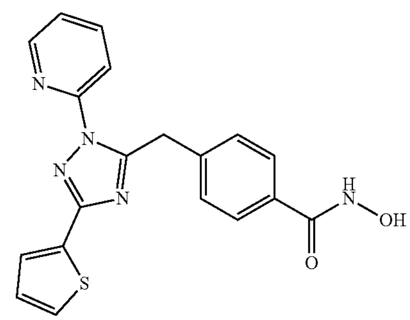 [SMILES: O=C(NO)c1ccc(Cc2nc(-c3cccs3)nn2-c2ccccn2)cc1] | 377.99 |
| 53 | 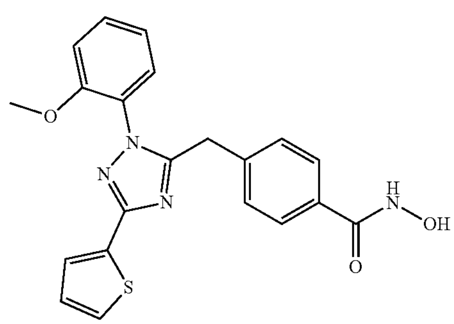 [SMILES: COc1ccccc1-n1nc(-c2cccs2)nc1Cc1ccc(C(=O)NO)cc1] | 407.04 |
| 216 | 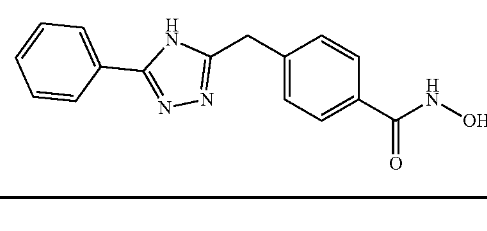 | 293.1 |

Example 10. Synthesis of 4-((5-(furan-2-yl)-2H-tetrazol-2-yl)methyl)-N-hydroxybenzamide (comp. 12)

Step A

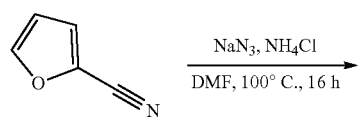

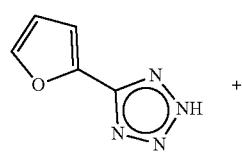

Furan-2-carbonitrile (500 mg, 1 eq) was dissolved in 10 ml of DMF. Sodium azide (770 mg, 2.2 eq) and ammonium chloride (631 mg, 2.2 eq) were added to the reaction mixture at room temperature under magnetic stirring. The suspension was heated at 120° C. and stirred overnight. The complete conversion of the starting material was observed by LC-MS.

The mixture was cooled to 0° C. with ice bath, diluted with 10 ml of water and acidified with 1M hydrochloric acid aqueous solution. The formed precipitate was collected by filtration and washed twice with water before drying under vacuum. 720 mg of product was obtained (International Patent Application WO2006/003096).

Step B

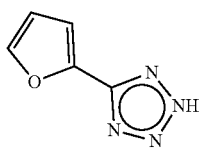

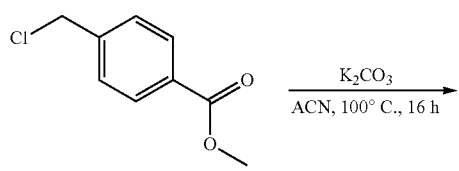

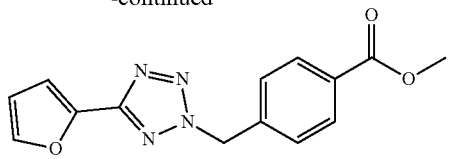

+

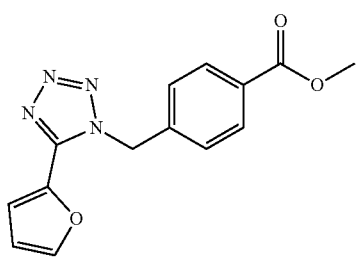

The reaction vessel was charged with potassium carbonate (742 mg, 1 eq) and 5 ml of acetonitrile. The tetrazole obtained in step A (364 mg, 1 eq) was added as a solid under magnetic stirring at room temperature, while methyl 4-choromethylbenzoate (1.1 eq) was added as a solution in 5 ml of acetonitrile. The mixture was heated at 100° C. and stirred overnight. The complete conversion of starting material into the two regioisomeric products was checked by LC-MS. Insoluble material was removed by filtration and the filtrate was evaporated under reduced pressure. The two regioisomers were isolated by column chromatography on silica gel (toluene:ethyl acetate). 384 mg of 2,5-disubstituted isomer and 234 mg of 1,5-disubstituted isomer were recovered (International Patent Application WO2012/106995).

Step C

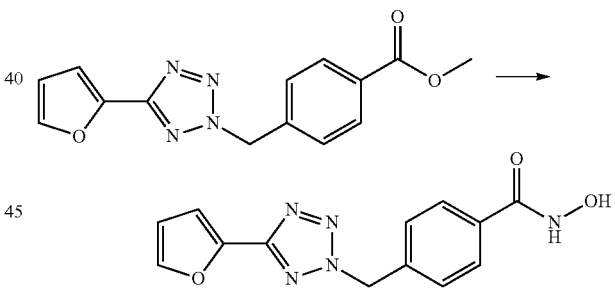

The ester obtained in step B (100 mg, 1 eq) was suspended in 10 ml of methanol and the resulting reaction mixture was cooled with ice bath at 0° C. and magnetically stirred. After hydroxylamine (50%, aqueous solution, 700 µl, 30 eq) addition, 1M sodium hydroxide (3.52 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 3.52 ml of 1M hydrochloric acid aqueous solution and 6 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 93.5 mg of clean product was recovered (m/z 286.02 [MH+]).

The following compounds were synthesized using this procedure:

| Comp. | Structure | m/z [MH+] |
|---|---|---|
| 8 | 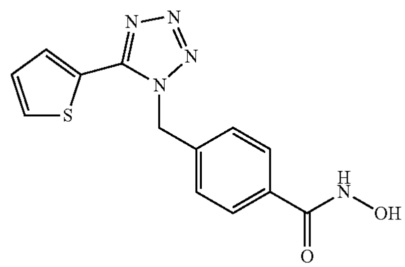 [SMILES: O=C(NO)c1ccc(Cn2nnnc2-c2cccs2)cc1] | 301.92 |
| 20 | 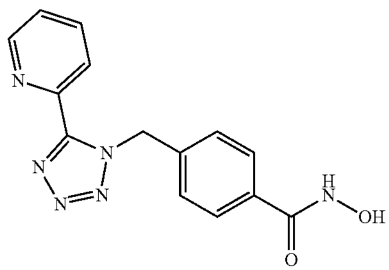 [SMILES: O=C(NO)c1ccc(Cn2nnnc2-c2ccccn2)cc1] | 297.01 |
| 23 | 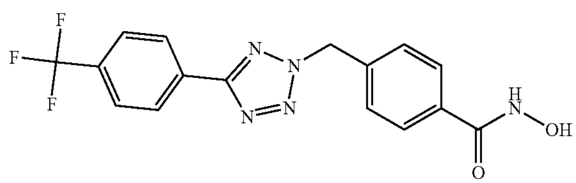 [SMILES: O=C(NO)c1ccc(Cn2nnc(-c3ccc(C(F)(F)F)cc3)n2)cc1] | 364.06 |
| 31 | 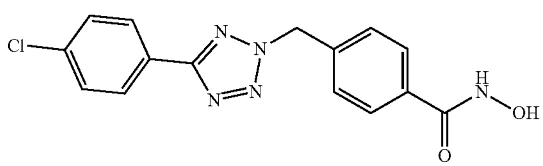 [SMILES: O=C(NO)c1ccc(Cn2nnc(-c3ccc(Cl)cc3)n2)cc1] | 330.12 |
| 32 | 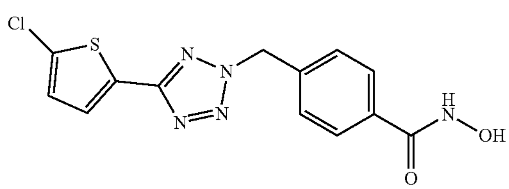 [SMILES: O=C(NO)c1ccc(Cn2nnc(-c3ccc(Cl)s3)n2)cc1] | 336.07 |
| 33 | 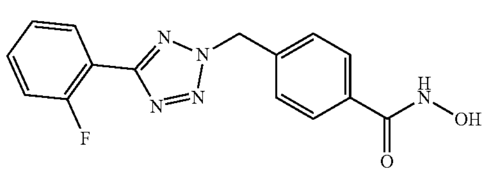 [SMILES: O=C(NO)c1ccc(Cn2nnc(-c3ccccc3F)n2)cc1] | 314.1 |
| 34 | 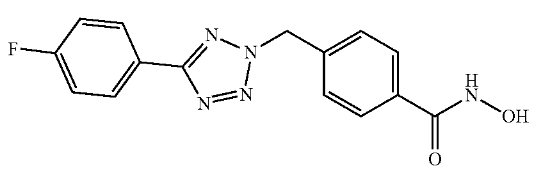 [SMILES: O=C(NO)c1ccc(Cn2nnc(-c3ccc(F)cc3)n2)cc1] | 314.1 |

-continued
| Comp. | Structure | m/z [MH+] |
|---|---|---|
| 35 | 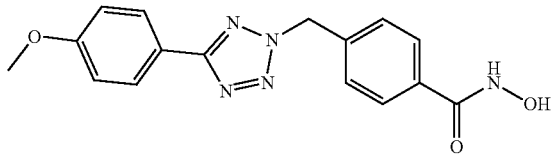 [SMILES: COc1ccc(-c2nnn(Cc3ccc(C(=O)NO)cc3)n2)cc1] | 326.13 |
| 36 | 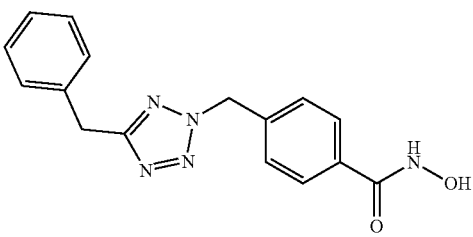 [SMILES: O=C(NO)c1ccc(Cn2nnc(Cc3ccccc3)n2)cc1] | 310.18 |
| 37 | 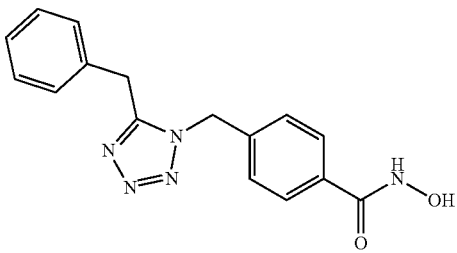 [SMILES: O=C(NO)c1ccc(Cn2nnnc2Cc2ccccc2)cc1] | 310.18 |
| 38 | 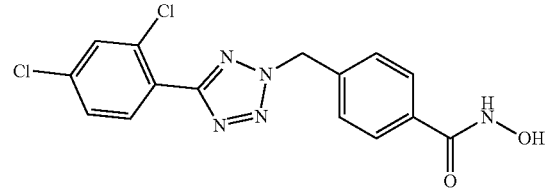 [SMILES: O=C(NO)c1ccc(Cn2nnc(-c3ccc(Cl)cc3Cl)n2)cc1] | 365.95 |
| 39 | 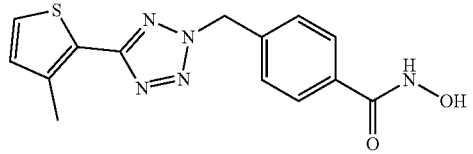 [SMILES: Cc1ccsc1-c1nnn(Cc2ccc(C(=O)NO)cc2)n1] | 316.12 |
| 41 | 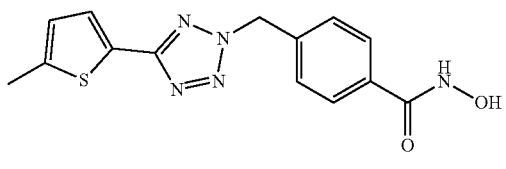 [SMILES: Cc1ccc(-c2nnn(Cc3ccc(C(=O)NO)cc3)n2)s1] | 316.05 |
| 42 | 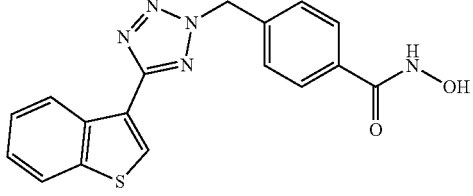 [SMILES: O=C(NO)c1ccc(Cn2nnc(-c3csc4ccccc34)n2)cc1] | 352.09 |

-continued

| Comp. | Structure | m/z [MH+] |
|---|---|---|
| 43 | 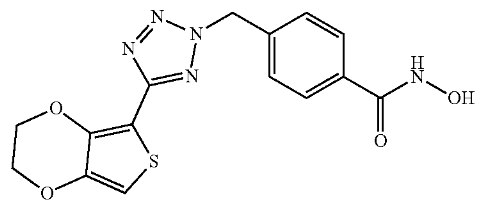 [SMILES: O=C(NO)c1ccc(Cn2nnc(-c3scc4c3OCCO4)n2)cc1] | 360.00 |
| 46 | 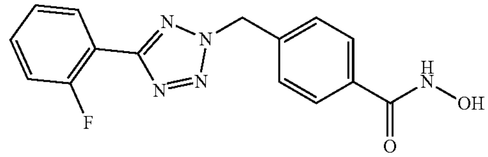 [SMILES: O=C(NO)c1ccc(Cn2nnc(-c3ccccc3F)n2)cc1] | 314.03 |
| 50 | 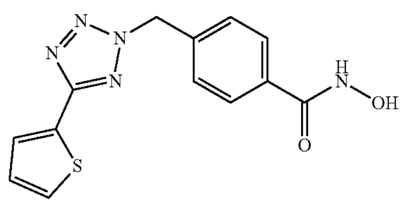 [SMILES: O=C(NO)c1ccc(Cn2nnc(-c3cccs3)n2)cc1] | 301.99 |
| 54 | 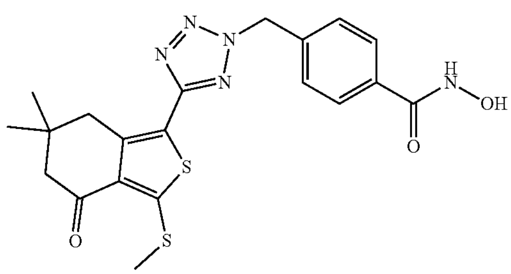 [SMILES: CSc1sc(-c2nnn(Cc3ccc(C(=O)NO)cc3)n2)c2c1C(=O)CC(C)(C)C2] | 444.00 |
| 55 | 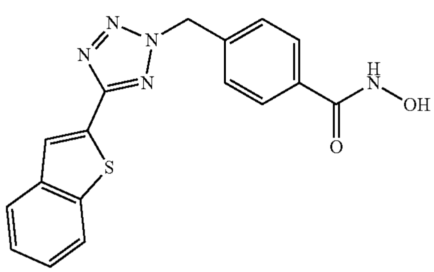 [SMILES: O=C(NO)c1ccc(Cn2nnc(-c3cc4ccccc4s3)n2)cc1] | 352.03 |
| 59 | 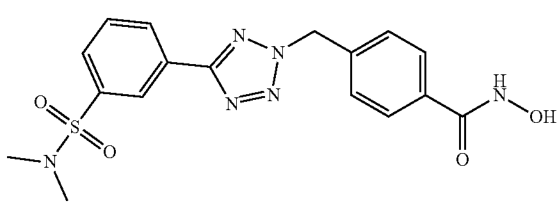 [SMILES: CN(C)S(=O)(=O)c1cccc(-c2nnn(Cc3ccc(C(=O)NO)cc3)n2)c1] | 403.12 |
| 70 | 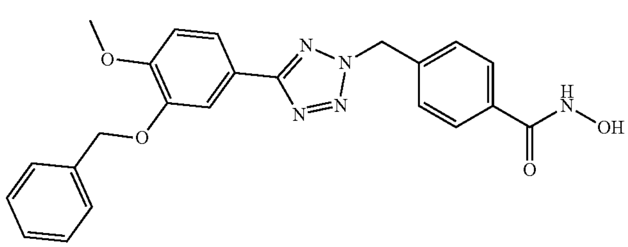 [SMILES: COc1ccc(-c2nnn(Cc3ccc(C(=O)NO)cc3)n2)cc1OCc1ccccc1] | 431.92 |

-continued

| Comp. | Structure | m/z [MH+] |
|---|---|---|
| 71 | 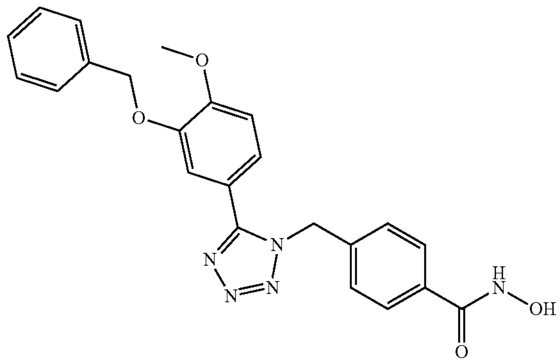 [SMILES: COc1ccc(-c2nnnn2Cc2ccc(C(=O)NO)cc2)cc1OCc1ccccc1] | 431.95 |
| 86 | 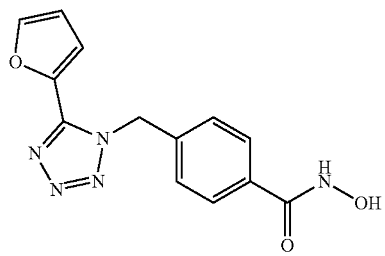 [SMILES: O=C(NO)c1ccc(Cn2nnnc2-c2ccco2)cc1] | 286.02 |
| 87 | 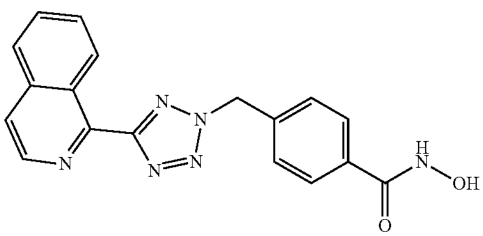 [SMILES: O=C(NO)c1ccc(Cn2nnc(-c3nccc4ccccc34)n2)cc1] | 347.01 |
| 88 | 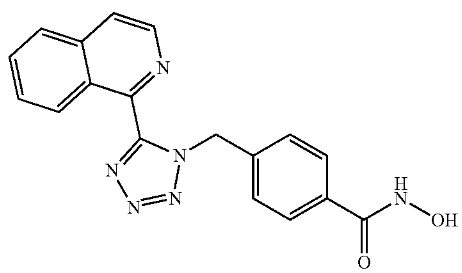 [SMILES: O=C(NO)c1ccc(Cn2nnnc2-c2nccc3ccccc23)cc1] | 347.02 |
| 89 | 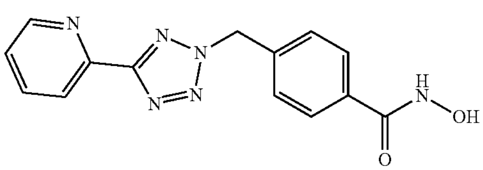 [SMILES: O=C(NO)c1ccc(Cn2nnc(-c3ccccn3)n2)cc1] | 297.03 |
| 90 | 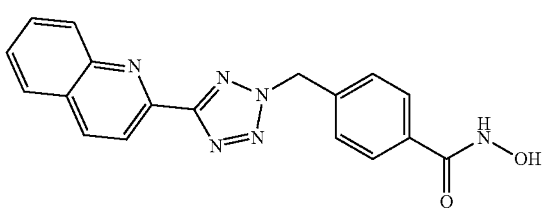 [SMILES: O=C(NO)c1ccc(Cn2nnc(-c3ccc4ccccc4n3)n2)cc1] | 347.02 |

| Comp. | Structure | m/z [MH+] |
|---|---|---|
| 91 | 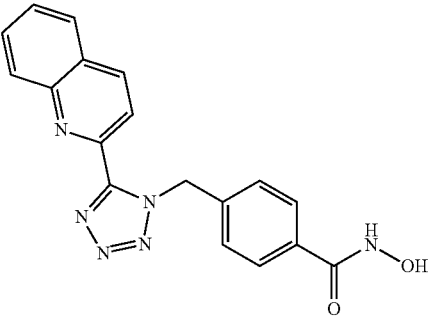 [SMILES: O=C(NO)c1ccc(Cn2nnnc2-c2ccc3ccccc3n2)cc1] | 347.01 |
| 106 | 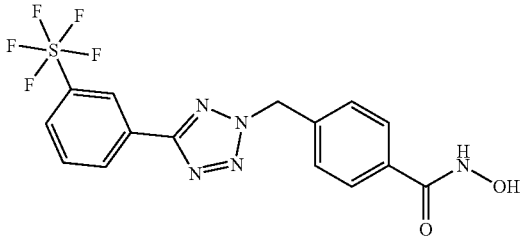 [SMILES: O=C(NO)c1ccc(Cn2nnc(-c3cccc(S(F)(F)(F)(F)F)c3)n2)cc1] | 421.94 |
| 107 | 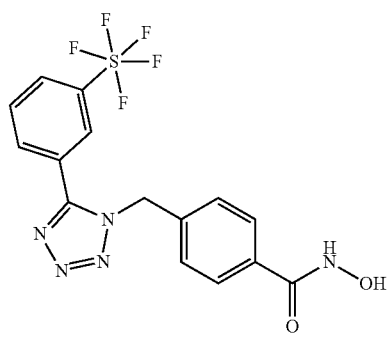 [SMILES: O=C(NO)c1ccc(Cn2nnnc2-c2cccc(S(F)(F)(F)(F)F)c2)cc1] | 421.94 |
| 110 | 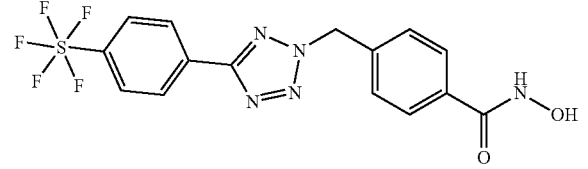 [SMILES: O=C(NO)c1ccc(Cn2nnc(-c3ccc(S(F)(F)(F)(F)F)cc3)n2)cc1] | 421.94 |
| 111 | 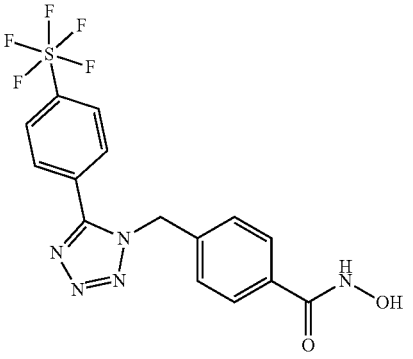 [SMILES: O=C(NO)c1ccc(Cn2nnnc2-c2ccc(S(F)(F)(F)(F)F)cc2)cc1] | 421.94 |

-continued
| Comp. | Structure | m/z [MH+] |
|---|---|---|
| 123 | 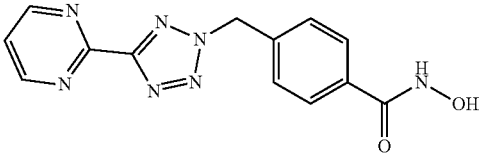 [SMILES: O=C(NO)c1ccc(Cn2nnc(-c3ncccn3)n2)cc1] | 297.98 |
| 124 | 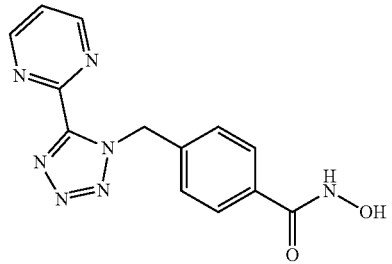 [SMILES: O=C(NO)c1ccc(Cn2nnnc2-c2ncccn2)cc1] | 297.99 |
| 126 | 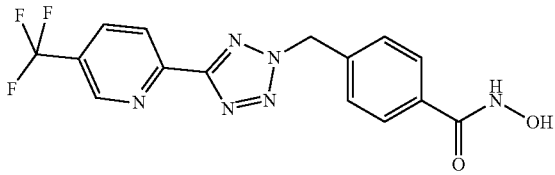 [SMILES: O=C(NO)c1ccc(Cn2nnc(-c3ccc(C(F)(F)F)cn3)n2)cc1] | 364.99 |
| 127 | 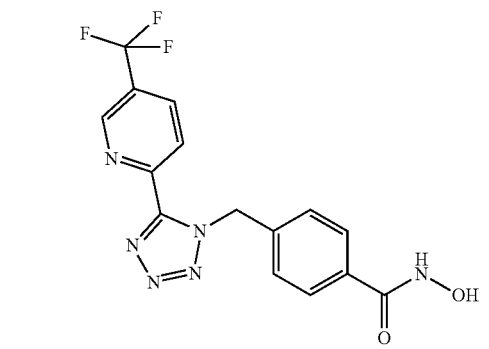 [SMILES: O=C(NO)c1ccc(Cn2nnnc2-c2ccc(C(F)(F)F)cn2)cc1] | 364.99 |
| 130 | 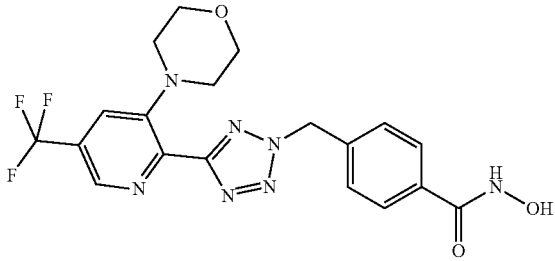 [SMILES: O=C(NO)c1ccc(Cn2nnc(-c3ncc(C(F)(F)F)cc3N3CCOCC3)n2)cc1] | 449.99 |
| 131 | 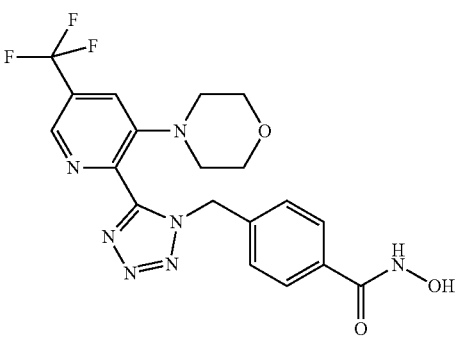 [SMILES: O=C(NO)c1ccc(Cn2nnnc2-c2ncc(C(F)(F)F)cc2N2CCOCC2)cc1] | 450.00 |

| Comp. | Structure | m/z [MH+] |
|---|---|---|
| 132 | 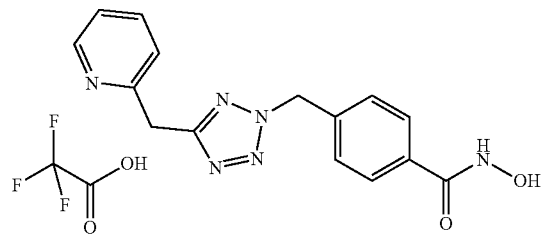 | 311.03 |
| 133 | 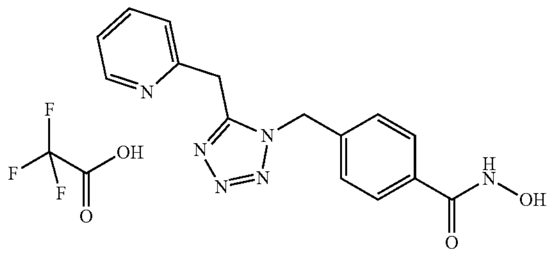 [SMILES: O=C(O)C(F)(F)F ; O=C(NO)c1ccc(Cn2nnnc2Cc2ccccn2)cc1] | 311.03 |
| 156 | 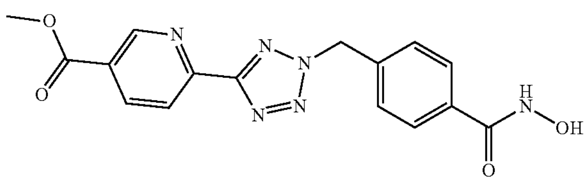 [SMILES: COC(=O)c1ccc(-c2nnn(Cc3ccc(C(=O)NO)cc3)n2)nc1] | 355.3 |
| 157 | 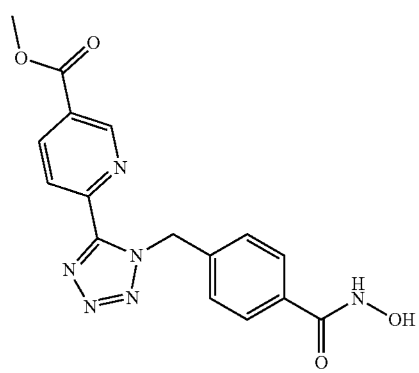 [SMILES: COC(=O)c1ccc(-c2nnnn2Cc2ccc(C(=O)NO)cc2)nc1] | 355.5 |
| 158 | 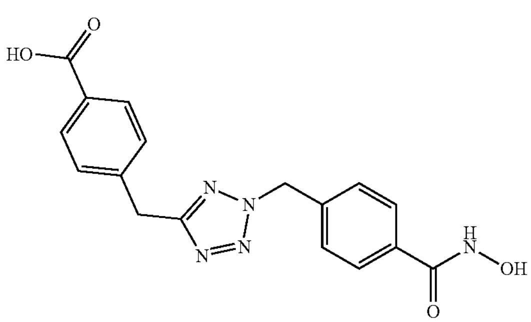 [SMILES: O=C(O)c1ccc(Cc2nnn(Cc3ccc(C(=O)NO)cc3)n2)cc1] | 354.2 |

-continued

| Comp. | Structure | m/z [MH+] |
|---|---|---|
| 159 | 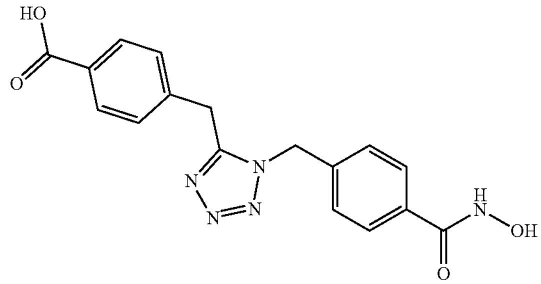 [SMILES: O=C(O)c1ccc(Cc2nnnn2Cc2ccc(C(=O)NO)cc2)cc1] | 354.4 |
| 162 | 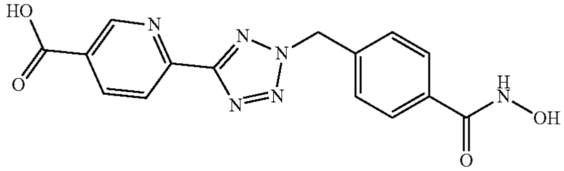 [SMILES: O=C(O)c1ccc(-c2nnn(Cc3ccc(C(=O)NO)cc3)n2)nc1] | 341.4 |
| 163 | 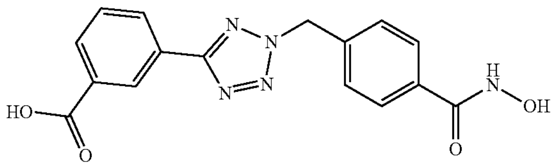 [SMILES: O=C(O)c1cccc(-c2nnn(Cc3ccc(C(=O)NO)cc3)n2)c1] | 340.4 |
| 169 | 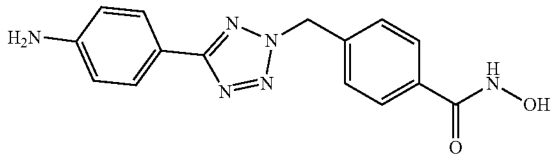 [SMILES: Nc1ccc(-c2nnn(Cc3ccc(C(=O)NO)cc3)n2)cc1] | 311.5 |
| 170 | 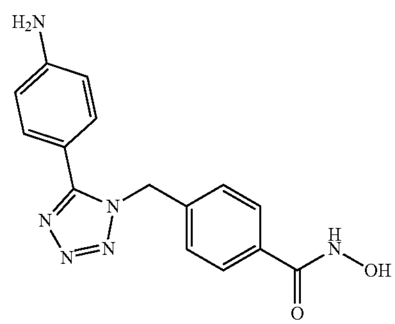 [SMILES: Nc1ccc(-c2nnnn2Cc2ccc(C(=O)NO)cc2)cc1] | 311.5 |
| 173 | 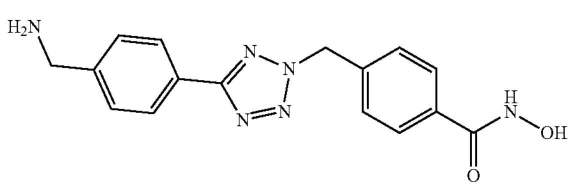 [SMILES: NCc1ccc(-c2nnn(Cc3ccc(C(=O)NO)cc3)n2)cc1] | 325.3 |
| 174 | 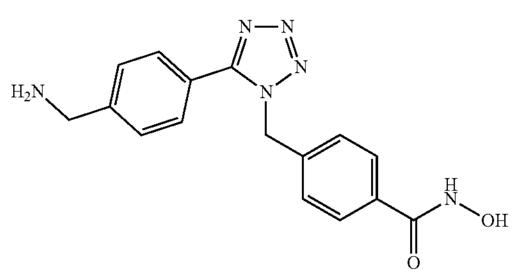 [SMILES: NCc1ccc(-c2nnnn2Cc2ccc(C(=O)NO)cc2)cc1] | 325.1 |

| Comp. | Structure | m/z [MH+] |
|---|---|---|
| 214 | 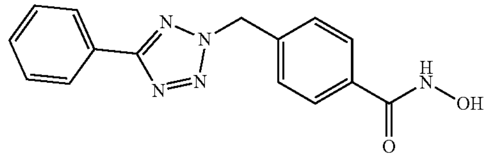 [SMILES: O=C(NO)c1ccc(Cn2nnc(-c3ccccc3)n2)cc1] | 296.08 |
| 215 | 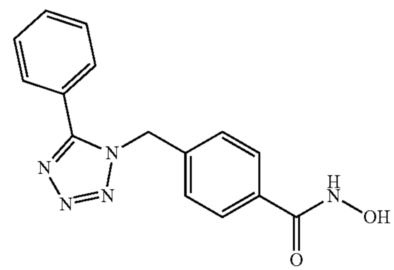 [SMILES: O=C(NO)c1ccc(Cn2nnnc2-c2ccccc2)cc1] | 294.0 |

Example 11. Synthesis of 4-((5-(2,3-dihydrothieno[3,4-b][1,4]dioxin-5-yl)-1H-tetrazol-1-yl)methyl)-3,5-difluoro-N-hydroxybenzamide (comp. 5)

Step A

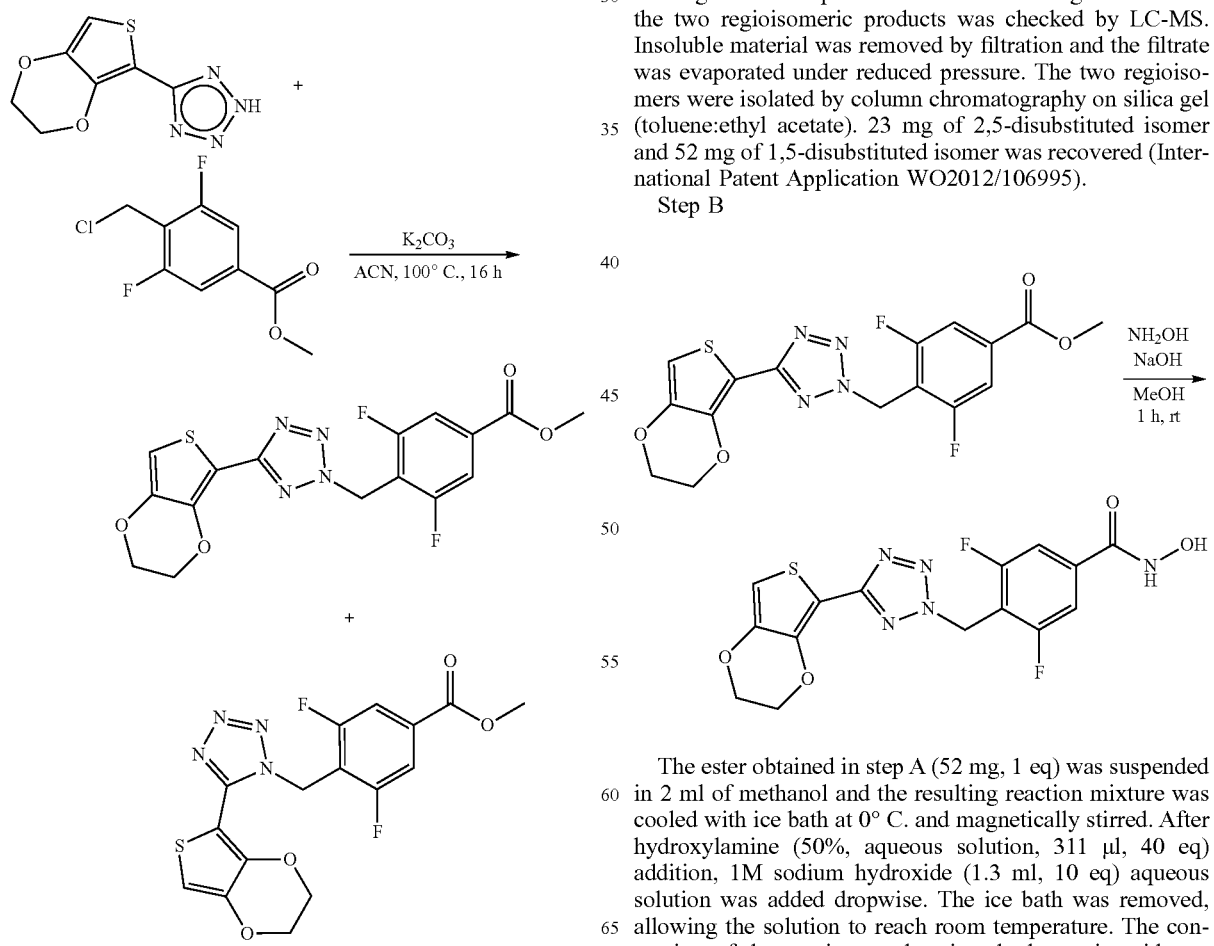

Step B

The reaction vessel was charged with potassium carbonate (85 mg, 1 eq) and 2 ml of acetonitrile. Tetrazole (105 mg, 1 eq) was added as a solid under magnetic stirring at room temperature, while methyl 3,5-difluoro-4-chloromethylbenzoate (122.3 mg, 1.1 eq) was added as a solution in 2 ml of acetonitrile. The mixture was heated at 100° C. and stirred overnight. The complete conversion of starting material into the two regioisomeric products was checked by LC-MS. Insoluble material was removed by filtration and the filtrate was evaporated under reduced pressure. The two regioisomers were isolated by column chromatography on silica gel (toluene:ethyl acetate). 23 mg of 2,5-disubstituted isomer and 52 mg of 1,5-disubstituted isomer was recovered (International Patent Application WO2012/106995).

The ester obtained in step A (52 mg, 1 eq) was suspended in 2 ml of methanol and the resulting reaction mixture was cooled with ice bath at 0° C. and magnetically stirred. After hydroxylamine (50%, aqueous solution, 311 μl, 40 eq) addition, 1M sodium hydroxide (1.3 ml, 10 eq) aqueous solution was added dropwise. The ice bath was removed, allowing the solution to reach room temperature. The conversion of the starting product into hydroxamic acid was confirmed by HPLC after 1 hour. The methanolic portion was removed by evaporation under reduced pressure, and the reaction was subsequently quenched by adding 1.3 ml of 1M hydrochloric acid aqueous solution and 2 ml of ethyl acetate. The phases were separated and the aqueous layer was re-extracted with additional ethyl acetate (3×). The organic phases were combined and washed with sodium bicarbonate saturated solution (2×), brine (2×), dried over sodium sulphate, filtered, and concentrated to dryness. 32 mg of clean product was recovered (m/z 395.91 [MH+]).

The following compounds were synthesized using this procedure:

| Comp. | Structure | m/z [MH+] |
|---|---|---|
| 6 | 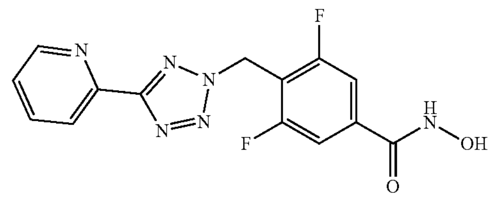 [SMILES: O=C(NO)c1cc(F)c(Cn2nnc(-c3ccccn3)n2)c(F)c1] | 333.02 |
| 7 | 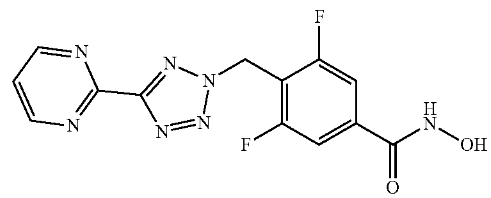 [SMILES: O=C(NO)c1cc(F)c(Cn2nnc(-c3ncccn3)n2)c(F)c1] | 333.96 |
| 13 | 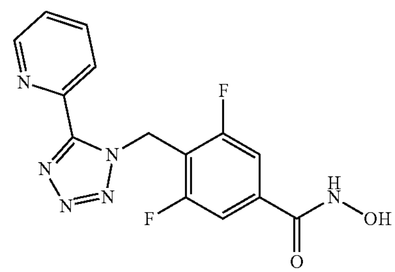 [SMILES: O=C(NO)c1cc(F)c(Cn2nnnc2-c2ccccn2)c(F)c1] | 333.02 |
| 15 | 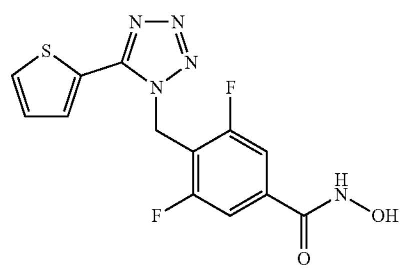 [SMILES: O=C(NO)c1cc(F)c(Cn2nnnc2-c2cccs2)c(F)c1] | 337.96 |
| 19 | 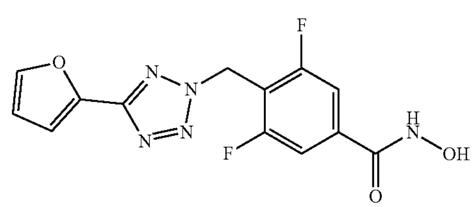 [SMILES: O=C(NO)c1cc(F)c(Cn2nnc(-c3ccco3)n2)c(F)c1] | 321.97 |
| 65 | 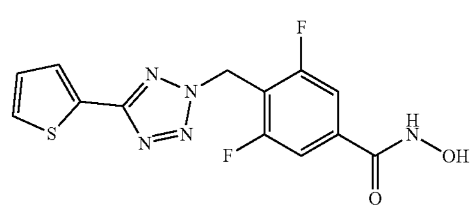 [SMILES: O=C(NO)c1cc(F)c(Cn2nnc(-c3cccs3)n2)c(F)c1] | 337.96 |

-continued

| Comp. | Structure | m/z [MH+] |
|---|---|---|
| 79 | 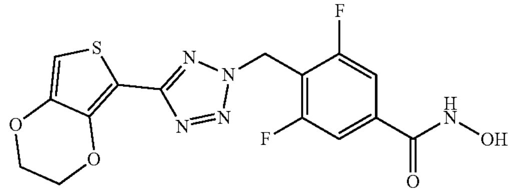 [SMILES: O=C(NO)c1cc(F)c(Cn2nnc(-c3scc4c3OCCO4)n2)c(F)c1] | 395.91 |
| 92 | 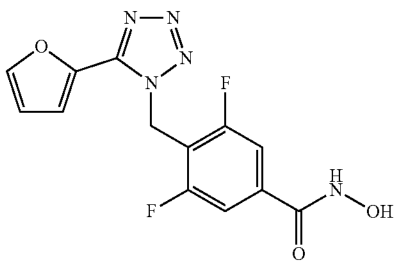 [SMILES: O=C(NO)c1cc(F)c(Cn2nnnc2-c2ccco2)c(F)c1] | 321.97 |
| 93 | 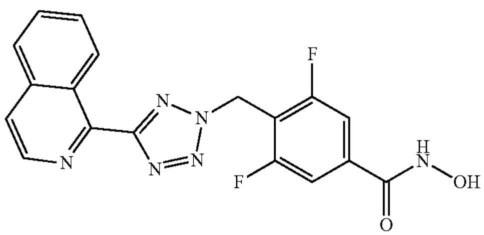 [SMILES: O=C(NO)c1cc(F)c(Cn2nnc(-c3nccc4ccccc34)n2)c(F)c1] | 382.97 |
| 94 | 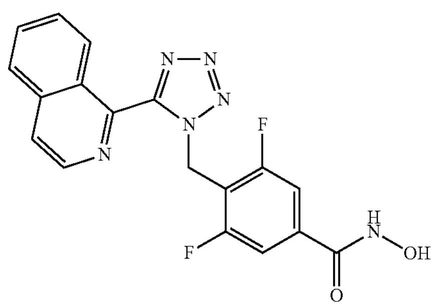 [SMILES: O=C(NO)c1cc(F)c(Cn2nnnc2-c2nccc3ccccc23)c(F)c1] | 382.97 |
| 95 | 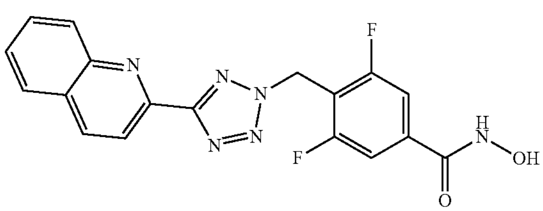 [SMILES: O=C(NO)c1cc(F)c(Cn2nnc(-c3ccc4ccccc4n3)n2)c(F)c1] | 382.98 |
| 96 | 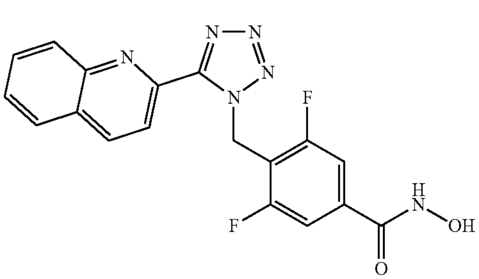 [SMILES: O=C(NO)c1cc(F)c(Cn2nnnc2-c2ccc3ccccc3n2)c(F)c1] | 382.97 |

-continued

| Comp. | Structure | m/z [MH+] |
|---|---|---|
| 108 | 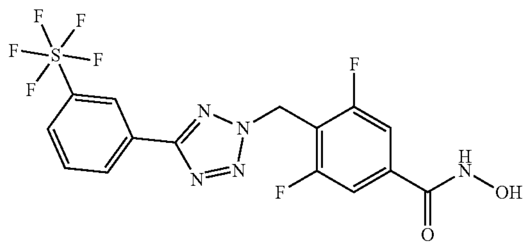 [SMILES: O=C(NO)c1cc(F)c(Cn2nnc(-c3cccc(S(F)(F)(F)(F)F)c3)n2)c(F)c1] | 457.91 |
| 109 | 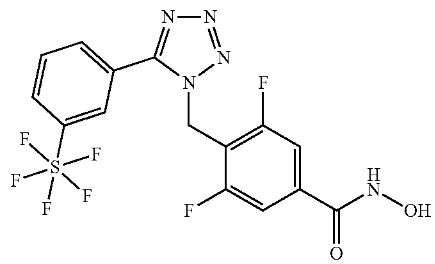 [SMILES: O=C(NO)c1cc(F)c(Cn2nnnc2-c2cccc(S(F)(F)(F)(F)F)c2)c(F)c1] | 457.91 |
| 112 | 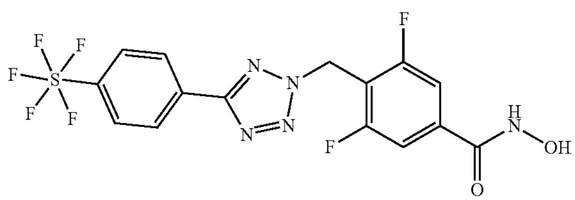 [SMILES: O=C(NO)c1cc(F)c(Cn2nnc(-c3ccc(S(F)(F)(F)(F)F)cc3)n2)c(F)c1] | 457.91 |
| 113 | 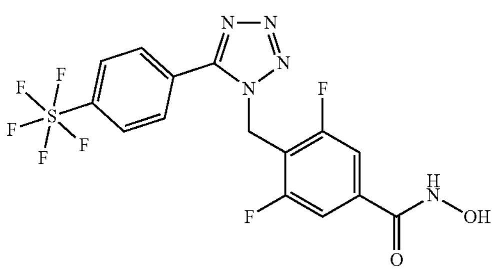 [SMILES: O=C(NO)c1cc(F)c(Cn2nnnc2-c2ccc(S(F)(F)(F)(F)F)cc2)c(F)c1] | 457.91 |
| 125 | 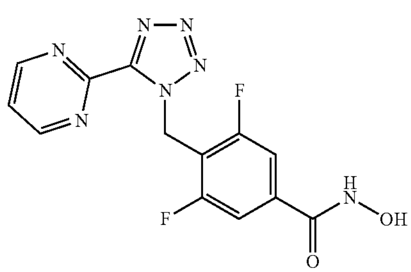 [SMILES: O=C(NO)c1cc(F)c(Cn2nnnc2-c2ncccn2)c(F)c1] | 333.95 |
| 128 | 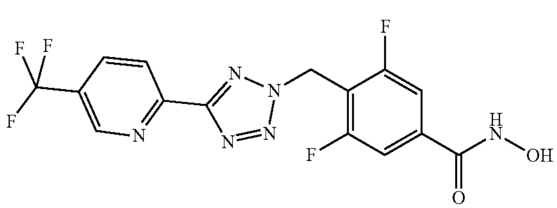 [SMILES: O=C(NO)c1cc(F)c(Cn2nnc(-c3ccc(C(F)(F)F)cn3)n2)c(F)c1] | 400.94 |

-continued

| Comp. | Structure | m/z [MH+] |
|---|---|---|
| 129 | 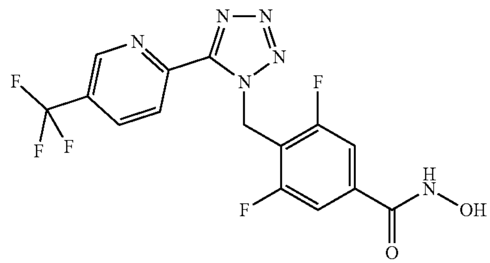 [SMILES: O=C(NO)c1cc(F)c(Cn2nnnc2-c2ccc(C(F)(F)F)cn2)c(F)c1] | 400.94 |
| 134 | 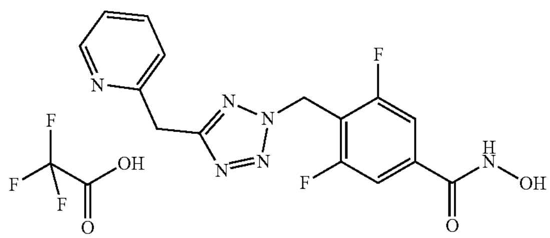 | 347.00 |
| 135 | 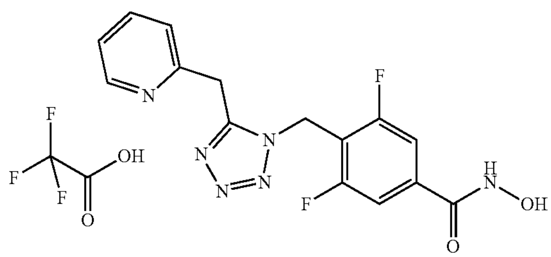 [SMILES: O=C(O)C(F)(F)F ; O=C(NO)c1cc(F)c(Cn2nnnc2Cc2ccccn2)c(F)c1] | 346.99 |
| 154 | 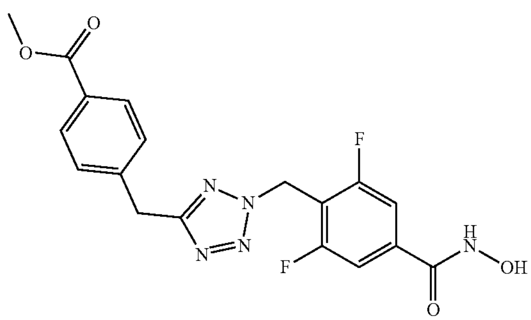 [SMILES: COC(=O)c1ccc(Cc2nnn(Cc3c(F)cc(C(=O)NO)cc3F)n2)cc1] | 404.4 |
| 155 | 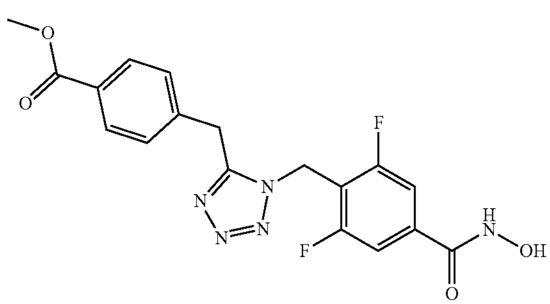 [SMILES: COC(=O)c1ccc(Cc2nnnn2Cc2c(F)cc(C(=O)NO)cc2F)cc1] | 404.5 |

-continued

| Comp. | Structure | m/z [MH+] |
|---|---|---|
| 160 | 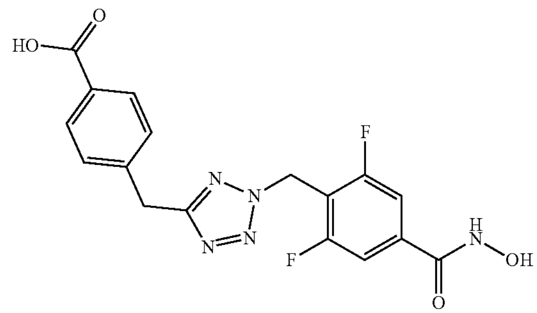 [SMILES: O=C(O)c1ccc(Cc2nnn(Cc3c(F)cc(C(=O)NO)cc3F)n2)cc1] | 390.3 |
| 161 | 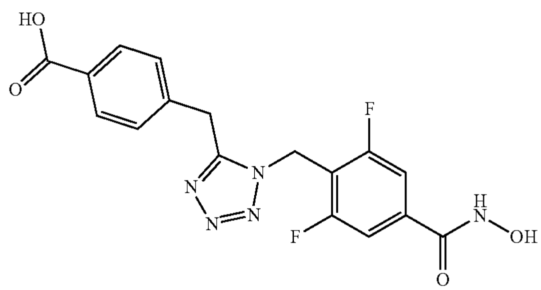 [SMILES: O=C(O)c1ccc(Cc2nnnn2Cc2c(F)cc(C(=O)NO)cc2F)cc1] | 390.4 |
| 171 | 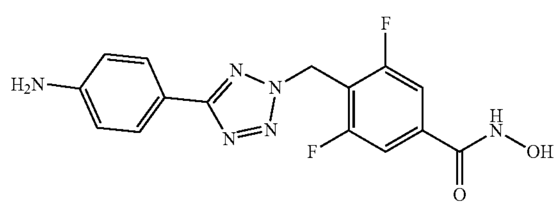 [SMILES: Nc1ccc(-c2nnn(Cc3c(F)cc(C(=O)NO)cc3F)n2)cc1] | 347.5 |
| 172 | 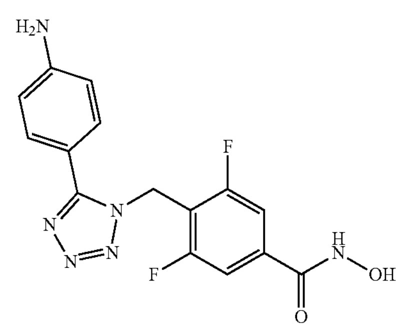 [SMILES: Nc1ccc(-c2nnnn2Cc2c(F)cc(C(=O)NO)cc2F)cc1] | 347.3 |
| 175 | 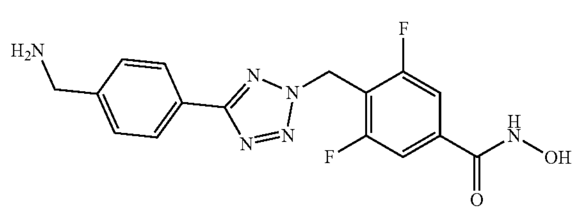 [SMILES: NCc1ccc(-c2nnn(Cc3c(F)cc(C(=O)NO)cc3F)n2)cc1] | 361.4 |

| Comp. | Structure | m/z [MH+] |
|---|---|---|
| 176 | 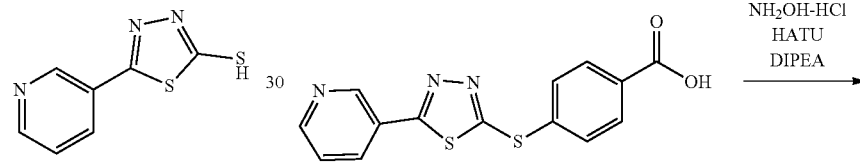 | 361.1 |

Example 12—Synthesis of 3,5-difluoro-N-hydroxy-4-((5-(pyridin-3-yl)-1,3,4-thiadiazol-2-yl)thio)benzamide (comp. 191)

Step A

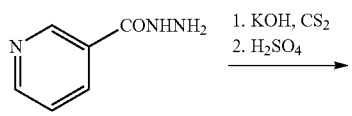

KOH (1.48 g, 26.47 mmol, 1.1 equiv) was dissolved in 45 mL of anhydrous ethanol. The hydrazide (3.30 g, 24.06 mmol, 1 equiv) was added and the reaction mixture was cooled to 0-5° C. CS₂ (1.66 mL, 27.67 mmol, 1.15 equiv) was added dropwise and the reaction mixture was stirred at 0-5° C. for 1 h. The resulted precipitate was collected, rinsed with cold acetone and dried affording 5.50 g of yellow solid. The obtained intermediate was added in small portions to 25 mL of sulfuric acid cooled to 0-5° C. After 1 h at 0-5° C. the reaction mixture was poured into ice water and the resulted precipitate was collected, rinsed with water and dried.

Step B

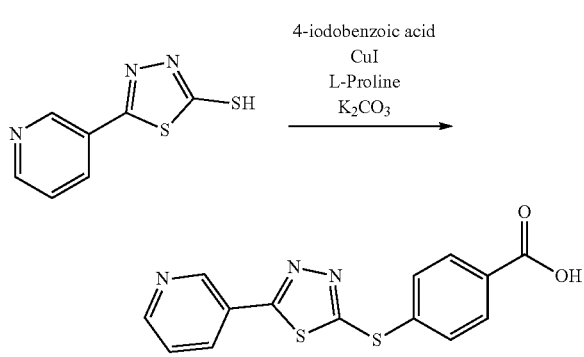

A mixture of 5-(pyridin-3-yl)-1,3,4-thiadiazole-2-thiol obtained in step A (0.8 g, 4.1 mmol, 1 equiv), 4-iodobenzoic acid (1.22 g, 4.92 mmol, 1.2 equiv), L-proline (0.047 g, 0.4 mmol, 0.1 equiv) and K₂CO₃ (2.26 g, 16.4 mmol, 4 equiv) in 20 mL of anhydrous DMF was degassed and CuI (0.039 g, 0.2 mmol, 0.05 equiv) was added. The reaction vessel was sealed and the reaction mixture was stirred at 120° C. for 48 h. Complete conversion of the starting thiole was monitored by LC-MS. The reaction mixture was poured into 150 mL of water and filtered through a pad of Celite. The filtrate was acidified with HCl. The formed precipitate was filtered and rinsed successively with water, acetonitrile and diethyl ether.

Step C

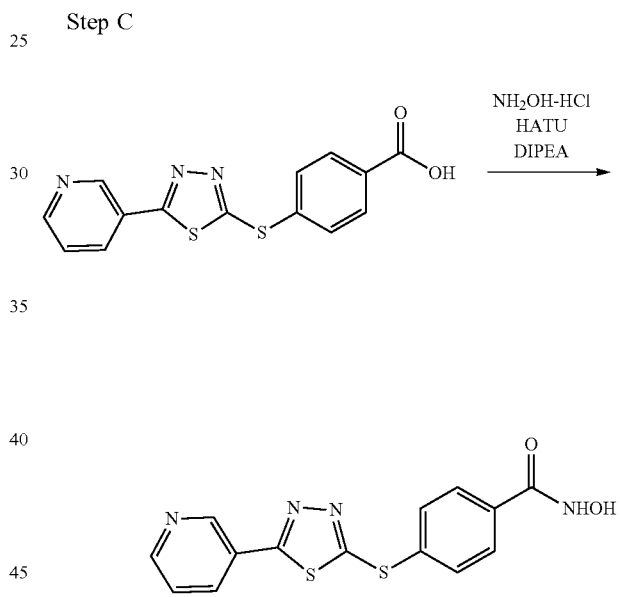

HATU (0.181 mg, 0.476 mmol, 1.5 equiv) was added to a solution of the carboxylic acid obtained in step B (0.1 g, 0.317 mmol, 1 equiv) and DIPEA (0.333 mL, 1.902 mmol, 6 equiv) in 2 mL of anhydrous DMF. The reaction mixture was stirred at room temperature and monitored by LC-MS for full conversion of the acid into the HATU-intermediate: after 1 h conversion was complete. NH₂OH—HCl (0.066 g, 0.951 mmol, 3 equiv) was added and the reaction mixture was stirred for 2 h more. The reaction was monitored by LC-MS. The reaction mixture was diluted with water to 50 mL of total volume and extracted with EtOAc (225 mL). After evaporation, 101 mg of very viscous orange oil was obtained. Trituration with acetonitrile (~15 min sonication) led to formation of a precipitate which was collected by filtration, rinsed with acetonitrile and diethyl ether and dried. 40 mg of pure product were obtained (m/z 366.99 [MH+]). LCMS: 94.5%. NMR: OK.

The following compounds were synthesized using this procedure:

| Comp. | Structure | m/z [MH+] |
|---|---|---|
| 196 | 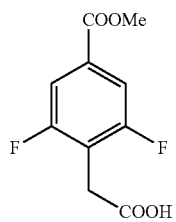 | 443.7 |
| 187 | 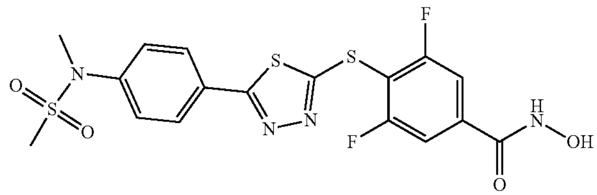 [SMILES: CN(c1ccc(-c2nnc(Sc3c(F)cc(C(=O)NO)cc3F)s2)cc1)S(C)(=O)=O] | 473.4 |

Example 13—Synthesis 3,5-difluoro-N-hydroxy-4-((5-phenyl-1,3,4-thiadiazol-2-yl)methyl)benzamide (comp. 198)

Step A

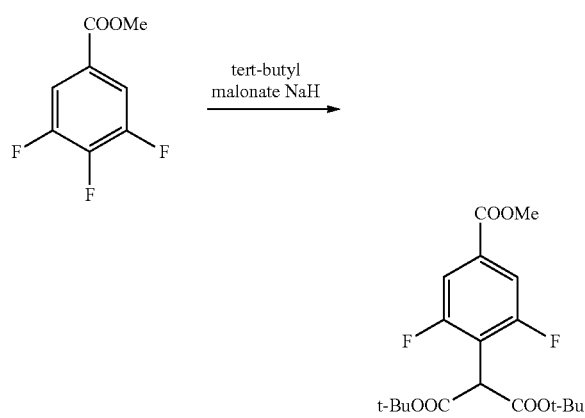

tert-Butyl malonate (11.4 g, 52.73 mmol, 2 equiv) was added dropwise to a suspension of NaH (1.5 equiv) in 70 mL of anhydrous DMF. After 5 min of stirring at rt, methyl 3,4,5-trifluorobenzoate (5 g, 26.3 mmol, 1 equiv) was added. The reaction mixture was stirred for 3 h at rt (formation of a white precipitate was observed), diluted with water and extracted with EtOAc. After concentration, the residue was purified by column chromatography. 11.0 g of inseparable mixture of the product and tert-Butyl malonate in 1:3 ratio (by NMR) was obtained. This mixture was used in the next step without further purification.

Step B

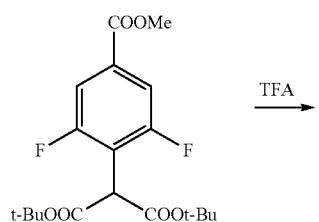

-continued

The mixture obtained in step A (8.6 g, 22 mmol, 1 equiv) and TFA (17 mL, 10 equiv) were dissolved in 10 mL of anhydrous DCE and refluxed o/n. After cooling, the solvent was evaporated and the residue was treated with hexane and the formed precipitate was collected. NMR analysis of the precipitate and of the filtrate revealed that a mixture of the product and malonic acid (in approx. the same 2:1 ratio in favor of the product) was obtained. The crops were combined and used in the next step.

Step C

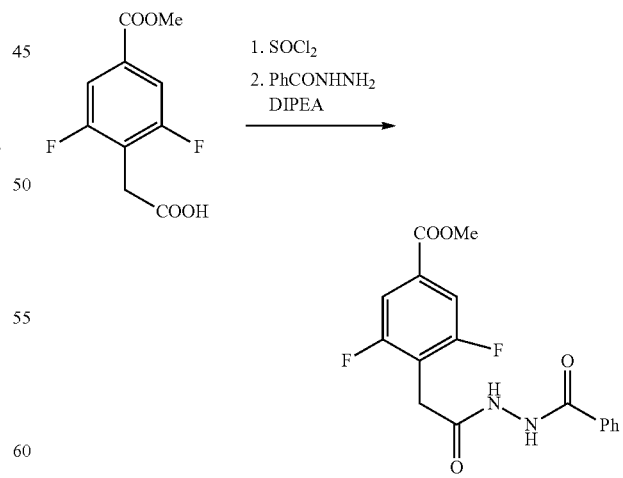

The mixture obtained in step B (0.5 g, 2.17 mmol, 1 equiv) was dissolved in 5 mL of SOCl₂, refluxed for 1 h and concentrated. The obtained crude chloroanhydride was mixed with benzoylhydrazine (0.643 g, 4.72 mmol, 2 equiv) in 10 mL of anhydrous DMF followed by addition of DIPEA (1.99 mL, 11.45 mmol, 5 equiv). After being stirred overnight, the reaction mixture was quenched with water, extracted with EtOAc and concentrated. The residue was treated with DCM and filtered.

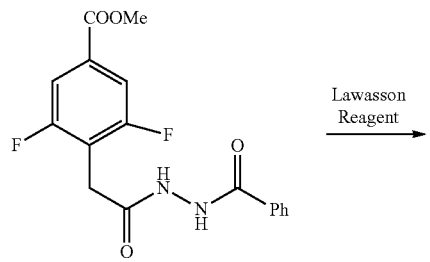

A mixture of the compound obtained in step C (0.277 g, 0.88 mmol, 1 equiv) and Lawesson Reagent (0.35 g, 0.86 mmol, 0.98 equiv) in 5 mL of toluene was stirred in the sealed vessel at 120° C. for 15 min. Full conversion of the starting material was monitored by UPLC. The solvent was evaporated and the residue was purified by column chromatography first using EtOAc in hexane (gradient 20% to 100%) then 5% MeOH in DCM.

Step E

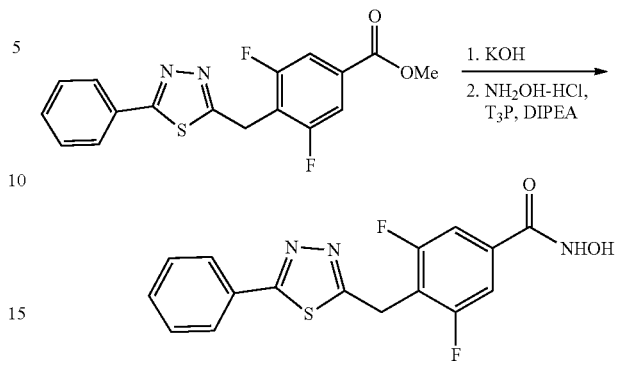

KOH (0.021 g, 0.37 mmol, 2 equiv) was added to a solution of the cyclic compound obtained in step D (0.06 g, 0.18 mmol, 1 equiv) in 14 mL of THF/water=4/1 mixture. The reaction mixture was stirred at rt overnight and acidified with 1M HCl. The obtained precipitate was collected and dried in vacuo. This solid was then dissolved in THF together with DIPEA (0.333 mL, 1.902 mmol, 6 equiv). HATU (0.181 mg, 0.476 mmol, 1.5 equiv) was added and the reaction mixture was stirred at rt and the full conversion of the acid to the HATU-intermediate was monitored by LC-MS. NH$_2$OH—HCl (0.066 g, 0.951 mmol, 3 equiv) was added and the reaction mixture was stirred for 2 h more. The reaction mixture was diluted with water to 50 mL of total volume and extracted with EtOAc (225 mL). After evaporation 101 mg of very viscous oil was obtained. Trituration with acetonitrile (~15 min sonication) led to formation of a precipitate which was collected by filtration, rinsed with acetonitrile and ether and dried. 33 mg of pure product were obtained (m/z 348.09 [MH+].

The following compounds were synthesized using this procedure:

| Comp. | Structure | m/z [MH+] |
|---|---|---|
| 190 | 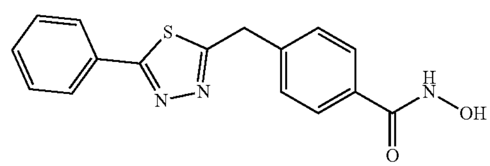 [SMILES: O=C(NO)c1ccc(Cc2nnc(-c3ccccc3)s2)cc1] | 312.12 |
| 195 | 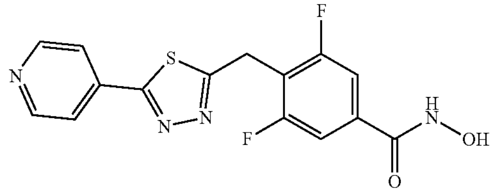 [SMILES: O=C(NO)c1cc(F)c(Cc2nnc(-c3ccncc3)s2)c(F)c1] | 349.11 |

| Comp. | Structure | m/z [MH+] |
|---|---|---|
| 197 | 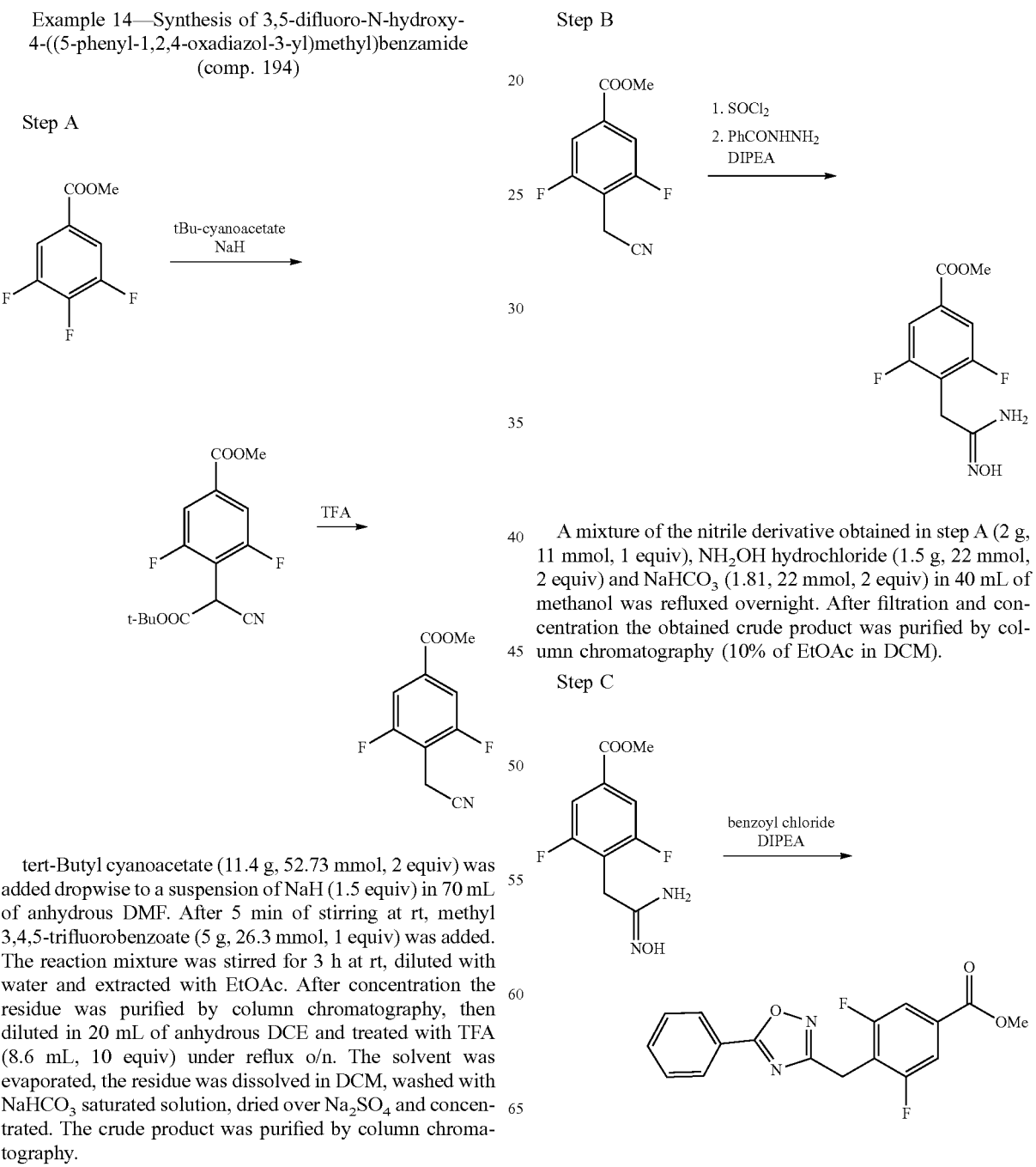 | 433.8 |

Example 14—Synthesis of 3,5-difluoro-N-hydroxy-4-((5-phenyl-1,2,4-oxadiazol-3-yl)methyl)benzamide (comp. 194)

Step A tert-Butyl cyanoacetate (11.4 g, 52.73 mmol, 2 equiv) was added dropwise to a suspension of NaH (1.5 equiv) in 70 mL of anhydrous DMF. After 5 min of stirring at rt, methyl 3,4,5-trifluorobenzoate (5 g, 26.3 mmol, 1 equiv) was added. The reaction mixture was stirred for 3 h at rt, diluted with water and extracted with EtOAc. After concentration the residue was purified by column chromatography, then diluted in 20 mL of anhydrous DCE and treated with TFA (8.6 mL, 10 equiv) under reflux o/n. The solvent was evaporated, the residue was dissolved in DCM, washed with $NaHCO_3$ saturated solution, dried over $Na_2SO_4$ and concentrated. The crude product was purified by column chromatography.

Step B

A mixture of the nitrile derivative obtained in step A (2 g, 11 mmol, 1 equiv), $NH_2OH$ hydrochloride (1.5 g, 22 mmol, 2 equiv) and $NaHCO_3$ (1.81, 22 mmol, 2 equiv) in 40 mL of methanol was refluxed overnight. After filtration and concentration the obtained crude product was purified by column chromatography (10% of EtOAc in DCM).

Step C

Benzoyl chloride (0.243 g, 1.73 mmol, 1.2 equiv) was added to a solution of methyl (Z)-4-(2-amino-2-(hydroxyimino)ethyl)-3,5-difluorobenzoate obtained in step B (0.3 g, 1.44 mmol, 1 equiv) and DIPEA (0.75 mL, 4.32 mmol, 3 equiv) in 2 mL of anhydrous DMF. After being stirred overnight the reaction mixture was quenched with water and extracted with EtOAc. Column chromatography purification (neat DCM) gave 41 mg of product.

Step D

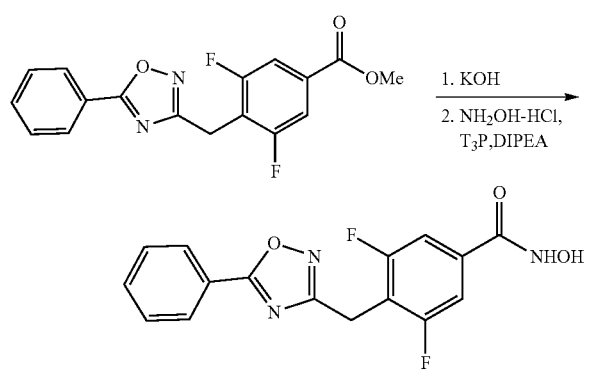

KOH (0.014 g, 0.24 mmol, 2 equiv) was added to a solution of the methyl ester obtained in step C (0.04 g, 0.12 mmol, 1 equiv) in 14 mL of THF/water=4/1 mixture. The reaction mixture was stirred at rt overnight and acidified with 1M HCl. The obtained precipitate was collected and dried in vacuo. The obtained carboxylic acid was dissolved in 2 mL of anhydrous THF. DIPEA (0.72 mmol, 6 equiv) and HATU (0.18 mmol, 1.5 equiv) were added. The reaction mixture was stirred at rt and monitored by LC-MS for full conversion of the acid to the HATU-intermediate. $NH_2OH$ hydrochloride (0.025 g, 0.36 mmol, 3 equiv) was added and the reaction mixture was stirred for 2 h more, then diluted with water to 50 mL of total volume and extracted with EtOAc (225 mL). After evaporation 101 mg of very viscous oil was obtained. Trituration with acetonitrile (~15 min sonication) led to formation of a precipitate which was collected by filtration, rinsed with acetonitrile and ether and dried. 20 mg of pure product were obtained (m/z 332.13 [MH+]).

The following compounds were synthesized using this procedure:

| Comp. | Structure | m/z [MH+] |
|---|---|---|
| 189 | 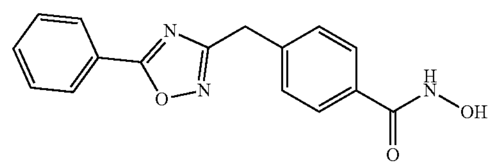 [SMILES: O=C(NO)c1ccc(Cc2noc(-c3ccccc3)n2)cc1] | 296.5 |
| 193 | 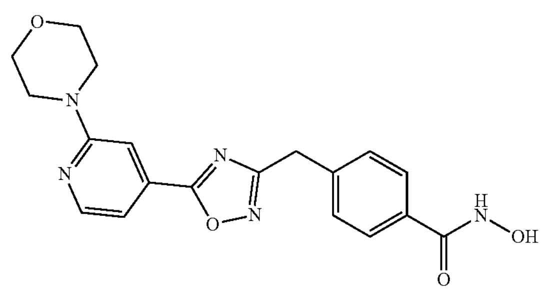 [SMILES: O=C(NO)c1ccc(Cc2noc(-c3ccnc(N4CCOCC4)c3)n2)cc1] | 382.13 |
| 200 | 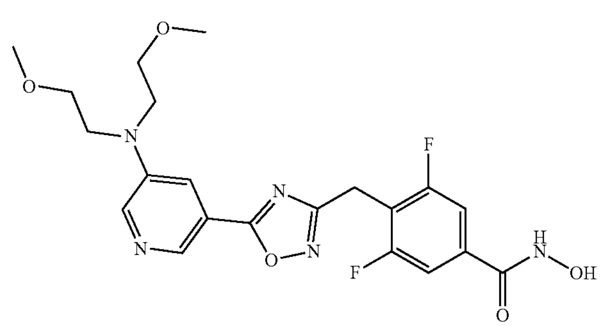 [SMILES: COCCN(CCOC)c1cncc(-c2nc(Cc3c(F)cc(C(=O)NO)cc3F)no2)c1] | 464.13 |

| Comp. | Structure | m/z [MH+] |
|---|---|---|
| 201 | 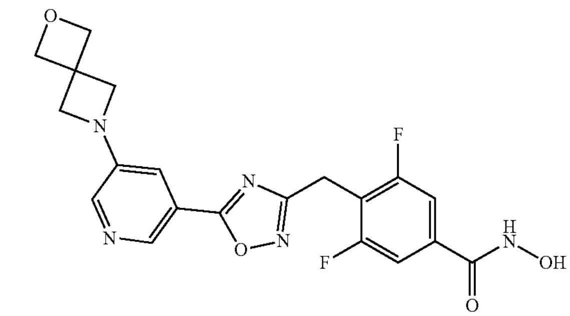 [SMILES: O=C(NO)c1cc(F)c(Cc2noc(-c3cncc(N4CC5(COC5)C4)c3)n2)c(F)c1] | 430.1 |
| 202 | 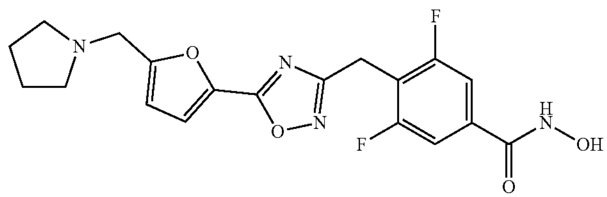 [SMILES: O=C(NO)c1cc(F)c(Cc2noc(-c3ccc(CN4CCCC4)o3)n2)c(F)c1] | 405.12 |

Example 15—Synthesis of N-hydroxy-4-((4-methyl-5-phenyl-4H-1,2,4-triazol-3-yl)methyl)benzamide (comp. 217)

Step A

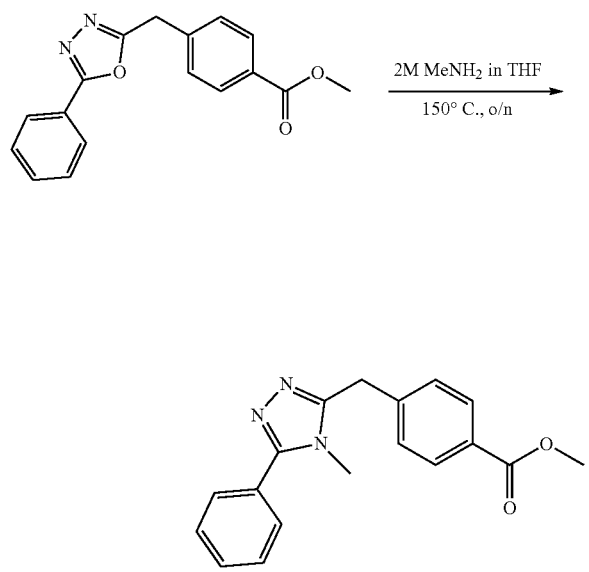

Acetic acid (0.3 mL) was added dropwise to a solution of crude methyl 4-((5-phenyl-1,3,4-oxadiazol-2-yl)methyl)benzoate (0.38 g, 1.29 mmol, 1 equiv) in 2M solution of MeNH₂ in THF (15 mL). The reaction vessel was sealed and the reaction mixture was allowed to stir at 150° C. overnight. After cooling, the solvent was evaporated; the residue was treated with water and extracted with EtOAc. The organic phase was dried and evaporated yielding 258 mg of orange oil which was used in the next step without further purification.

Step B

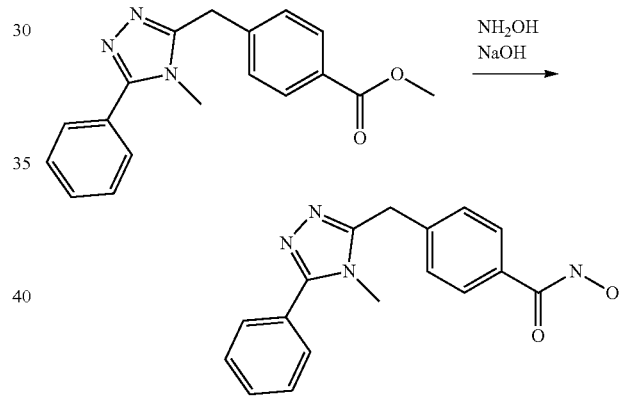

The methyl ester obtained in step A (0.041 g, 0.139 mmol, 1 equiv) was suspended in 8 mL of methanol and the resulted solution was cooled with ice bath. 50% solution of NH₂OH in water (0.34 mL, 40 equiv) was added followed by slow addition of 1M NaOH solution (1.4 mL, 10 equiv). The reaction mixture was stirred allowing to reach rt (about 1 h) and acidified with 1M HCl. The white precipitate was collected by filtration. Prep. HPLC purification gave 24 mg of pure product (m/z 309.12 [MH+]).

Example 16—Synthesis of 4-((3-((1H-indol-3-yl)methyl)-5-(thiophen-2-yl)-4H-1,2,4-triazol-4-yl)methyl)-N-hydroxybenzamide (comp. 183)

Step A

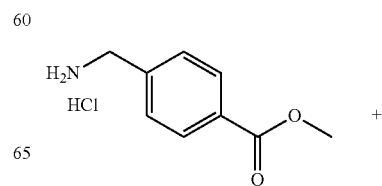

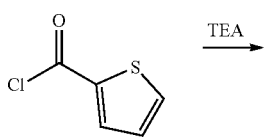

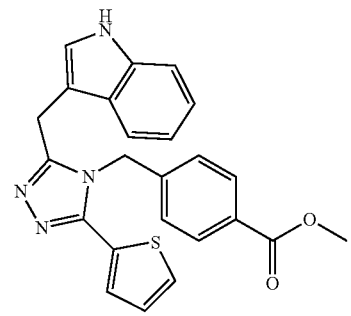

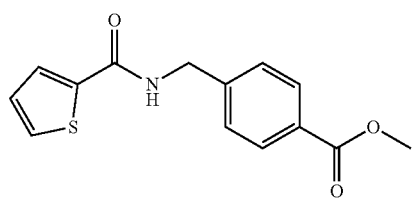

Methyl 4-((thiophene-2-carboxamido)methyl)benzoate (1 mmol, 1 eq.) was suspended in tionyl chloride (4 ml, 5.5 eq) under argon, and stirred at reflux temperature overnight. The mixture was concentrated at reduced pressure to remove the excess of SOCl$_2$. The crude imidoyl chloride thus obtained was suspended in dry toluene, and indole-3-acetic acid hydrazide (189 mg, 1 mmol, 1 eq) was added as a solid. The resulting mixture was heated up to 120° C. and agitated over weekend. The mixture was concentrated by rotary evaporation. Product was precipitated from EtOAc/MeOH 1% and collected by filtration. 113 mg of product were obtained.

Step C

Methyl 4-(aminomethyl)benzoate hydrochloride (402 mg, 2 mmol, 1 eq.) was dissolved in dichloromethane (8 ml) in presence of trimethylamine (616 uL, 4.4 mmol, 2.2 eq.). 2-Thiophenecarbonyl chloride (236 uL, 2.2 mmol, 1.1 eq.) was then added and the mixture was stirred at r.t. overnight.

Upon completion, reaction mixture was diluted with dichloromethane and washed with water. Organic layer was dried over Na$_2$SO$_4$, filtered and concentrated affording a crude product which was used for the subsequent step without any further purification.

Step B

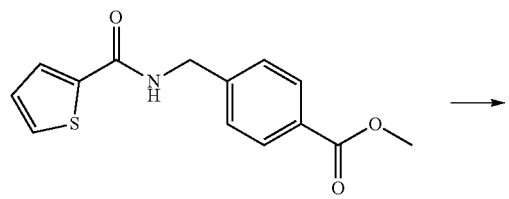

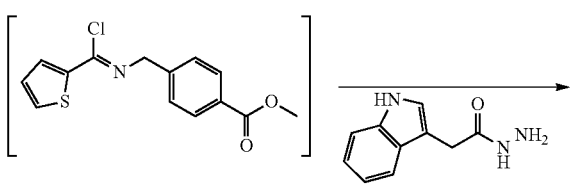

The methyl ester obtained in step B (0.041 g, 0.139 mmol, 1 equiv) was suspended in 8 mL of methanol and the resulted solution was cooled with ice bath. 50% solution of NH$_2$OH in water (0.34 mL, 40 equiv) was added followed by slow addition of 1M NaOH solution (1.4 mL, 10 equiv). The reaction mixture was stirred allowing to reach rt (about 1 h) and acidified with 1M HCl. The white precipitate was collected by filtration. Prep. HPLC purification gave pure product (m/z 430.3 [MH+]).

The following compound was synthesized using this procedure

| Comp. | Structure | m/z [MH+] |
|---|---|---|
| 185 | (3,4-dimethoxybenzyl triazole thiophene benzyl hydroxamic acid structure) | 451.3 |

Example 17—Enzymatic Screening

Enzymatic activity on recombinant human HDAC6 and HDAC3 was evaluated (Table 2) for each synthesized compound. Compounds that showed good HDAC6 selectivity, defined as log of the $IC_{50}$ ratio between HDAC6 and another isoform less than −2, were also screened on all other isoforms in order to obtain the full profile (Table 3).

For each test compound, solutions at five different concentrations (usually in the range 3-30000 nM) 5× concentrated in the reaction buffer (25 mM Tris-HCl, pH 8, 130 mM NaCl, 0.05% Tween-20, 10% Glycerol) plus DMSO normalized to the amount present in the more concentrated inhibitor solution, usually 0.75% equivalent to the final 0.15% in the plate were prepared. 10 µL of triplicate solution for each test compound concentration were placed on a 96-well plate and 15 µL of 3,33× concentrated enzyme solution in the reaction buffer (25 mM Tris-HCl, pH 8, 130 mM NaCl 0.05% Tween-20 10% glycerol, 1 mg/ml BSA or 2 mg/ml for HDAC4, HDAC5 and HDAC9—note: for HDAC7, 50 mM TRIS-HCl, pH 8, 137 mM NaCl, 2.7 mM KCl, and 1 mM $MgCl_2$ were used) were added to each well. After a period of incubation at 30° C. (incubation times vary for different isoforms and are shown in table 1) 25 µL of solution containing the substrate were added. As substrate, FLUOR DE LYS® deacetylase substrate (Enzo Life Sciences, cat #BML-K1104, FdL), FLUOR DE LYS®-Green substrate (Enzo Life Sciences, cat #BML-K1572 FdL_G) and trifluoroacetyl-L-lysine (Tfal)-2× concentrated solution in 25 mM Tris-HCl, pH 8, 130 mM NaCl 0.05% Tween-20 10% glycerol) were used. Following a reaction period at 30° C. (reaction times vary for different isoforms and are reported in Table 1), 50 µL of the development solution consisting of concentrate FLUOR DE LYS® developer I (Enzo Life Sciences, cat #BML-K1105), diluted 200 times in HAB plus 2 µM TSA was added and, after 25 minutes at room temperature in the dark, using the Victor 1420 Multilabel Counter Perkin Elmer Wallac instrument, the fluorescence reading was carried out.

TABLE 1

Operational details for the enzymatic test of each individual isoform

| Isoform | Source | Concentration | Substrate | Preincubation | Reaction | Reading method λ ex/λ em (0.1 s) |
|---|---|---|---|---|---|---|
| HDAC1 | BPS cat 50051 | 1.6 nM | 150 µM FdL | 30 minutes at 30° C. | 30 minutes at 30° C. | 355/460 nm |
| HDAC2 | BPS cat 50002 | 3 nM | 150 µM FdL | 30 minutes at 30° C. | 30 minutes at 30° C. | 355/460 nm |
| HDAC3 | BPS cat 50003 | 400 pM | 60 µM FdL | 30 minutes at 30° C. | 30 minutes at 30° C. | 355/460 nm |
| HDAC4 | BPS cat 50004 | 32 pM | 20 µM Tfal | 30 minutes at 30° C. | 80 minutes at 30° C. | 355/460 nm |
| HDAC5 | BPS cat 50005 | 700 pM | 20 µM Tfal | 30 minutes at 30° C. | 60 minutes at 30° C. | 355/460 nm |
| HDAC6 | BPS cat 50006 | 1.5 nM | 60 µM FdL | 30 minutes at 30° C. | 30 minutes at 30° C. | 355/460 nm |
| HDAC7 | BPS cat 50007 | 14 pM | 20 µM Tfal | 30 minutes at 30° C. | 30 minutes at 30° C. | 355/460 nm |
| HDAC8 | BPS cat 50008 | 3.9 nM | 25 µM FdL_G | 55 minutes at RT | 25 minutes at 30° C. | 485/535 nm |
| HDAC9 | BPS cat 50009 | 900 pM | 20 µM Tfal | 30 minutes at 30° C. | 80 minutes at 30° C. | 355/460 nm |
| HDAC10 | BPS cat 50010 | 13 nM | 150 µM FdL | 30 minutes at 30° C. | 180 minutes at 30° C. | 355/460 nm |
| HDAC11 | BML cat SE560 | 25 nM | 150 µM FdL | 30 minutes at 30° C. | 240 minutes at 30° C. | 355/460 nm |

Data on HDAC6 and HDAC3 enzymatic inhibition of synthesized compounds are shown in Table 2. Complete inhibition profiles on all isoforms for selected compounds are shown in Table 3. Molecules showed good HDAC6 activity and marked selectivity against other isoforms.

TABLE 2

Enzyme Inhibitory Activity Assay on HDAC6 ($IC_{50}$ nM) and selectivity vs. HDAC3 (log of ratio between $IC_{50}$s on the two enzymes)

| Comp. | Selectivity vs HDAC3 | HDAC6 $IC_{50}$ (nM) |
|---|---|---|
| 1 | −1.6 | 81 |
| 2 | −2.7 | 16 |
| 3 | −1.6 | 11 |
| 4 | −3.0 | 20 |
| 5 | −2.8 | 17 |
| 6 | −3.0 | 7 |
| 7 | −3.0 | 5 |
| 8 | −1.6 | 19 |
| 9 | −2.9 | 79 |
| 10 | −1.8 | 8 |
| 12 | −2.0 | 4 |
| 13 | −2.8 | 4 |
| 14 | −2.7 | 8 |
| 15 | −2.5 | 19 |
| 16 | −2.7 | 5 |
| 17 | −2.5 | 9 |
| 19 | −2.9 | 4 |
| 20 | −2.0 | 4 |
| 21 | −1.4 | 116 |
| 22 | −1.8 | 5 |
| 23 | −1.7 | 11 |
| 24 | −1.4 | 56 |
| 25 | −1.7 | 47 |
| 26 | −0.4 | 258 |
| 27 | −1.1 | 77 |
| 28 | −1.6 | 10 |
| 29 | −1.1 | 19 |
| 30 | −1.7 | 25 |
| 31 | −1.5 | 14 |
| 32 | −1.4 | 6 |
| 33 | −1.7 | 3 |
| 34 | −1.6 | 7 |
| 35 | −1.6 | 5 |
| 36 | −1.4 | 52 |
| 37 | −1.4 | 212 |
| 38 | −1.6 | 10 |
| 39 | −1.5 | 3 |
| 40 | −1.6 | 7 |
| 41 | −1.4 | 4 |
| 42 | −0.9 | 5 |
| 43 | −1.7 | 3 |
| 44 | −0.7 | 415 |
| 45 | −1.1 | 68 |
| 46 | −1.7 | 5 |
| 47 | −1.5 | 6 |
| 48 | −1.6 | 257 |
| 49 | −1.6 | 7 |
| 50 | −1.9 | 2 |
| 51 | −1.4 | 368 |
| 52 | −1.6 | 344 |
| 53 | −1.2 | 333 |
| 54 | −1.5 | 18 |
| 55 | −1.2 | 6 |
| 57 | −1.5 | 8 |
| 58 | −1.5 | 6 |
| 59 | −1.8 | 7 |
| 60 | −1.0 | 136 |
| 61 | −1.7 | 9 |
| 62 | −1.5 | 127 |
| 63 | −1.0 | 682 |
| 64 | −1.4 | 13 |
| 65 | −2.5 | 6 |
| 66 | −2.2 | 6 |
| 67 | −1.8 | 70 |
| 68 | −1.5 | 4 |
| 69 | −1.5 | 11 |
| 70 | −1.6 | 9 |
| 71 | −0.7 | 52 |
| 72 | −1.1 | 162 |
| 73 | −1.7 | 8 |
| 74 | −1.8 | 17 |
| 75 | −1.7 | 4 |
| 76 | −2.3 | 28 |
| 77 | −1.8 | 17 |
| 78 | −1.8 | 20 |
| 79 | −2.3 | 8 |
| 80 | −2.1 | 16 |
| 82 | −1.7 | 27 |
| 83 | −1.1 | 22 |
| 84 | −1.7 | 21 |
| 85 | −1.9 | 5 |
| 86 | −1.7 | 39 |
| 87 | −2.1 | 20 |
| 88 | −1.3 | 2 |
| 89 | −2.3 | 9 |
| 90 | −0.9 | 20 |
| 91 | −1.9 | 3 |
| 92 | −2.5 | 27 |
| 93 | −2.8 | 22 |
| 94 | −1.7 | 7 |
| 95 | −1.8 | 10 |
| 96 | −2.3 | 7 |
| 97 | −2.4 | 51 |
| 98 | −2.2 | 61 |
| 99 | −2.4 | 7 |
| 100 | −2.6 | 7 |
| 101 | −2.4 | 18 |
| 102 | −2.6 | 33 |
| 103 | −2.4 | 56 |
| 104 | −2.2 | 48 |
| 106 | −1.5 | 26 |
| 107 | −1.2 | 162 |
| 108 | −2.1 | 108 |
| 109 | −2.1 | 35 |
| 100 | −2.6 | 7 |
| 110 | −1.7 | 25 |
| 111 | −0.2 | 271 |
| 112 | −2.2 | 123 |
| 113 | −1.6 | 158 |
| 114 | −3.1 | 256 |
| 115 | −2.5 | 122 |
| 116 | −2.6 | 25 |
| 117 | −2.7 | 17 |
| 118 | −2.4 | 6 |
| 121 | −2.7 | 12 |
| 122 | −2.1 | 12 |
| 123 | −2.1 | 8 |
| 124 | −2.0 | 72 |
| 125 | −2.8 | 17 |
| 126 | −1.4 | 86 |
| 127 | −1.8 | 9 |
| 128 | −2.4 | 45 |
| 129 | −2.5 | 13 |
| 130 | −1.2 | 837 |
| 131 | −1.1 | 57 |
| 132 | −2.2 | 25 |
| 133 | −1.8 | 283 |
| 134 | −3.1 | 10 |
| 135 | −2.5 | 93 |
| 136 | −2.6 | 40 |
| 137 | −2.8 | 14 |
| 138 | −2.8 | 12 |
| 139 | −2.9 | 18 |
| 140 | −2.6 | 14 |
| 141 | −2.5 | 25 |
| 142 | −2.3 | 20 |
| 143 | −1.9 | 25 |
| 144 | −2.3 | 12 |
| 145 | −2.6 | 16 |

TABLE 2-continued

Enzyme Inhibitory Activity Assay on HDAC6 (IC$_{50}$ nM) and selectivity vs. HDAC3 (log of ratio between IC$_{50}$s on the two enzymes)

| Comp. | Selectivity vs HDAC3 | HDAC6 IC$_{50}$ (nM) |
|---|---|---|
| 146 | −2.9 | 20 |
| 147 | −2.9 | 16 |
| 148 | −2.1 | 6 |
| 149 | −2.6 | 11 |
| 150 | −2.1 | 24 |
| 151 | −2.8 | 9 |
| 152 | −2.5 | 22 |
| 153 | −2.9 | 25 |
| 154 | −2.2 | 32 |
| 155 | −2.0 | 172 |
| 156 | −1.2 | 61 |
| 157 | −1.2 | 27 |
| 158 | −1.6 | 231 |
| 159 | −1.5 | 1370 |
| 160 | −2.5 | 115 |
| 161 | −2.5 | 327 |
| 162 | −1.1 | 138 |
| 163 | −1.6 | 12 |
| 164 | −1.8 | 45 |
| 165 | −2.6 | 8 |
| 166 | −2.5 | 9 |
| 167 | −2.7 | 6 |
| 168 | −2.6 | 7 |
| 169 | −1.9 | 1 |
| 170 | −1.5 | 8 |
| 171 | −2.2 | 4 |
| 172 | −2.4 | 8 |
| 173 | −1.5 | 2 |
| 174 | −0.8 | 129 |
| 175 | −2.0 | 4 |
| 176 | −1.7 | 55 |
| 177 | −2.8 | 21 |
| 178 | −2.7 | 23 |
| 179 | −3.1 | 11 |
| 180 | −2.7 | 6 |
| 181 | −2.7 | 10 |
| 182 | −2.5 | 16 |
| 183 | −2.2 | 212 |
| 184 | −2.1 | 17 |
| 185 | −1.9 | 1004 |
| 186 | −3.3 | 23 |
| 187 | −2.4 | 55 |
| 188 | −1.2 | 7 |
| 189 | −1.6 | 9 |
| 190 | −1.7 | 3 |
| 191 | −2.7 | 22 |
| 192 | −2.2 | 31 |
| 193 | −1.8 | 6 |
| 194 | −2.4 | 11 |
| 195 | −2.7 | 4 |
| 196 | −2.4 | 53 |
| 197 | −2.2 | 10 |
| 198 | −2.1 | 5 |
| 199 | −2.5 | 6 |
| 200 | −2.7 | 8 |
| 201 | −1.6 | 16 |
| 202 | −3.0 | 9 |
| 203 | −1.8 | 14 |
| 204 | −2.3 | 7 |
| 205 | −2.4 | 5 |
| 206 | −2.6 | 7 |
| 207 | −2.5 | 7 |
| 208 | −2.2 | 4 |
| 209 | −1.9 | 11 |
| 210 | −2.7 | 7 |
| 211 | −2.5 | 8 |
| 212 | −2.5 | 6 |
| 213 | −2.6 | 13 |
| 214 | −1.9 | 3 |
| 215 | −1.9 | 9 |

Preferred compounds of the present invention show HDAC6 IC$_{50}$ values below 20 nM and a selectivity index vs HDAC3 below −1.6.

TABLE 3

Complete inhibition profile on all HDACs for some preferred compounds according to the invention (IC$_{50}$ nM)

| Comp | HDAC 1 | 2 | 3 | 8 | 6 | 4 | 5 | 7 | 9 | 10 | 11 |
|---|---|---|---|---|---|---|---|---|---|---|---|
| 1 | 1927 | 6663 | 2866 | 710 | 81 | 10113 | 12042 | 3528 | 5866 | 2477 | 2681 |
| 2 | 11585 | >30000 | 8648 | #N/D | 16 | 1459 | 1854 | 1087 | 592 | 14100 | 8050 |
| 6 | 7512 | 27504 | 7255 | 1024 | 7 | 1036 | 1046 | 750 | 756 | 10879 | 5172 |
| 8 | 1094 | 4017 | 979 | 1355 | 27 | 2994 | 2690 | 1484 | 1733 | 2008 | 1373 |
| 10 | 1015 | 4449 | 487 | 506 | 9 | 2502 | 2678 | 817 | 1084 | 2818 | 981 |
| 13 | 2886 | 11374 | 2492 | 490 | 4 | 606 | 512 | 623 | 640 | 2680 | 1470 |
| 15 | 7091 | 8799 | 6293 | 999 | 19 | 660 | 706 | 473 | 659 | 8625 | 4589 |
| 17 | 3991 | 16022 | 2827 | 193 | 9 | 1393 | 1538 | 550 | 496 | 6863 | 2289 |
| 19 | 2517 | 9478 | 2635 | 647 | 4 | 675 | 597 | 1017 | 592 | 2697 | 798 |
| 22 | 416 | 1561 | 271 | 933 | 5 | 3459 | 3742 | 1202 | 1854 | 684 | 423 |
| 23 | 616 | 2033 | 568 | 2831 | 11 | 4242 | 4812 | 6674 | 2686 | 1099 | 486 |
| 28 | 426 | 1568 | 373 | 270 | 10 | 1331 | 1170 | 1029 | 328 | 636 | 568 |
| 33 | 232 | 810 | 138 | 413 | 3 | 1914 | 2360 | 608 | 948 | 441 | 225 |
| 50 | 254 | 958 | 154 | 455 | 2 | 1950 | 1955 | 611 | 800 | 398 | 245 |
| 58 | 364 | 1748 | 206 | 1001 | 6 | 3930 | 3688 | 1511 | 2170 | 591 | 282 |
| 59 | 353 | 2315 | 448 | 547 | 7 | 2487 | 4125 | 820 | 1545 | 542 | 515 |
| 61 | 495 | 6911 | 488 | 494 | 9 | 1593 | 2515 | 529 | 884 | 991 | 904 |
| 65 | 2411 | 17667 | 1856 | 1081 | 6 | 831 | 1194 | 1076 | 995 | 1454 | 975 |
| 66 | 747 | 1035 | 921 | 419 | 6 | 481 | 325 | 214 | 168 | 1339 | 1006 |
| 77 | 581 | 5233 | 1152 | 795 | 17 | 2650 | 4467 | 1362 | 1732 | 2812 | 1441 |
| 79 | 2315 | 6747 | 1649 | #N/D | 8 | 541 | 687 | 1306 | 514 | 1912 | 659 |

TABLE 3-continued

Complete inhibition profile on all HDACs for some preferred compounds according to the invention (IC$_{50}$ nM)

| Comp | HDAC 1 | 2 | 3 | 8 | 6 | 4 | 5 | 7 | 9 | 10 | 11 |
|---|---|---|---|---|---|---|---|---|---|---|---|
| 80 | 4641 | 13782 | 1866 | 548 | 16 | 731 | 1281 | 764 | 426 | 5577 | 2816 |
| 85 | 469 | 1704 | 339 | 216 | 5 | 1030 | 559 | 514 | 452 | 954 | 557 |
| 98 | 1009 | 4236 | 8926 | 186 | 61 | 1614 | 2657 | 1990 | 844 | 1478 | 2086 |

Example 18—Cytotoxicity

Cytotoxic activity was evaluated on B 697 promyelocytic cell line for all synthesized compounds and on peripheral blood mononuclear cells (PBMCs) for compounds showing a good potency/selectivity profile.

Cells were seeded in plate ($2 \times 10^4$ cells per well for 697, $5 \times 10^5$ cells per well for PBMCs). The test compounds (concentrations from 1.5 nM to 10000 nM for PBMCs and from 1 nM to 10000 nM for 697) were added after 24 hours and incubated 72 hours. The molecules cytotoxic activity was evaluated using CellTiter 96© Aqueous One Solution Cell Proliferation Assay (Promega), which measures the mitochondria function, following the manufacturer's instructions.

IC$_{50}$ values are shown in Table 4. Most of the molecules shows a low toxicity.

TABLE 4

Cell Cytotoxicity on 697 cell line and PBMC (IC50 nM)

| comp. | 697 TOXICITY | PBMC TOXICITY (72 h) |
|---|---|---|
| 1 | 10390 | 7000 |
| 2 | 6079 | >1000 |
| 3 | 2878 | 735 |
| 4 | >10000 | 10000 > X > 1000 |
| 5 | 88692 | 10000 > X > 1000 |
| 6 | >10000 | 20000 |
| 7 | 4188 | 10000 |
| 8 | 8881 | 3500 |
| 9 | >10000 | >10000 |
| 10 | 4329 | 4500 |
| 12 | >10000 | 10000 > X > 1000 |
| 13 | 10000 > X > 1000 | 10000 > X > 1000 |
| 14 | 3941 | >10000 |
| 15 | 8723 | >10000 |
| 16 | 7882 | 7500 |
| 17 | 5203 | 9000 |
| 19 | 1164 | >10000 |
| 20 | 1121 | 2000 |
| 74 | 2283 | 2000 |
| 75 | 1199 | 514 |
| 76 | >10000 | >10000 |
| 77 | 11086 | 2000 |
| 78 | 22173 | 6000 |
| 79 | 22173 | 3000 |
| 82 | 6504 | n.a |
| 84 | 5203 | 4500 |
| 85 | 1157 | 2000 |
| 87 | 6656 | 6000 |
| 91 | 783 | 812 |
| 92 | >10000 | >10000 |
| 93 | >10000 | >10000 |
| 94 | 908 | n.a |
| 100 | 7092 | 10000 |
| 121 | 5911 | n.a |
| 122 | 1028 | n.a |
| 123 | 1970 | n.a |
| 125 | >10000 | >10000 |
| 129 | 13175 | n.a |
| 134 | >10000 | n.a |
| 141 | >10000 | n.a |
| 146 | >10000 | n.a |
| 147 | >10000 | n.a |
| 149 | 794 | n.a |
| 150 | 1256 | n.a |
| 151 | 287 | n.a |
| 152 | 1447 | n.a |
| 154 | 22668 | >10000 |
| 155 | 22670 | n.a |
| 156 | 1567 | >10000 |
| 157 | 913 | 940 |
| 158 | 16947 | n.a |
| 159 | 16945 | n.a |
| 160 | 16945 | n.a |
| 161 | 16945 | n.a |
| 162 | 16945 | n.a |
| 163 | 48981 | n.a |
| 164 | 1403 | 661 |
| 165 | 55283 | >10000 |
| 166 | 61437 | >10000 |
| 167 | 42998 | >10000 |
| 168 | 36855 | 7001 |
| 169 | 271 | 24 |
| 170 | 61431 | n.a |
| 171 | 6143 | >10000 |
| 172 | 61425 | >10000 |
| 173 | 1886 | 948 |
| 174 | 50287 | n.a |
| 175 | 10055 | 1261 |
| 176 | 50287 | 5302 |
| 177 | 50287 | >10000 |
| 178 | 50287 | >10000 |
| 179 | 50287 | >10000 |
| 180 | 40221 | >10000 |
| 181 | 50287 | >10000 |
| 182 | 50287 | 100000 |
| 183 | 50287 | n.a |
| 184 | 14691 | 100000 |
| 185 | 10448 | n.a |
| 186 | 10448 | 100000 |
| 189 | 291 | 1050 |
| 190 | 333 | 983 |
| 195 | 3124 | >10000 |
| 203 | 15161 | >10000 |
| 204 | 15369 | n.a |
| 205 | 15369 | n.a |
| 208 | 15369 | n.a |
| 209 | 15369 | n.a |
| 210 | 10414 | >10000 |
| 212 | 15369 | n.a |
| 213 | 15369 | n.a |
| 214 | 409 | n.a |
| 215 | 340 | n.a |
| 216 | 288 | n.a | n.a = not available

Preferred compounds of the present invention show $IC_{50}$ value for 697 cell line over 1000 nM and for PBMC over 5000 nM.

Example 19—Stability to Phase I Metabolism in Rat and Human S9 Liver Fraction

Test compounds were incubated in rat and human liver S9 fraction at 37° C. up to 90 minutes in order to evaluate their stability to Phase I metabolism by hepatic enzymes. Each test compound was incubated at μM concentration (50 μM when the samples were analysed by UV/HPLC, 1 or 2 μM when the samples were analysed by LC-MS/MS) with S9 fraction (protein content 2 mg/mL) in 100 mM phosphate buffer (pH 7.4), 3.3 mM $MgCl_2$ and 1.3 mM NADPH for 0, 10, 30, 60 and 90 minutes at 37° C. in a thermostated oscillating bath. The reaction was stopped placing samples on ice bath and adding acidified acetonitrile. After centrifugation (10 minutes at 14000 rpm) an aliquot of the supernatant was diluted water, filtered with 0.45 μm regenerated cellulose syringe filters and injected in HPLC-UV or in LC-MS/MS. The percentages of the amount remaining at the various incubation times with respect to the initial amount were calculated. The intrinsic clearance was also calculated.

Example 20—Stability in Rat and Human Plasma

In order to evaluate the stability to circulating enzymes, test compounds were incubated in human and rat plasma at 37° C. in a thermostated oscillating bath. Each test compound was incubated at μM (50 μM when the samples were analysed by UV/HPLC, 1 or 2 μM when the samples were analysed by LC-MS/MS) concentration for 0, 15, 30 min and 1, 2 and 4 hours. The reaction was stopped placing tubes on ice bath and adding acidified acetonitrile. After centrifugation for 10 minutes at 14000 rpm, an aliquot of the supernatant was diluted with water, filtered with 0.45 μm syringe filters and injected in HPLC-UV or in LC-MS/MS. The percentages of amount remaining at the various times of incubation with respect to initial amount were calculated. The half-life in plasma was also calculated.

In vitro metabolic stability data are summarized in Tables 5 and 5'. Most of the molecules showed a good stability.

TABLE 5

In vitro enzymatic stability assay of preferred compounds (residual percentage in S9 after 90 min and in plasma after 4 hours).

| comp. | rat plasma | human plasma | rat S9 fraction | human S9 fraction |
|---|---|---|---|---|
| 1 | 86 | 102 | 70 | 81 |
| 2 | 79 | 71 | 1 | 78 |
| 3 | 79 | 100 | 66 | 93 |
| 4 | 106 | n.a. | 34 | n.a. |
| 5 | 97 | n.a. | 36 | n.a. |
| 6 | 87 | 96 | 96.6 | 85.6 |
| 7 | 77 | 93 | 96 | 89 |
| 8 | 62 | 91 | 82 | 100 |
| 9 | 106 | n.a. | 75 | n.a. |
| 10 | 86 | 99 | 82 | 95 |
| 12 | 87 | n.a. | 44 | n.a. |
| 13 | 96.7 | 94 | 90.9 | 98 |
| 14 | 38 | 77 | 88 | 87 |
| 15 | 78 | 91 | 60 | 83 |
| 16 | 75 | n.a. | 74 | n.a. |
| 17 | 87 | 98 | 71 | 83 |
| 19 | 96 | 100 | 68 | 94 |
| 20 | 98.5 | 94.3 | 88 | 101.7 |
| 68 | 77 | n.a. | 34 | n.a. |
| 74 | 94 | 100 | 61 | 84 |
| 75 | 116 | n.a. | 75 | n.a. |
| 76 | 98 | 96 | 76 | 77 |
| 77 | n.a. | n.a. | 40 | n.a. |
| 79 | 99 | n.a. | 73 | n.a. |
| 85 | 76 | n.a. | 75 | n.a. |
| 87 | 0 | n.a. | 77 | n.a. |
| 91 | 93 | n.a. | 8 | n.a. |
| 92 | 79 | n.a. | 71 | n.a. |
| 93 | 10 | n.a. | 53 | n.a. |
| 94 | 75 | n.a. | 22 | n.a. |
| 95 | 75 | n.a. | 41 | n.a. |
| 100 | 80 | 92 | 30 | 76 |
| 121 | 100 | n.a. | 25 | n.a. |
| 122 | 94 | n.a. | 47 | n.a. |
| 123 | 99 | n.a. | 99 | n.a. |
| 125 | 78 | 77 | 90 | 83 |
| 129 | 93 | n.a. | 45 | n.a. |
| 134 | 76 | n.a. | 95 | n.a. |
| 138 | n.a. | n.a. | 79 | n.a. |
| 140 | 85 | n.a. | 12 | n.a. |
| 141 | 73 | n.a. | 36 | n.a. |
| 145 | 79 | n.a. | 7 | n.a. |
| 146 | n.a. | n.a. | 59 | n.a. |
| 147 | 89 | n.a. | 76 | n.a. |
| 149 | n.a. | n.a. | 84 | n.a. |
| 150 | 92 | n.a. | 35 | n.a. |
| 151 | 87 | n.a. | 62 | n.a. |
| 152 | 113 | n.a. | 31 | n.a. |
| 153 | 76 | n.a. | 91 | n.a. |
| 167 | 85 | 91 | 55 | 78 |
| 169 | 68 | n.a. | 44 | n.a. |
| 171 | 77 | 88 | 48 | 74 |
| 179 | 98 | 100 | 58 | 79 |
| 180 | 100 | 97 | 70 | 80 |
| 186 | 75 | n.a. | 9 | n.a. |
| 187 | 101 | 92 | 17 | 54 |
| 188 | 93 | 90 | 7 | 49 |
| 189 | 78 | 100 | 5 | 72 |
| 190 | 73 | 99 | 9 | 64 |
| 191 | 92 | 93 | 35 | 42 |
| 192 | 90 | 100 | 17 | 43 |
| 193 | 81 | 100 | 63 | 71 |
| 194 | 89 | 99 | 3 | 29 |
| 195 | 84 | 93 | 32 | 68 |
| 196 | 99 | 89 | 23 | 26 |
| 197 | 82 | 96 | 62 | 86 |
| 198 | 63 | 95 | 6 | 51 |
| 199 | 92 | 90 | 57 | 75 |
| 200 | 96 | 102 | 32 | 37 |
| 201 | 95 | 88 | 34 | 75 |
| 203 | 94 | 95 | 58 | 74 |
| 204 | 89 | 79 | 72 | 84 |
| 205 | 89 | 80 | 71 | 95 |
| 206 | 88 | 92 | 50 | 97 |
| 208 | 81 | 87 | 81 | 81 |
| 209 | 69 | 77 | 84 | 100 |
| 210 | 84 | 79 | 71 | 80 |
| 211 | 86 | 76 | 67 | 59 |
| 212 | 81 | 83 | 60 | 75 |
| 213 | 80 | 97 | 58 | 63 |
| 214 | 60 | 92 | 9 | 73 |
| 215 | 57 | 90 | 65 | 82 |
| 216 | 89 | 91 | 62 | 84 | n.a. = not available

Preferred compounds of the present invention show residual percentage in rat S9 fraction over 25%, in human S9 fraction over 85%, in rat plasma over 75% and in human plasma over 90%.

TABLE 5'

In vitro Enzyme stability assay (residual percentage in S9 after 90 min and in plasma after 4 h)

| comp. | rat plasma | rat S9 fraction |
|---|---|---|
| 22 | 81 | 6 |
| 23 | 77 | 8 |
| 25 | 77 | 9 |
| 28 | 90 | 68 |
| 29 | 103 | 74 |
| 30 | 49 | 63 |
| 31 | 76 | 0 |
| 33 | 52 | 2 |
| 36 | 60 | 38 |
| 37 | 6 | 82 |
| 38 | n.a. | 1 |
| 39 | 63 | 0 |
| 42 | n.a. | 16 |
| 44 | 32 | 87 |
| 45 | 81 | 69 |
| 47 | 76 | 0 |
| 49 | 82 | 57 |
| 54 | n.a. | 0 |
| 55 | n.a. | 46 |
| 57 | 94 | 71 |
| 58 | 106 | 15 |
| 59 | 53 | 8 |
| 61 | 71 | 49 |
| 62 | 83 | 55 |
| 65 | 88 | 8 |
| 66 | 66 | 54 |
| 67 | 101 | 44 |
| 70 | 79 | 18 |
| 71 | 4 | 58 |
| 80 | 77 | 32 |
| 83 | 76 | 92 |
| 89 | 70 | 97 |
| 96 | 99 | 41 |
| 98 | 89 | 88 |
| 99 | 91 | 108 |
| 101 | 73 | 9 |
| 102 | 82 | 16 |
| 103 | 79 | 5 |
| 109 | 10 | 72 |
| 110 | 92 | 16 |
| 115 | 73 | 57 |
| 116 | 78 | 65 |
| 117 | 82 | 88 |
| 135 | 78 | 96 |
| 137 | 100 | 52 |
| 139 | 90 | 40 | n.a. = not available

Preferred compounds of the present invention show residual percentage in rat S9 fraction over 25% and in rat plasma over 75%.

Example 21—In Vitro α-Tubulin and H3 Histone Acetylation in 697 Cell Line

The in vitro α-tubulin and H3 histone acetylation determination was evaluated on B 697 promyelocytic cell line.

The test molecules were diluted from 20 mM stock solution in DMSO with RPMI 10% FCS+0.01% DMSO medium at 20× concentration compared to the final concentration, added to the cells ($15 \times 10^6$ cells in a total volume of 30 ml in RPMI medium 10% FCS+0.01% DMSO) to obtain the final concentrations of 1000, 333, 111 and 37 nM and incubated at 37° C., 5% $CO_2$ for 16 hours.

At the end of the incubation period, $5 \times 10^6$ cells were taken from each sample, centrifuged for 5 minutes at 1100 rpm and washed in 0.9% NaCl at 4° C. The resulting pellet was lysed by treating at 4° C. for 30 minutes with 150 μl of Complete Lysis-M (Roche, cat-04719956051) containing protease inhibitors and phosphatase (Complete Easy Pack proteinase inhibitor cocktail tablets cat: 04693116001, Phostop easypack phosphatase inhibitor cocktails, cat: 01906837001—Roche), then centrifuged 10 minutes at 14,000 rpm (20817×g). 0.150 μg of supernatant (total protein extract) were diluted in 100 μl of 1×PBS and immobilized in Maxisorp F96 NUN-IMMUNO Plate (Nunc cat #5442404) at room temperature overnight. Plates were washed twice with Wash Buffer (PBS1X+0.005% tween 20) and saturated for 1 hour at room temperature with 300 μL of 1×PBS containing 10 FCS. After washing with buffer (1×PBS containing 0.005% tween), the plates were incubated for two hours at room temperature in the presence of anti-acetylated-α-tubulin antibody (Monoclonal Anti-acetylated-tubulin clone 6-11B-1, mouse ascites fluid, cat #T6793 Sigma, 100 μl diluted 1:1000 in 1×PBS containing 10% FCS) or with total anti-α-tubulin antibody (Monoclonal Anti alpha-tubulin produced in mouse, cat #T6074 Sigma). After washing, 100 μl per well of TMB substrate kit was added for 10 minutes at room temperature in the dark. The reaction was stopped by adding 50 μl of 2N $H_2SO_4$. The plates were read at Multiskan Spectrum spectrophotometer at a wavelength of 450 nm.

The degree of acetylation was calculated by dividing the absorbance obtained for acetylated α-tubulin by the absorbance of total α-tubulin.

The remaining cells ($10 \times 10^6$) were treated by acid extraction of histones (Kazuhiro et al., PNAS (2002), 99 (13) 8921-8926). Cells were centrifuged 5 min at 1100 rpm at 4° C. and washed once in 0.9% NaCl. The resulting pellet was lysed with lysine buffer (10 mM Tris.HCl, pH 6.5/50 mM sodium bisulphite, 1% Triton X-100/10 mM $MgCl_2$/8.6% saccharose containing the protease inhibitor mixture (Roche)) for 20 min at 4° C. The resulting nucleus pellet was repeatedly washed in buffer until supernatant clarification (centrifuged at 7,500×g, 5 minutes after each wash) and finally washed in nucleus buffer (10 mM Tris.HCl/13 mm EDTA, pH 7, 4) and resuspended in 250 μl of 0.2 M HCl/$H_2SO_4$. Histone proteins were extracted in an acidic environment by incubating overnight at 4° C. under gentle shaking. After centrifugation at 14,000 rpm at 4° C. for 10 minutes, 1250 μl of cold acetone was added to the supernatant and incubated overnight at −20° C., resulting in the precipitation of histone proteins. The pellet obtained after centrifugation for 10 minutes at 14000 rpm and 4° C. was washed with cold acetone, evaporated to dryness and resuspended in 50 μl distilled water. The protein content determination of both total and histone extracts was carried out by a colorimetric assay using a BCA Protein Assay Kit (Pierce cat: 23227).

H3 histone acetylation and total H3 amount were quantified by commercial ELISA assays PathScan acetylated histone H3 Sandwich Elisa kit, cat #7232C and PathScan total histone H3 Sandwich Elisa Kit, cat #7253C Cell Signaling) according to supplier reported method and by detecting absorbance at 450 nm wavelength using Multiskan Spectrum. ELISA tests were performed by analysing 0.250 μg and 0.500 μg of histone extract of each sample. The degree of acetylation was calculated by dividing H3 histone absorbance by histone total absorbance.

Test results of tubulin and H3 histone acetylation, expressed as fold increase of ratio of acetylated α-tubulin/total α-tubulin and H3Ac/H3Tot, respectively, of each sample relative to the control sample (untreated) are summarized in Tables 6 and 6'. The molecules showed a good tubulin acetylation and a poor H3 histone acetylation.

Givinostat, a pan-HDAC inhibitor, has been used as a reference compound. As expected, the reference compound showed a good acetylation of both tubulin and H3 histone. Example 43 of WO 2012/106343, a HDAC inhibitor, has been used as comparative compound in order to show the unexpected effects of the compounds of the invention over a compound of the prior art having the following formula:

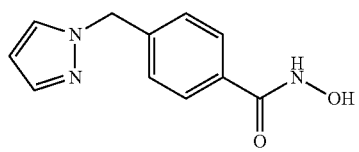 [SMILES: O=C(NO)c1ccc(Cn2cccn2)cc1]

Example 43

TABLE 6

Tubulin acetylation in 697 cell line (fold increase of the ratio of acetylated tubulin and total tubulin towards control).

| Comp. | Conc (nM) | | | |
|---|---|---|---|---|
| | 1000 | 333 | 111 | 37 |
| 8 | 12 | 9 | 4 | 3 |
| 10 | 16 | 13 | 7 | 3 |
| 15 | 12 | 5 | 3 | 1 |
| 17 | 10 | 9 | 8 | 3 |
| 19 | 17 | 21 | 15 | 7 |
| 100 | 14 | 9 | 3 | 2 |
| 7 | 11 | 8 | 3 | 2 |
| 125 | 14 | 6 | 3 | 1 |
| 167 | 13 | 9 | 3 | 2 |
| 168 | 16 | 19 | 11 | 3 |
| 171 | 22 | 20 | 19 | 10 |
| 179 | 14 | 6 | 7 | 2 |
| 180 | 19 | 15 | 7 | 2 |
| 195 | 14 | 10 | 11 | 6 |
| Example 43 (prior art) | 7 | 3 | 1 | 1 |
| Givinostat | 18 | 12 | 4 | 1 |

Relative to Example 43, the molecules of the invention showed a higher acetylation of tubulin.

TABLE 6'

Acetylation of H3 histone in 697 cell line (fold increase of the report between acetylated H3 and total H3 towards control).

| comp. | Conc (nM) | | |
|---|---|---|---|
| | 1000 | 333 | 111 |
| 8 | 3 | 2 | 1 |
| 10 | 2 | 1 | 1 |
| 17 | 2 | 1 | 2 |
| 15 | 1 | 1 | 1 |
| 19 | 2 | 2 | 1 |
| 100 | 2 | 3 | 1 |
| 7 | 1 | 1 | 1 |
| 125 | 1 | 1 | 1 |
| 167 | 2 | 1 | 1 |
| 168 | 2 | 1 | 1 |
| 171 | 3 | n.a. | n.a. |
| 179 | 1 | n.a. | n.a. |
| 180 | 1 | n.a. | n.a. |

TABLE 6'-continued

Acetylation of H3 histone in 697 cell line (fold increase of the report between acetylated H3 and total H3 towards control).

| comp. | Conc (nM) | | |
|---|---|---|---|
| | 1000 | 333 | 111 |
| 195 | 1 | 1 | 1 |
| Example 43 (prior art) | 1 | 1 | 1 |
| Givinostat | 23 | 17 | 8 | n.a. = not available

With the exception of Givinostat, all the molecules showed a poor acetylation of the H3 histone.

Example 22—Pharmacokinetics

Plasma levels and main pharmacokinetic parameters of test compounds were evaluated after single intravenous and oral administration to the mouse.

The doses administered were 1.3-2.6 mg/kg via intravenous route and 2.6-5.2 mg/kg by oral gavage. The formulations were prepared in a mixture of DMSO/PEG400/$H_2O$. Blood was collected at the following sampling times: 5, 10, 15, 30 minutes, 1, 2, 4 and 6 hours after administration. Plasma samples (100 µL) were deproteinized by addition of 1% formic acid in ACN, then vortex mixed and centrifuged. For each sample, an aliquot of the supernatant was collected and diluted with water, filtered with 0.45 µm regenerated cellulose filter and analysed by LC-MS/MS. Plasma levels of the test compounds were calculated on a calibration curve prepared in the range 0.5-200 ng/mL.

Pharmacokinetic parameters were calculated on the mean plasma concentration curve using the software Kinetica™ v. 5.1, with a non-compartmental method.

Main parameters are summarized in Table 7. The three molecules tested showed good oral bioavailability.

TABLE 7

Pharmacokinetic parameters in mouse for three preferred compounds

| | comp. 8 | | comp. 17 | | comp. 10 | |
|---|---|---|---|---|---|---|
| | i.v. | Os | i.v. | Os | i.v. | Os |
| Dose (mg/kg) | 2.6 | 5.2 | 1.3 | 2.6 | 2.6 | 5.2 |
| Cmax (ng/mL) | — | 238 | — | 60 | — | 144 |
| Tmax (h) | — | 0.08 | — | 0.08 | — | 0.25 |
| $AUC_{tot}$ (ng*h/mL) | 253 | 94 | 114 | 42 | 239 | 123 |
| C0 (ng/mL) | 1287 | — | 727 | — | 949 | — |
| CL (L/h*kg) | 10.3 | — | 11.4 | — | 10.9 | — |
| Vd (L/kg) | 15.3 | — | 16.8 | — | 20.5 | — |
| $T_{1/2}$ (h) | 1 | — | 1 | — | 1.3 | — |
| F % | | 18.5 | | 18.4 | | 25.8 |

Example 23—Evaluation of Maximum Tolerated Dose (MTD)

Following chronic intraperitoneal administration in C57BL/6 mice, compounds MTD was estimated by clinical (body weight and behaviour) and blood (white blood cells and platelets) parameters evaluation. The compounds were administered after dissolution in a $H_2O$/PEG400 mixture in ratio 1:1 w/w containing 5% DMSO (for compound 17, 20% DMSO was used).

All animals were weighed the day before the treatment (day 0) and the average body weight was determined.

Animals (8 animals per group) were treated once a day starting from Day 1 during 5 consecutive days per week with:
 a) the compounds at doses of 10, 30, 50 mg/kg ip,
 b) Givinostat at 100 mg/kg (internal control) and
 c) the vehicle solutions used for solubilizing the substances.

The volume of the solutions administered was 10 mL/Kg. The treatment was repeated for 2 weeks, for a total of 10 treatments/group.

On a daily basis any clinical sign (skin appearance, mobility and animal reactivity, respiration, etc.) indicating a possible toxicity of the compounds has been reported. The animal weight was evaluated on days 2, 4, 9 and 11.

On Day 1, 3, 5, 8, 10 and 12, blood sample (about 50 µL) were taken from the tail of the animal to evaluate the effect of the substances on blood parameters. Withdrawals were performed on 4 animals per group on alternate days.

Samples were harvested in tubes containing EDTA, appropriately diluted in physiological solution and analysed with a cell counter.

At the end of the study (day 12) the animals were sacrificed 60 minutes after the last treatment. Gross necropsy evaluation was performed to detect any internal organ abnormalities. Table 8 summarizes the data obtained in MTD determination experiments for some of the compounds according to the invention. Givinostat is a HDAC pan inhibitor and was used as a reference. The tested molecules are well tolerated.

TABLE 8

Day 12 values of parameters monitored in the MTD experiment on mouse for four of the preferred compounds according to the invention

|  | Body weight % vs control | Platelet % vs control | White blood cells % vs control |
|---|---|---|---|
| Compound 8 50 mg/kg | −0.3 | 12 | −15 |
| Compound 10 50 mg/kg | 1.7 | 3.6 | −30 |
| Compound 17 30 mg/kg | −6 | −17 | −22 |
| Compound 50 50 mg/kg | 0 | −0.1 | −47 |
| Givinostat 100 mg/Kg | 0.9 | −7 | −72 |

Example 24—T CD4 Lymphocyte Proliferation Mediated by Mouse Regulatory T Cells Suppression Assay To evaluate the ability of the molecules under this patent to increase regulatory T cell (Treg, $CD4^+CD25^+$) suppression activity a T-cell (responder T cells, Teff) proliferation suppression assay was used. Treg cells at different concentrations were cultured with Teff cells ($CD4^+CD25^-$) in the presence of proliferative stimuli. T cells need of two stimuli to proliferate: the first given by the recognition of antigen associated with MHC by T cell receptor (TCR) and the second one derived from co-stimulatory molecules such as CD28. In the absence of a specific antigen, TCR activation can take place with an antibody recognizing one of the composing subunits, CD3ε. In this assay, anti-CD3ε monoclonal antibody and CD4 T cell depleted splenocytes were used as activator stimuli. Therefore, the ability to reduce Teff cells proliferation by Tregs in the presence or absence of HDAC6 inhibitors was assessed.

Treg and Teff cells were separated using the Treg isolation kit based on magnetic beads separation technique (Miltenyi Biotec) through an initial negative selection and a final positive selection process.

Single cell suspension was obtained from spleen of C57BL/6 mice using a 70 µm strainer.

Cell suspension was treated with ACK buffer to lyse red blood cells and then centrifuged for 5 minutes at 300×g. After centrifugation, the cells were resuspended in PBS (Phosphate Buffered Saline, Gibco) and counted. Subsequently, splenocytes were resuspended in a buffer consisting of PBS, 0.5% BSA and 2 mM EDTA.

To proceed with the first step of Treg separation, CD4 negative cells were indirectly magnetically labeled with a cocktail of biotin-conjugated antibodies against CD8a, CD11b, CD45R, CD49b, Ter-119 and Anti-Biotin Micro-Beads CD4+ cells were thus obtained by negative selection as flow-through of a magnetic MACS column.

Cells bound to microbeads were eluted and conserved for their use as antigen presenting cells (APC) in the proliferation assay.

Figure 6:
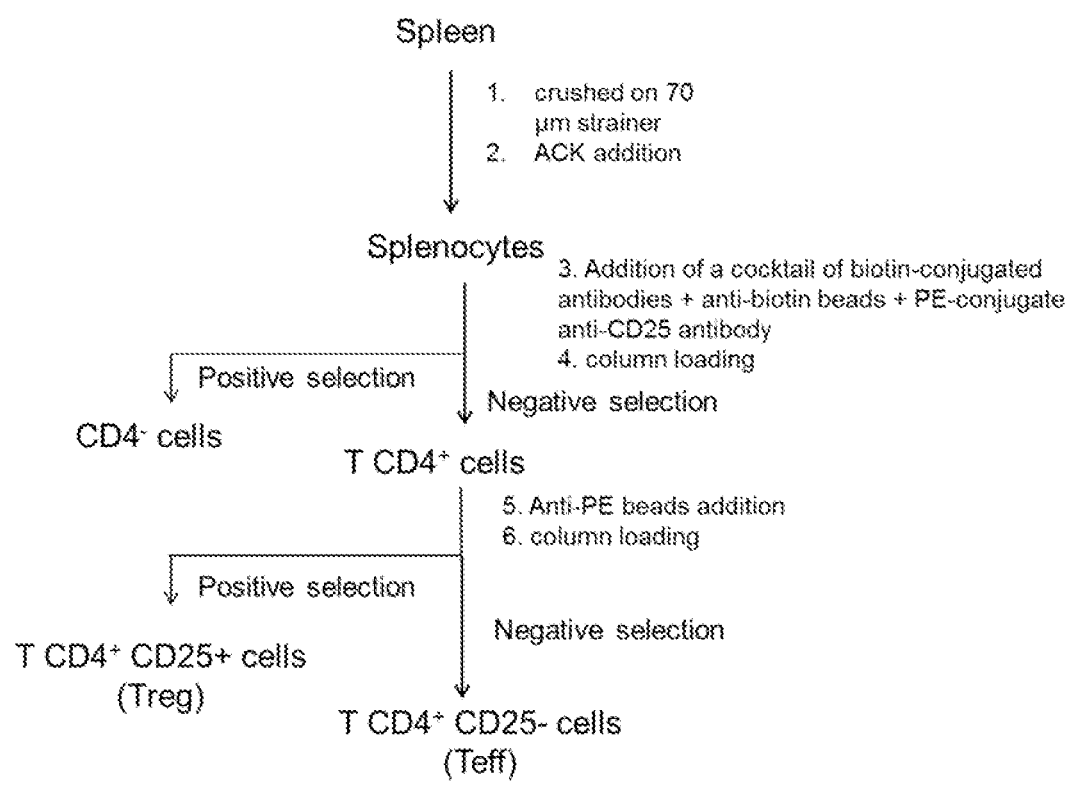
FIG. 6: Purification scheme for Treg and Teff cell purification.

In the second step of Treg purification, pre-enriched CD4+ cells were labelled with an R-phycoerythrin (PE)-conjugated anti-CD25 antibody that preferentially binds to Treg cells and magnetic beads coupled with an anti PE antibody. The cell suspension was then loaded on a column. The Teff cells pass through the column without binding (negative selection), while beads-bound Treg cells adhere through the magnetic beads (positive selection). Treg cells were then eluted from the column by buffer flow using a plunger. Treg and Teff cell purification is summarized in FIG. 6.

CD4− cells from first positive selection as APC
 Treg CD4+ CD25+ as suppressor cells
 Teff CD4+ CD25− as responder/proliferating cells $CD4^-$ cells were treated with mitomycin C (50 µg/ml, Sigma) for 30 min at 37° C. to prevent their proliferation They were then resuspended at a concentration of $4.0\times10^5$/50 µl in complete medium (RPMI, FBS10%, penicillin/streptomycin 1×, 50 µM beta mercaptoethanol). Teffs were labeled with carboxy fluorescein succinimidyl ester (CFSE) at a concentration of 2 µM in PBS at 37° C., and after 10 minutes incubation, the reaction was blocked with a 10% FBS PBS solution. CFSE labelling allows covalent modification of Teff cell to analyse their proliferation by fluorescence dilution. The labelled Teffs were then centrifuged and resuspended at the final concentration of $5.0\times10^4$/50 µl in complete medium. Finally, the Tregs obtained by purification were diluted to the final concentration of $5.0\times10^4$/50 µl in complete medium.

Then a co-culture of Teff ($5.0\times10^4$), T CD4− ($4.0\times10^5$) was prepared and Treg cells in different ratios (1:1, 1:2, 1:4, 1:8 ratio Teff to Treg cells) were added thereto. The test compounds at different concentrations or DMSO vehicle were added to the cell suspension. Finally, an anti-CD3ε monoclonal antibody (Miltenyi Biotec) was added at a concentration of 1 µg/ml. Cells were plated in flat bottom 96-well plates and each condition was set up in a technical duplicate. To determine how the different substances directly influence cell proliferation, the effect of the compounds on a labelled Teff and CD4 cells− co-culture in the presence of stimulus provided by anti-CD3ε monoclonal antibody, in the absence of Treg cells, was evaluated. The cell proliferation negative control has been determined only on labelled Teffs which, in the absence of T CD4⁻ and anti-CD3ε monoclonal antibody should not proliferate.

After 72 h incubation, the co-cultured cells were labelled with a PE/Cy5-labelled anti-CD4 antibody (1:200 dilution, Biolegend) for 15 minutes at room temperature (RT). After labelling, the cells were washed and resuspended in 200 µl of PBS.

The percentage of proliferated Teff was detected by flow cytometry by observing the dilution of the signal from CFSE within the T CD4+ cells population. CFSE labelling is inherited by daughters cells after mitosis induced by cell activation. CSFE fluorescence signal analysis allows to obtain the percentage of proliferating cells which are represented by populations with lower fluorescence with respect to non-proliferating population.

In this assay, direct antiproliferative activity of the substances tested must be excluded. Thus, a threshold has been established whereby, if a proliferation reduction >10% in Teff cells without Treg is observed, the proliferation inhibitory cannot entirely be attributed to the induction of Treg's suppressor activity alone.

To compare compounds effect on Treg's suppressive ability, the standardized proliferation rate was calculated by applying the min-max standardization to proliferation rates for each sample compared to control. The obtained values were converted into a standardized suppression percentage:

Standardized suppression=100−(% standardized proliferation)

The area under the curve (AUC) of the plot of the standard suppression percentage values was then calculated. The relative suppression given by formula: (AUC drug/AUC control) is the value that allows the comparison of the activity of the compounds. The above procedures have been performed by data processing using the GraphPad Prism 7 software.

Further details of the entire procedure can be found in Akimova et al., Methods Mol Biol (2016), 1371: 43-78.

The results of Treg cell suppression assay are reported in Tables 9 and 10. A compound with RS greater than 1.5 induces a good suppression activity in Treg cells. RS values above 2.5 indicate a high activity in this assay. Many of the tested molecules show high activity.

TABLE 9

Relative T-reg suppression for some of the preferred compounds of the invention

| Comp. | Concentration, µM | # of experiments | RS |
|---|---|---|---|
| 8 | 0.25 | 2 | 1.5 |
| 8 | 0.5 | 1 | 2.24 |
| 8 | 1 | 1 | 2.1 |
| 10 | 1 | 4 | 5.2 |
| 10 | 0.75 | 3 | 7.4 |
| 10 | 0.5 | 5 | 3.2 |
| 15 | 1 | 3 | 3.0 |
| 17 | 1 | 6 | 1.9 |
| 17 | 0.5 | 3 | 1.7 |
| 19 | 1 | 2 | 2.3 |
| 6 | 1 | 3 | 1.7 |
| 13 | 1 | 3 | 1.9 |
| 77 | 1 | 3 | 2.4 |
| 79 | 1 | 1 | 1.7 |
| 85 | 1 | 2 | 3.8 |

TABLE 9-continued

Relative T-reg suppression for some of the preferred compounds of the invention

| Comp. | Concentration, µM | # of experiments | RS |
|---|---|---|---|
| 85 | 0.5 | 3 | 3.0 |
| 85 | 0.25 | 3 | 2.0 |
| ctrl | 1.5 | 23 | 1.8 |

TABLE 10

Relative T-reg suppression for other compounds according to the invention

| Comp. | Concentration, µM | # of experiments | RS |
|---|---|---|---|
| 22 | 0.25 | 5 | 4.2 |
| 23 | 0.25 | 3 | 4.2 |
| 28 | 0.25 | 1 | 2.9 |
| 33 | 0.10 | 2 | 4.6 |
| 50 | 0.25 | 5 | 4.2 |
| 58 | 0.25 | 1 | 3.4 |
| 59 | 0.5 | 1 | 4.8 |
| 61 | 1 | 3 | 1.1 |
| 65 | 1 | 3 | 4.4 |
| 66 | 1 | 3 | 2.6 |
| ctrl | 1.5 | 23 | 1.8 |

Example 25—Mixed Lymphocytes Reaction (MLR) with Human PBMCs

In order to study HDAC6 inhibitors ability to inhibit the activation of allogenic T CD4+ cells, a Mixed Lymphocytes Reaction (MLR or mixed lymphocyte culture, CLM) assay was performed. This is a reaction involving blast transformation of in vitro cultured lymphocytes in the presence of allogeneic lymphocytes. There is the so-called "two-way" reaction wherein the two lymphocyte populations stimulate each other to proliferate, and the so-called "one way" reaction, wherein the proliferation of one of the two populations is inhibited by mitomycin C or irradiation, these cells provide proliferation stimulus (stimulator) to the so-called "responder" cells.

Human peripheral blood mononuclear cells (PBMCs) used in MLR were obtained by Ficoll gradient separation from Buffy Coat of healthy donors.

We used a two-way MLR. The cells from the two donors were plated at 1:1 ratio (allogenic stimulation) to the final concentration of $2 \times 10^5$ per well in U-bottom 96 well plates in RPMI 1640 medium with 10% FBS and antibiotics. As a control we individually plated the cells from each donor (singenic stimulus). The experiment for each inhibitor was set in deduplicate for allogeneic stimuli and in quintuplicate for singenic stimuli. The cells were cultured for 6 days in an incubator at 37° C.

After 6 days the effect of the test compounds was evaluated by measuring the production of pro-inflammatory cytokines recognized to be characteristics of this assay.

For this purpose, the culture supernatant was harvested and used for IFN-γ, TNF-α and IL-6 inflammatory cytokine assay.

The results of MLR tests are summarized in Tables 11 and 12. The JAK inhibitor ruxolitinib was used as the active reference compound in the test.

TABLE 11

MLR test for some preferred compounds according to the invention

| comp. | Concentration µM | MLR exp # | IFN-γ | TNF-α | IL-6 |
|---|---|---|---|---|---|
| 8 | 1 | 2 | 15.7 | 28.1 | −1.5 |
| 8 | 0.5 | 3 | 35.3 | 35.1 | −13.0 |
| 8 | 0.25 | 2 | 24.1 | 54.7 | −33.1 |
| 10 | 1 | 7 | 25.6 | 49.4 | 20.6 |
| 15 | 1 | 6 | 21.0 | 33.9 | 22.9 |
| 17 | 1 | 3 | 41.6 | 39.4 | 31.2 |
| 19 | 1 | 2 | −7.85 | 25.9 | 4.62 |
| 6 | 1 | 3 | −6.5 | 13.5 | 15.5 |
| 13 | 1 | 3 | −10.9 | 37.2 | 38.3 |
| 77 | 1 | 4 | 32.1 | 64.2 | 34.3 |
| 79 | 1 | 3 | 27.5 | 50.9 | 38.6 |
| 85 | 1 | 5 | 51.8 | 73.8 | 66.9 |
| ctrl | 1.5 | 17 | 20.6 | 32.0 | 13.8 |
| ruxolitinib | 0.05 | 15 | 87.9 | 61.2 | 73.3 |

Values in the table indicate the inhibition percentages. Negative values indicate an induction.

TABLE 12

MLR Test for Other Compounds according to the Invention

| comp. | Concentration, µM | MLR exp # | IFN-γ | TNF-α | IL-6 |
|---|---|---|---|---|---|
| 58 | 0.25 | n.a | n.a | n.a | n.a |
| 59 | 0.5 | n.a | n.a | n.a | n.a |
| 61 | 1 | 1 | 16 | n.a | −21 |
| 65 | 1 | 2 | 45.0 | 67.3 | 5.4 |
| 66 | 1 | 3 | 53.0 | 42.8 | 12.9 |
| ctrl | 1.5 | 17 | 20.6 | 32.0 | 13.8 |
| ruxolitinib | 0.05 | 15 | 87.9 | 61.2 | 73.3 |

Example 26—Inhibition of the Expression of PD-L1 in In Vitro Derived Dendritic Cells The current literature describes that selective HDAC6 inhibitors have a great potential as immune modulators to be used in cancer immunotherapy (Tavares M T et al. ACS Med Chem Lett. 2017; 8(10):1031-1036).

Solid tumors are known to have a strong myeloid component that contributes to tumor development, progression and dissemination.

Dendritic Cells (DCs) are professional antigen-presenting cells (APCs) which play a crucial role in the regulation of the adaptive immune response. They can efficiently present neo tumor antigens in the context of MHC class I and II to stimulate T cell responses against the tumor. However, in the tumor microenvironment, cancer cells can dampen the activation of T cells via DCs in various ways. This activity is exemplified by the induction of the expression of the immune checkpoint inhibitor PD-L1 on the DC surface. PD-L1 can interact with PD-1 expressed on T cells and repress their activation. Thus, reduction of PD-L1 expression on the DC may represent a means to counter this process.

We hypothesized that selective HDAC6 inhibition could reduce the expression of PD-L1 on DCs, thus increasing their T cell stimulatory activity.

To obtain in vitro derived DCs, human monocytes purified from PBMC, were treated for 5 days with GMCSF (50 ng/ml) and IL-4 (10 ng/ml) in the presence of two selective HDAC6 inhibitors described in this invention (compounds 10 and 19) and the HDAC inhibitor example 43 of WO 2012/106343. Control cells were treated with the inhibitor's vehicle. This procedure induces the formation of immature dendritic cells (iDCs) that express PD-L1 (Brown J A et al. J Immunol. 2003; 170:1257-66). After 5 days, iDCs were analyzed for the expression of the inhibitory marker PD-1.

As shown in FIG. 1 compounds 10 and 19 of this invention, reduced the PD-L1 expression in a statistically significant way. Conversely, example 43 of WO 2012/106343 was not able to reduce PD-L1 expression, indicating a different biological activity of this molecule compared to what observed for compounds 10 and 19.

Example 27—In Vivo Murine Tumor Models

Four different immune-oncology mouse models of cancer were used to evaluate the in vivo efficacy of compounds 8 and 10 of this invention. In this experiment, we compared the efficacy of an anti PD-1 antibody with that shown by the HDAC6 inhibitors. Anti PD-1 targets the immune checkpoint PD-1/PD-L1 axis and is an established immunotherapy in a growing number of malignancies (Pardoll D. M., Nature Reviews Cancer, 2012, 12: 252-264).

Tumors were induced in immunocompetent mice using the following cell lines:
- EMT6 (murine breast cancer)
- CT26 (murine colon cancer
- 4T1 (triple negative murine breast cancer)

According to the literature, the sensitivity of these murine tumors to anti PD-1 treatment is summarized in the following table:

| Cell line | Expected sensitivity to anti-PD-1 in vivo |
|---|---|
| EMT6 | ++++ |
| CT26 | +++ |
| 4T1 | ++ |

Therapeutic treatment started when tumor nodules reached approximately 3 mm in diameter.

Compounds 8 and 10 were administered by oral gavage once a day for 5 days a week at 50 mg/kg.

Anti PD-1 antibody was administered three times a week by ip injection at 10 mg/kg.

Figure 2:
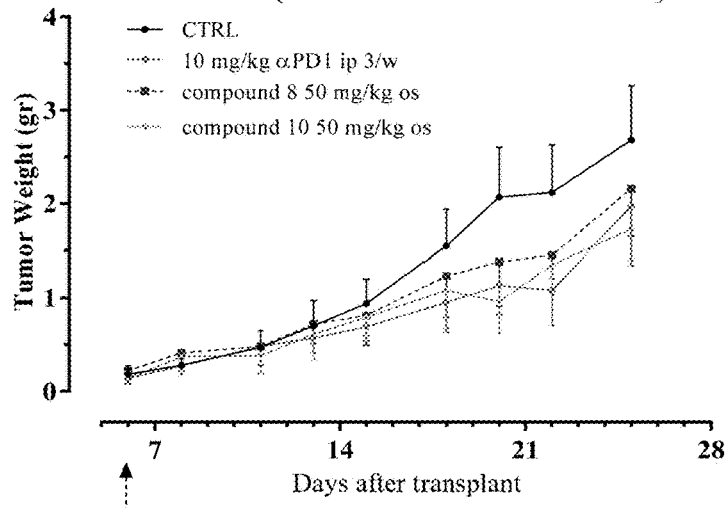
FIG. 2: Compounds 8 and 10 reduce tumor growth in vivo and have comparable efficacy of an anti PD-1 antibody. The arrow indicates the treatment starting day.
Figure 2:
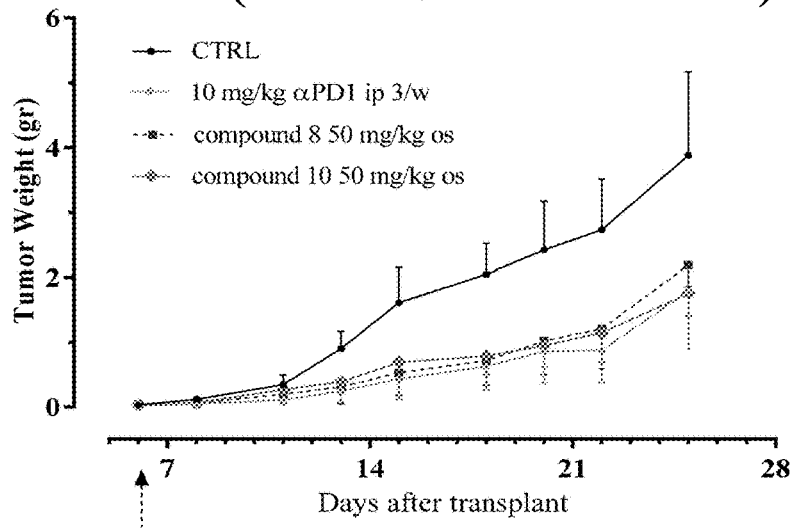
Figure 2:
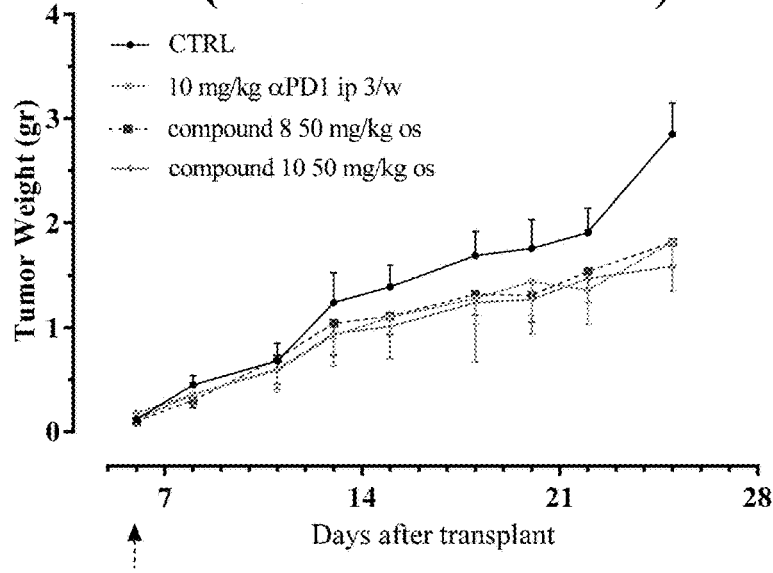

The results of the experiments are shown in FIG. 2. Compounds 8, 10 and the anti PD1 antibody had comparable efficacy in reducing tumor growth. The results are also in agreement with the expected efficacy of anti PD-1 antibody. The selective HDAC6 inhibitors of this invention have reduced direct anti-tumor activity as exemplified by the lack of cytotoxic activity in vitro. Therefore, the in vivo results in these immune-oncology models suggest that treatment with selective HDAC6 inhibitors leads to a possible activation of anti-tumor immune response.

To demonstrate that the in vivo antitumor activity of compounds 8 and 10 is mediated by an activation of the immune system, we carried out further experiments using the CT-26 murine model.

Adult BALB/c mice were injected s.c. with $1 \times 10^6$ CT26 tumor cells (diluted to 100 ul with phosphate-buffered saline). One week later, mice were given daily compounds 8 and 10 p.o. at 50 mg/Kg and/or injected with anti-PD1 antibody at 10 mg/Kg. At time of sacrifice, spleens were taken to analyze ex vivo, the tumor immune response. Spleen cells were stimulated with a mixture of CT-26 tumor specific peptides recognized in the context of both MHC I and MHC II. Thus, using this ex vivo stimulation, a specific tumor response mediated by CD4 and CD8 T cells can be detected.

Figure 3:
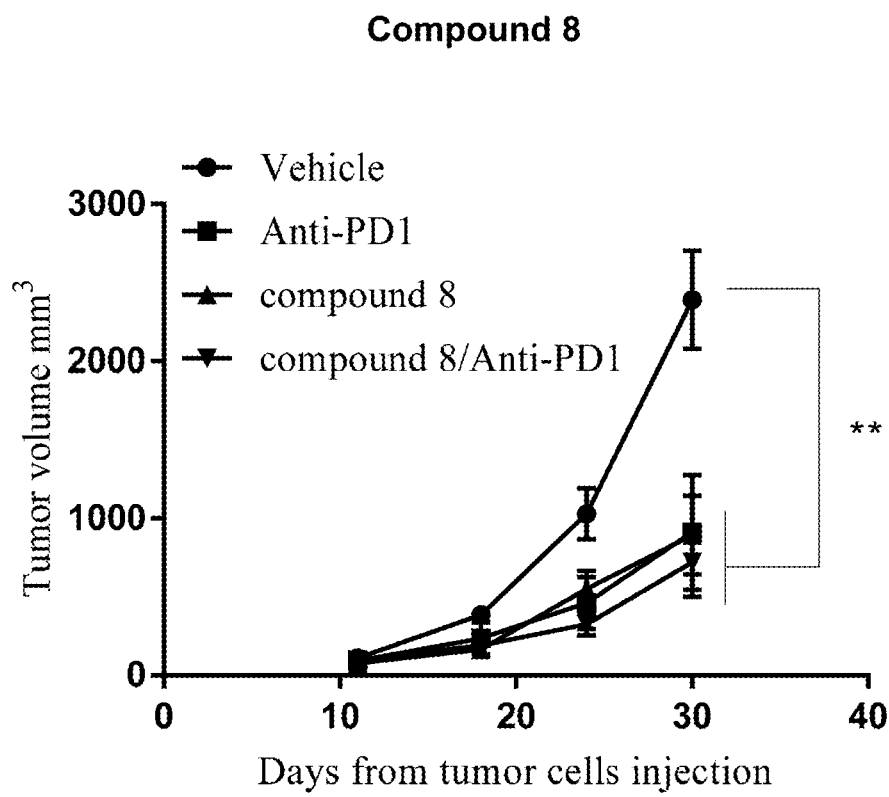
FIG. 3: HDAC6 inhibitors reduces CT-26 tumor growth in vivo and their activity can be improved by combined treatment with anti PD-1 antibody. Statistics was evaluated at day 30 by Student's t test. *, P<0.05; , P<0.01; *, P<0.001. See text for further details.
Figure 3:
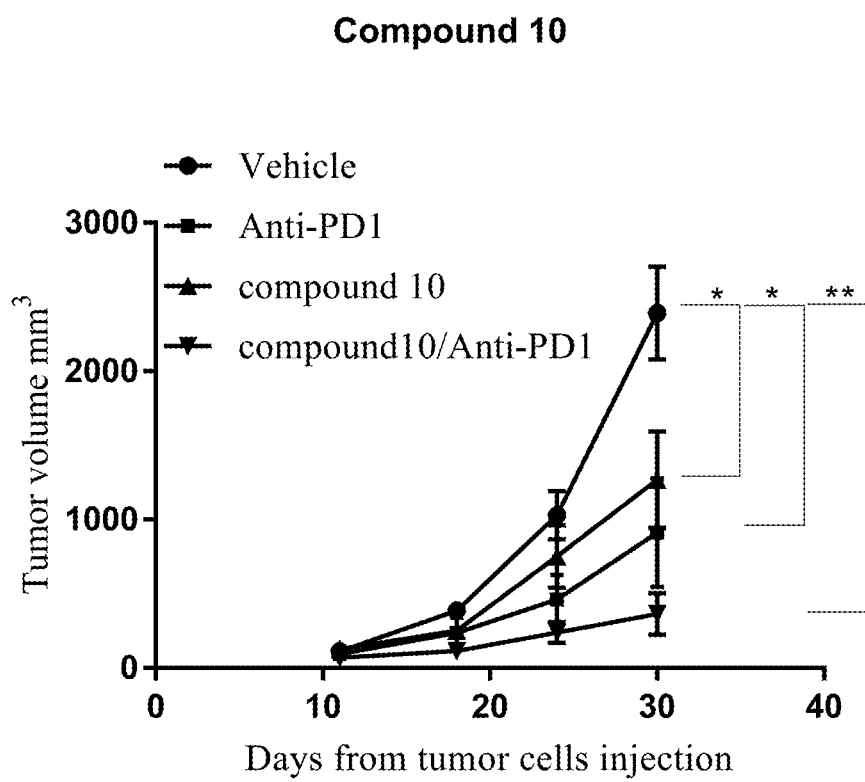

The results shown in FIG. 3 confirm the previous data of efficacy of our molecules as single agents in reducing tumor growth. This reduction was again comparable to that obtained with anti PD-1 antibody. Additionally, combination treatment of anti PD-1 antibody and HDAC6 inhibitors lead to further improvement, especially with compound 10.

To demonstrate specific activation of immune system against the tumor, spleens of the animals were isolated and splenocytes were cultured in the presence of specific CT-26 peptides recognized by both CD4 and CD8 T cells (Kreiter S. et al. Nature, 2015, 520:692-696).

Figure 4:
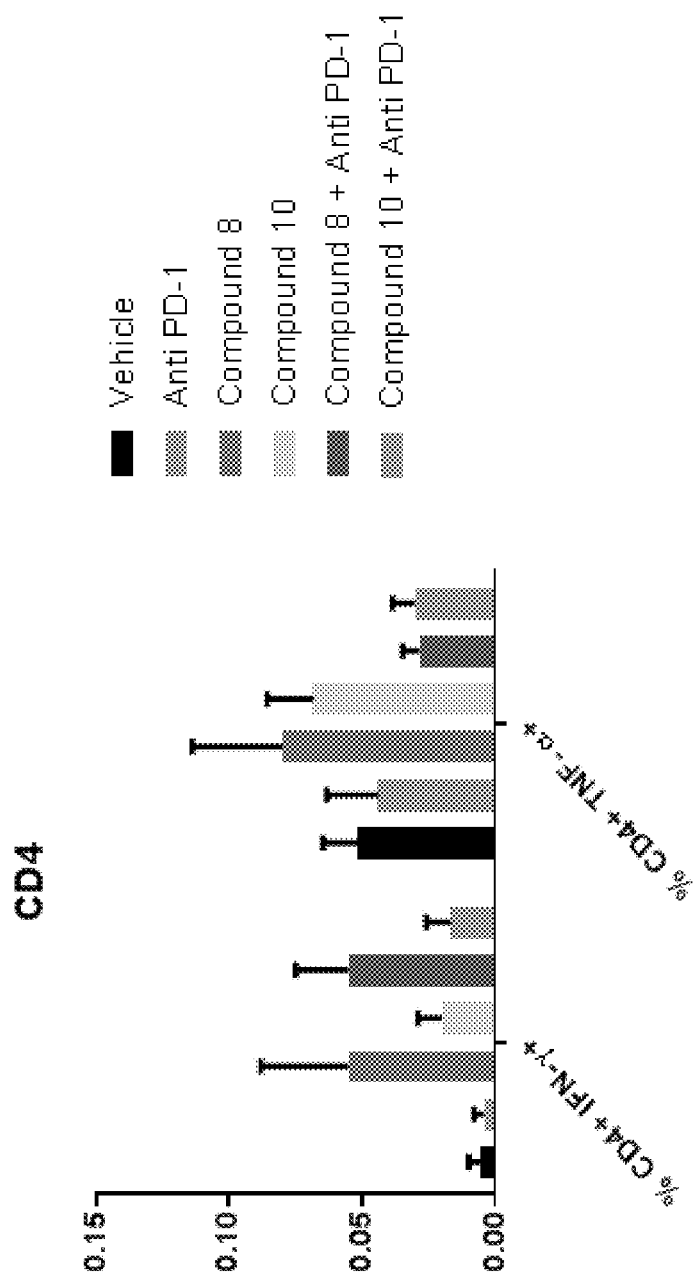
FIG. 4: In vivo Treatment with selective HDAC6 inhibitors induced specific T cell response. Splenocytes of animal treated with Compounds 8 and 10 and the combination with anti PD-1 Ab were stimulated with CT-26 derived tumor peptides and the production of IFN-γ and TNF-α by CD4 T cells was quantified by ELISPOT.
Figure 5:
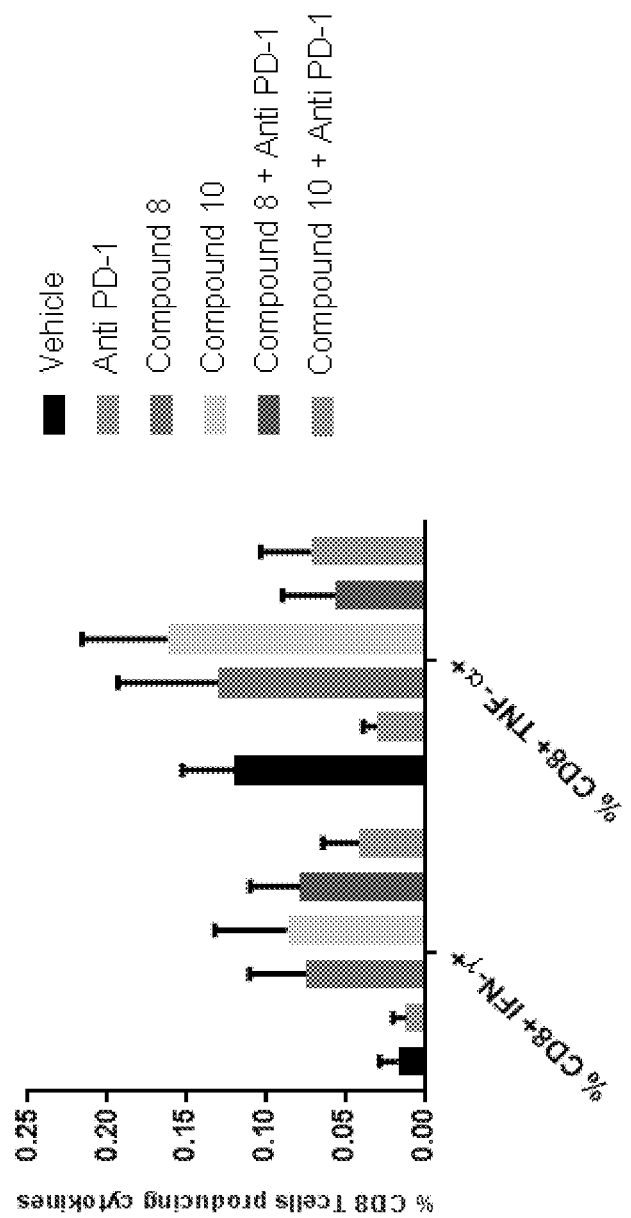
FIG. 5: In vivo Treatment with selective HDAC6 inhibitors induced specific T cell response. Splenocytes of animal treated with Compound 8 and 10 and the combination with anti PD-1 Ab were stimulated with CT-26 derived tumor peptides and the production of IFN-γ and TNF-α by CD8 Tcells was quantified by ELISPOT.

The results are shown in FIGS. 4 and 5 where the percentage of CD4 and CD8 T cells that produce IFN-γ and TNF-α are indicated for each treatment group.

In summary, the results shown in FIGS. 3-5, indicate that:
The selective HDAC6 inhibitors 8 and 10 can significantly reduce CT-26 tumor progression.
The efficacy of the two compounds is comparable to that of the anti PD-1 antibody.
Combination of compound 10 with anti PD-1 antibody further improves tumor growth inhibition.
Ex vivo stimulation with CT-26 specific peptides indicate that treatment with HDAC6 inhibitors, alone and in combination with anti PD-1 antibody, elicited a specific antitumor T cell mediated immune response.
The results of the ex vivo assay indicate that a greater neo antigen immune response was achieved with compounds 8 and 10 compared to anti PD-1 antibody.

The invention claimed is:

1. A compound of formula (I) or formula (II), or a pharmaceutically acceptable salt, stereoisomer or prodrug thereof:

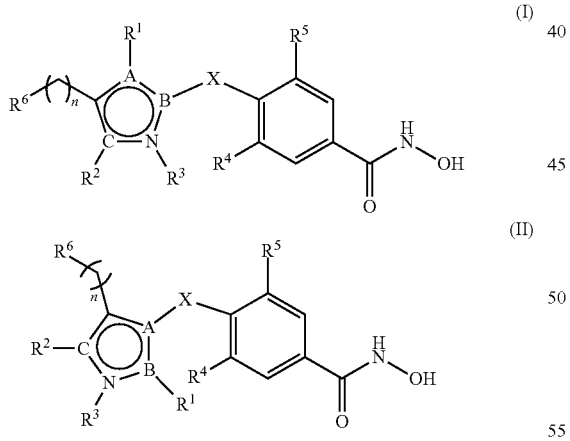

wherein
A represents N, O, or S;
B represents C or N;
C represents N or O;
X represents $CH_2$, S, NH, O, or $CD_2$;
n is 0 or 1,
when n is 1, the carbon atom may be substituted with $R^{12}$ and $R^{13}$, which are independently selected from the group consisting of H, D, Me, -phenyl, —F and —OH, or $R^{12}$ and $R^{13}$, together with the carbon atom to which they are attached, form a saturated cyclic moiety;
when n=1, $R^6$ is not absent;
$R^4$ and $R^5$ independently represent H or F;
$R^1$ is absent or is selected from the group consisting of —H, —$NH_2$, C1-C4 alkyl, phenyl, phenyl substituted with one or more halogens, arylalkyl, cycloalkyl, methylfuran, cyclobutylmethyl, tetrahydrofuran-2-yl-methyl, 3-(diethylamino)propyl, 2-methoxyethyl, vinyl, 2-(methylsulfanyl)ethyl, 1-cyclopropylethyl, pyridin-2-yl, (pyridin-3-yl)methyl, 2-(pyridin-2-yl)ethyl, 2-(thiophen-2-yl)ethyl, 3,4-dimethoxyphenyl, 4-methoxyphenyl, methylpheny, 2-chloro-5-(morpholin-4-sulfonyl)phenyl, 4-[(difluoromethyl)sulfanyl]phenyl, 4-(morpholin-4-sulfonyl)phenyl, 5-(dimethylsulfamoyl)-2-methylphenyl, 3-(trifluoromethyl)phenyl, 4-(trifluoromethyl)phenyl, 2-(morpholin-4-yl) ethyl, 3-(morpholin-4-yl)propyl, 1-naphthyl, 2,3-dihydro-1,4-benzodioxin-6-yl, benzhydryl, 5-indanyl, thiophene and methylthiophene;
$R^2$ is absent or is selected from the group consisting of H, alkyl, cycloalkyl, cycloalkyl-methyl, heteroaryl, phenyl, phenyl substituted with one or more halogens, phenyl substituted with one or more alkoxy groups, phenyl substituted with one or more nitro groups, benzyl, alkyl-substituted benzyl, (2,2-difluorocyclopentyl)methyl, 2-bromo-3-fluorophenyl, (2,2-dimethylcyclopropyl)methyl, 4-hydroxyphenyl, 2-(benzyloxy)ethyl, 2-bromo-4-methoxyphenyl, 2-methylquinoline, 3-methylpyridin-4-yl, 4-methanesulfonyl-2-methylphenyl, 2-chloro-4,6-dinitrophenyl, 1,3-benzodioxol-5-ylmethyl, and 2-benzyloxyphenyl;
$R^3$ is absent or is selected from the group consisting of H, alkoxyaryl, phenyl, phenyl substituted with $CF_3$, benzyl, pyridyl, alkyl, cycloalkyl, cycloalkyl-methyl, heteroaryl, phenyl substituted with one or more halogens, phenyl substituted with one or more alkoxy groups, phenyl substituted with one or more nitro groups, alkyl-substituted benzyl, (2,2-difluorocyclopentyl) methyl, 2-bromo-3-fluorophenyl, (2,2-dimethylcyclopropyl)methyl, 4-hydroxyphenyl, 2-(benzyloxy)ethyl, 2-bromo-4-methoxyphenyl, methyl-2-quinoline, 3-methylpyridin-4-yl, 4-methanesulfonyl-2-methylphenyl, 2-chloro-4,6-dinitrophenyl, 1,3-benzodioxol-5-ylmethyl, and 2-benzyloxyphenyl;
$R^6$ is a substituted or non-substituted mono or polycyclic residue, optionally partially or totally unsaturated, comprising carbon atoms and optionally one or more heteroatoms selected from the group consisting of N, S and O;
or $R^6$ is:

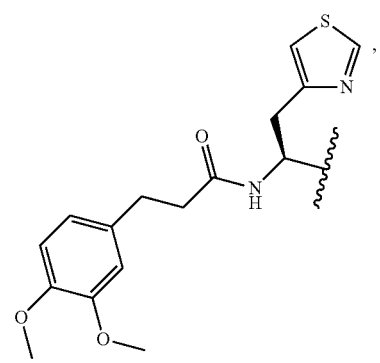

-continued

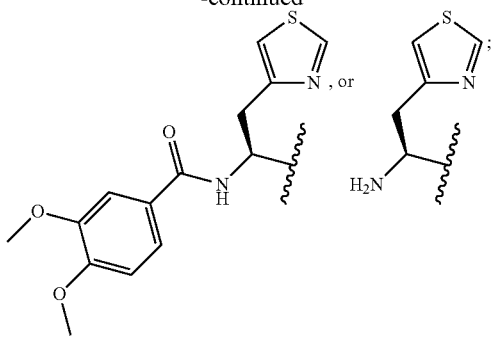

with the proviso that in the compound of formula (I), when the pentaheterocyclic core is 1,3,4-oxadiazole, $R^6$ is not naphthyl.

2. The compound according to claim 1, wherein:

A represents N, O, or S;

B represents C or N;

C represents N or O;

X represents $CH_2$ or S;

n is 0 or 1, when n is 1, the carbon atom may be substituted with $R^{12}$ and $R^{13}$, which are independently selected from the group consisting of H, -Me, -phenyl, —F and —OH, or $R^{12}$ and $R^{13}$, together with the carbon atom to which they are attached, form a saturated cyclic moiety;

when n is 1, $R^6$ is not absent;

$R^4$ and $R^5$ independently represent H or F;

$R^1$ is absent or is selected from the group consisting of —H, —$NH_2$, —$CH_3$, —$CH_2CH_3$, phenyl, p-fluorophenyl, m-chlorophenyl, p-chlorophenyl, benzyl, methylfuran, cyclopropyl, isobutyl, methylphenyl, trifluorophenyl, thiophene and 2-(morpholin-4-yl) ethyl;

$R^2$ is absent or is selected from the group consisting of H, phenyl, and p-dichlorophenyl;

$R^3$ is absent or is selected from the group consisting of H, o-methoxyphenyl, p-trifluoromethylphenyl, benzyl, and pyridyl;

$R^6$ is selected from the group consisting of:

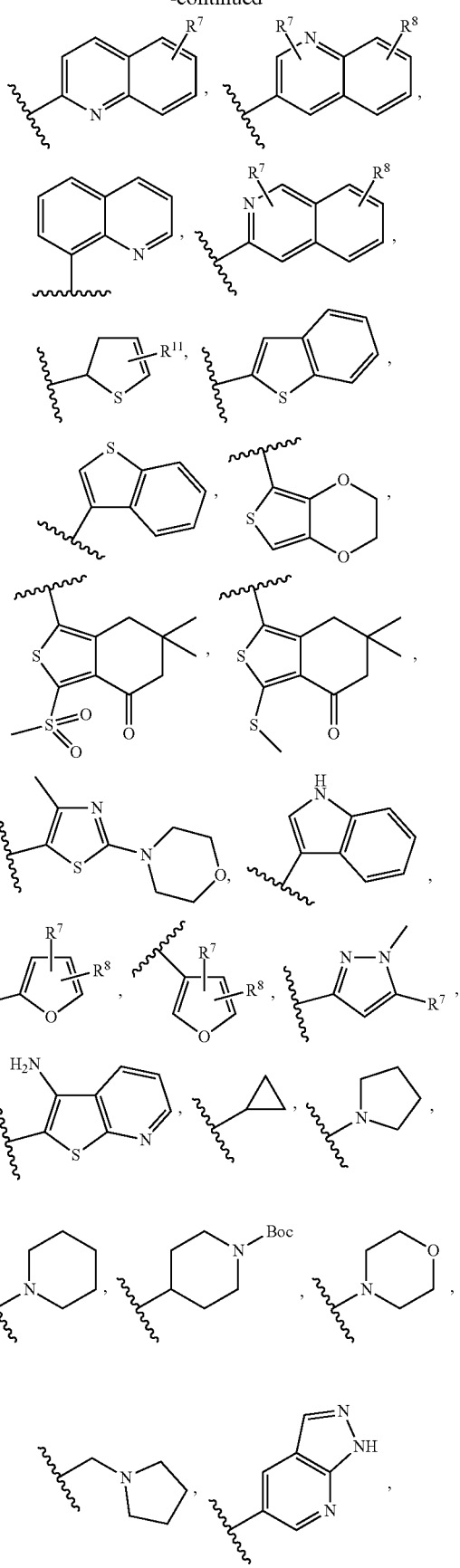

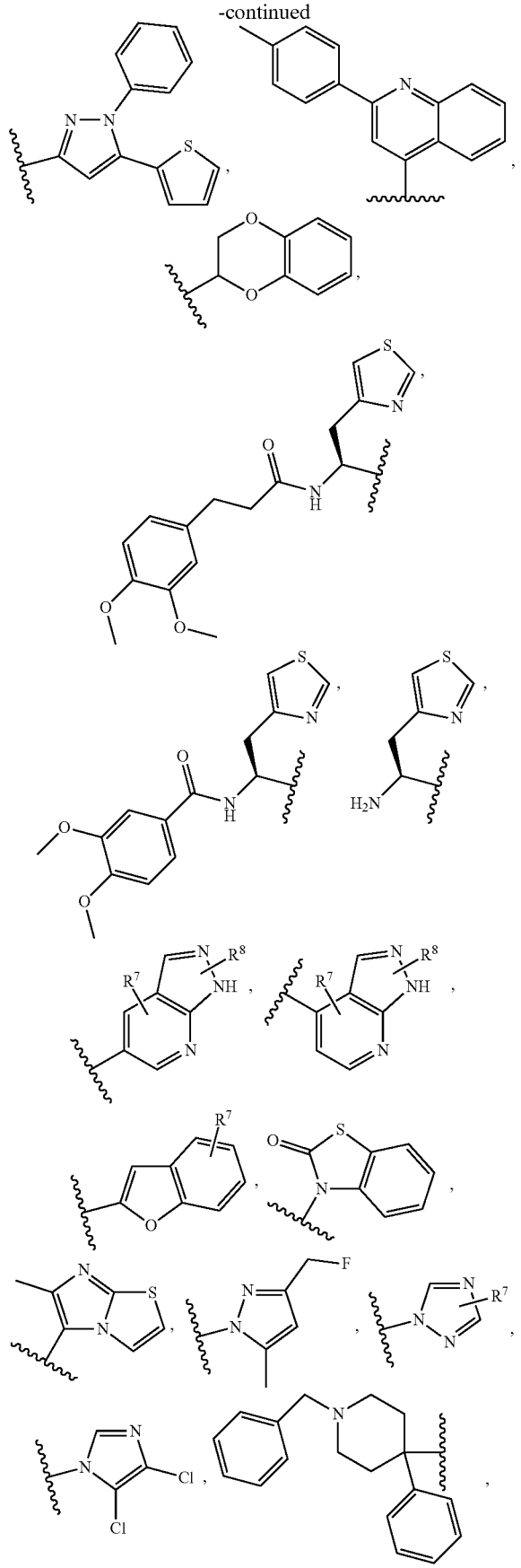

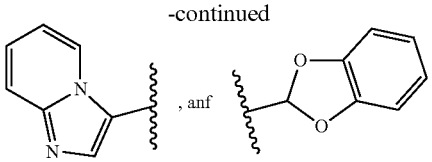

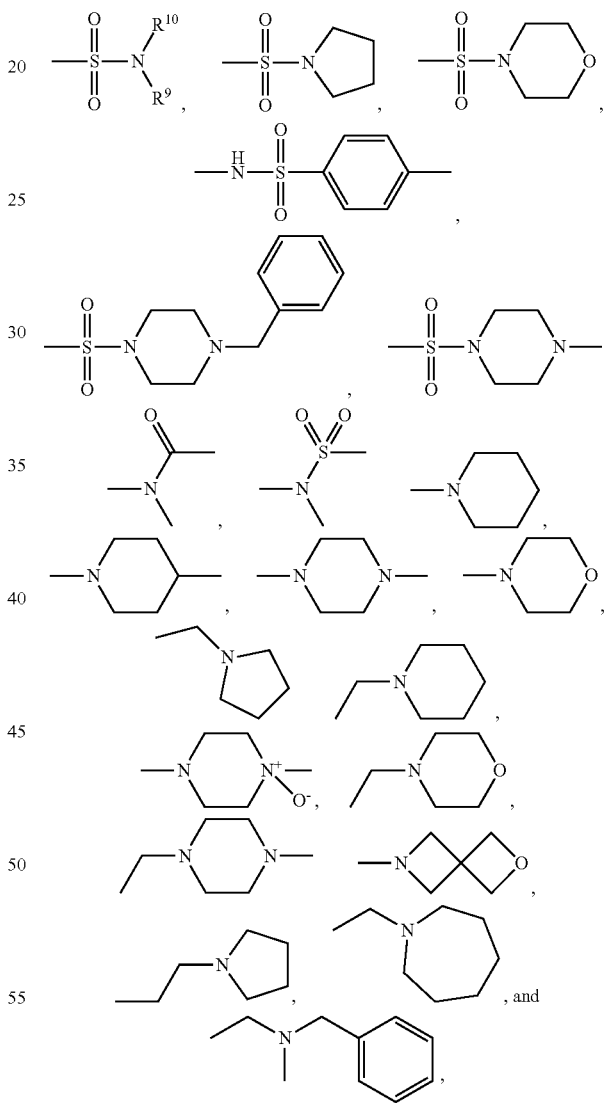

wherein:
$R^7$ and $R^8$ are independently selected from the group consisting of H, D, —Cl, —F, —Br, —CF$_3$, -Me, -Et, —OMe, —OMe, —OBenzyl, —SF$_5$, —OCH$_2$F, —CH$_2$NH$_2$, —CH$_2$NMe$_2$, —NH$_2$, —NMe$_2$, —N(CH$_2$CH$_2$OCH$_3$)$_2$, —COOH, —COOMe, —OH, —NHNH$_2$, —NO$_2$, —OEt, —OCHF$_2$, —OiPr, —CHF$_2$, —NEt$_2$, or $R^7$ and $R^8$ together form a heteropentacyclic moiety (—OCH$_2$O—);
$R^9$ and $R^{19}$ independently represent —H, -Me, or -Et;
$R^{11}$ is selected from the group consisting of —H, —Cl, —CH$_3$, —NO$_2$ and —Br.

3. The compound according to claim 1, which is selected from the group consisting of:

(S)—N-(1-(3-(4-(hydroxycarbamoyl)benzyl)-1,2,4-oxadiazol-5-yl)-2-(thiazol-4-yl)ethyl)-3,4-dimethoxybenzamide (comp. 1);
3,5-difluoro-N-hydroxy-4-((4-methyl-5-(naphthalen-1-yl)-4H-1,2,4-triazol-3-yl)thio)benzamide (comp. 2);
4-((5-(3-(N,N-dimethylsulfamoyl)phenyl)-1,3,4-oxadiazol-2-yl)methyl)-N-hydroxybenzamide (comp. 3);
3,5-difluoro-N-hydroxy-4-((4-methyl-5-(2-phenylpropan-2-yl)-4H-1,2,4-triazol-3-yl)thio)benzamide (comp. 4);
4-((5-(2,3-dihydrothieno[3,4-b][1,4]dioxin-5-yl)-1H-tetrazol-1-yl)methyl)-3,5-difluoro-N-hydroxybenzamide (comp. 5);
3,5-difluoro-N-hydroxy-4-((5-(pyridin-2-yl)-2H-tetrazol-2-yl)methyl)benzamide (comp. 6);
difluoro-N-hydroxy-4-((5-(pyrimidin-2-yl)-2H-tetrazol-2-yl)methyl)benzamide (comp. 7);
N-hydroxy-4-((5-(thiophen-2-yl)-1H-tetrazol-1-yl)methyl)benzamide (comp. 8);
3,5-difluoro-N-hydroxy-4-((4-methyl-5-(4-methyl-2-morpholinothiazol-5-yl)-4H-1,2,4-triazol-3-yl)thio)benzamide (comp. 9);
N-hydroxy-4-((4-methyl-5-(thiophen-2-yl)-4H-1,2,4-triazol-3-yl)thio)benzamide (comp. 10);
4-((5-(furan-2-yl)-2H-tetrazol-2-yl)methyl)-N-hydroxybenzamide (comp. 12);
3,5-difluoro-N-hydroxy-4-((5-(pyridin-2-yl)-1H-tetrazol-1-yl)methyl)benzamide (comp. 13);
3,5-difluoro-N-hydroxy-4-((4-methyl-5-(pyridin-2-yl)-4H-1,2,4-triazol-3-yl)thio)benzamide (comp. 14);
3,5-difluoro-N-hydroxy-4-((5-(thiophen-2-yl)-1H-tetrazol-1-yl)methyl)benzamide (comp. 15);
3,5-difluoro-N-hydroxy-4-((4-methyl-5-(4-(piperidin-1-ylmethyl)phenyl)-4H-1,2,4-triazol-3-yl)thio)benzamide (comp. 16);
3,5-difluoro-N-hydroxy-4-((4-methyl-5-(thiophen-2-yl)-4H-1,2,4-triazol-3-yl)thio)benzamide (comp. 17);
3,5-difluoro-4-((5-(furan-2-yl)-2H-tetrazol-2-yl)methyl)-N-hydroxybenzamide (comp. 19);
N-hydroxy-4-((5-(pyridin-2-yl)-1H-tetrazol-1-yl)methyl)benzamide (comp. 20);
3-(3,4-dimethoxyphenyl)-N-[(1S)-1-[3-[[4-(hydroxycarbamoyl)phenyl]methyl]-1,2,4-oxadiazol-5-yl]-2-thiazol-4-yl-ethyl]propanamide (comp. 21);
4-[[5-[4-(trifluoromethyl)phenyl]tetrazol-2-yl]methyl]benzenecarbohydroxamic acid (comp. 23);
4-[(4,5-diphenyl-1,2,4-triazol-3-yl)sulfanyl]benzenecarbohydroxamic acid (comp. 24);
4-[[4-(2-furylmethyl)-5-(1H-indol-3-yl)-1,2,4-triazol-3-yl]sulfanyl]benzenecarbohydroxamic acid;2,2,2-trifluoroacetic acid (comp. 25);
4-[5-[(3,4-dimethoxyphenyl)methyl]-1,3,4-oxadiazol-2-yl]benzenecarbohydroxamic acid (comp. 26);
4-[[5-benzyl-4-(4-fluorophenyl)-1,2,4-triazol-3-yl]sulfanyl]benzenecarbohydroxamic acid (comp. 27);
4-[[4-amino-5-[4-(difluoromethoxy)phenyl]-1,2,4-triazol-3-yl]sulfanyl]benzenecarbohydroxamic acid (comp. 28);
4-[[5-(4-fluorophenyl)-4H-1,2,4-triazol-3-yl]sulfanyl]benzenecarbohydroxamic acid (comp. 29);
4-[[4-ethyl-5-(4-fluorophenyl)-1,2,4-triazol-3-yl]sulfanyl]benzenecarbohydroxamic acid (comp. 30);
4-[[5-(4-chlorophenyl)tetrazol-2-yl]methyl]benzenecarbohydroxamic acid (comp. 31);
4-[[5-(5-chloro-2-thienyl)tetrazol-2-yl]methyl]benzenecarbohydroxamic acid (comp. 32);
4-[[5-(2-fluorophenyl)tetrazol-2-yl]methyl]benzenecarbohydroxamic acid (comp. 33);
4-[[5-(4-fluorophenyl)tetrazol-2-yl]methyl]benzenecarbohydroxamic acid (comp. 34);
4-[[5-(4-methoxyphenyl)tetrazol-2-yl]methyl]benzenecarbohydroxamic acid (comp. 35);
4-[(5-benzyltetrazol-2-yl)methyl]benzenecarbohydroxamic acid (comp. 36);
4-[(5-benzyltetrazol-1-yl)methyl]benzenecarbohydroxamic acid (comp. 37);
4-[[5-(2,4-dichlorophenyl)tetrazol-2-yl]methyl]benzenecarbohydroxamic acid (comp. 38);
4-[[5-(3-methyl-2-thienyl)tetrazol-2-yl]methyl]benzenecarbohydroxamic acid (comp. 39);
4-[[5-(5-methyl-2-thienyl)tetrazol-2-yl]methyl]benzenecarbohydroxamic acid (comp. 41);
4-[[5-(benzothiophen-3-yl)tetrazol-2-yl]methyl]benzenecarbohydroxamic acid (comp. 42);
4-[[5-(2,3-dihydrothieno[3,4-b][1,4]dioxin-5-yl)tetrazol-2-yl]methyl]benzenecarbohydroxamic acid (comp. 43);
4-[[5-[(3,4-dimethoxyphenyl)methyl]-2-[4-(trifluoromethyl)phenyl]-1,2,4-triazol-3-yl]methyl]benzenecarbohydroxamic acid (comp. 44);
4-[[5-[(3,4-dimethoxyphenyl)methyl]-1,3,4-oxadiazol-2-yl]methyl]benzenecarbohydroxamic acid (comp. 45);
4-[[5-(2-fluorophenyl)tetrazol-2-yl]methyl]benzenecarbohydroxamic acid (comp. 46);
4-[[5-[(1S)-1-amino-2-thiazol-4-yl-ethyl]-1,2,4-oxadiazol-3-yl]methyl]benzenecarbohydroxamic acid;2,2,2-trifluoroacetic acid (comp. 48);
4-[[5-(3,4-dimethoxyphenyl)-1,2,4-oxadiazol-3-yl]methyl]benzenecarbohydroxamic acid (comp. 49);
4-[[5-(2-thienyl)tetrazol-2-yl]methyl]benzenecarbohydroxamic acid (comp. 50);
4-[[2-benzyl-5-(4-chlorophenyl)-1,2,4-triazol-3-yl]methyl]benzenecarbohydroxamic acid (comp. 51);
4-[[2-(2-pyridyl)-5-(2-thienyl)-1,2,4-triazol-3-yl]methyl]benzenecarbohydroxamic acid (comp. 52);
4-[[2-(2-methoxyphenyl)-5-(2-thienyl)-1,2,4-triazol-3-yl]methyl]benzenecarbohydroxamic acid (comp. 53);
4-[[5-(6,6-dimethyl-3-methylsulfanyl-4-oxo-5,7-dihydro-2-benzothiophen-1-yl)tetrazol-2-yl]methyl]benzenecarbohydroxamic acid (comp. 54);
4-[[5-(benzothiophen-2-yl)tetrazol-2-yl]methyl]benzenecarbohydroxamic acid (comp. 55);
4-[[5-(3,4-dimethoxyphenyl)-1,3,4-oxadiazol-2-yl]methyl]benzenecarbohydroxamic acid (comp. 57);
4-[[5-(2,4-difluorophenyl)-1,3,4-oxadiazol-2-yl]methyl]benzenecarbohydroxamic acid (comp. 58);
4-[[5-[3-(dimethylsulfamoyl)phenyl]tetrazol-2-yl]methyl]benzenecarbohydroxamic acid (comp. 59);
4-[(5-phenyl-1,3,4-oxadiazol-2-yl)amino]benzenecarbohydroxamic acid (comp. 60);
4-[[4-amino-5-[3-(diethylsulfamoyl)phenyl]-1,2,4-triazol-3-yl]sulfanyl]benzenecarbohydroxamic acid (comp. 61);
4-[[5-(3-pyrrolidin-1-ylsulfonylphenyl)-1,3,4-oxadiazol-2-yl]amino]benzenecarbohydroxamic acid (comp. 63);
4-[[5-(3-morpholinosulfonylphenyl)-1,3,4-oxadiazol-2-yl]methyl]benzenecarbohydroxamic acid (comp. 64);
3,5-difluoro-4-[[5-(2-thienyl)tetrazol-2-yl]methyl]benzenecarbohydroxamic acid (comp. 65);
4-[[5-[3-(diethylsulfamoyl)phenyl]-4-methyl-1,2,4-triazol-3-yl]sulfanyl]benzenecarbohydroxamic acid (comp. 66);

4-[[4-methyl-5-[2-(p-tolyl)-4-quinolyl]-1,2,4-triazol-3-yl]sulfanyl]benzenecarbohydroxamic acid (comp. 67);

4-[(5-phenyl-1,3,4-oxadiazol-2-yl)methyl]benzenecarbohydroxamic acid (comp. 68);

4-[[5-(4-pyrrolidin-1-ylsulfonylphenyl)-1,3,4-oxadiazol-2-yl]methyl]benzenecarbohydroxamic acid (comp. 69);

4-[[5-(3-benzyloxy-4-methoxy-phenyl)tetrazol-2-yl]methyl]benzenecarbohydroxamic acid (comp. 70);

4-[[5-(3-benzyloxy-4-methoxy-phenyl)tetrazol-1-yl]methyl]benzenecarbohydroxamic acid (comp. 71);

4-[(5-cyclopropyl-1-phenyl-1,2,4-triazol-3-yl)sulfanyl]benzenecarbohydroxamic acid (comp. 72);

4-[[5-[4-(dimethylamino)phenyl]-4-methyl-1,2,4-triazol-3-yl]sulfanyl]benzenecarbohydroxamic acid (comp. 73);

4-[[5-(6,6-dimethyl-3-methylsulfonyl-4-oxo-5,7-dihydro-2-benzothiophen-1-yl)tetrazol-2-yl]methyl]benzenecarbohydroxamic acid (comp. 74);

4-[5-(4-methyl-2-morpholino-thiazol-5-yl)-1,3,4-oxadiazol-2-yl]methyl]benzenecarbohydroxamic acid (comp. 75);

4-[[5-[5-(dimethylsulfamoyl)-2-fluoro-phenyl]-4-methyl-1,2,4-triazol-3-yl]sulfanyl]benzenecarbohydroxamic acid (comp. 76);

4-[[5-[3-(dimethylamino)phenyl]-4-methyl-1,2,4-triazol-3-yl]sulfanyl]benzenecarbohydroxamic acid (comp. 77);

4-[[5-(3-methoxyphenyl)-4-methyl-1,2,4-triazol-3-yl]sulfanyl]benzenecarbohydroxamic acid (comp. 78);

4-[[5-(2,3-dihydrothieno[3,4-b][1,4]dioxin-5-yl)tetrazol-2-yl]methyl]-3,5-difluoro-benzenecarbohydroxamic acid (comp. 79);

4-[[5-[3-(dimethylamino)phenyl]-4-methyl-1,2,4-triazol-3-yl]sulfanyl]-3,5-difluoro-benzenecarbohydroxamic acid (comp. 80);

tert-butyl 4-[5-[4-(hydroxycarbamoyl)phenyl]sulfanyl-4-methyl-1,2,4-triazol-3-yl]piperidine-1-carboxylate (comp. 82);

4-[[5-(2,3-dihydro-1,4-benzodioxin-3-yl)-4-methyl-1,2,4-triazol-3-yl]sulfanyl]benzenecarbohydroxamic acid (comp. 83);

4-[[5-(1,3-benzodioxol-5-yl)-4-methyl-1,2,4-triazol-3-yl]sulfanyl]benzenecarbohydroxamic acid (comp. 84);

4-[[5-(1,5-dimethylpyrazol-3-yl)-4-methyl-1,2,4-triazol-3-yl]sulfanyl]benzenecarbohydroxamic acid (comp. 85);

4-[[5-(2-furyl)tetrazol-1-yl]methyl]benzenecarbohydroxamic acid (comp. 86);

4-[[5-(1-isoquinolyl)tetrazol-2-yl]methyl]benzenecarbohydroxamic acid (comp. 87);

4-[[5-(1-isoquinolyl)tetrazol-1-yl]methyl]benzenecarbohydroxamic acid (comp. 88);

4-[[5-(2-pyridyl)tetrazol-2-yl]methyl]benzenecarbohydroxamic acid (comp. 89);

4-[[5-(2-quinolyl)tetrazol-2-yl]methyl]benzenecarbohydroxamic acid (comp. 90);

4-[[5-(2-quinolyl)tetrazol-1-yl]methyl]benzenecarbohydroxamic acid (comp. 91);

3,5-difluoro-4-[[5-(2-furyl)tetrazol-1-yl]methyl]benzenecarbohydroxamic acid (comp. 92);

3,5-difluoro-4-[[5-(1-isoquinolyl)tetrazol-2-yl]methyl]benzenecarbohydroxamic acid (comp. 93);

3,5-difluoro-4-[[5-(1-isoquinolyl)tetrazol-1-yl]methyl]benzenecarbohydroxamic acid (comp. 94);

3,5-difluoro-4-[[5-(2-quinolyl)tetrazol-2-yl]methyl]benzenecarbohydroxamic acid (comp. 95);

3,5-difluoro-4-[[5-(2-quinolyl)tetrazol-1-yl]methyl]benzenecarbohydroxamic acid (comp. 96);

3,5-difluoro-4-[[5-(2-thienyl)-4H-1,2,4-triazol-3-yl]sulfanyl]benzenecarbohydroxamic acid (comp. 97);

4-[(5-benzhydryl-4-methyl-1,2,4-triazol-3-yl)sulfanyl]-3,5-difluoro-benzenecarbohydroxamic acid (comp. 98);

4-[[5-(3-aminothieno[2,3-b]pyridin-2-yl)-4-methyl-1,2,4-triazol-3-yl]sulfanyl]-3,5-difluoro-benzenecarbohydroxamic acid (comp. 99);

4-[[5-(1,5-dimethyl pyrazol-3-yl)-4-methyl-1,2,4-triazol-3-yl]sulfanyl]-3, 5-difluoro-benzenecarbohydroxamic acid (comp. 100);

3,5-difluoro-4-[[4-methyl-5-(1-phenylcyclobutyl)-1,2,4-triazol-3-yl]sulfanyl]benzenecarbohydroxamic acid (comp. 101);

3,5-difluoro-4-[[5-[1-(3-fluorophenyl)cyclopentyl]-4-methyl-1,2,4-triazol-3-yl]sulfanyl]benzenecarbohydroxamic acid (comp. 102);

3,5-difluoro-4-[[5-[1-(4-methoxyphenyl)cyclohexyl]-4-methyl-1,2,4-triazol-3-yl]sulfanyl]benzenecarbohydroxamic acid (comp. 103);

3,5-difluoro-4-[[5-[1-(4-methoxyphenyl)cyclopropyl]-4-methyl-1,2,4-triazol-3-yl]sulfanyl]benzenecarbohydroxamic acid (comp 104);

4-[[5-[3-(pentafluoro-lambda6-sulfanyl)phenyl]tetrazol-2-yl]methyl]benzenecarbohydroxamic acid (comp. 106);

4-[[5-[3-(pentafluoro-lambda6-sulfanyl)phenyl]tetrazol-1-yl]methyl]benzenecarbohydroxamic acid (comp. 107);

3,5-difluoro-4-[[5-[3-(pentafluoro-lambda6-sulfanyl)phenyl]tetrazol-2-yl]methyl]benzenecarbohydroxamic acid (comp. 108);

3,5-difluoro-4-[[5-[3-(pentafluoro-lambda6-sulfanyl)phenyl]tetrazol-1-yl]methyl]benzenecarbohydroxamic acid (comp. 109);

4-[[5-[4-(pentafluoro-lambda6-sulfanyl)phenyl]tetrazol-2-yl]methyl]benzenecarbohydroxamic acid (comp. 110);

4-[[5-[4-(pentafluoro-lambda6-sulfanyl)phenyl]tetrazol-1-yl]methyl]benzenecarbohydroxamic acid (comp. 111);

3,5-difluoro-4-[[5-[4-(pentafluoro-lambda6-sulfanyl)phenyl]tetrazol-2-yl]methyl]benzenecarbohydroxamic acid (comp. 112);

3,5-difluoro-4-[[5-[4-(pentafluoro-lambda6-sulfanyl)phenyl]tetrazol-1-yl]methyl]benzenecarbohydroxamic acid (comp. 113);

3,5-difluoro-4-[[4-methyl-5-[3-(4-methyl-4-oxido-piperazin-4-ium-1-yl)phenyl]-1,2,4-triazol-3-yl]sulfanyl]benzenecarbohydroxamic acid (comp. 114);

3,5-difluoro-4-[[4-(4-fluorophenyl)-5-(1-piperidylmethyl)-1,2,4-triazol-3-yl]sulfanyl]benzenecarbohydroxamic acid (comp. 115);

3,5-difluoro-4-[[4-(2-furylmethyl)-5-pyrrolidin-1-yl-1,2,4-triazol-3-yl]sulfanyl]benzenecarbohydroxamic acid (comp. 116);

4-[(4-benzyl-5-morpholino-1,2,4-triazol-3-yl)sulfanyl]-3,5-difluoro-benzenecarbohydroxamic acid (comp. 117);

4-[[5-(2,3-dihydrothieno[3,4-b][1,4]dioxin-5-yl)-4-methyl-1,2,4-triazol-3-yl]sulfanyl]-3,5-difluoro-benzenecarbohydroxamic acid (comp. 118);

3,5-difluoro-4-[[5-(1-isoquinolyl)-4-methyl-1,2,4-triazol-3-yl]sulfanyl]benzenecarbohydroxamic acid (comp. 121);

3,5-difluoro-4-[[4-methyl-5-(2-quinolyl)-1,2,4-triazol-3-yl]sulfanyl]benzenecarbohydroxamic acid (comp. 122);
4-[(5-pyrimidin-2-yltetrazol-2-yl)methyl]benzenecarbohydroxamic acid (comp. 123);
4-[(5-pyrimidin-2-yltetrazol-1-yl)methyl]benzenecarbohydroxamic acid (comp. 124);
3,5-difluoro-4-[(5-pyrimidin-2-yltetrazol-1-yl)methyl]benzenecarbohydroxamic acid (comp. 125);
4-[[5-[5-(trifluoromethyl)-2-pyridyl]tetrazol-2-yl]methyl]benzenecarbohydroxamic acid (comp. 126);
4-[[5-[5-(trifluoromethyl)-2-pyridyl]tetrazol-1-yl]methyl]benzenecarbohydroxamic acid (comp. 127);
3,5-difluoro-4-[[5-[5-(trifluoromethyl)-2-pyridyl]tetrazol-2-yl]methyl]benzenecarbohydroxamic acid (comp. 128);
3,5-difluoro-4-[[5-[5-(trifluoromethyl)-2-pyridyl]tetrazol-1-yl]methyl]benzenecarbohydroxamic acid (comp. 129);
4-[[5-[3-morpholino-5-(trifluoromethyl)-2-pyridyl]tetrazol-2-yl]methyl]benzenecarbohydroxamic acid (comp. 130);
4-[[5-[3-morpholino-5-(trifluoromethyl)-2-pyridyl]tetrazol-1-yl]methyl]benzenecarbohydroxamic acid (comp. 131);
4-[[5-(2-pyridylmethyl)tetrazol-2-yl]methyl]benzenecarbohydroxamic acid;2,2,2-trifluoroacetic acid (comp. 132);
4-[[5-(2-pyridylmethyl)tetrazol-1-yl]methyl]benzenecarbohydroxamic acid;2,2,2-trifluoroacetic acid (comp. 133);
3,5-difluoro-4-[[5-(2-pyridyl methyl)tetrazol-2-yl]methyl]benzenecarbohydroxamic acid;2,2,2-trifluoroacetic acid (comp. 134);
3,5-difluoro-4-[[5-(2-pyridylmethyl)tetrazol-1-yl]methyl]benzenecarbohydroxamic acid;2,2,2-trifluoroacetic acid (comp. 135);
3,5-difluoro-4-[[4-methyl-5-[1-phenyl-5-(2-thienyl)pyrazol-3-yl]-1,2,4-triazol-3-yl]sulfanyl]benzenecarbohydroxamic acid (comp. 136);
3,5-difluoro-4-[[5-(6-fluoro-2-methyl-3-quinolyl)-4-methyl-1,2,4-triazol-3-yl]sulfanyl]benzenecarbohydroxamic acid (comp. 137);
3,5-difluoro-4-[[5-(4-fluorophenyl)-4-(2-morpholinoethyl)-1,2,4-triazol-3-yl]sulfanyl]benzenecarbohydroxamic acid (comp. 138);
3,5-difluoro-4-[[4-(2-furylmethyl)-5-pyrazin-2-yl-1,2,4-triazol-3-yl]sulfanyl]benzenecarbohydroxamic acid (comp. 139);
3,5-difluoro-4-[[4-(2-furylmethyl)-5-(2-pyridyl)-1,2,4-triazol-3-yl]sulfanyl]benzenecarbohydroxamic acid (comp. 140);
4-[[4-benzyl-5-(pyrrolidin-1-ylmethyl)-1,2,4-triazol-3-yl]sulfanyl]-3,5-difluoro-benzenecarbohydroxamic acid (comp. 141);
4-[[4-benzyl-5-(2-furyl)-1,2,4-triazol-3-yl]sulfanyl]-3,5-difluoro-benzenecarbohydroxamic acid (comp. 142);
4-[[4-benzyl-5-(2-thienyl)-1,2,4-triazol-3-yl]sulfanyl]-3,5-difluoro-benzenecarbohydroxamic acid (comp. 143);
3,5-difluoro-4-[[4-(2-furylmethyl)-5-(2-thienyl)-1,2,4-triazol-3-yl]sulfanyl]benzenecarbohydroxamic acid (comp. 144);
3,5-difluoro-4-[[5-(2-fluorophenyl)-4-(2-furylmethyl)-1,2,4-triazol-3-yl]sulfanyl]benzenecarbohydroxamic acid (comp. 145);
3,5-difluoro-4-[[4-(2-furylmethyl)-5-(4-pyridyl)-1,2,4-triazol-3-yl]sulfanyl]benzenecarbohydroxamic acid (comp. 146);
3,5-difluoro-4-[[4-(2-furylmethyl)-5-(3-pyridyl)-1,2,4-triazol-3-yl]sulfanyl]benzenecarbohydroxamic acid (comp. 147);
3,5-difluoro-4-[[5-(3-isoquinolyl)-4-methyl-1,2,4-triazol-3-yl]sulfanyl]benzenecarbohydroxamic acid (comp. 148);
3,5-difluoro-4-[(5-imidazo[1,2-a]pyridin-3-yl-4-methyl-1,2,4-triazol-3-yl)sulfanyl]benzenecarbohydroxamic acid (comp. 149);
4-[[5-(1-benzyl-4-phenyl-4-piperidyl)-4-methyl-1,2,4-triazol-3-yl]sulfanyl]-3,5-difluoro-benzenecarbohydroxamic acid (comp. 150);
3,5-difluoro-4-[[4-methyl-5-[3-(4-methylpiperazin-1-yl)sulfonylphenyl]-1,2,4-triazol-3-yl]sulfanyl]benzenecarbohydroxamic acid (comp. 151);
4-[[5-[3-(4-benzylpiperazin-1-yl)sulfonylphenyl]-4-methyl-1,2,4-triazol-3-yl]sulfanyl]-3,5-difluoro-benzenecarbohydroxamic acid (comp. 152);
3,5-difluoro-4-[[4-methyl-5-(3-pyridyl)-1,2,4-triazol-3-yl]sulfanyl]benzenecarbohydroxamic acid (comp. 153);
methyl 4-[[2-[[2,6-difluoro-4-(hydroxycarbamoyl)phenyl]methyl]tetrazol-5-yl]methyl]benzoate (comp. 154);
methyl 4-[[1-[[2,6-difluoro-4-(hydroxycarbamoyl)phenyl]methyl]tetrazol-5-yl]methyl]benzoate (comp. 155);
methyl 6-[2-[[4-(hydroxycarbamoyl)phenyl]methyl]tetrazol-5-yl]pyridine-3-carboxylate (comp. 156);
methyl 6-[1-[[4-(hydroxycarbamoyl)phenyl]methyl]tetrazol-5-yl]pyridine-3-carboxylate (comp. 157);
4-[[2-[[4-(hydroxycarbamoyl)phenyl]methyl]tetrazol-5-yl]methyl]benzoic acid (comp. 158);
4-[[1-[[4-(hydroxycarbamoyl)phenyl]methyl]tetrazol-5-yl]methyl]benzoic acid (comp. 159);
4-[[2-[[2,6-difluoro-4-(hydroxycarbamoyl)phenyl]methyl]tetrazol-5-yl]methyl]benzoic acid (comp. 160);
4-[[1-[[2,6-difluoro-4-(hydroxycarbamoyl)phenyl]methyl]tetrazol-5-yl]methyl]benzoic acid (comp. 161);
6-[2-[[4-(hydroxycarbamoyl)phenyl]methyl]tetrazol-5-yl]pyridine-3-carboxylic acid (comp. 162);
3-[2-[[4-(hydroxycarbamoyl)phenyl]methyl]tetrazol-5-yl]benzoic acid (comp. 163);
3,5-difluoro-4-[[4-methyl-5-(8-quinolylmethyl)-1,2,4-triazol-3-yl]sulfanyl]benzenecarbohydroxamic acid (comp. 164);
4-[[5-(2,6-difluorophenyl)-4-methyl-1,2,4-triazol-3-yl]sulfanyl]-3,5-difluoro-benzenecarbohydroxamic acid (comp. 165);
3,5-difluoro-4-[[4-methyl-5-[3-(4-methylpiperazin-1-yl)phenyl]-1,2,4-triazol-3-yl]sulfanyl]benzenecarbohydroxamic acid (comp. 166);
4-[[5-[3-(azepan-1-ylmethyl)phenyl]-4-methyl-1,2,4-triazol-3-yl]sulfanyl]-3,5-difluoro-benzenecarbohydroxamic acid (comp. 167);
4-[[5-[4-(azepan-1-ylmethyl)phenyl]-4-methyl-1,2,4-triazol-3-yl]sulfanyl]-3,5-difluoro-benzenecarbohydroxamic acid (comp. 168);
4-[[5-(4-aminophenyl)tetrazol-2-yl]methyl]benzenecarbohydroxamic acid (comp. 169);
4-[[5-(4-aminophenyl)tetrazol-1-yl]methyl]benzenecarbohydroxamic acid (comp. 170);
4-[[5-(4-aminophenyl)tetrazol-2-yl]methyl]-3,5-difluoro-benzenecarbohydroxamic acid (comp. 171);
4-[[5-(4-aminophenyl)tetrazol-1-yl]methyl]-3,5-difluoro-benzenecarbohydroxamic acid (comp. 172);

4-[[5-[4-(aminomethyl)phenyl]tetrazol-2-yl]methyl]benzenecarbohydroxamic acid (comp. 173);
4-[[5-[4-(aminomethyl)phenyl]tetrazol-1-yl]methyl]benzenecarbohydroxamic acid (comp. 174);
4-[[5-[4-(aminomethyl)phenyl]tetrazol-2-yl]methyl]-3,5-difluoro-benzenecarbohydroxamic acid (comp. 175);
4-[[5-[4-(aminomethyl)phenyl]tetrazol-1-yl]methyl]-3,5-difluoro-benzenecarbohydroxamic acid (comp. 176);
3,5-difluoro-4-[[4-methyl-5-[1-(2-pyridyl)cyclopropyl]-1,2,4-triazol-3-yl]sulfanyl]benzenecarbohydroxamic acid (comp. 177);
3,5-difluoro-4-[[4-methyl-5-[1-(3-pyridyl)cyclopropyl]-1,2,4-triazol-3-yl]sulfanyl]benzenecarbohydroxamic acid (comp. 178);
3,5-difluoro-4-[(4-methyl-5-pyridazin-3-yl-1,2,4-triazol-3-yl)sulfanyl]benzenecarbohydroxamic acid (comp. 179);
3,5-difluoro-4-[[5-(3-fluoro-2-pyridyl)-4-methyl-1,2,4-triazol-3-yl]sulfanyl]benzenecarbohydroxamic acid (comp. 180);
3,5-difluoro-4-[[4-methyl-5-[3-(1-piperidylmethyl)phenyl]-1,2,4-triazol-3-yl]sulfanyl]benzenecarbohydroxamic acid (comp. 181);
3,5-difluoro-4-[[4-methyl-5-[3-(morpholinomethyl)phenyl]-1,2,4-triazol-3-yl]sulfanyl]benzenecarbohydroxamic acid (comp. 182);
4-((3-((1H-indol-3-yl)methyl)-5-(thiophen-2-yl)-4H-1,2,4-triazol-4-yl)methyl)-N-hydroxybenzamide (comp. 183);
4-[[5-[3-[[benzyl(methyl)amino]methyl]phenyl]-4-methyl-1,2,4-triazol-3-yl]sulfanyl]-3,5-difluoro-benzenecarbohydroxamic acid (comp. 184);
4-[[3-[(3,4-dimethoxyphenyl)methyl]-5-(2-thienyl)-1,2,4-triazol-4-yl]methyl]benzenecarbohydroxamic acid (comp. 185);
3,5-difluoro-4-[[4-methyl-5-[1-methyl-1-(3-pyridyl)ethyl]-1,2,4-triazol-3-yl]sulfanyl]benzenecarbohydroxamic acid (comp. 186);
3,5-difluoro-4-[[5-[4-[methyl(methylsulfonyl)amino]phenyl]-1,3,4-thiadiazol-2-yl]sulfanyl]benzenecarbohydroxamic acid (comp. 187);
4-[(5-phenyl-1,3,4-oxadiazol-2-yl)sulfanyl]benzenecarbohydroxamic acid (comp. 188);
4-[(5-phenyl-1,2,4-oxadiazol-3-yl)methyl]benzenecarbohydroxamic acid (comp. 189);
4-[(5-phenyl-1,3,4-thiadiazol-2-yl)methyl]benzenecarbohydroxamic acid (comp. 190);
3,5-difluoro-N-hydroxy-4-((5-(pyridin-3-yl)-1,3,4-thiadiazol-2-yl)thio)benzamide (comp. 191);
3,5-difluoro-4-[(5-phenyl-1,3,4-oxadiazol-2-yl)sulfanyl]benzenecarbohydroxamic acid (comp. 192);
4-[[5-(2-morpholino-4-pyridyl)-1,2,4-oxadiazol-3-yl]methyl]benzenecarbohydroxamic acid (comp. 193);
3,5-difluoro-N-hydroxy-4-((5-phenyl-1,2,4-oxadiazol-3-yl)methyl)benzamide (comp. 194);
3,5-difluoro-4-[[5-(4-pyridyl)-1,3,4-thiadiazol-2-yl]methyl]benzenecarbohydroxamic acid (comp. 195);
4-[[5-(5-bromo-3-pyridyl)-1,3,4-thiadiazol-2-yl]sulfanyl]-3,5-difluoro-benzenecarbohydroxamic acid (comp. 196);
3,5-difluoro-4-[[5-(5-morpholino-3-pyridyl)-1,3,4-thiadiazol-2-yl]methyl]benzenecarbohydroxamic acid (comp. 197);
3,5-difluoro-N-hydroxy-4-((5-phenyl-1,3,4-thiadiazol-2-yl)methyl)benzamide (comp. 198);
3,5-difluoro-4-[[5-(2-furyl)-4-methyl-1,2,4-triazol-3-yl]sulfanyl]benzenecarbohydroxamic acid (comp. 199);
4-[[5-[5-[bis(2-methoxyethyl)amino]-3-pyridyl]-1,2,4-oxadiazol-3-yl]methyl]-3,5-difluoro-benzenecarbohydroxamic acid (comp. 200);
3,5-difluoro-4-[[5-[5-(2-oxa-6-azaspiro[3.3]heptan-6-yl)-3-pyridyl]-1,2,4-oxadiazol-3-yl]methyl]benzenecarbohydroxamic acid (comp. 201);
3,5-difluoro-4-[[5-[5-(pyrrolidin-1-ylmethyl)-2-furyl]-1,2,4-oxadiazol-3-yl]methyl]benzenecarbohydroxamic acid (comp. 202);
3,5-difluoro-4-[[4-methyl-5-[5-(morpholinomethyl)-3-furyl]-1,2,4-triazol-3-yl]sulfanyl]benzenecarbohydroxamic acid (comp. 203);
3,5-difluoro-4-[[4-methyl-5-[5-(morpholinomethyl)-2-furyl]-1,2,4-triazol-3-yl]sulfanyl]benzenecarbohydroxamic acid (comp. 204);
3,5-difluoro-4-[[4-methyl-5-[5-[(4-methylpiperazin-1-yl)methyl]-2-furyl]-1,2,4-triazol-3-yl]sulfanyl]benzenecarbohydroxamic acid (comp. 205);
4-[[5-[5-[(dimethylamino)methyl]-2-furyl]-4-methyl-1,2,4-triazol-3-yl]sulfanyl]-3,5-difluoro-benzenecarbohydroxamic acid (comp. 206);
3,5-difluoro-4-[[4-methyl-5-[5-(pyrrolidin-1-ylmethyl)-2-furyl]-1,2,4-triazol-3-yl]sulfanyl]benzenecarbohydroxamic acid (comp. 207);
4-[[5-[5-ethyl-4-(pyrrolidin-1-ylmethyl)-2-furyl]-4-methyl-1,2,4-triazol-3-yl]sulfanyl]-3,5-difluoro-benzenecarbohydroxamic acid (comp. 208);
4-[[4-methyl-5-[5-[(4-methylpiperazin-1-yl)methyl]-2-furyl]-1,2,4-triazol-3-yl]sulfanyl]benzenecarbohydroxamic acid (comp. 209);
3,5-difluoro-4-[[4-methyl-5-[6-(2-pyrrolidin-1-ylethyl)-3-pyridyl]-1,2,4-triazol-3-yl]sulfanyl]benzenecarbohydroxamic acid (comp. 210);
4-[[5-[5-(diethylaminomethyl)-2-furyl]-4-methyl-1,2,4-triazol-3-yl]sulfanyl]-3,5-difluoro-benzenecarbohydroxamic acid (comp. 211);
3,5-difluoro-4-[[4-methyl-5-[5-(1-piperidylmethyl)-2-furyl]-1,2,4-triazol-3-yl]sulfanyl]benzenecarbohydroxamic acid (comp. 212);
4-[[5-[5-(diethylaminomethyl)-2-methyl-3-furyl]-4-methyl-1,2,4-triazol-3-yl]sulfanyl]-3,5-difluoro-benzenecarbohydroxamic acid (comp. 213);
4-[(5-phenyltetrazol-2-yl)methyl]benzenecarbohydroxamic acid (comp. 214);
4-[(5-phenyltetrazol-1-yl)methyl]benzenecarbohydroxamic acid (comp. 215);
4-[(5-phenyl-4H-1,2,4-triazol-3-yl)methyl]benzenecarbohydroxamic acid (comp. 216); and
N-hydroxy-4-((4-methyl-5-phenyl-4H-1,2,4-triazol-3-yl)methyl)benzamide (comp. 217).

4. A combination comprising the compound according to claim 1, and a drug selected from the group consisting of proteasome inhibitors, immune checkpoint inhibitors, steroids, bromodomain inhibitors, epigenetic drugs, traditional chemotherapy, and kinase inhibitors.

5. A method for treating cancer, comprising the step of administering the compound according to claim 1 to a subject suffering from cancer.

6. A pharmaceutical composition comprising a therapeutically effective quantity of at least one compound according to claim 1, or a pharmaceutically acceptable salt, stereoisomer or prodrug thereof, together with at least one pharmaceutically acceptable excipient.

7. The pharmaceutical composition according to claim 6, in a form suitable to be administered by enteral route, parenteral route, oral route, topical route, or inhalatory route.

8. The pharmaceutical composition according to claim 6, in the form of a liquid or a solid.

9. The compound according to claim 1, wherein $R^{12}$ and $R^{13}$, together with the carbon atom to which they are attached form a saturated cyclic moiety selected from the group consisting of cyclopropane, cyclobutane, cyclopentane, and cyclohexane.

10. The compound according to claim 2, wherein $R^{12}$ and $R^{13}$, together with the carbon atom to which they are attached form a saturated cyclic moiety selected from the group consisting of cyclopropane, cyclobutane, cyclopentane, and cyclohexane.

11. The compound according to claim 3, which is selected from the group consisting of:
- (S)—N-(1-(3-(4-(hydroxycarbamoyl)benzyl)-1,2,4-oxadiazol-5-yl)-2-(thiazol-4-yl)ethyl)-3,4-dimethoxybenzamide (comp. 1);
- 3,5-difluoro-N-hydroxy-4-((4-methyl-5-(naphthalen-1-yl)-4H-1,2,4-triazol-3-yl)thio)benzamide (comp. 2);
- 4-((5-(3-(N,N-dimethylsulfamoyl)phenyl)-1,3,4-oxadiazol-2-yl)methyl)-N-hydroxybenzamide (comp. 3);
- 3,5-difluoro-N-hydroxy-4-((4-methyl-5-(2-phenylpropan-2-yl)-4H-1,2,4-triazol-3-yl)thio)benzamide (comp. 4);
- 4-((5-(2,3-dihydrothieno[3,4-b][1,4]dioxin-5-yl)-1H-tetrazol-1-yl)methyl)-3,5-difluoro-N-hydroxybenzamide (comp. 5);
- 3,5-difluoro-N-hydroxy-4-((5-(pyridin-2-yl)-2H-tetrazol-2-yl)methyl)benzamide (comp. 6);
- difluoro-N-hydroxy-4-((5-(pyrimidin-2-yl)-2H-tetrazol-2-yl)methyl)benzamide (comp. 7);
- N-hydroxy-4-((5-(thiophen-2-yl)-1H-tetrazol-1-yl)methyl)benzamide (comp. 8);
- 3,5-difluoro-N-hydroxy-4-((4-methyl-5-(4-methyl-2-morpholinothiazol-5-yl)-4H-1,2,4-triazol-3-yl)thio)benzamide (comp. 9);
- N-hydroxy-4-((4-methyl-5-(thiophen-2-yl)-4H-1,2,4-triazol-3-yl)thio)benzamide (comp. 10);
- 4-((5-(furan-2-yl)-2H-tetrazol-2-yl)methyl)-N-hydroxybenzamide (comp. 12);
- 3,5-difluoro-N-hydroxy-4-((5-(pyridin-2-yl)-1H-tetrazol-1-yl)methyl)benzamide (comp. 13);
- 3,5-difluoro-N-hydroxy-4-((4-methyl-5-(pyridin-2-yl)-4H-1,2,4-triazol-3-yl)thio)benzamide (comp. 14);
- 3,5-difluoro-N-hydroxy-4-((5-(thiophen-2-yl)-1H-tetrazol-1-yl)methyl)benzamide (comp. 15);
- 3,5-difluoro-N-hydroxy-4-((4-methyl-5-(4-(piperidin-1-ylmethyl)phenyl)-4H-1,2,4-triazol-3-yl)thio)benzamide (comp. 16);
- 3,5-difluoro-N-hydroxy-4-((4-methyl-5-(thiophen-2-yl)-4H-1,2,4-triazol-3-yl)thio)benzamide (comp. 17);
- 3,5-difluoro-4-((5-(furan-2-yl)-2H-tetrazol-2-yl)methyl)-N-hydroxybenzamide (comp. 19);
- N-hydroxy-4-((5-(pyridin-2-yl)-1H-tetrazol-1-yl)methyl)benzamide (comp. 20);
- 4-[(5-phenyl-1,3,4-oxadiazol-2-yl)methyl]benzenecarbohydroxamic acid (comp. 68);
- 4-[[5-(6,6-dimethyl-3-methylsulfonyl-4-oxo-5,7-dihydro-2-benzothiophen-1-yl)tetrazol-2-yl]methyl]benzenecarbohydroxamic acid (comp. 74);
- 4-[[5-(4-methyl-2-morpholino-thiazol-5-yl)-1,3,4-oxadiazol-2-yl]methyl]benzenecarbohydroxamic acid (comp. 75);
- 4-[[5-[5-(dimethylsulfamoyl)-2-fluoro-phenyl]-4-methyl-1,2,4-triazol-3-yl]sulfanyl]benzenecarbohydroxamic acid (comp. 76);
- 4-[[5-[3-(dimethylamino)phenyl]-4-methyl-1,2,4-triazol-3-yl]sulfanyl]benzenecarbohydroxamic acid (comp. 77);
- 4-[[5-(3-methoxyphenyl)-4-methyl-1,2,4-triazol-3-yl]sulfanyl]benzenecarbohydroxamic acid (comp. 78);
- 4-[[5-(2,3-dihydrothieno[3,4-b][1,4]dioxin-5-yl)tetrazol-2-yl]methyl]-3,5-difluoro-benzenecarbohydroxamic acid (comp. 79);
- tert-butyl 4-[5-[4-(hydroxycarbamoyl)phenyl]sulfanyl-4-methyl-1,2,4-triazol-3-yl]piperidine-1-carboxylate (comp. 82);
- 4-[[5-(1,3-benzodioxol-5-yl)-4-methyl-1,2,4-triazol-3-yl]sulfanyl]benzenecarbohydroxamic acid (comp. 84);
- 4-[[5-(1,5-dimethylpyrazol-3-yl)-4-methyl-1,2,4-triazol-3-yl]sulfanyl]benzenecarbohydroxamic acid (comp. 85);
- 4-[[5-(1-isoquinolyl)tetrazol-2-yl]methyl]benzenecarbohydroxamic acid (comp. 87);
- 4-[[5-(2-quinolyl)tetrazol-1-yl]methyl]benzenecarbohydroxamic acid (comp. 91);
- 3,5-difluoro-4-[[5-(2-furyl)tetrazol-1-yl]methyl]benzenecarbohydroxamic acid (comp. 92);
- 3,5-difluoro-4-[[5-(1-isoquinolyl)tetrazol-2-yl]methyl]benzenecarbohydroxamic acid (comp. 93);
- 3,5-difluoro-4-[[5-(1-isoquinolyl)tetrazol-1-yl]methyl]benzenecarbohydroxamic acid (comp. 94);
- 3,5-difluoro-4-[[5-(2-quinolyl)tetrazol-2-yl]methyl]benzenecarbohydroxamic acid (comp. 95);
- 3,5-difluoro-4-[[5-(1-isoquinolyl)-4-methyl-1,2,4-triazol-3-yl]sulfanyl]benzenecarbohydroxamic acid (comp. 121);
- 3,5-difluoro-4-[[4-methyl-5-(2-quinolyl)-1,2,4-triazol-3-yl]sulfanyl]benzenecarbohydroxamic acid (comp. 122);
- 4-[(5-pyrimidin-2-yltetrazol-2-yl)methyl]benzenecarbohydroxamic acid (comp. 123);
- 3,5-difluoro-4-[(5-pyrimidin-2-yltetrazol-1-yl)methyl]benzenecarbohydroxamic acid (comp. 125);
- 3,5-difluoro-4-[[5-[5-(trifluoromethyl)-2-pyridyl]tetrazol-1-yl]methyl]benzenecarbohydroxamic acid (comp. 129);
- 3,5-difluoro-4-[[5-(2-pyridylmethyl)tetrazol-2-yl]methyl]benzenecarbohydroxamic acid;2,2,2-trifluoroacetic acid (comp. 134);
- 3,5-difluoro-4-[[5-(4-fluorophenyl)-4-(2-morpholinoethyl)-1,2,4-triazol-3-yl]sulfanyl]benzenecarbohydroxamic acid (comp. 138);
- 3,5-difluoro-4-[[4-(2-furylmethyl)-5-(2-pyridyl)-1,2,4-triazol-3-yl]sulfanyl]benzenecarbohydroxamic acid (comp. 140);
- 4-[[4-benzyl-5-(pyrrolidin-1-ylmethyl)-1,2,4-triazol-3-yl]sulfanyl]-3,5-difluoro-benzenecarbohydroxamic acid (comp. 141);
- 3,5-difluoro-4-[[5-(2-fluorophenyl)-4-(2-furylmethyl)-1,2,4-triazol-3-yl]sulfanyl]benzenecarbohydroxamic acid (comp. 145);
- 3,5-difluoro-4-[[4-(2-furylmethyl)-5-(4-pyridyl)-1,2,4-triazol-3-yl]sulfanyl]benzenecarbohydroxamic acid (comp. 146);
- 3,5-difluoro-4-[[4-(2-furylmethyl)-5-(3-pyridyl)-1,2,4-triazol-3-yl]sulfanyl]benzenecarbohydroxamic acid (comp. 147);
- 3,5-difluoro-4-[(5-imidazo[1,2-a]pyridin-3-yl-4-methyl-1,2,4-triazol-3-yl)sulfanyl]benzenecarbohydroxamic acid (comp. 149);

4-[[5-(1-benzyl-4-phenyl-4-piperidyl)-4-methyl-1,2,4-triazol-3-yl]sulfanyl]-3,5-difluoro-benzenecarbohydroxamic acid (comp. 150);

3,5-difluoro-4-[[4-methyl-5-[3-(4-methylpiperazin-1-yl)sulfonylphenyl]-1,2,4-triazol-3-yl]sulfanyl]benzenecarbohydroxamic acid (comp. 151);

4-[[5-[3-(4-benzylpiperazin-1-yl)sulfonylphenyl]-4-methyl-1,2,4-triazol-3-yl]sulfanyl]-3,5-difluoro-benzenecarbohydroxamic acid (comp. 152);

3,5-difluoro-4-[[4-methyl-5-(3-pyridyl)-1,2,4-triazol-3-yl]sulfanyl]benzenecarbohydroxamic acid (comp. 153);

4-[[5-(2,6-difluorophenyl)-4-methyl-1,2,4-triazol-3-yl]sulfanyl]-3,5-difluoro-benzenecarbohydroxamic acid (comp. 165);

3,5-difluoro-4-[[4-methyl-5-[3-(4-methylpiperazin-1-yl)phenyl]-1,2,4-triazol-3-yl]sulfanyl]benzenecarbohydroxamic acid (comp. 166);

4-[[5-[3-(azepan-1-ylmethyl)phenyl]-4-methyl-1,2,4-triazol-3-yl]sulfanyl]-3,5-difluoro-benzenecarbohydroxamic acid (comp. 167);

4-[[5-[4-(azepan-1-ylmethyl)phenyl]-4-methyl-1,2,4-triazol-3-yl]sulfanyl]-3,5-difluoro-benzenecarbohydroxamic acid (comp. 168);

4-[[5-(4-aminophenyl)tetrazol-2-yl]methyl]benzenecarbohydroxamic acid (comp. 169);

4-[[5-(4-aminophenyl)tetrazol-2-yl]methyl]-3,5-difluoro-benzenecarbohydroxamic acid (comp. 171);

4-[[5-(4-aminophenyl)tetrazol-1-yl]methyl]-3,5-difluoro-benzenecarbohydroxamic acid (comp. 172);

4-[[5-[4-(aminomethyl)phenyl]tetrazol-2-yl]methyl]-3,5-difluoro-benzenecarbohydroxamic acid (comp. 175);

3,5-difluoro-4-[[4-methyl-5-[1-(2-pyridyl)cyclopropyl]-1,2,4-triazol-3-yl]sulfanyl]benzenecarbohydroxamic acid (comp. 177);

3,5-difluoro-4-[[4-methyl-5-[1-(3-pyridyl)cyclopropyl]-1,2,4-triazol-3-yl]sulfanyl]benzenecarbohydroxamic acid (comp. 178);

3,5-difluoro-4-[(4-methyl-5-pyridazin-3-yl-1,2,4-triazol-3-yl)sulfanyl]benzenecarbohydroxamic acid (comp. 179);

3,5-difluoro-4-[[5-(3-fluoro-2-pyridyl)-4-methyl-1,2,4-triazol-3-yl]sulfanyl]benzenecarbohydroxamic acid (comp. 180);

3,5-difluoro-4-[[4-methyl-5-[3-(1-piperidylmethyl)phenyl]-1,2,4-triazol-3-yl]sulfanyl]benzenecarbohydroxamic acid (comp. 181);

3,5-difluoro-4-[[4-methyl-5-[3-(morpholinomethyl)phenyl]-1,2,4-triazol-3-yl]sulfanyl]benzenecarbohydroxamic acid (comp. 182);

3,5-difluoro-4-[[4-methyl-5-[1-methyl-1-(3-pyridyl)ethyl]-1,2,4-triazol-3-yl]sulfanyl]benzenecarbohydroxamic acid (comp. 186);

3,5-difluoro-N-hydroxy-4-((5-(pyridin-3-yl)-1,3,4-thiadiazol-2-yl)thio)benzamide (comp. 191);

3,5-difluoro-4-[[5-(4-pyridyl)-1,3,4-thiadiazol-2-yl]methyl]benzenecarbohydroxamic acid (comp. 195);

3,5-difluoro-4-[[5-(5-morpholino-3-pyridyl)-1,3,4-thiadiazol-2-yl]methyl]benzenecarbohydroxamic acid (comp. 197);

3,5-difluoro-N-hydroxy-4-((5-phenyl-1,3,4-thiadiazol-2-yl)methyl)benzamide (comp. 198);

3,5-difluoro-4-[[5-(2-furyl)-4-methyl-1,2,4-triazol-3-yl]sulfanyl]benzenecarbohydroxamic acid (comp. 199);

4-[[5-[5-[bis(2-methoxyethyl)amino]-3-pyridyl]-1,2,4-oxadiazol-3-yl]methyl]-3,5-difluoro-benzenecarbohydroxamic acid (comp. 200);

3,5-difluoro-4-[[5-[5-(pyrrolidin-1-ylmethyl)-2-furyl]-1,2,4-oxadiazol-3-yl]methyl]benzenecarbohydroxamic acid (comp. 202);

3,5-difluoro-4-[[4-methyl-5-[5-(morpholinomethyl)-2-furyl]-1,2,4-triazol-3-yl]sulfanyl]benzenecarbohydroxamic acid (comp. 204);

3,5-difluoro-4-[[4-methyl-5-[5-[(4-methylpiperazin-1-yl)methyl]-2-furyl]-1,2,4-triazol-3-yl]sulfanyl]benzenecarbohydroxamic acid (comp. 205);

4-[[5-[5-[(dimethylamino)methyl]-2-furyl]-4-methyl-1,2,4-triazol-3-yl]sulfanyl]-3,5-difluoro-benzenecarbohydroxamic acid (comp. 206);

3,5-difluoro-4-[[4-methyl-5-[5-(pyrrolidin-1-ylmethyl)-2-furyl]-1,2,4-triazol-3-yl]sulfanyl]benzenecarbohydroxamic acid (comp. 207);

4-[[5-[5-ethyl-4-(pyrrolidin-1-ylmethyl)-2-furyl]-4-methyl-1,2,4-triazol-3-yl]sulfanyl]-3,5-difluoro-benzenecarbohydroxamic acid (comp. 208);

4-[[4-methyl-5-[5-[(4-methylpiperazin-1-yl)methyl]-2-furyl]-1,2,4-triazol-3-yl]sulfanyl]benzenecarbohydroxamic acid (comp. 209);

3,5-difluoro-4-[[4-methyl-5-[6-(2-pyrrolidin-1-ylethyl)-3-pyridyl]-1,2,4-triazol-3-yl]sulfanyl]benzenecarbohydroxamic acid (comp. 210);

4-[[5-[5-(diethylaminomethyl)-2-furyl]-4-methyl-1,2,4-triazol-3-yl]sulfanyl]-3,5-difluoro-benzenecarbohydroxamic acid (comp. 211);

3,5-difluoro-4-[[4-methyl-5-[5-(1-piperidylmethyl)-2-furyl]-1,2,4-triazol-3-yl]sulfanyl]benzenecarbohydroxamic acid (comp. 212);

4-[[5-[5-(diethylaminomethyl)-2-methyl-3-furyl]-4-methyl-1,2,4-triazol-3-yl]sulfanyl]-3,5-difluoro-benzenecarbohydroxamic acid (comp. 213);

4-[(5-phenyltetrazol-2-yl)methyl]benzenecarbohydroxamic acid (comp. 214); and

4-[(5-phenyltetrazol-1-yl)methyl]benzenecarbohydroxamic acid (comp. 215).

12. The combination according to claim 4, wherein drug is a JAK family inhibitor, a CTLA4 inhibitor, a PD1 inhibitor or a PDL1 checkpoints inhibitor.

13. The pharmaceutical composition according to claim 8 in the form of a capsule, tablet, coated tablet, granule, cream, or ointment.

14. The method according to claim 5, wherein the cancer is multiple myeloma or non-Hodgkin's lymphoma.

* * * * *

UNITED STATES PATENT AND TRADEMARK OFFICE
CERTIFICATE OF CORRECTION

PATENT NO.       : 11,351,178 B2
APPLICATION NO.  : 16/491827
DATED            : June 7, 2022
INVENTOR(S)      : Vergani et al.

Page 1 of 1

It is certified that error appears in the above-identified patent and that said Letters Patent is hereby corrected as shown below:

In the Claims

Column 157, Claim 1, Lines 48-55: Formula (II) should read:

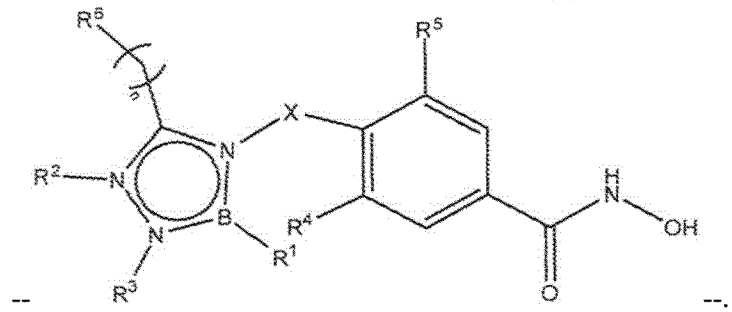

Column 162, Claim 2, Line 5: "anf" should read -- and --.

Column 165, Claim 3, Line 54: "pyridyptetrazol" should read -- pyridyl)tetrazol --.

Signed and Sealed this
Second Day of August, 2022

Katherine Kelly Vidal
*Director of the United States Patent and Trademark Office*